United States Patent
Kim et al.

(10) Patent No.: US 12,433,150 B2
(45) Date of Patent: Sep. 30, 2025

(54) ORGANIC ELECTROLUMINESCENCE DEVICE AND POLYCYCLIC COMPOUND FOR ORGANIC ELECTROLUMINESCENCE DEVICE

(71) Applicant: Samsung Display Co., Ltd., Yongin-si (KR)

(72) Inventors: Hyeongmin Kim, Suwon-si (KR); HeeChoon Ahn, Seoul (KR); Hyunah Um, Seoul (KR); Yeseul Lee, Busan (KR); Yirang Im, Daejeon (KR); Soo-Byung Ko, Yongin-si (KR); Jongwoo Kim, Hwaseong-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 614 days.

(21) Appl. No.: 16/922,862

(22) Filed: Jul. 7, 2020

(65) Prior Publication Data

US 2021/0020854 A1    Jan. 21, 2021

(30) Foreign Application Priority Data

Jul. 17, 2019 (KR) .......................... 10-2019-0086568

(51) Int. Cl.
*H10K 85/40* (2023.01)
*C07D 405/14* (2006.01)
(Continued)

(52) U.S. Cl.
CPC .......... *H10K 85/40* (2023.02); *C07D 405/14* (2013.01); *C07D 409/14* (2013.01);
(Continued)

(58) Field of Classification Search
None
See application file for complete search history.

(56) References Cited

U.S. PATENT DOCUMENTS 8,614,010 B2   12/2013   Yabunouchi et al.
8,895,966 B2   11/2014   Numata et al.
(Continued)

FOREIGN PATENT DOCUMENTS

KR   10-2011-0097784 A   8/2011
KR   10-2014-0024734 A   3/2014
(Continued)

OTHER PUBLICATIONS

Iani S. Pereteanu et al. "Synthesis and electronic properties of 3,7-dianilino substituted N-hexyl phenothiazines", Org. Biomol. Chem. 2013, vol. 11, p. 5127-5135 (Year: 2013).*
(Continued)

*Primary Examiner* — Seokmin Jeon
(74) *Attorney, Agent, or Firm* — Womble Bond Dickinson (US) LLP

(57) ABSTRACT

The present disclosure relates to an organic electroluminescence device in which a polycyclic compound represented
(Continued)

by Formula 1 below is included in at least one functional layer of a plurality of functional layers, and to the polycyclic compound represented by Formula 1 below:

[Formula 1]

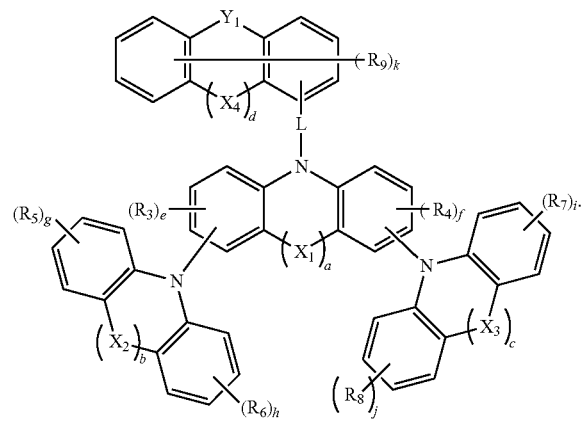

5 Claims, 2 Drawing Sheets

(51) Int. Cl.
  *C07D 409/14* (2006.01)
  *C07D 413/14* (2006.01)
  *C07D 417/14* (2006.01)
  *C07F 7/08* (2006.01)
  *H10K 50/11* (2023.01)
  *H10K 85/60* (2023.01)
  *H10K 101/10* (2023.01)

(52) U.S. Cl.
  CPC ......... *C07D 413/14* (2013.01); *C07D 417/14* (2013.01); *C07F 7/0812* (2013.01); *C07F 7/0816* (2013.01); *H10K 85/631* (2023.02); *H10K 85/636* (2023.02); *H10K 85/657* (2023.02); *H10K 85/6572* (2023.02); *H10K 85/6574* (2023.02); *H10K 85/6576* (2023.02); *H10K 50/11* (2023.02); *H10K 2101/10* (2023.02)

(56) References Cited

U.S. PATENT DOCUMENTS

| | | | |
|---|---|---|---|
| 9,196,842 B2 | 11/2015 | Kato et al. | |
| 2014/0042412 A1* | 2/2014 | Ryu | H01L 51/0071 |
| | | | 257/40 |
| 2017/0117488 A1 | 4/2017 | Ahn et al. | |
| 2017/0244049 A1* | 8/2017 | Aspuru-Guzik | H01L 51/0072 |
| 2018/0072945 A1 | 3/2018 | Otsu et al. | |
| 2018/0159050 A1* | 6/2018 | Kim | H01L 51/0072 |

FOREIGN PATENT DOCUMENTS

| | | |
|---|---|---|
| KR | 10-2015-0072644 A | 6/2015 |
| KR | 10-2016-0079415 A | 7/2016 |
| KR | 10-2016-0149879 A | 12/2016 |
| KR | 10-2017-0131537 A | 11/2017 |
| KR | 10-2018-0027468 A | 3/2018 |
| KR | 10-1862881 B1 | 5/2018 |
| WO | WO 2014/002873 A1 | 1/2014 |

OTHER PUBLICATIONS

English version of WO 2007/043484 A and the original WO 2007/043484 A, Tadao Yagi, Apr. 19, 2007 (Year: 2007).*
The screen shot of the compound information of FIrpic from Ossila, webpage address (https://www.ossila.com/products/firpic?_pos=1&_sid=a465273be&_ss=r) (Year: 2024).*
English translation of JP 2008/109103 A and the original JP 2008/109103 A, Rei Takeda, May 8, 2008 (Year: 2008).*
Pamela Schrogel et al. "A series of CBP-derivatives as host materials for blue phosphorescent organic light-emitting diodes", J. Mater. Chem. 2011, vol. 21, p. 2266-2273 (Year: 2011).*

* cited by examiner

ORGANIC ELECTROLUMINESCENCE DEVICE AND POLYCYCLIC COMPOUND FOR ORGANIC ELECTROLUMINESCENCE DEVICE

CROSS-REFERENCE TO RELATED APPLICATION

This application claims priority to and the benefit of Korean Patent Application No. 10-2019-0086568, filed on Jul. 17, 2019, the entire content of which is hereby incorporated by reference.

BACKGROUND

1. Field

The present disclosure herein relates to an organic electroluminescence device and a polycyclic compound utilized therein.

2. Description of the Related Art

The development of an organic electroluminescence display as an image display is being actively conducted. The organic electroluminescence display is a so-called self-luminescent display (which is different from a liquid crystal display), and in which holes and electrons injected from a first electrode and a second electrode recombine in an emission layer to form excitons. A light emission material (that is an organic compound) included in the emission layer emits light when the excitons transition from an excited state to a ground state.

For example, an organic material containing device which includes a first electrode, a hole transport layer disposed on the first electrode, an emission layer disposed on the hole transport layer, an electron transport layer disposed on the emission layer, and a second electrode disposed on the electron transport layer is known as an organic electroluminescence display. Holes are injected from the first electrode, and the injected holes are moved through the hole transport layer and injected into the emission layer. Meanwhile, electrons are injected from the second electrode, and the injected electrons are moved through the electron transport layer and injected into the emission layer. The holes and electrons injected into the emission layer are recombined with each other to form excitons in the emission layer. The organic electroluminescence display emits light generated when the excitons fall to a ground state.

In the application of an organic electroluminescence device to a display, the increase of the life (e.g., lifespan) of the organic electroluminescence device is desired, and development on materials for an organic electroluminescence device which is capable of stably meeting the desired lifespan is being continuously researched.

SUMMARY

Aspects according to embodiments of the present disclosure are directed toward an organic electroluminescence device and a polycyclic compound utilized therein.

An organic electroluminescence device according to an embodiment of the present disclosure may include a first electrode, a second electrode, and a plurality of functional layers. The second electrode may be on the first electrode. The plurality of functional layers may be between the first electrode and the second electrode. The first electrode and the second electrode each independently include at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides thereof. At least one functional layer of the plurality of functional layers may include a polycyclic compound represented by Formula 1 below:

[Formula 1]

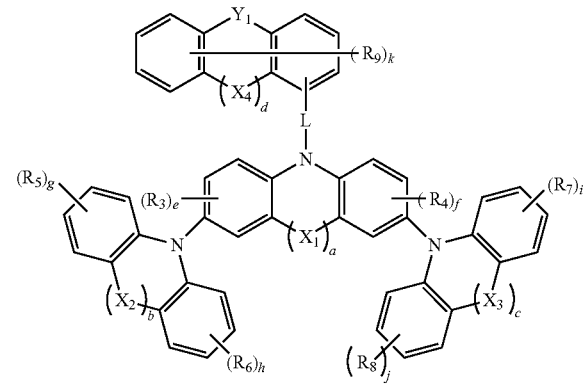

In Formula 1 above, $X_1$ to $X_4$ each independently may be a direct linkage, O, or S. $Y_1$ may be O, S, or $SiR_1R_2$. L may be a direct linkage, a substituted or unsubstituted alkylene group having 1 to 10 carbon atoms, a substituted or unsubstituted arylene group having 6 to 30 carbon atoms to form a ring, or a substituted or unsubstituted heteroarylene group having 2 to 30 carbon atoms to form a ring. $R_1$ and $R_2$ may be each independently a hydrogen atom, a deuterium atom, a substituted or unsubstituted alkyl group having 1 to 20 carbon atoms, a substituted or unsubstituted aryl group having 6 to 30 carbon atoms to form a ring, or a substituted or unsubstituted heteroaryl group having 2 to 30 carbon atoms to form a ring; $R_1$ and $R_2$ may be each optionally combined with an adjacent group to form a ring. $R_3$ to $R_9$ may be each independently a hydrogen atom, a deuterium atom, a halogen atom, a cyano group, a substituted or unsubstituted amine group, a substituted or unsubstituted silyl group, a substituted or unsubstituted oxy group having 1 to 20 carbon atoms, a substituted or unsubstituted alkyl group having 1 to 20 carbon atoms, a substituted or unsubstituted aryl group having 6 to 30 carbon atoms to form a ring, or a substituted or unsubstituted heteroaryl group having 2 to 30 carbon atoms to form a ring; $R_3$ to $R_9$ may be each optionally combined with an adjacent group to form a ring. a to d may be each independently 0 or 1. e and f may be each independently an integer of 0 to 3. g and j may be each independently an integer of 0 to 4. k may be an integer of 0 to 7. When $Y_1$ is O or S, and when $X_4$ is a direct linkage, at least one selected from $X_1$ to $X_3$ may be O or S. Alternatively, when $Y_1$ is O or S, and when $X_4$ is a direct linkage, at least one selected from a to c may be 0.

In an embodiment, the polycyclic compound represented by Formula 1 above may be represented by Formula 2-1 below:

[Formula 2-1]

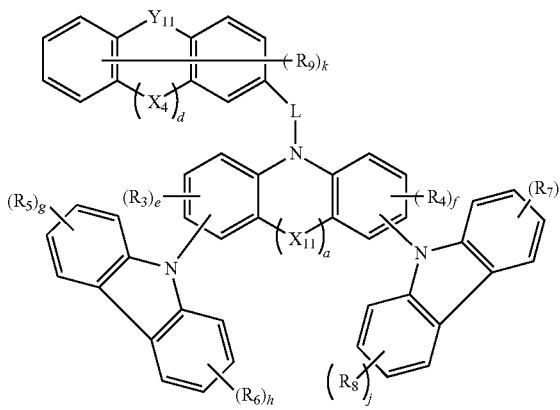

In Formula 2-1 above, $X_{11}$ and $Y_{11}$ may be each independently O or S. $X_4$, L, $R_3$ to $R_9$, a, and d to k may be the same as respectively defined in connection with Formula 1 above.

The polycyclic compound represented by Formula 2-1 above may be represented by at least one selected from Formula 2-1-1 to Formula 2-1-3 below:

[Formula 2-1-1]

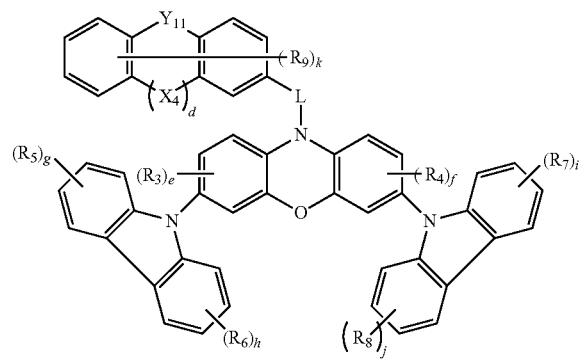

[Formula 2-1-2]

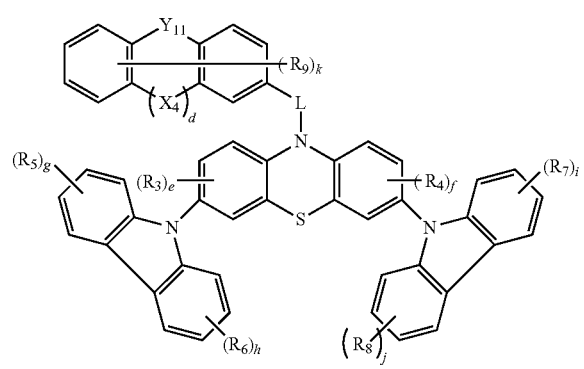

[Formula 2-1-3]

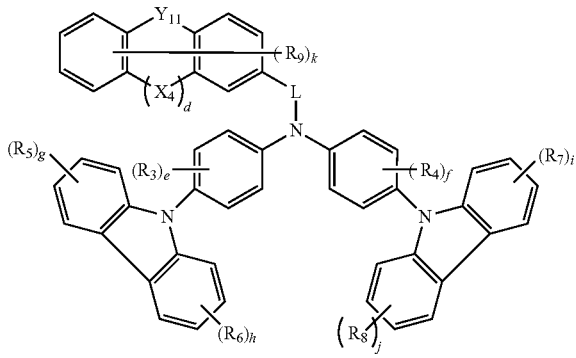

In Formula 2-1-1 to Formula 2-1-3 above, $X_4$, $Y_{11}$, L, $R_3$ to $R_9$, and d to k may be the same as respectively defined in connection with Formula 2-1 above.

In an embodiment, the polycyclic compound represented by Formula 1 above may be represented by Formula 2-2 below:

[Formula 2-2]

In Formula 2-2 above, $X_{21}$, $X_{31}$, and $Y_{11}$ may be each independently O or S. $X_4$, L, $R_3$ to $R_9$, and b to k may be the same as respectively defined in connection with Formula 1 above.

In an embodiment, the polycyclic compound represented by Formula 1 above may be represented by Formula 3 below:

[Formula 3]

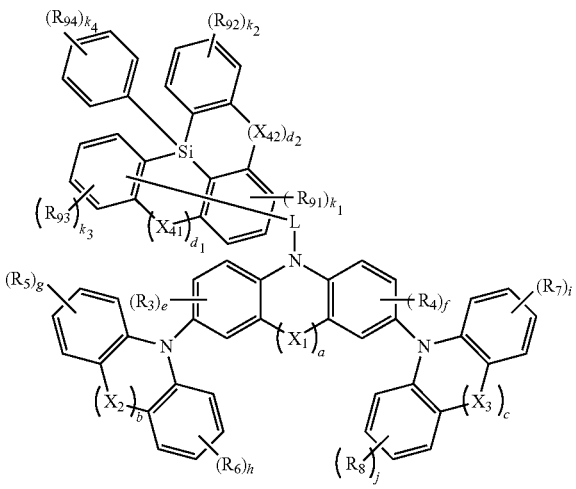

In Formula 3 above, $X_{41}$ and $X_{42}$ may each be O. $R_{91}$ to $R_{94}$ may be each independently a hydrogen atom, a deuterium atom, a halogen atom, a cyano group, a substituted or unsubstituted amine group, a substituted or unsubstituted silyl group, a substituted or unsubstituted oxy group having 1 to 20 carbon atoms, a substituted or unsubstituted alkyl group having 1 to 20 carbon atoms, a substituted or unsubstituted aryl group having 6 to 30 carbon atoms to form a ring, or a substituted or unsubstituted heteroaryl group having 2 to 30 carbon atoms to form a ring. $d_1$ and $d_2$ may be each independently 0 or 1. $k_1$ may be an integer of 0 to 3. $k_2$ and $k_3$ may be each independently an integer of 0 at 4. $k_4$ may be an integer of 0 to 5. $X_1$, to $X_3$, L, $R_3$ to $R_8$, a to c, and e to j may be the same as respectively defined in connection with Formula 1 above.

At least one selected from $d_1$ and $d_2$ may be 1.

In an embodiment, the polycyclic compound represented by Formula 3 above may be represented by Formula 3-1 below:

[Formula 3-1]

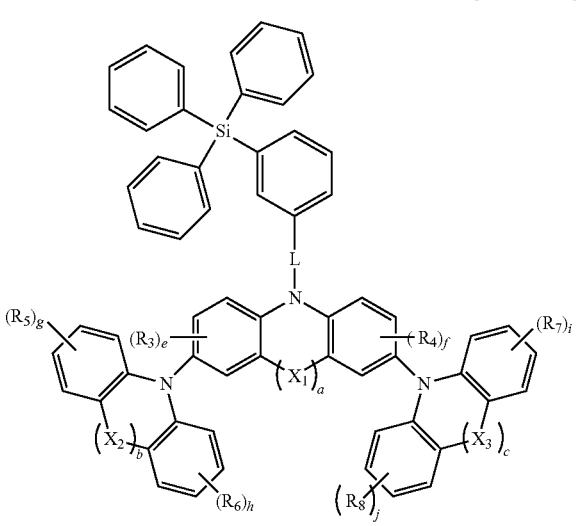

In Formula 3-1 above, $X_1$ to $X_3$, L, $R_3$ to $R_8$, a to c, and e to j may be the same as respectively defined in connection with Formula 3 above.

The polycyclic compound represented by Formula 3-1 above may be represented by at least one selected from Formula 3-1-1 to Formula 3-1-3 below:

[Formula 3-1-1]

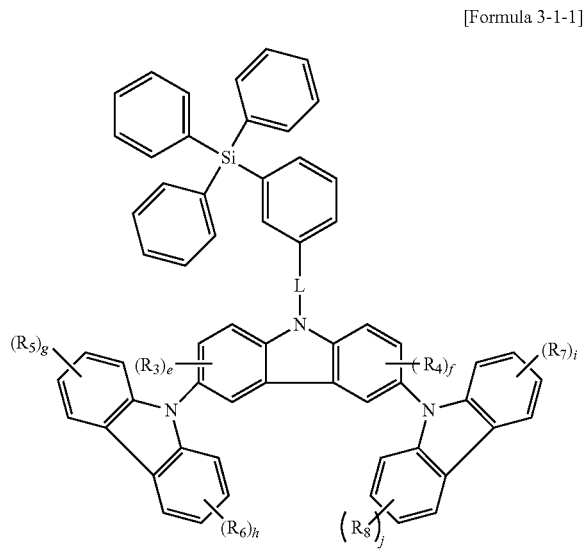

[Formula 3-1-2]

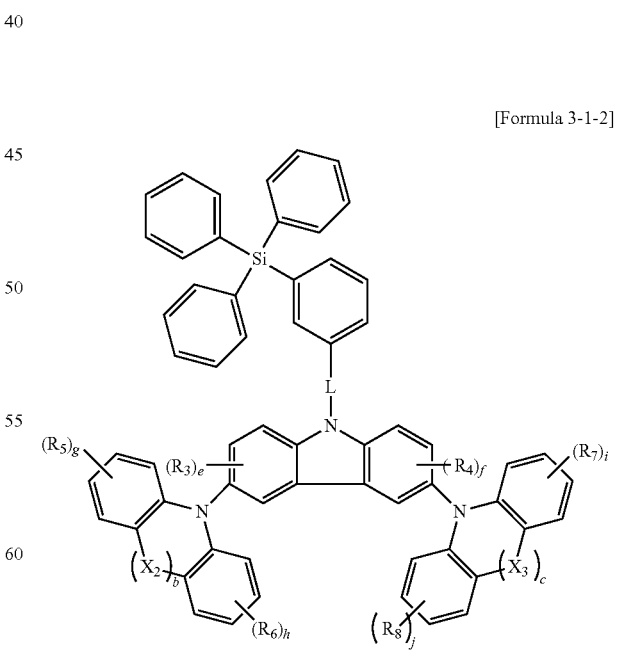

[Formula 3-1-3]
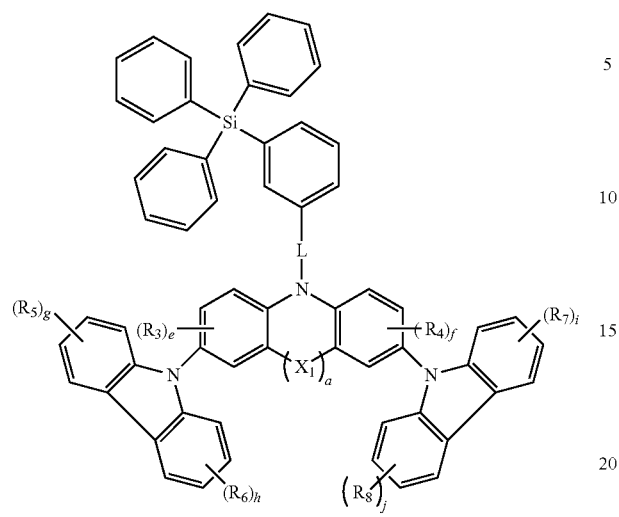
In Formula 3-1-1 to Formula 3-1-3 above, $X_1$ to $X_3$, L, $R_3$ to $R_8$, a to c, and e to j may be the same as respectively defined in connection with Formula 3-1 above.
The polycyclic compound may be any one selected from the compounds represented in Compound Group 1 below:
[Compound Group 1]
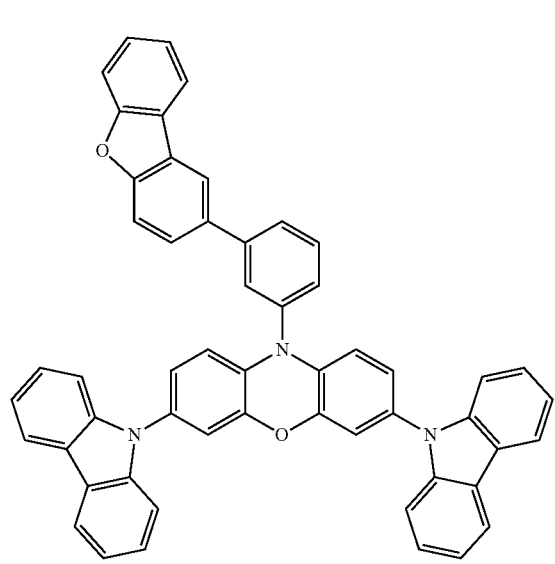
1
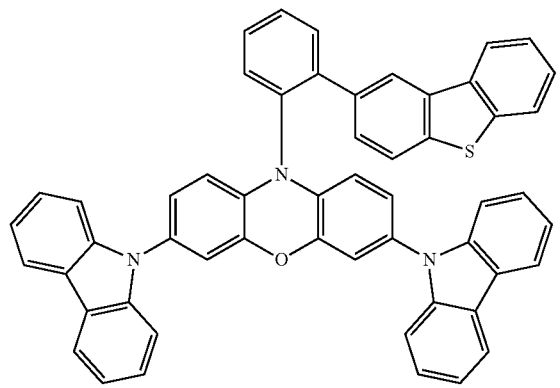
2

-continued
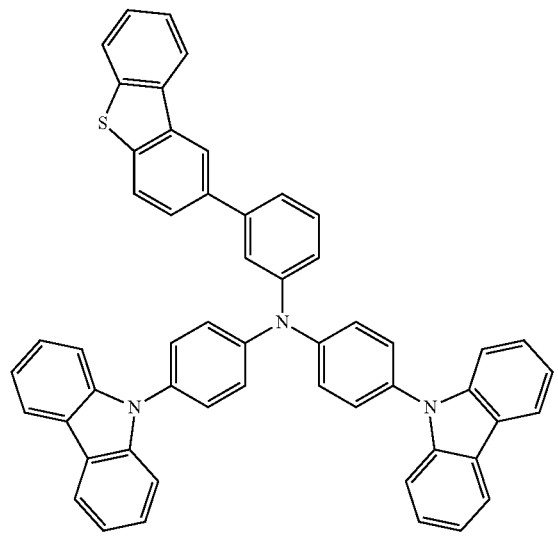
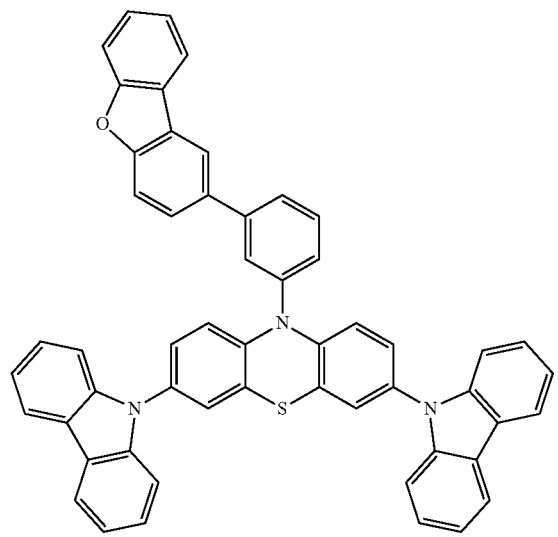
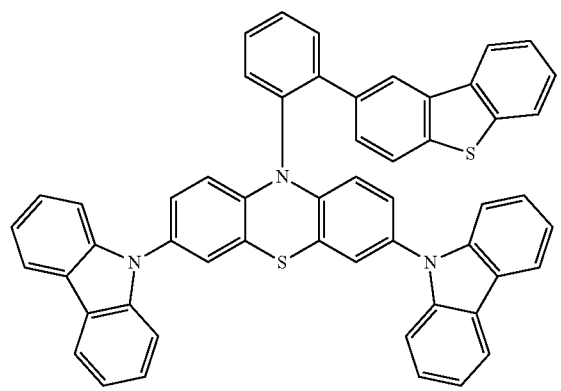
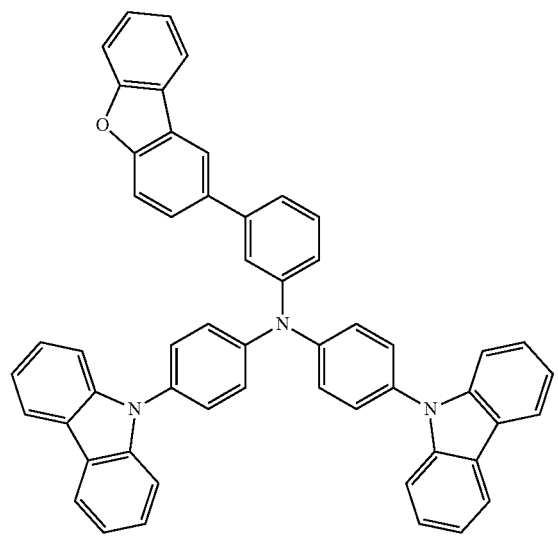

-continued
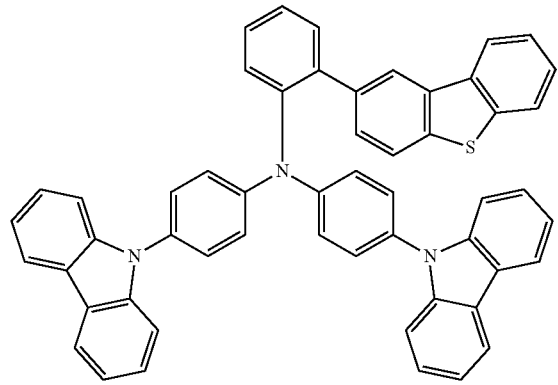
9
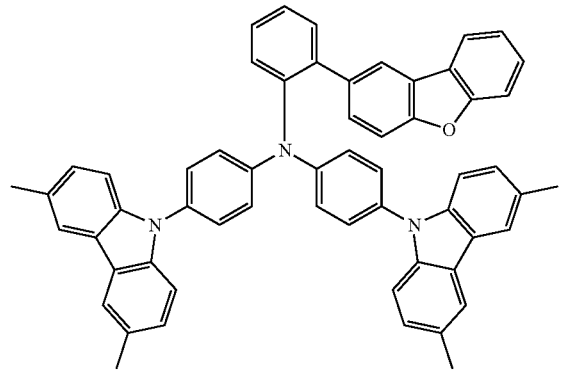
10
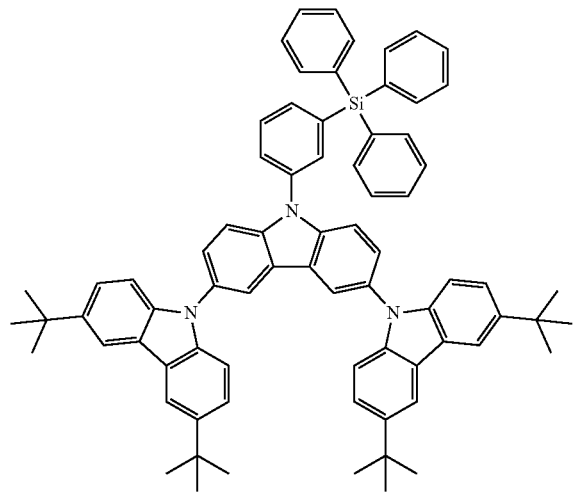
11
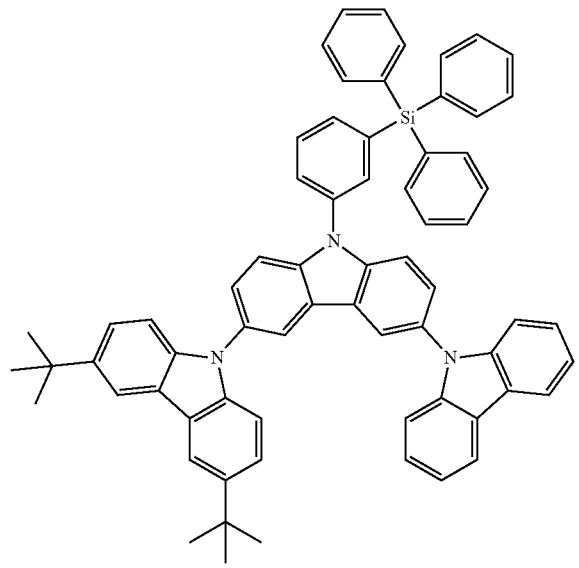
12
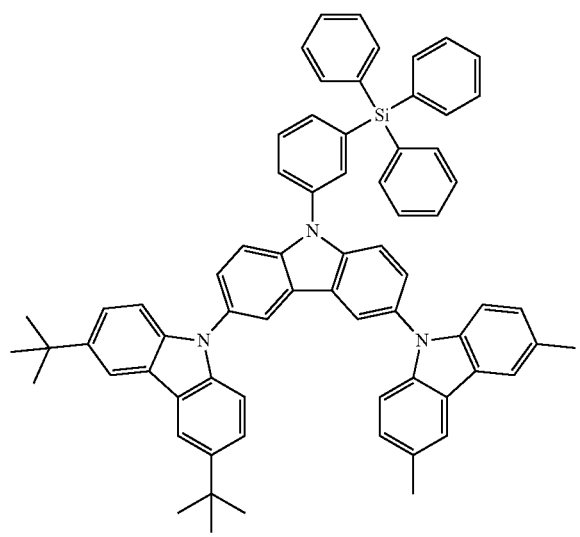
13

15
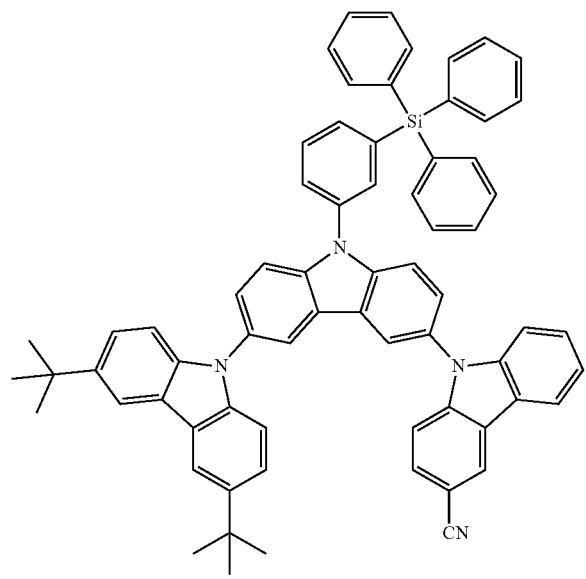
16
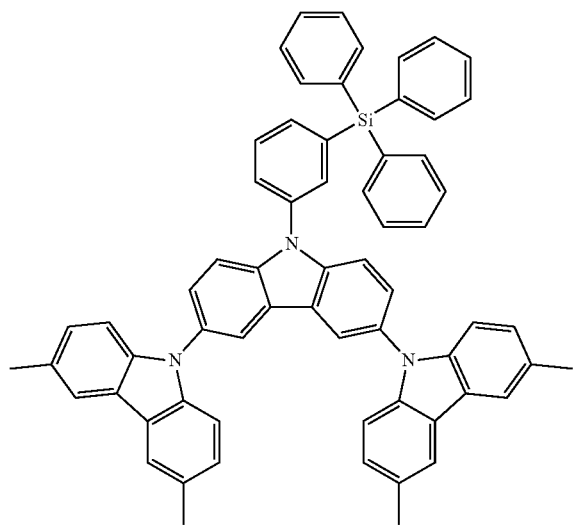
17
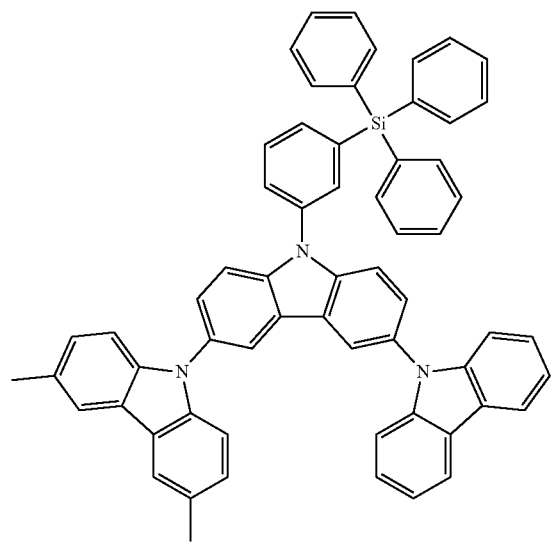
18
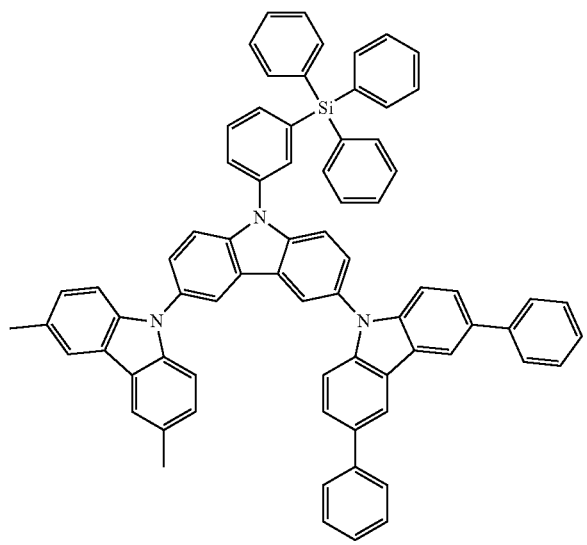

-continued
19
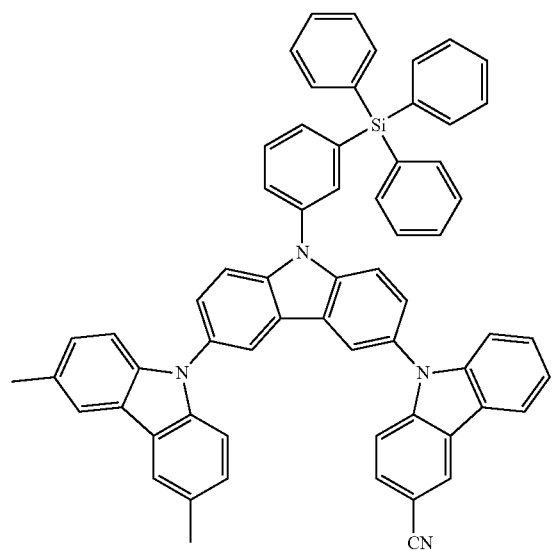
20
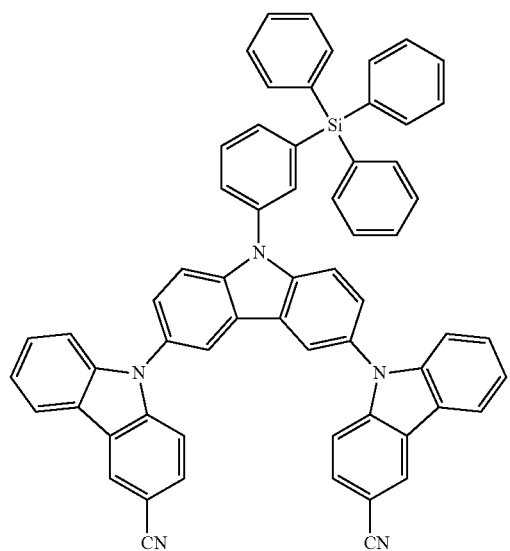
21
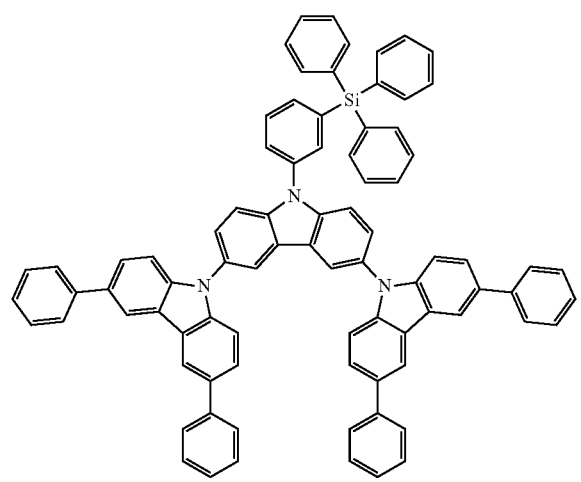
22
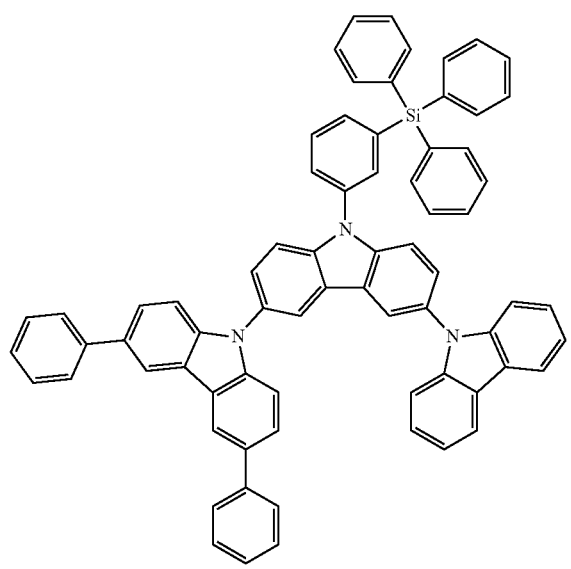

-continued
23
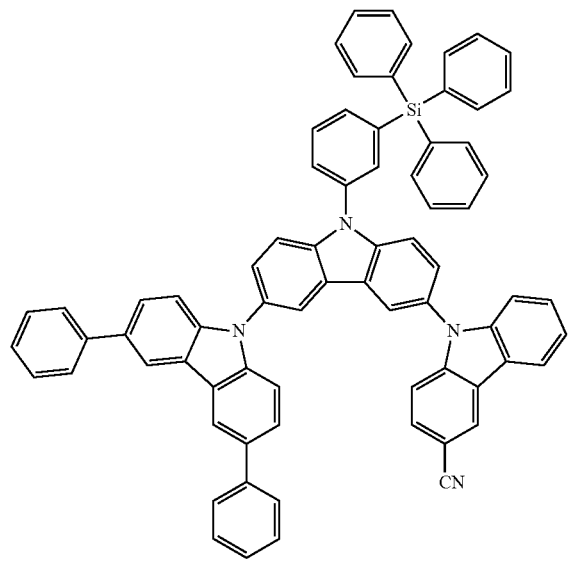
24
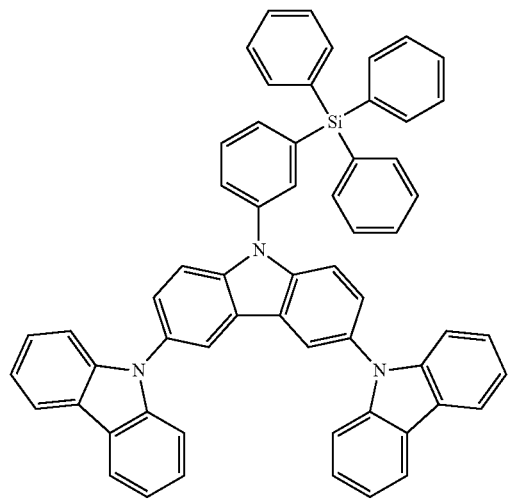
25
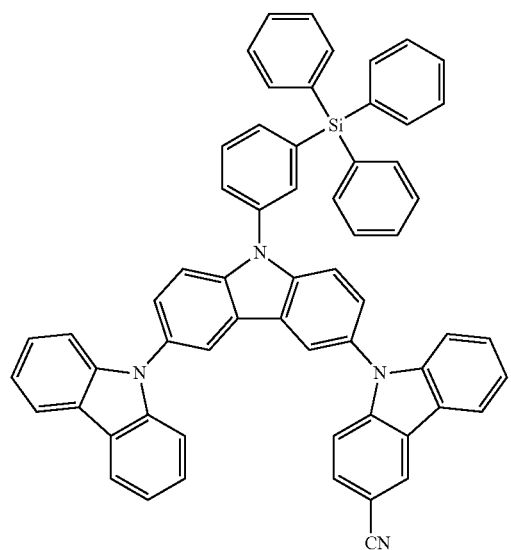
26
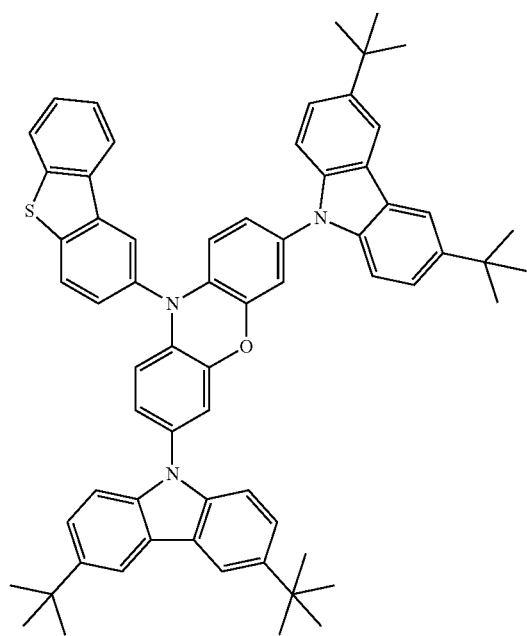

-continued
27
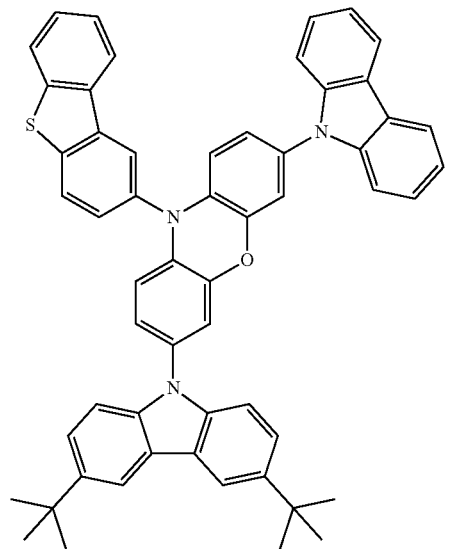
28
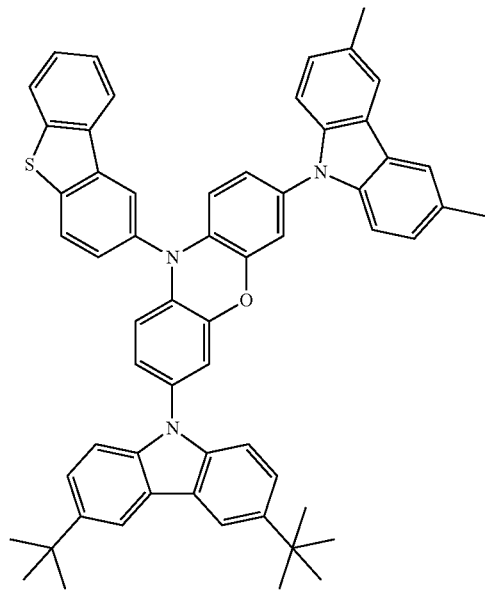
29
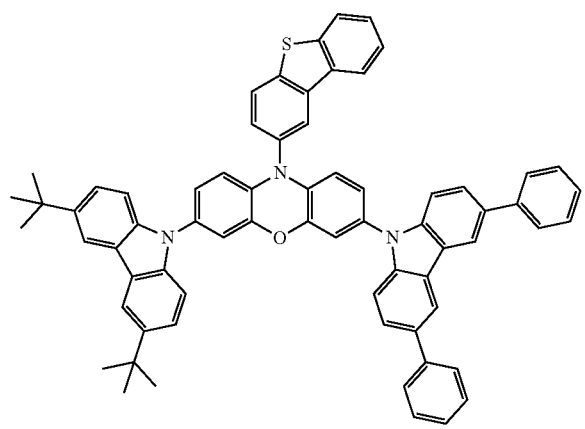
30
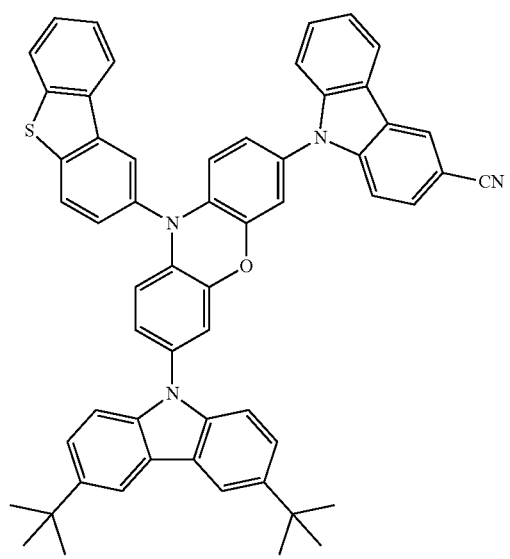

-continued
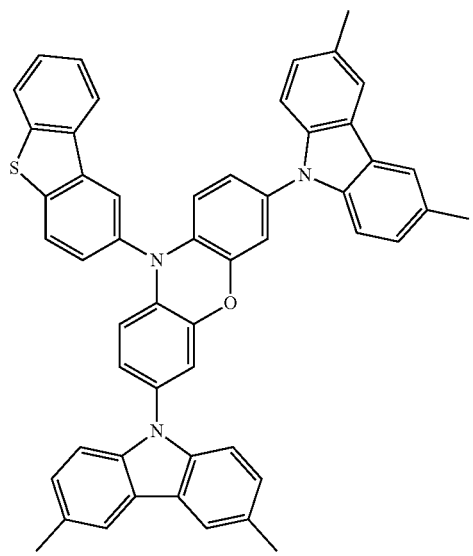
31
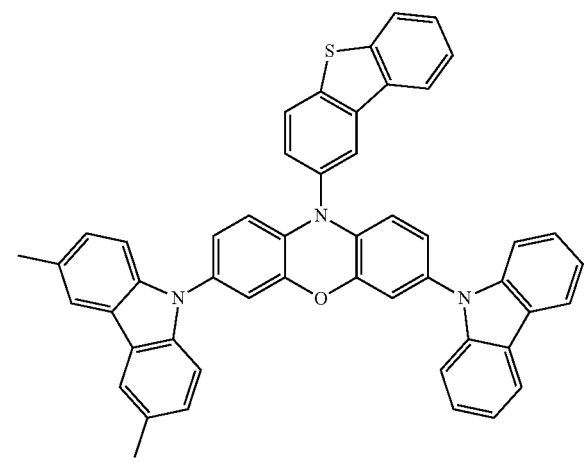
32
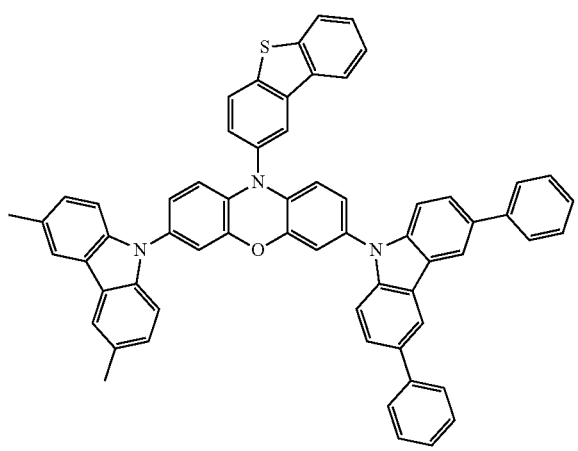
33
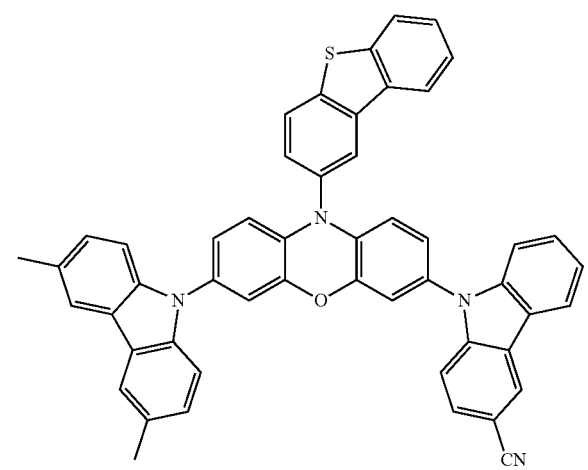
34
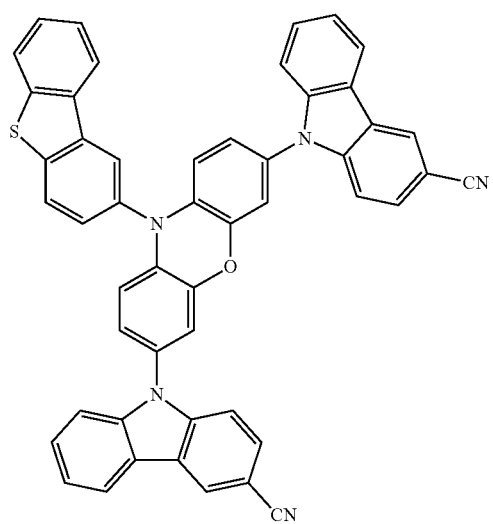
35

36
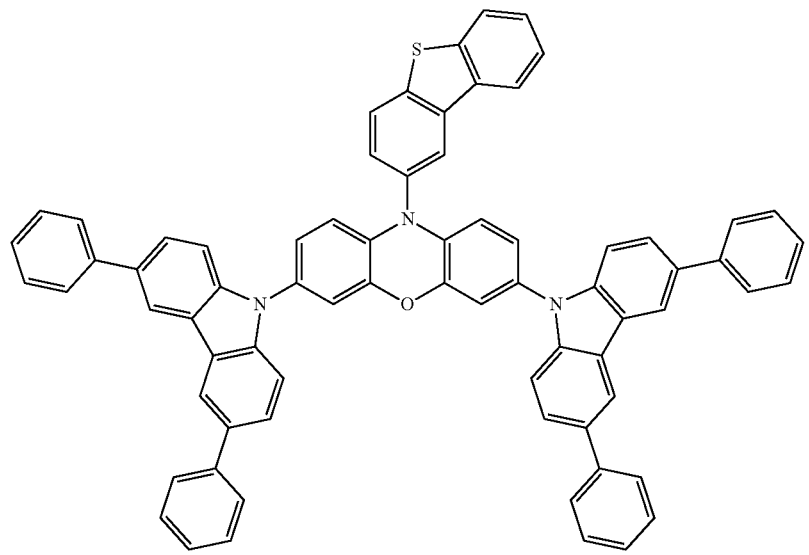
37
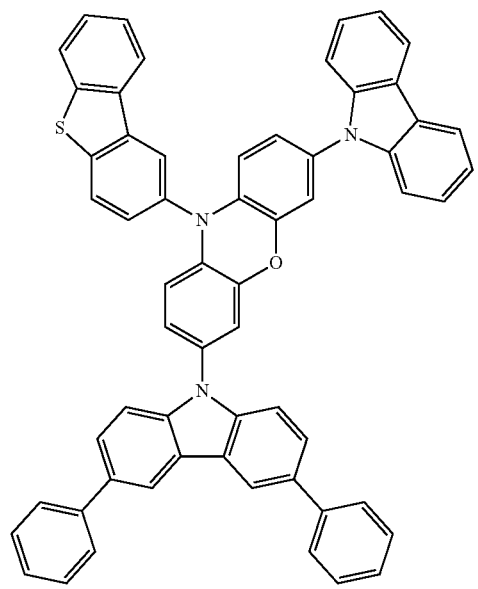
38
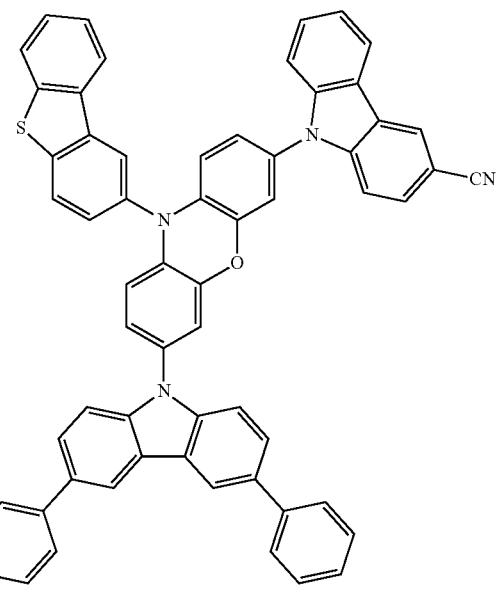
39
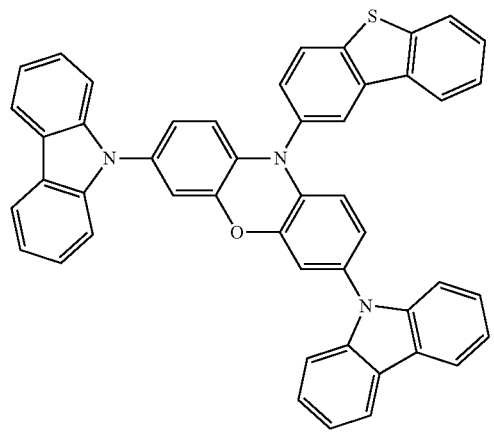
40
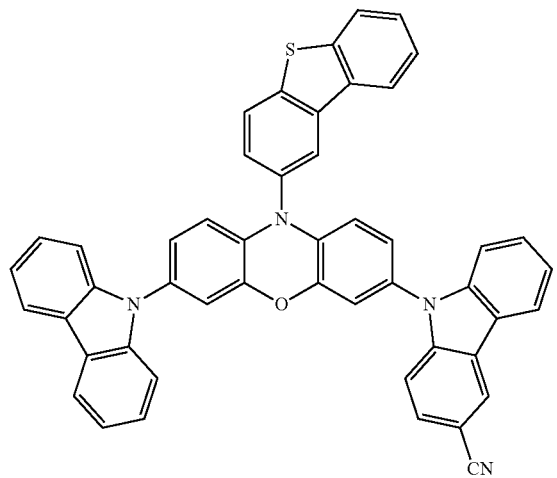

-continued
41
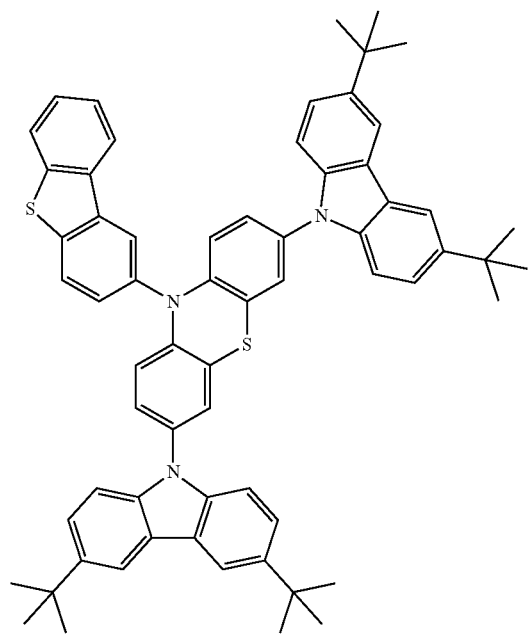
42
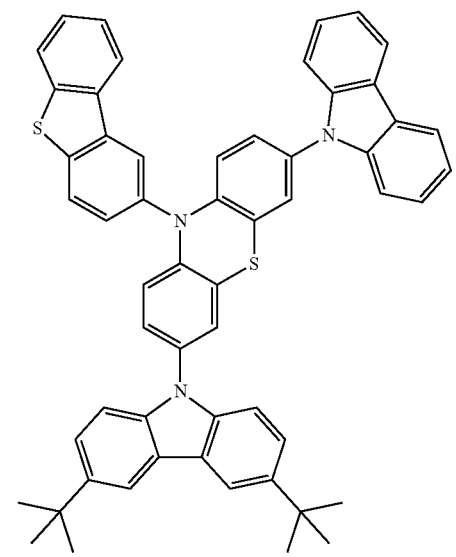
43
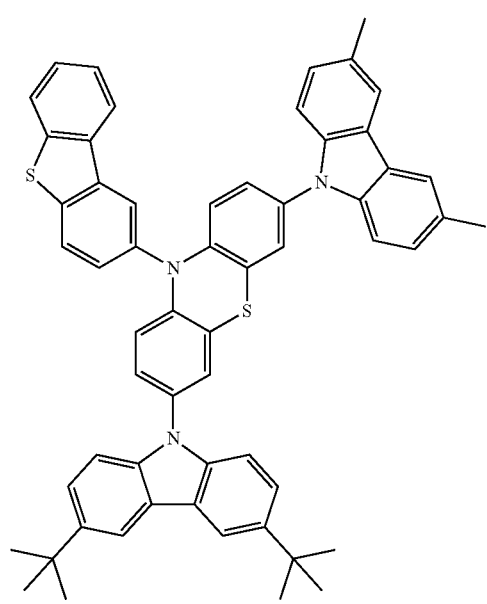
44
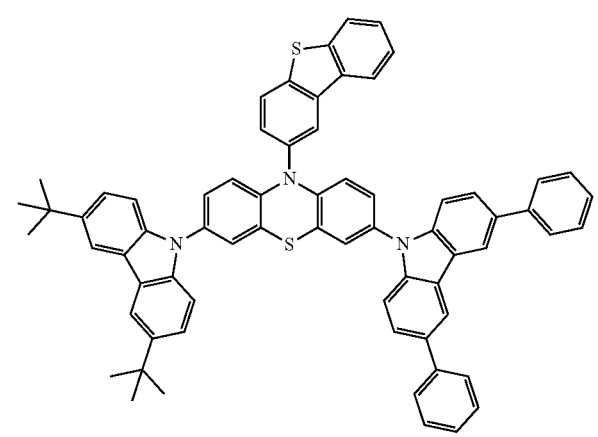

-continued
45
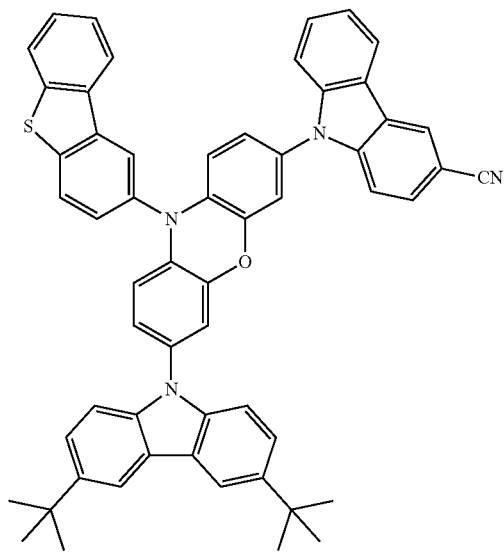
46
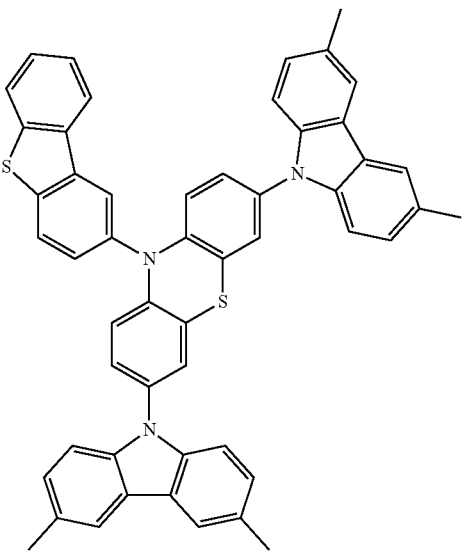
47
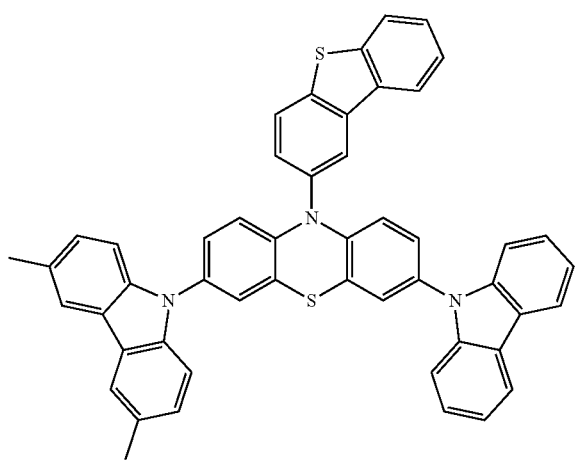
48
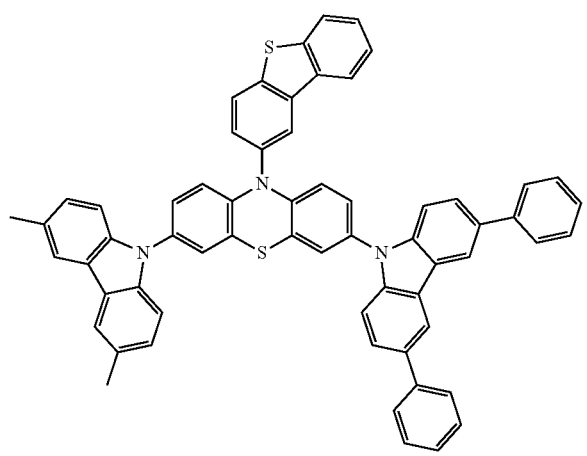
49
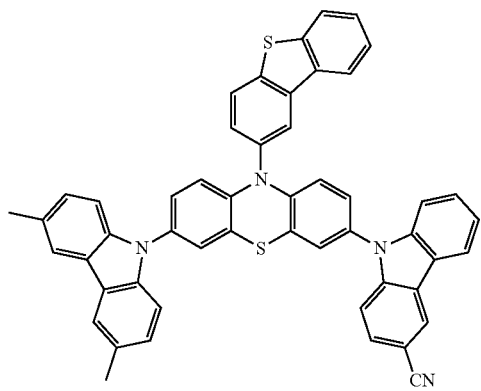
50
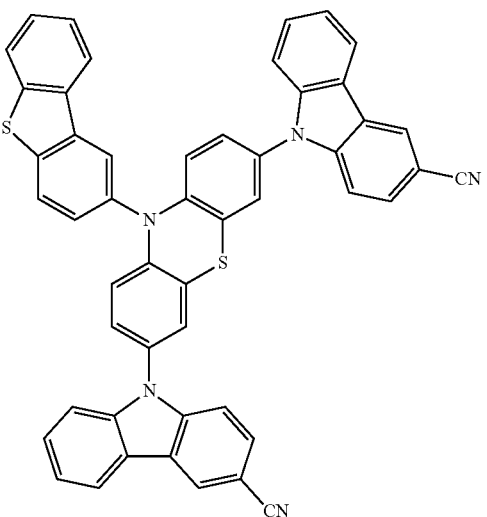

-continued
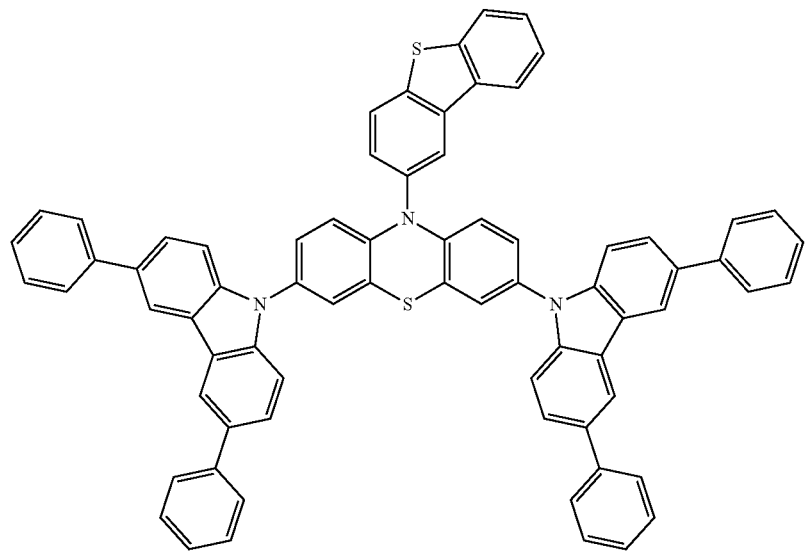
51
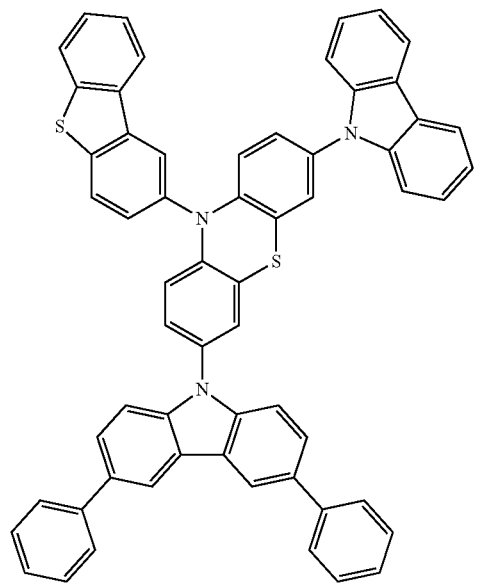
52
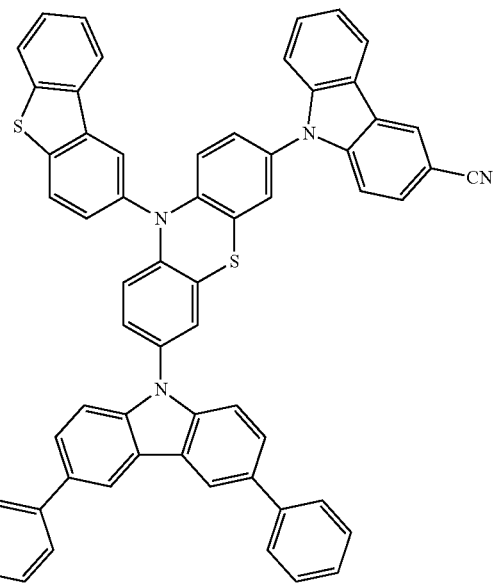
53
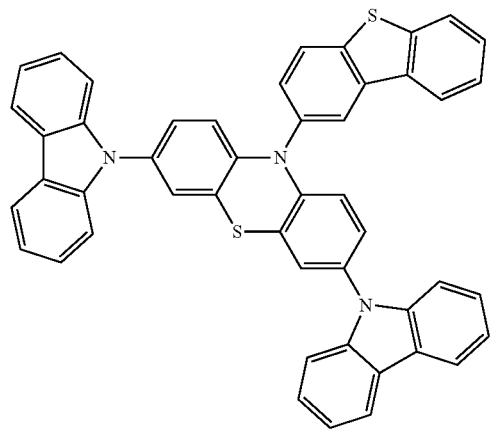
54
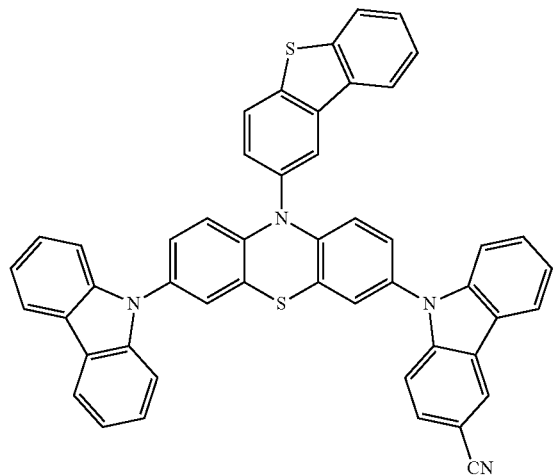
55

56
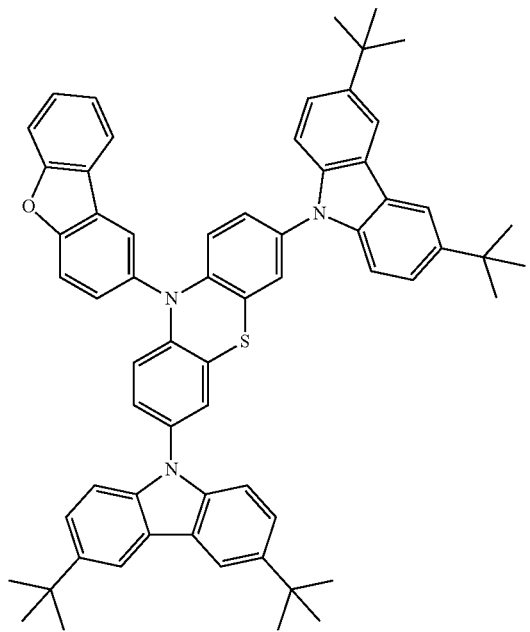
57
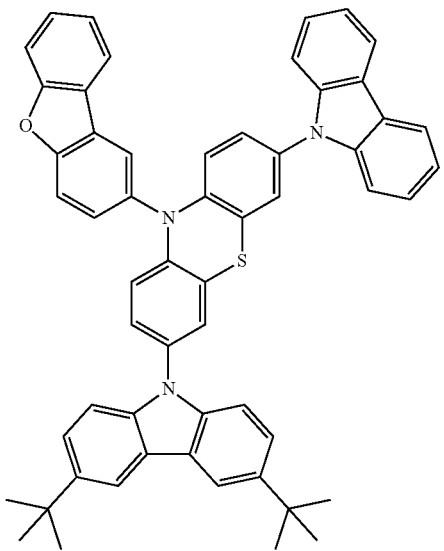
58
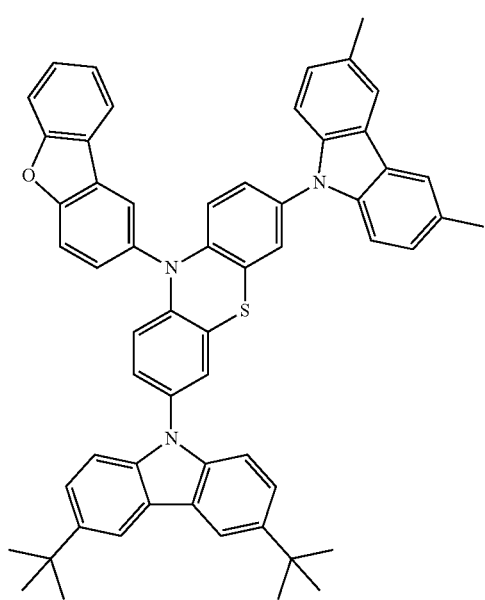
59
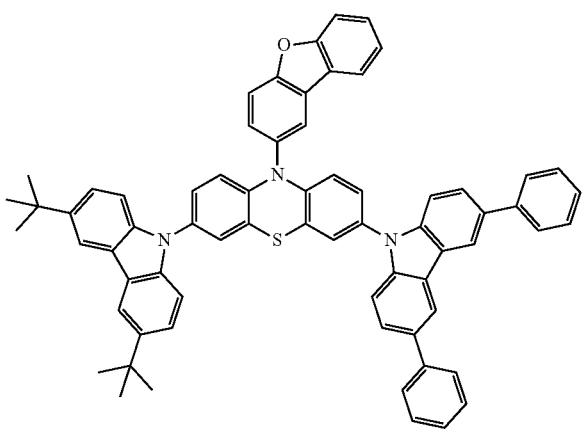

60
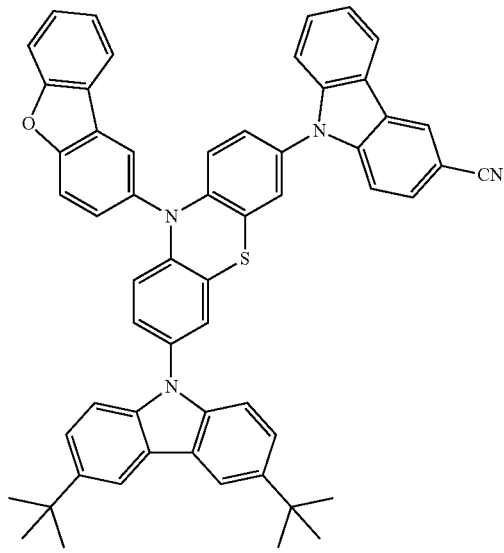
61
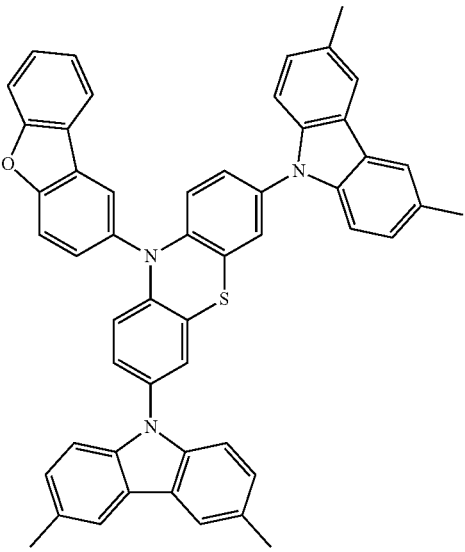
62
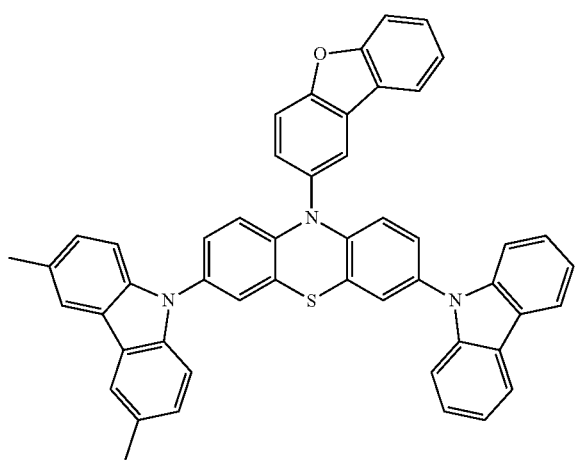
63
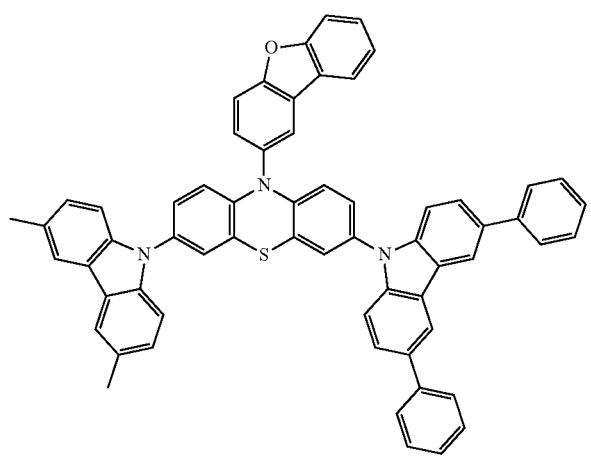
64
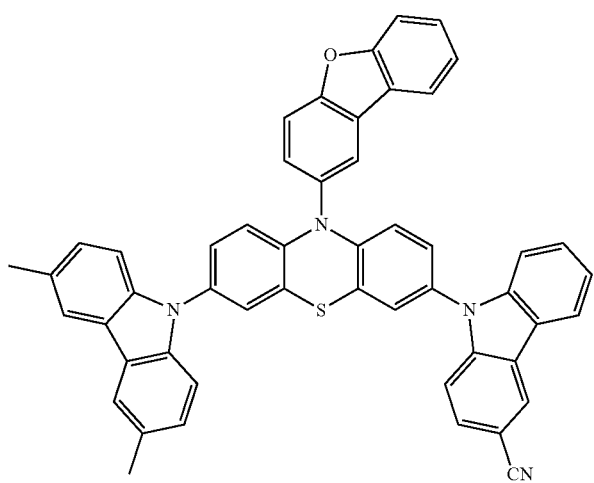
65
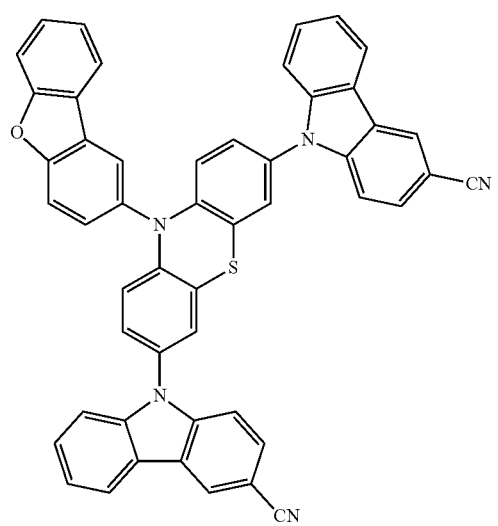

-continued
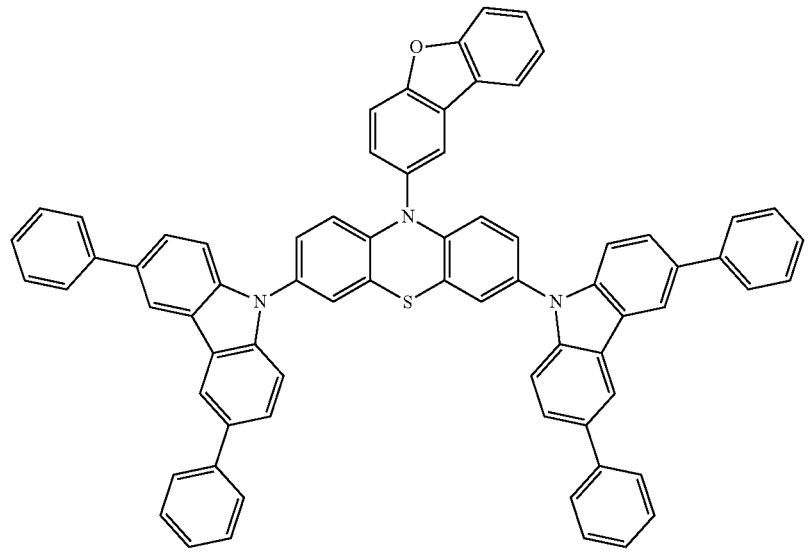
66
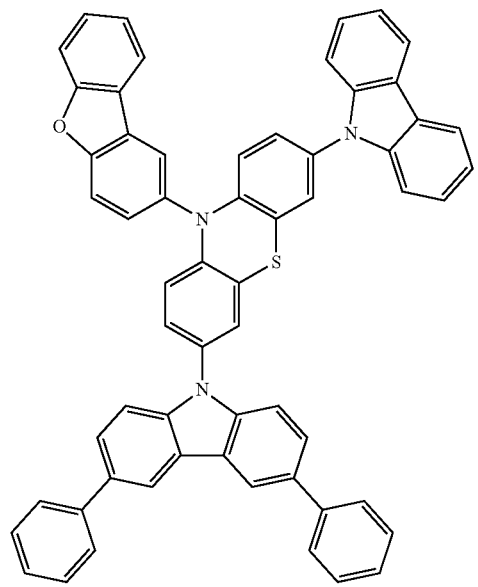
67
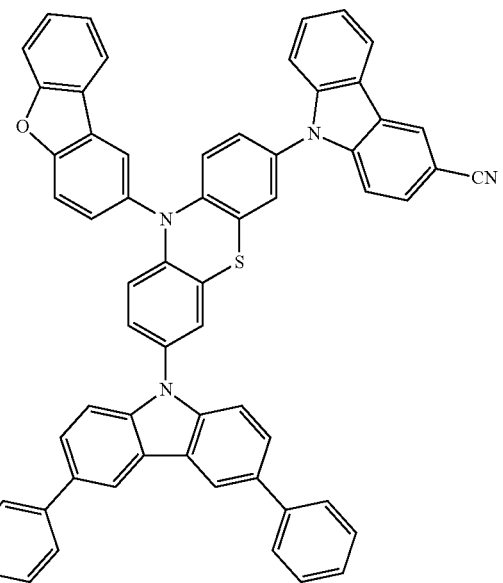
68
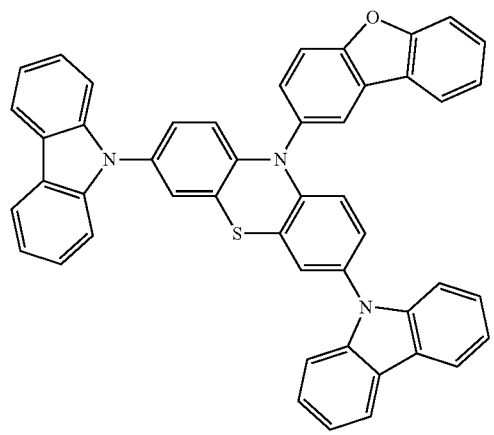
69
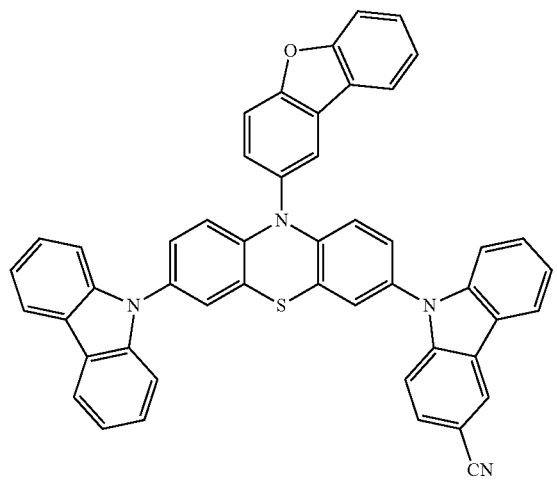
70

-continued
71
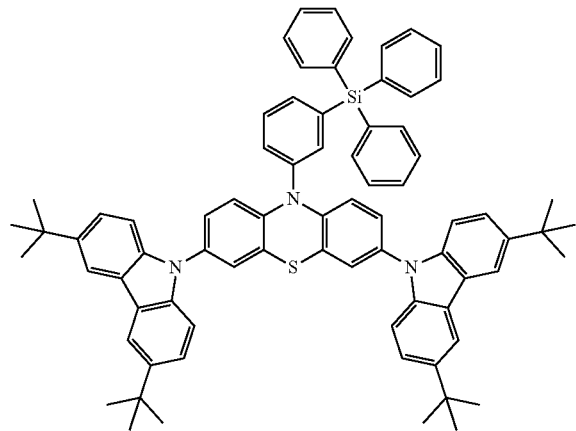
72
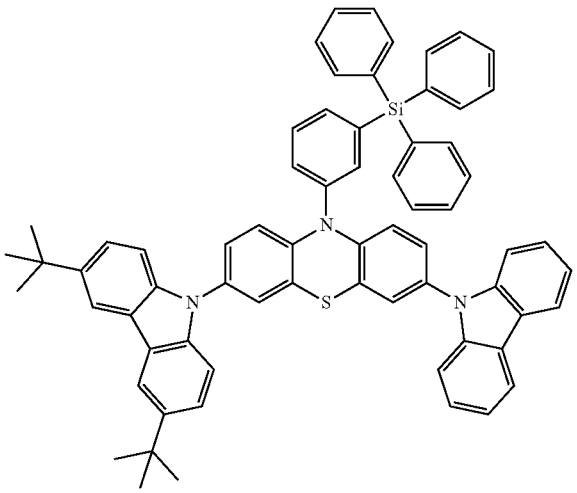
73
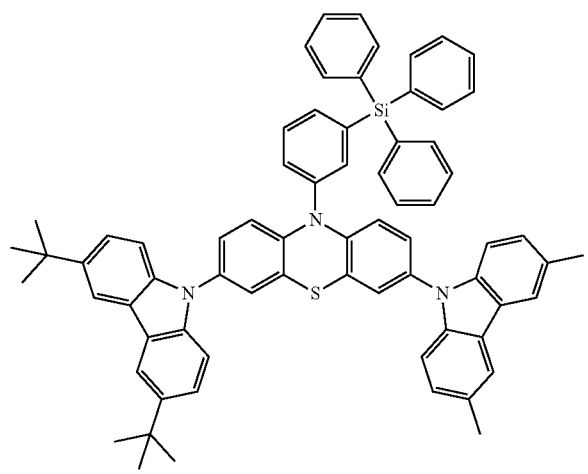
74
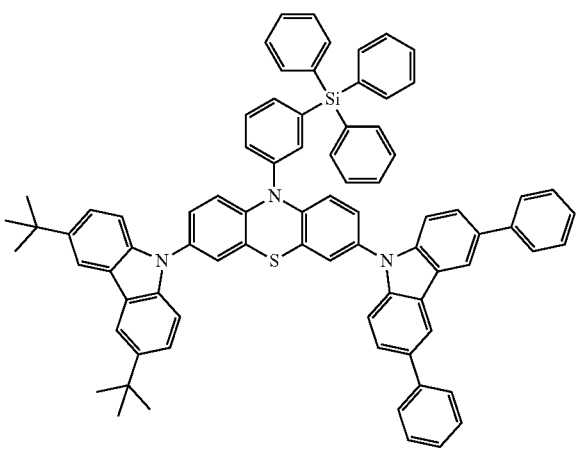
75
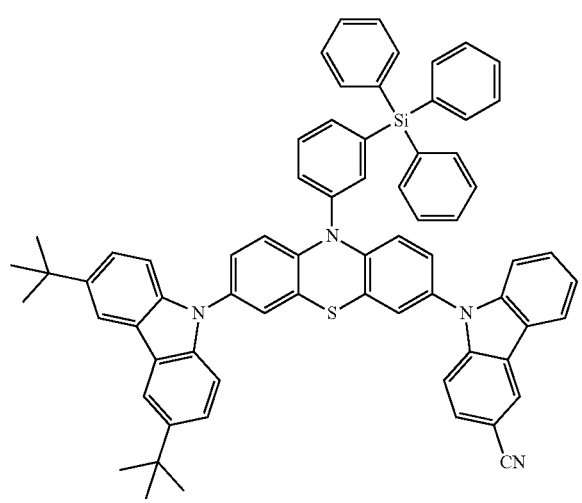
76
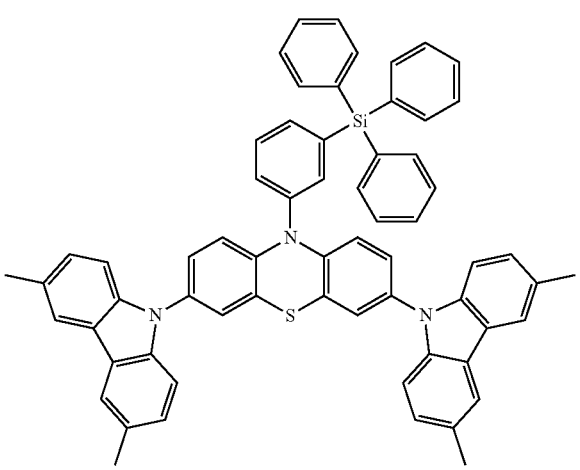

-continued
77
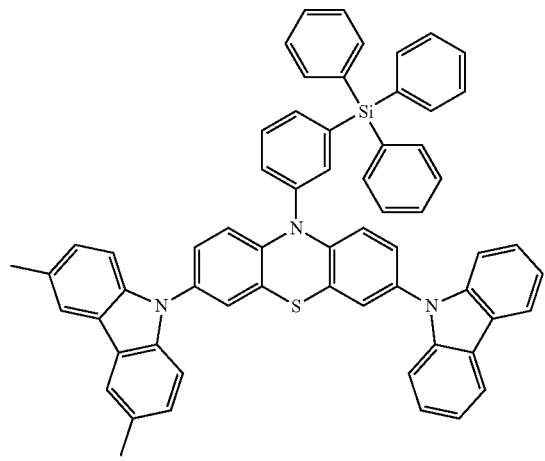
78
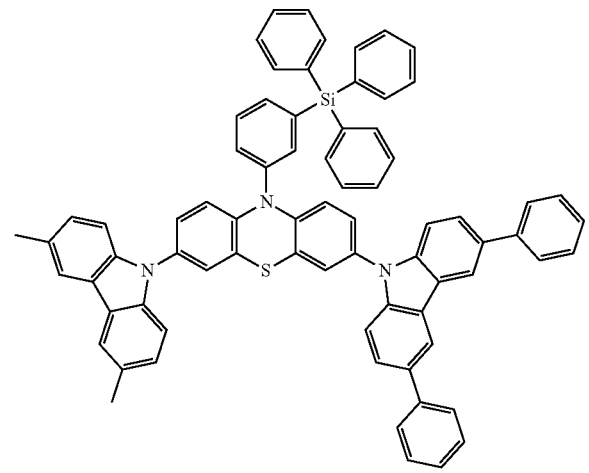
79
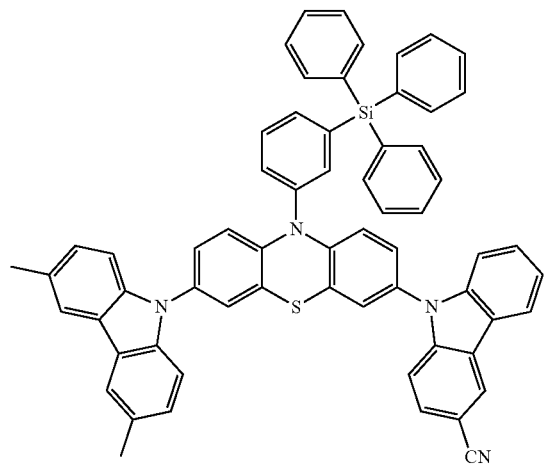
80
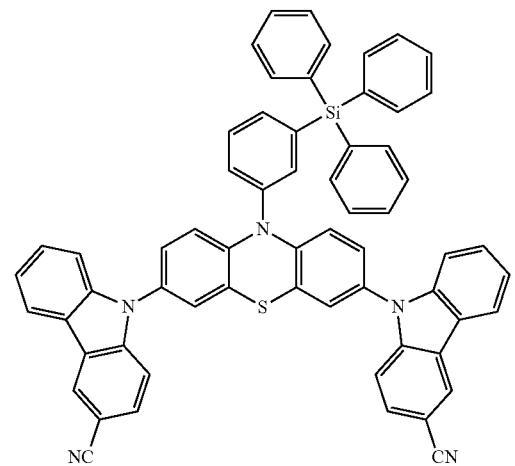
81
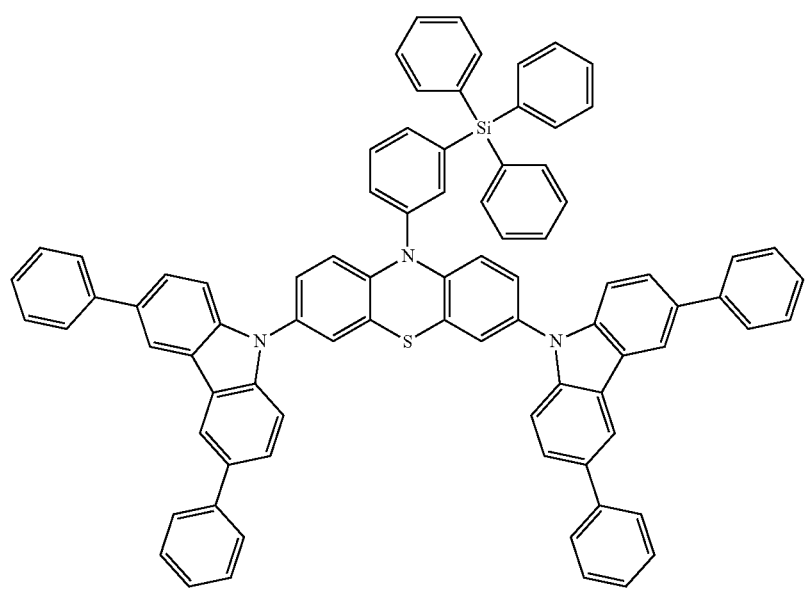

82
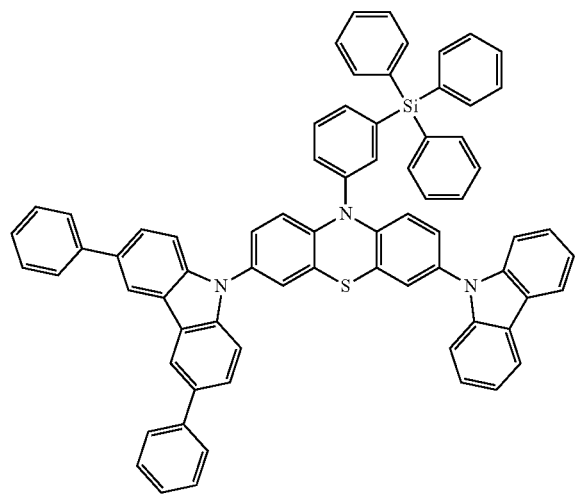
83
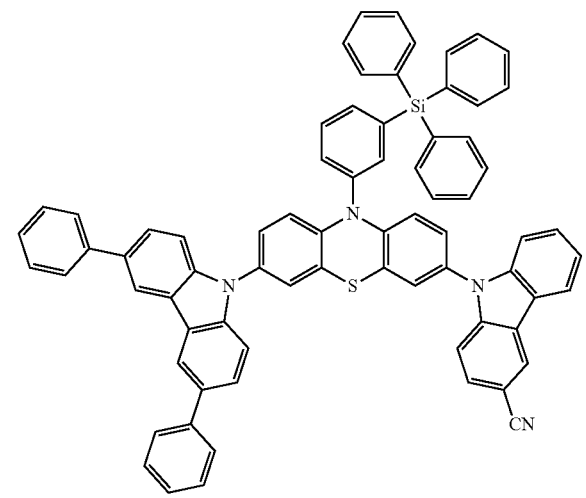
84
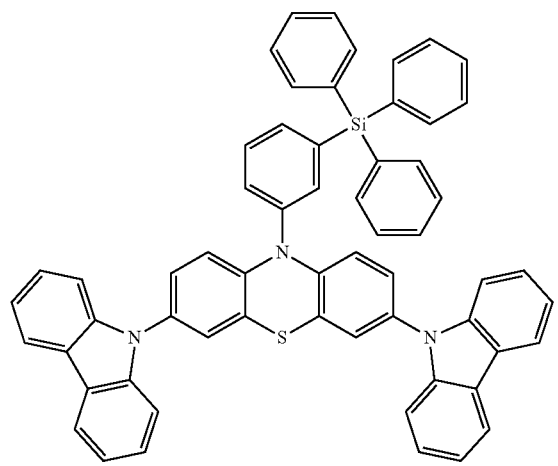
85
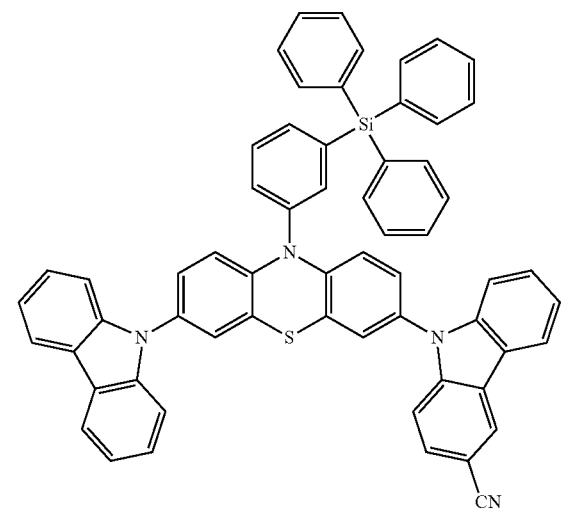
86
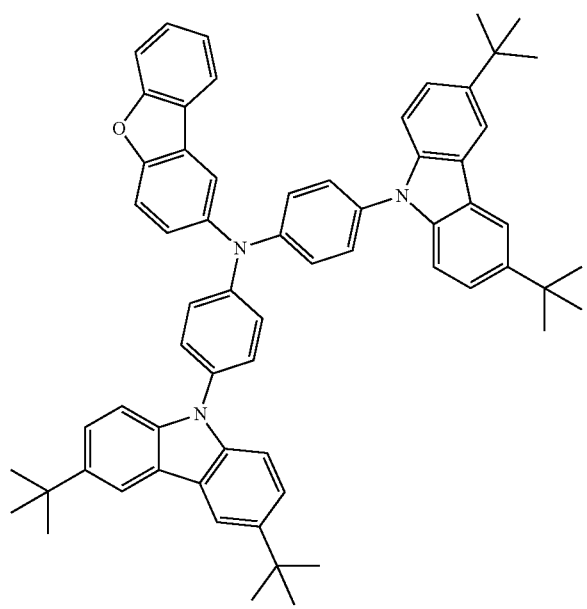
87
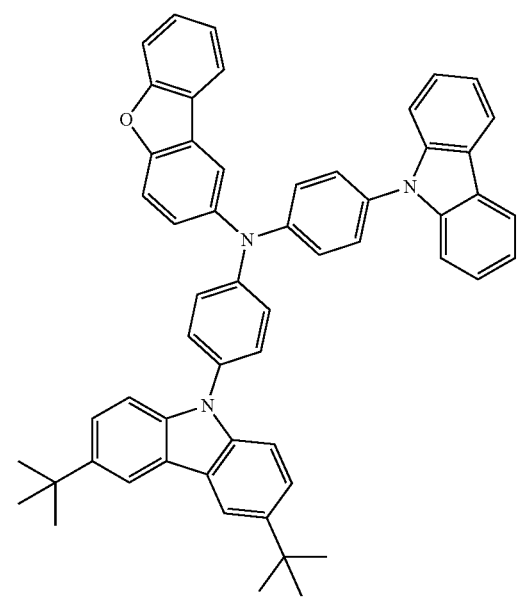

88
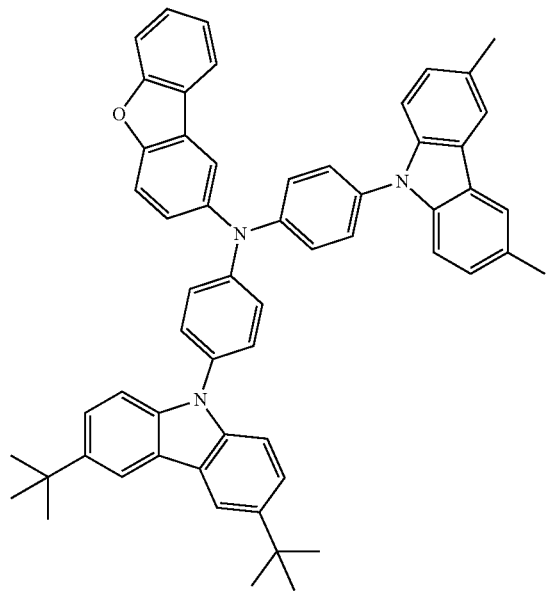
89
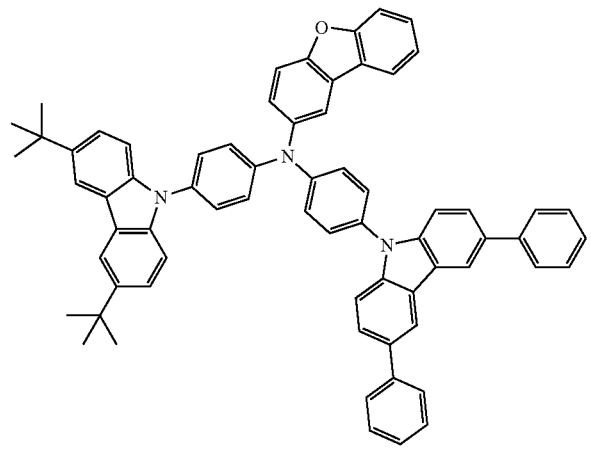
90
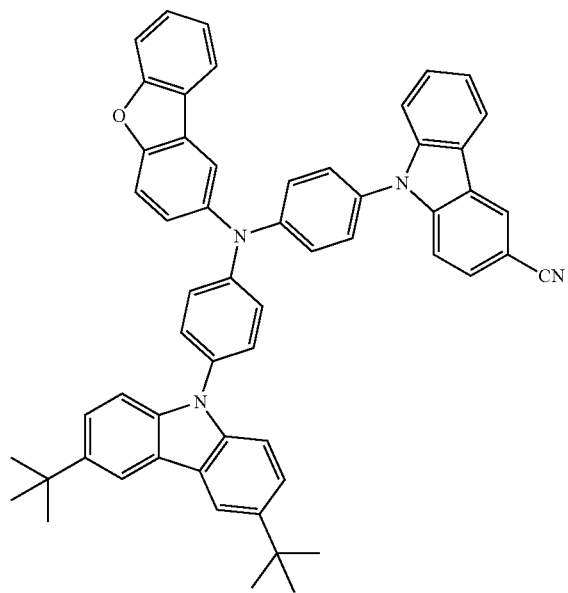
91
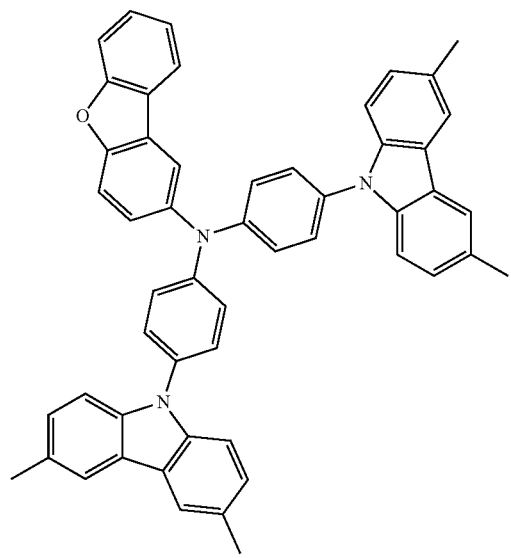

92
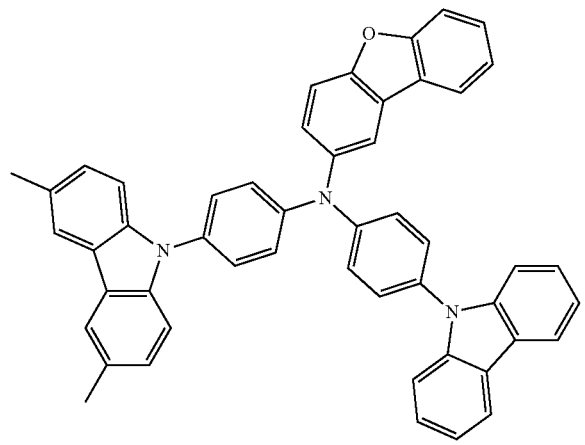
93
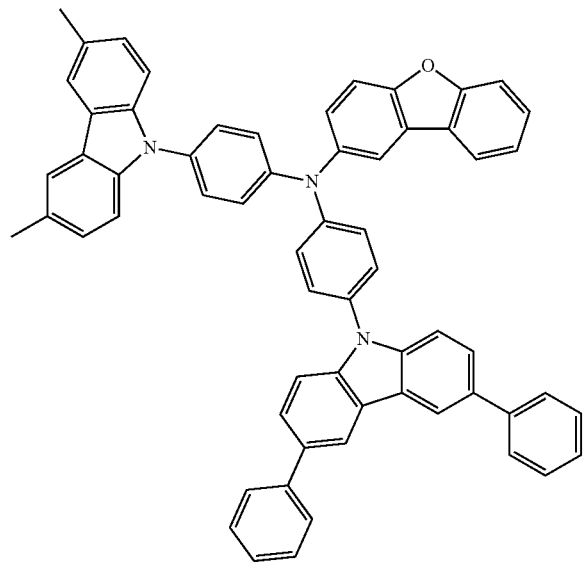
94
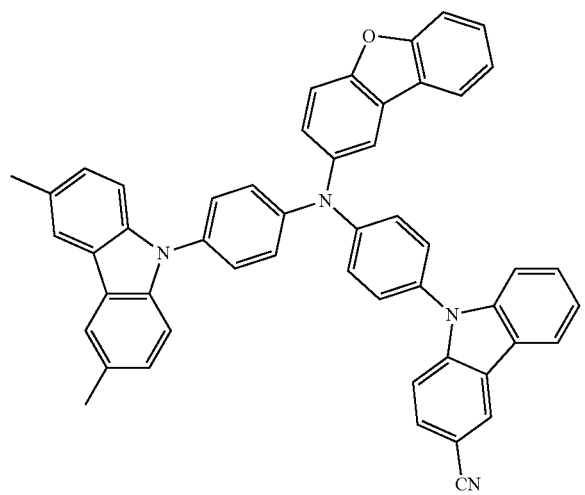
95
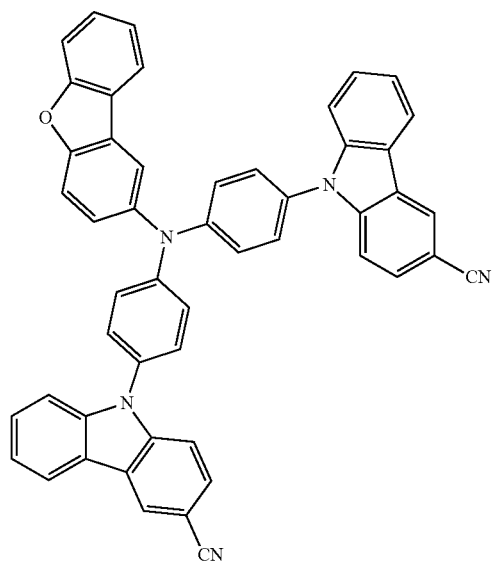

96
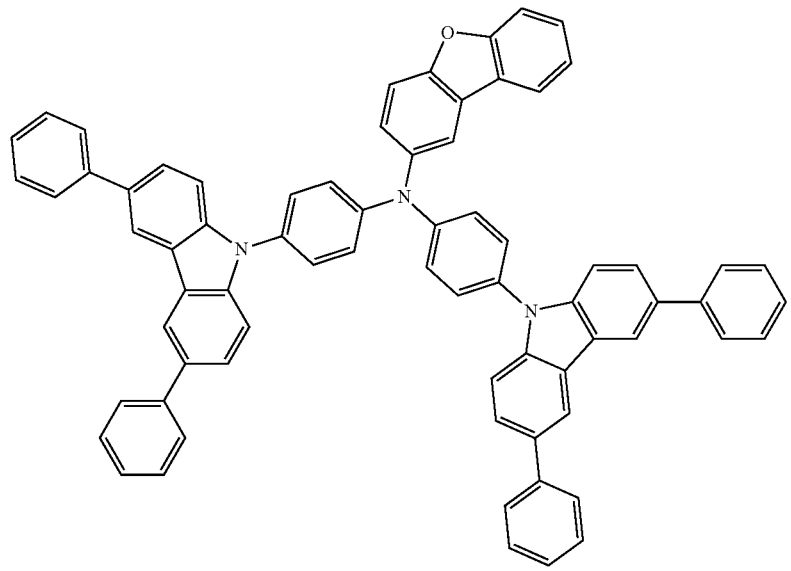
97  98
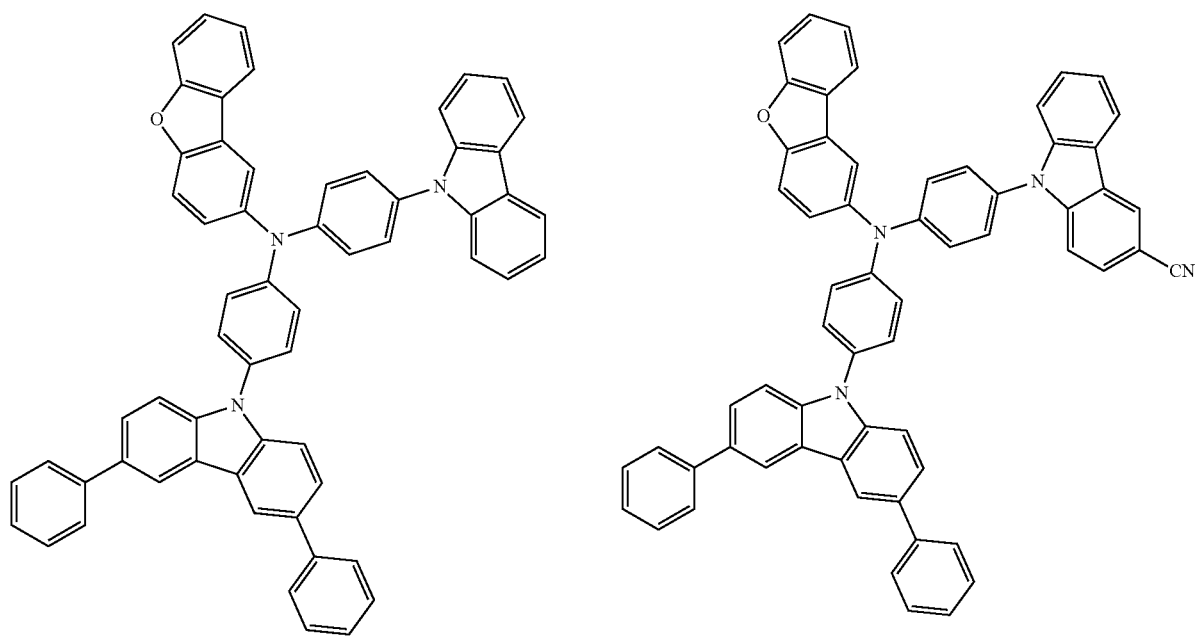

-continued
99
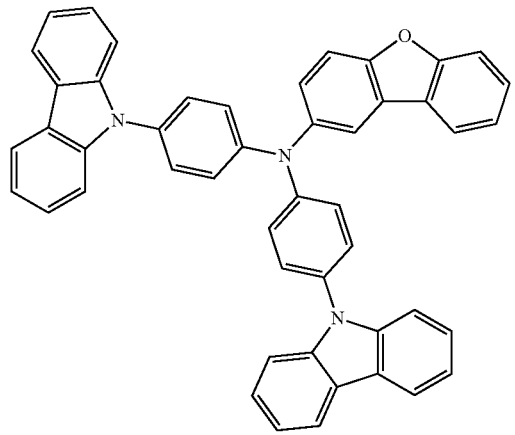
100
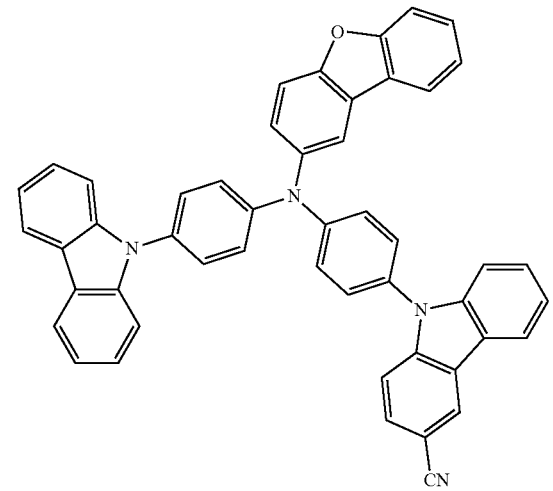
101
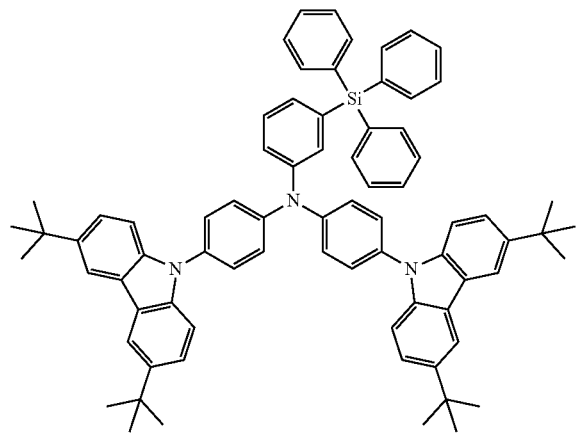
102
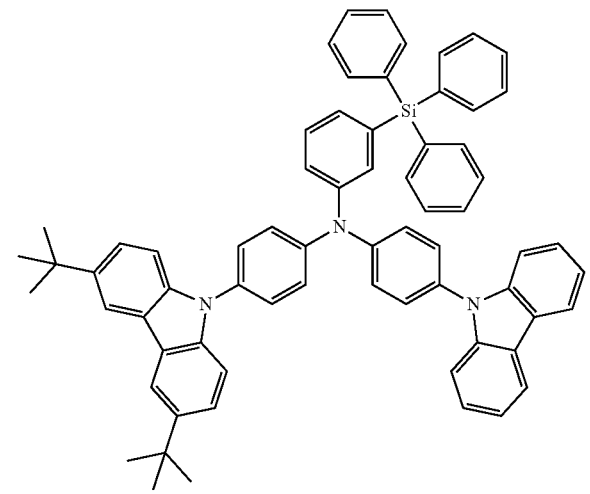
103
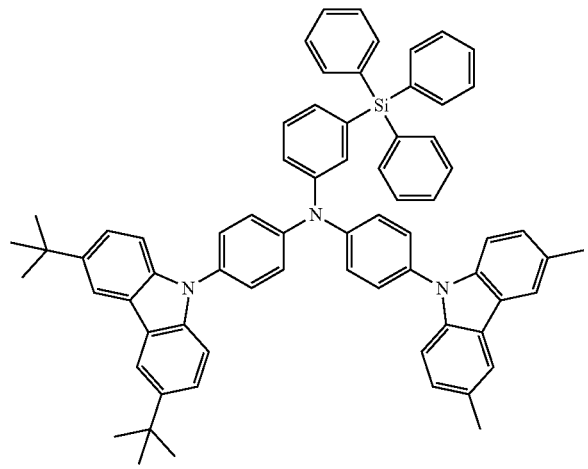
104
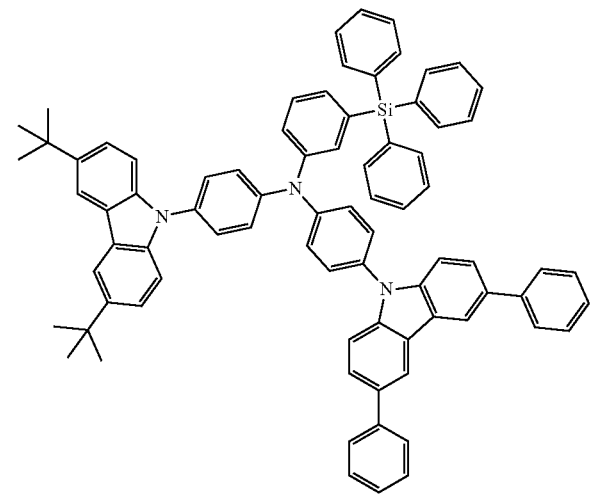

-continued
105
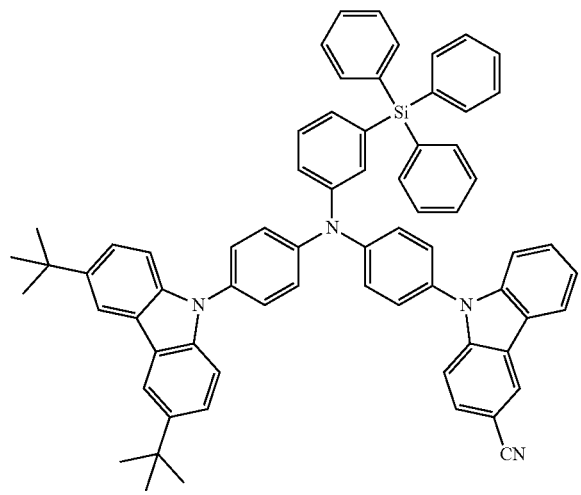
106
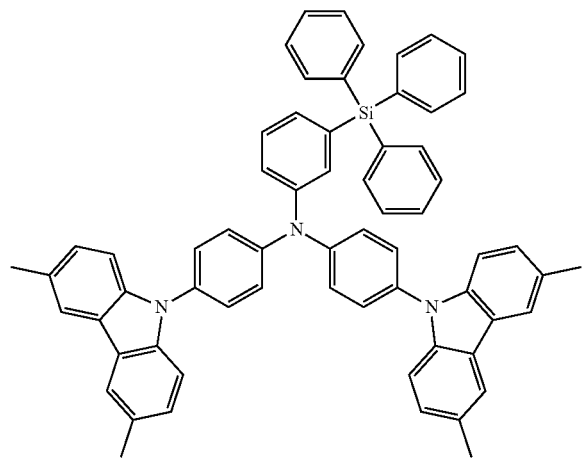
107
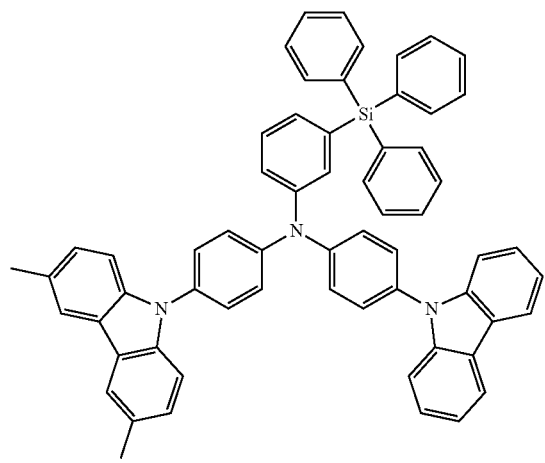
108
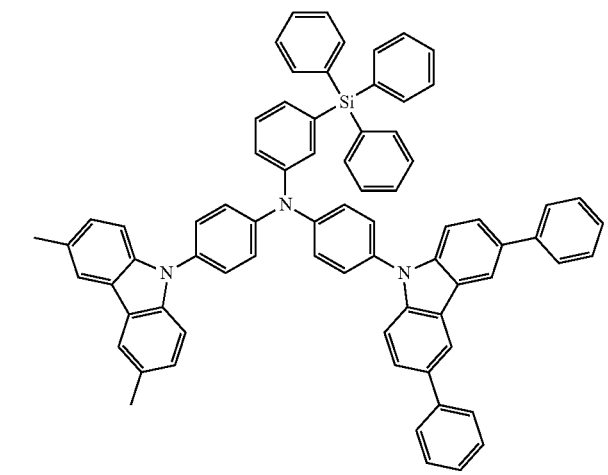
109
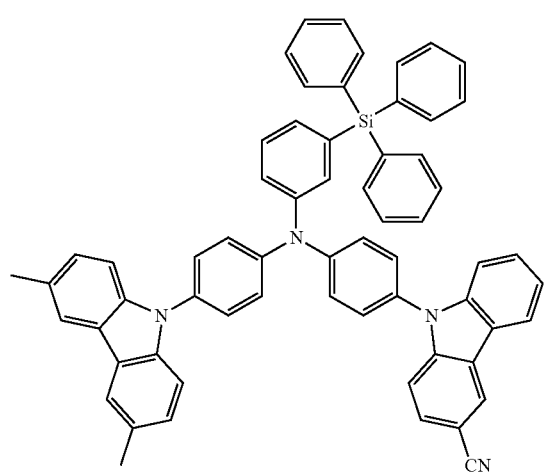
110
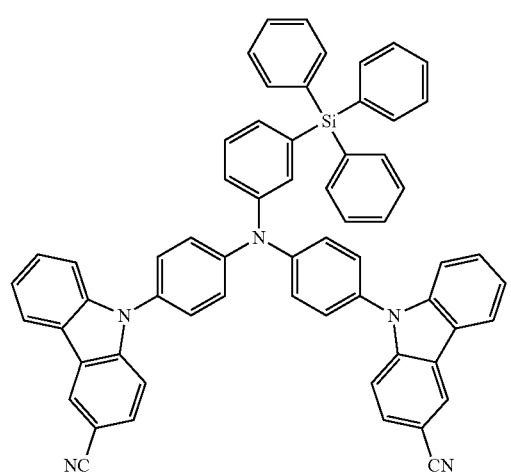

-continued
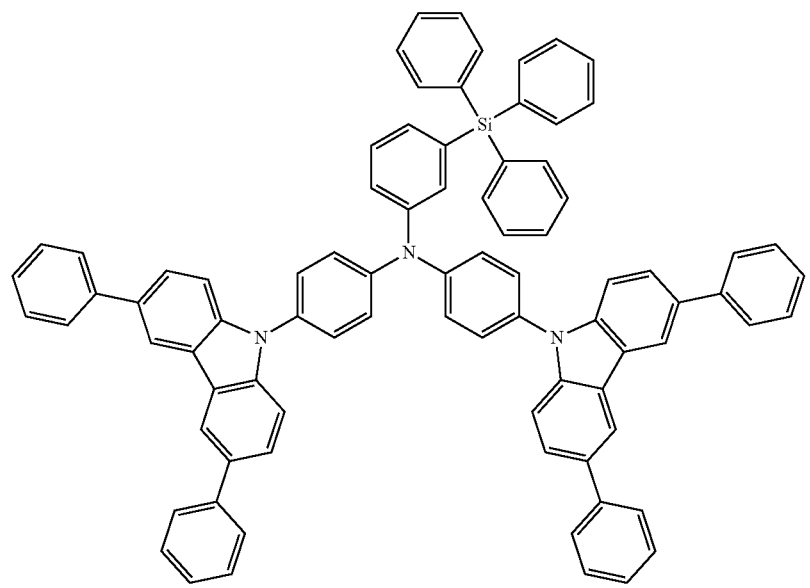
111
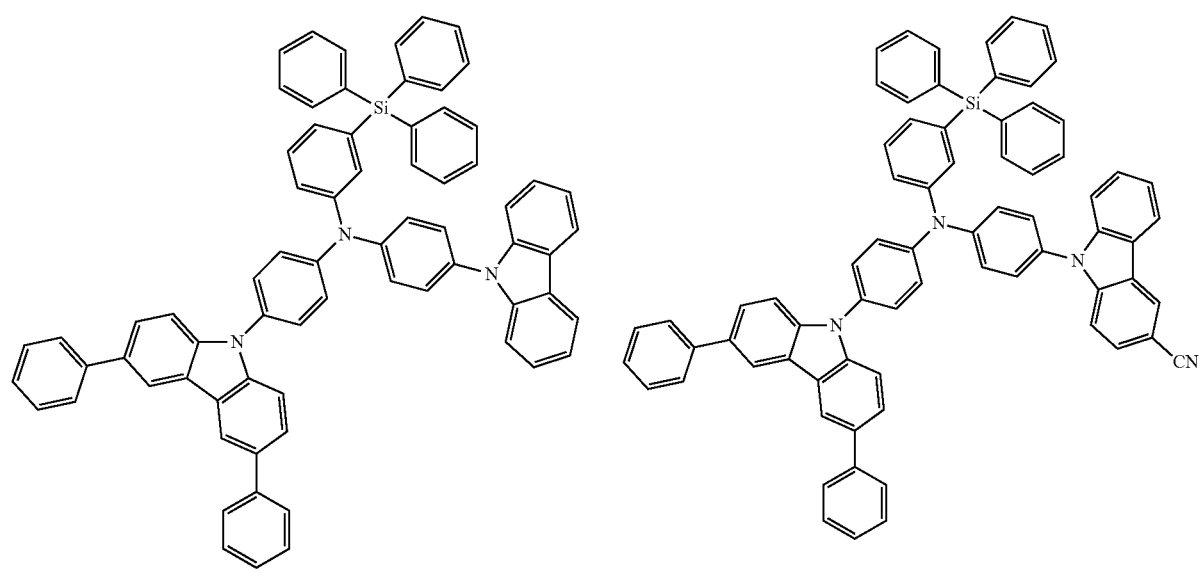
112
113

-continued
114
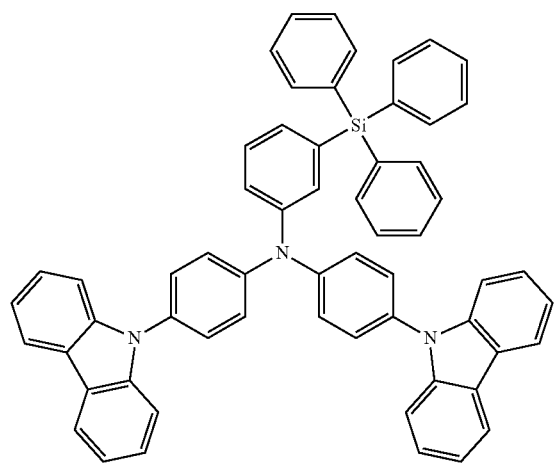
115
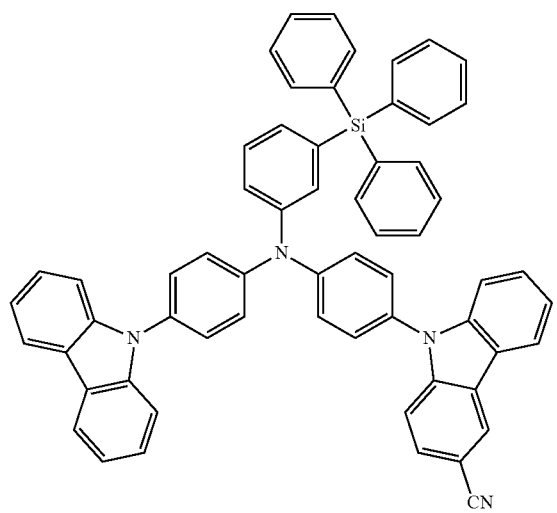
116
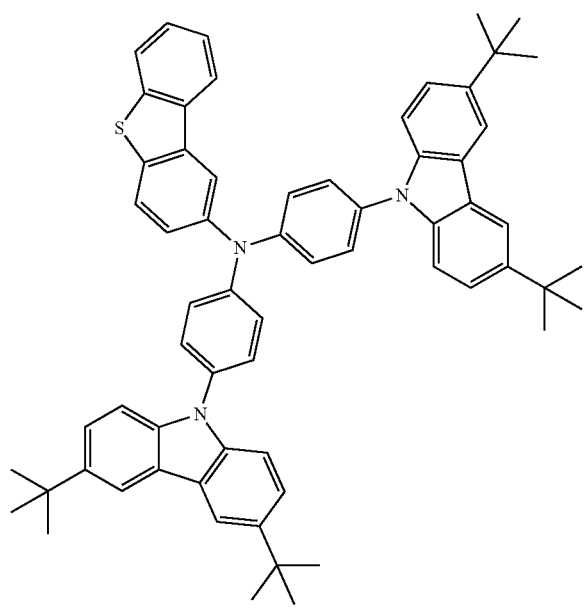
117
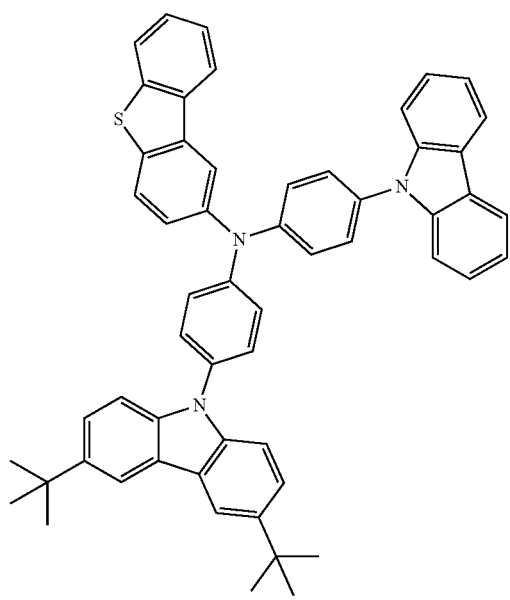

118
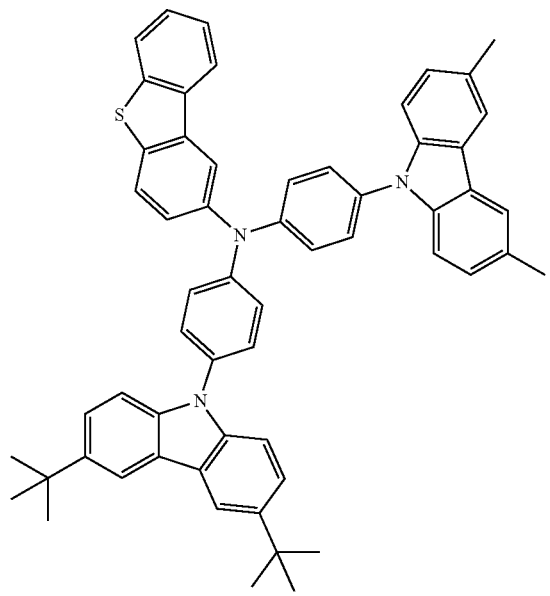
119
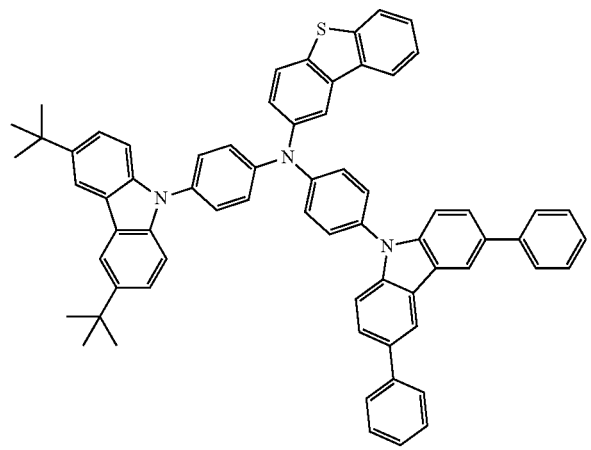
120
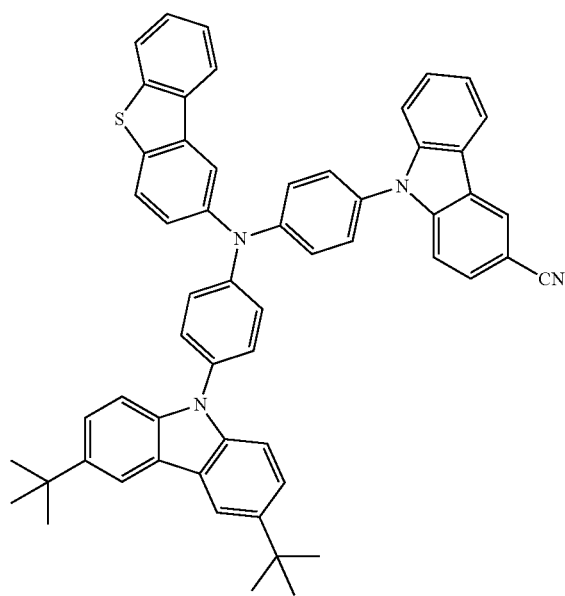
121
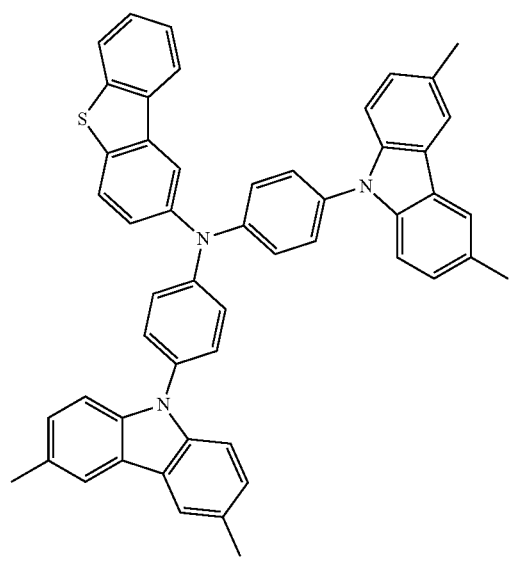

-continued
122
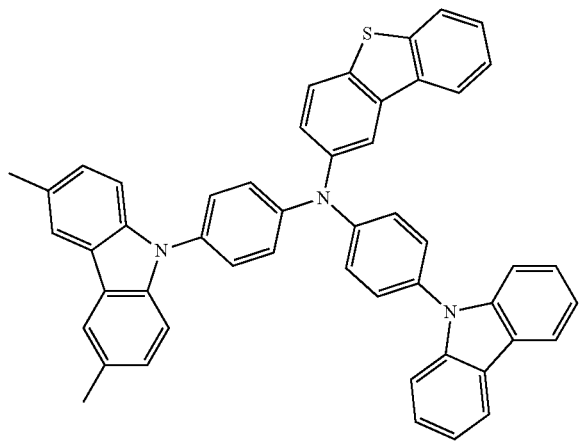
123
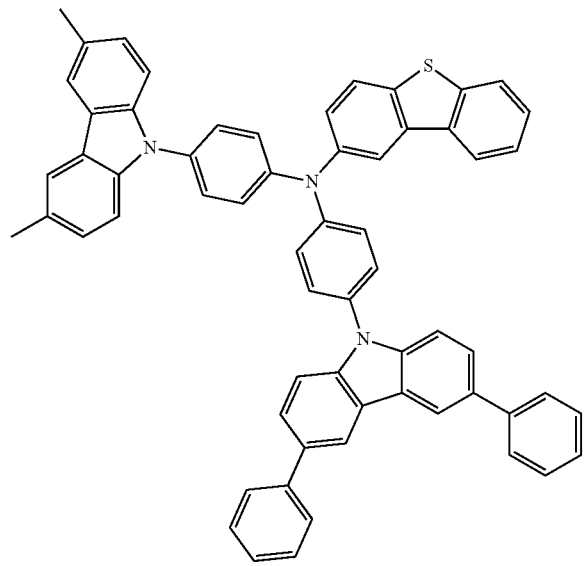
124
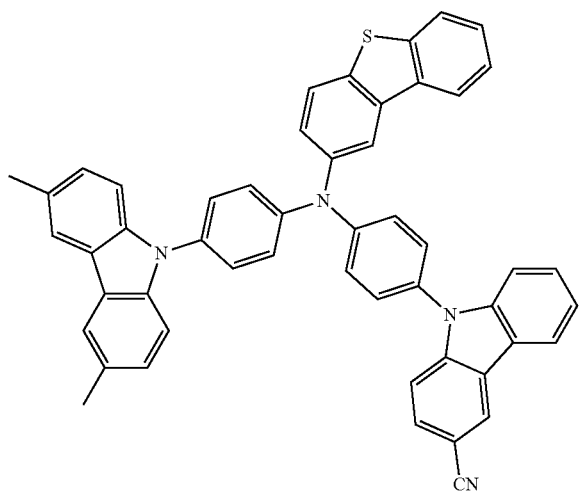
125
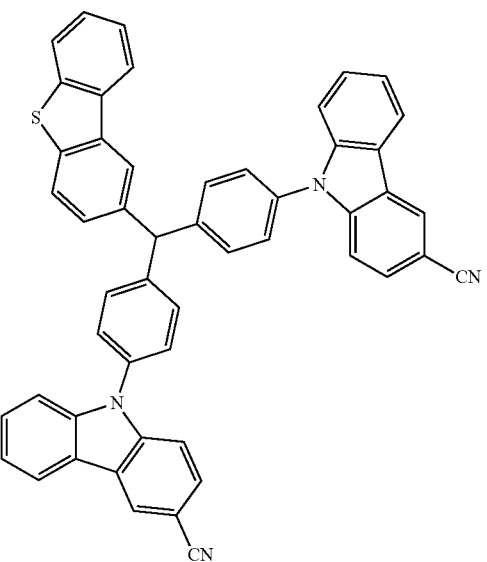

126
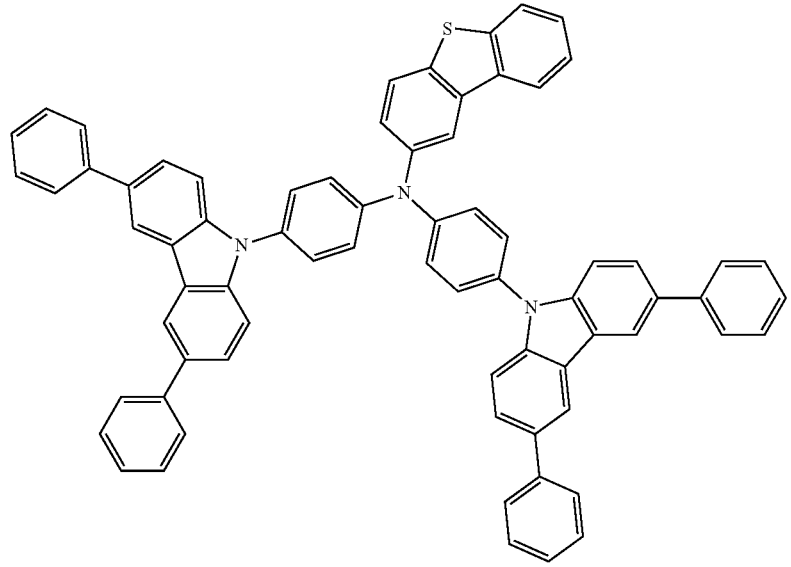
127
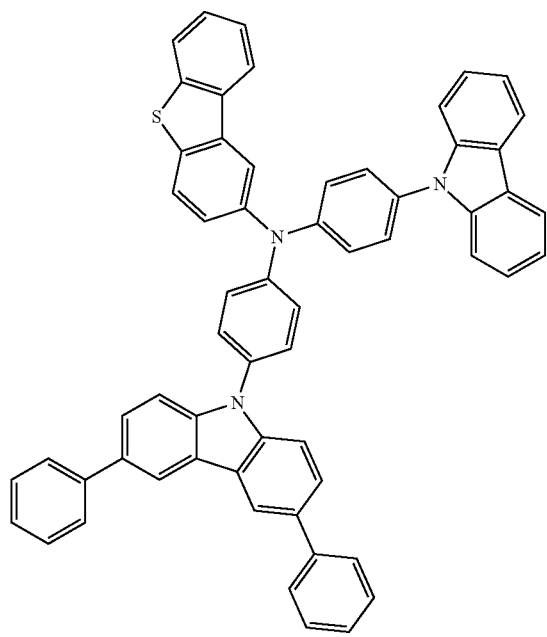
128
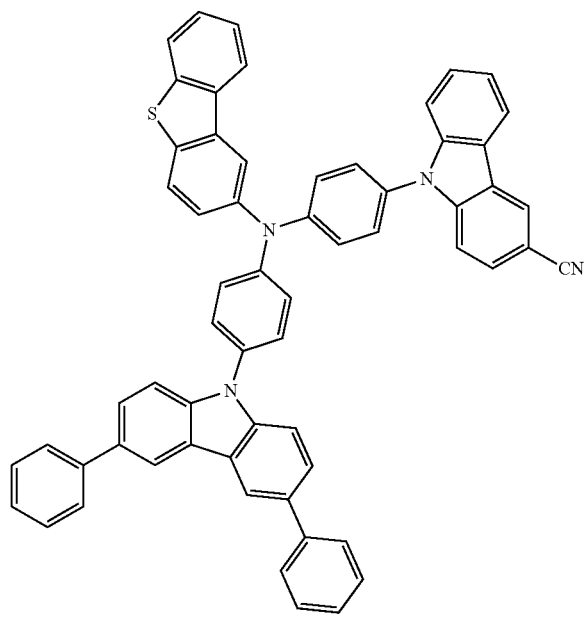

129
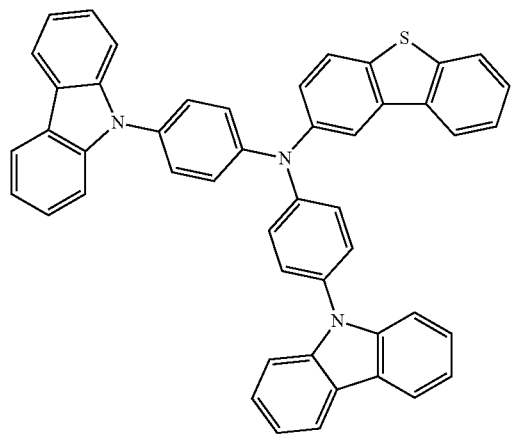
130
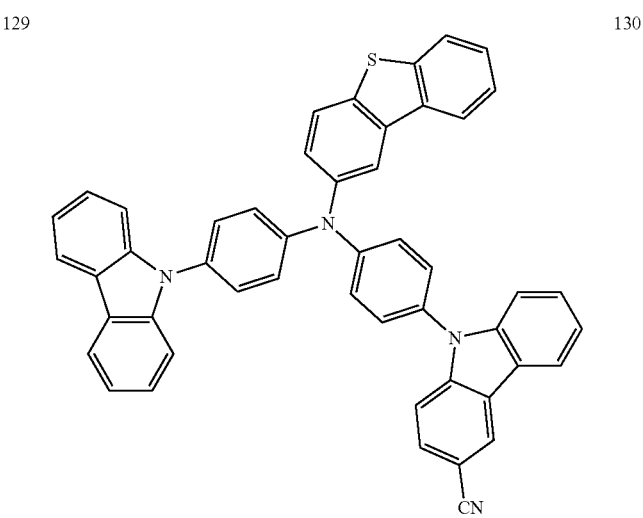
131
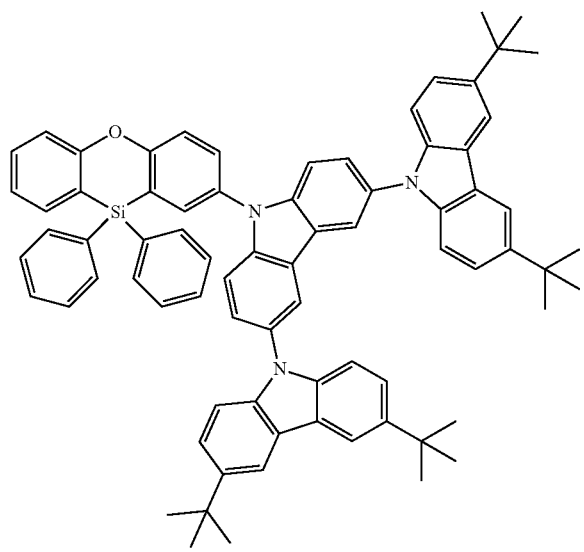
132
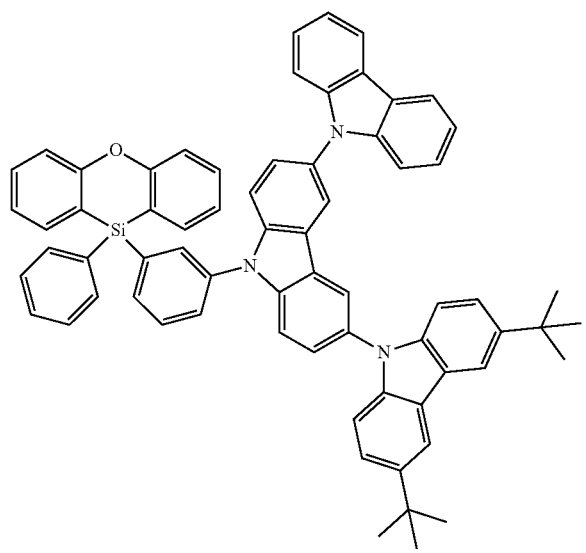
133
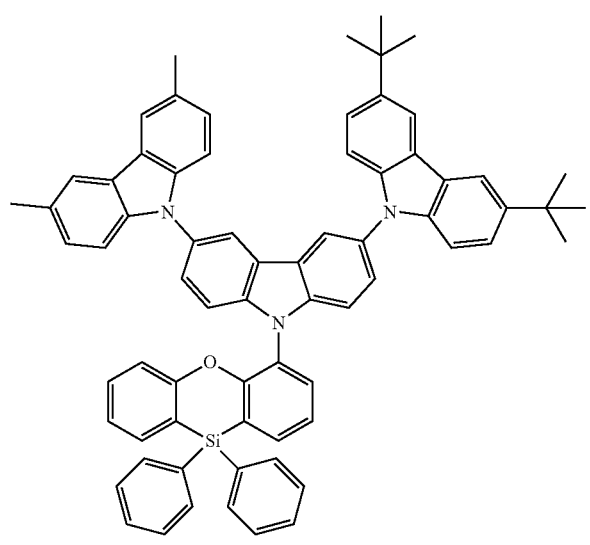
134
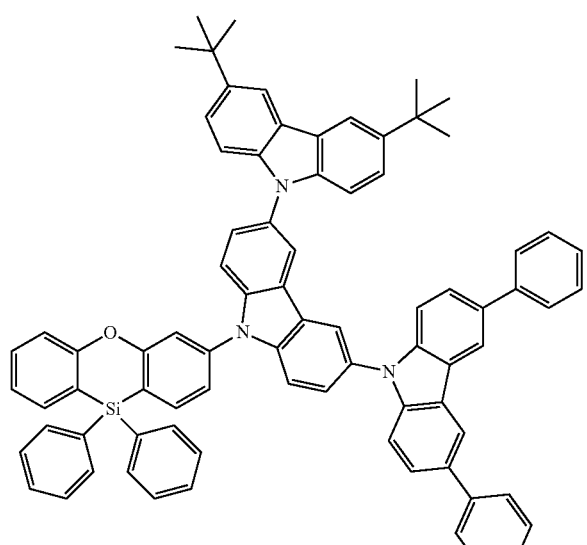

135
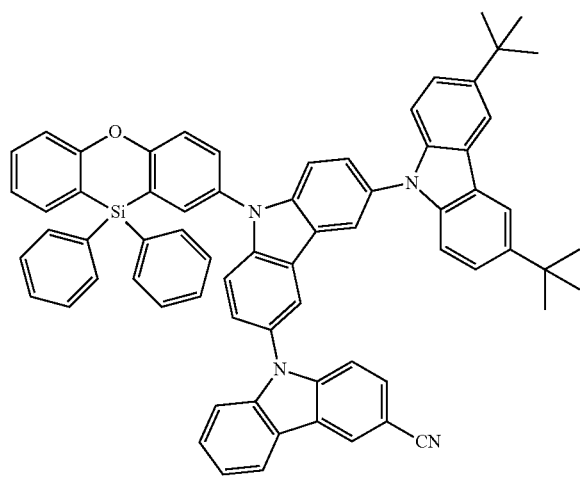
136
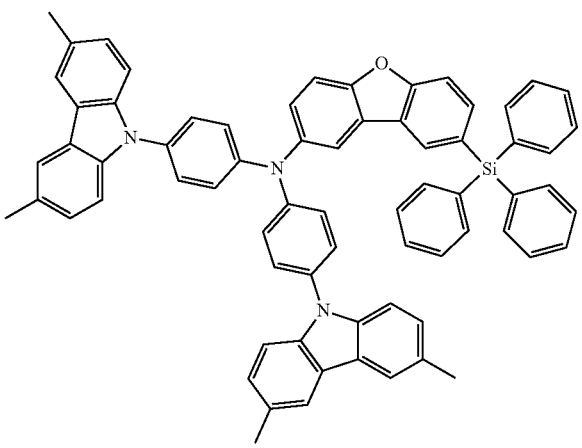
137
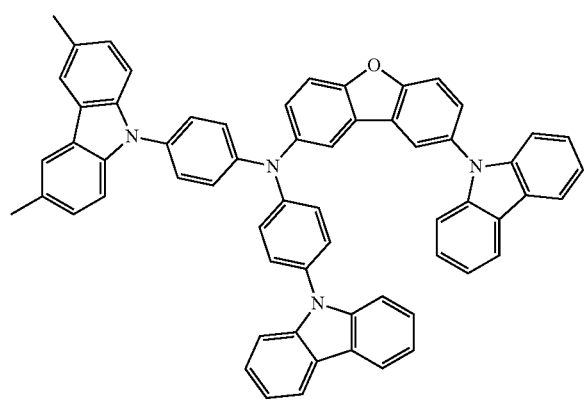
138
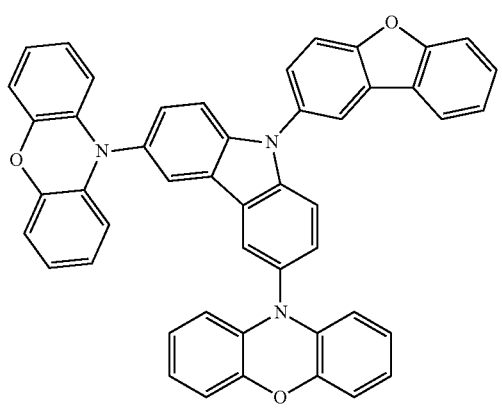
139
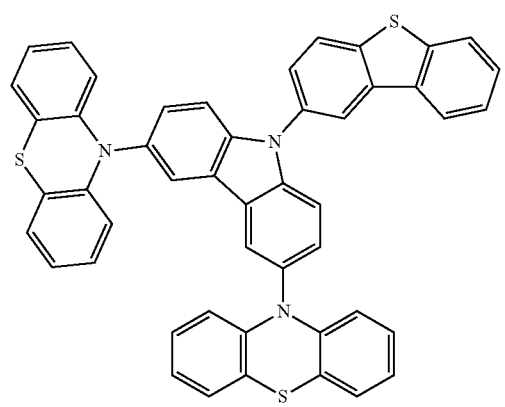
140
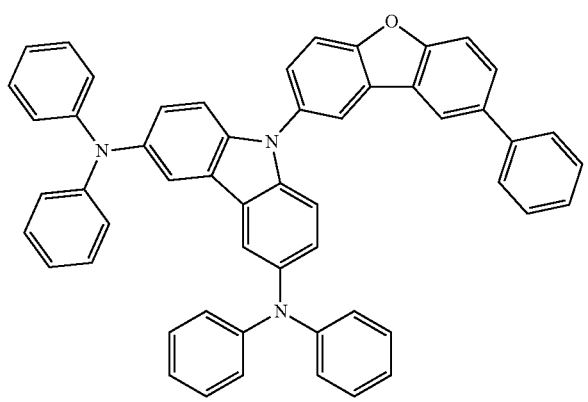

-continued
141
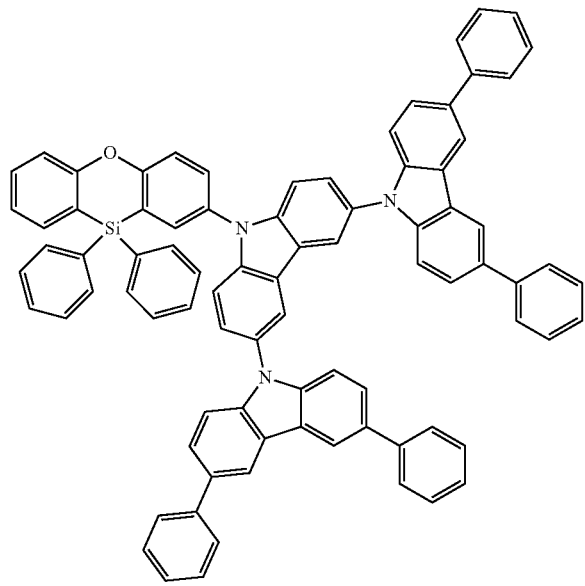
142
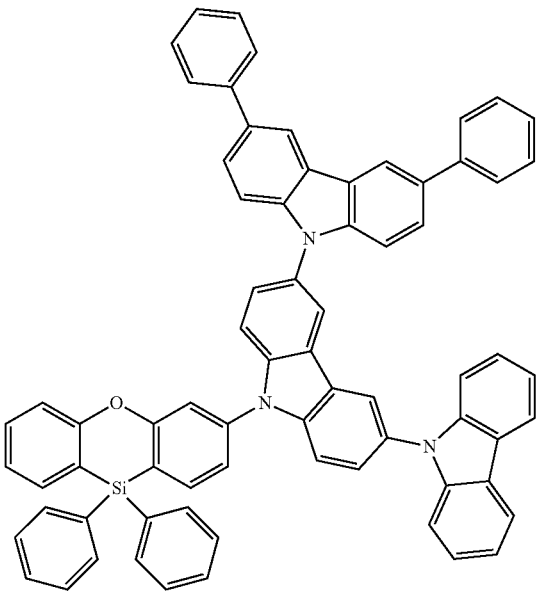
143
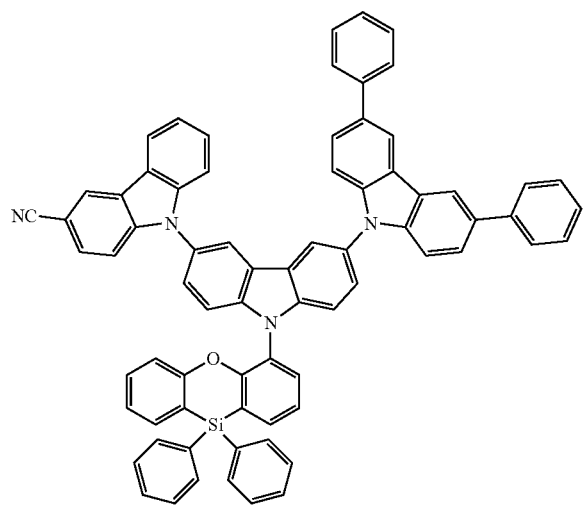
144
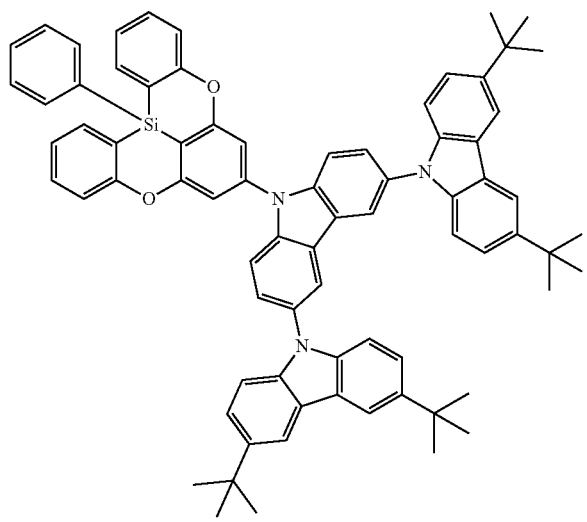
145
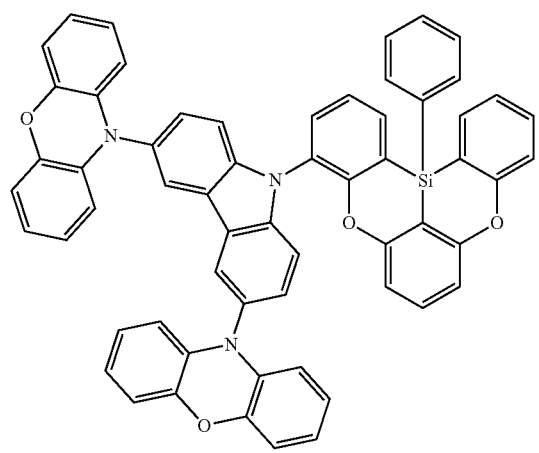

-continued
146
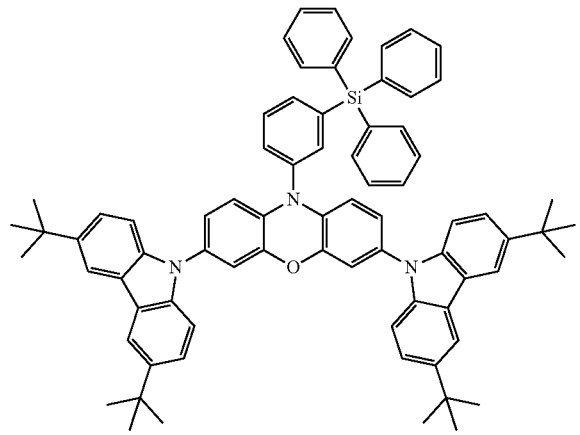
147
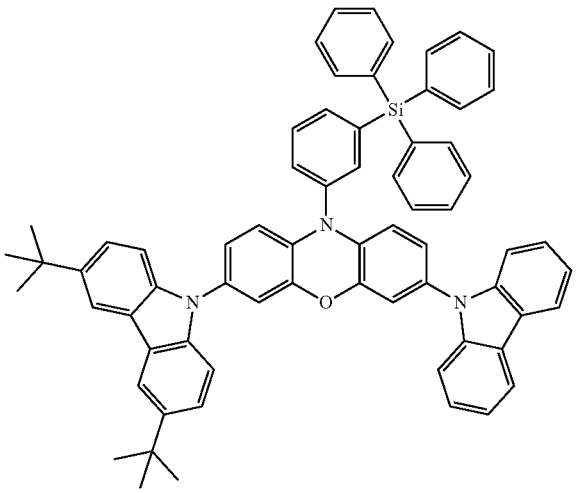
148
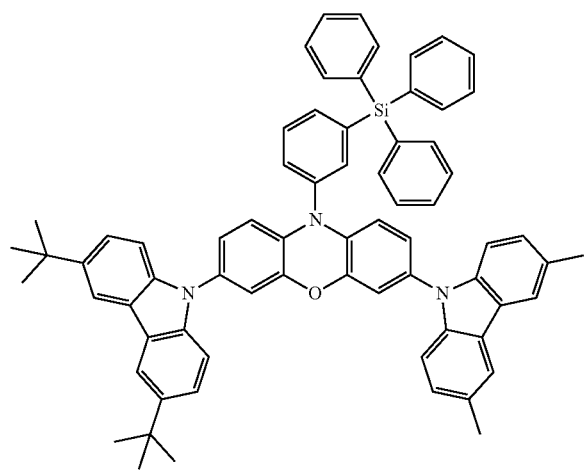
149
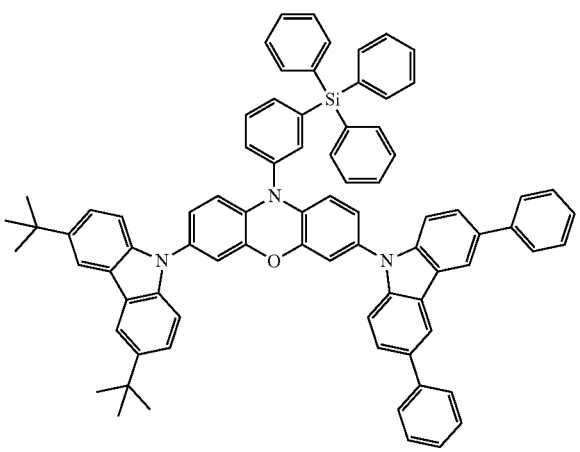
150
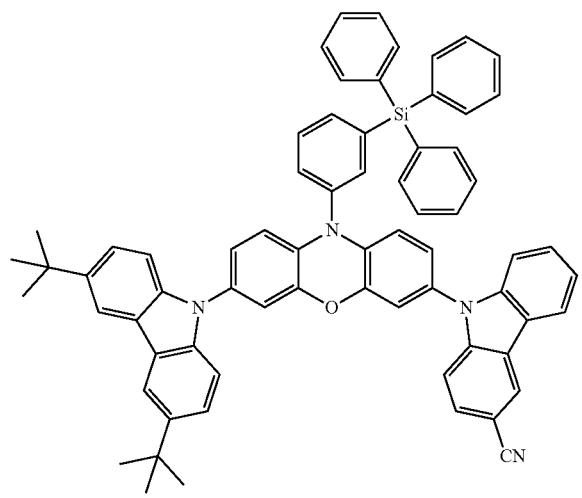
151
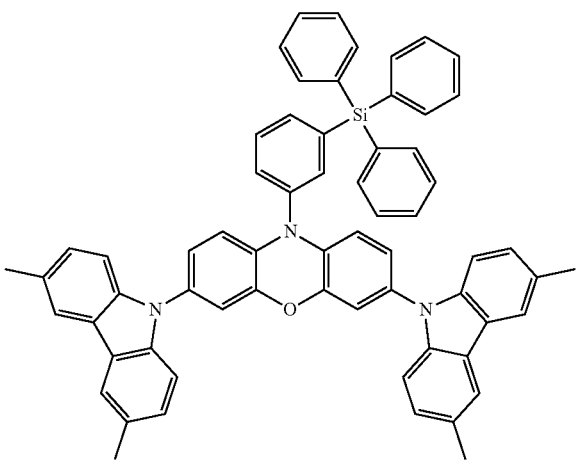

-continued
152
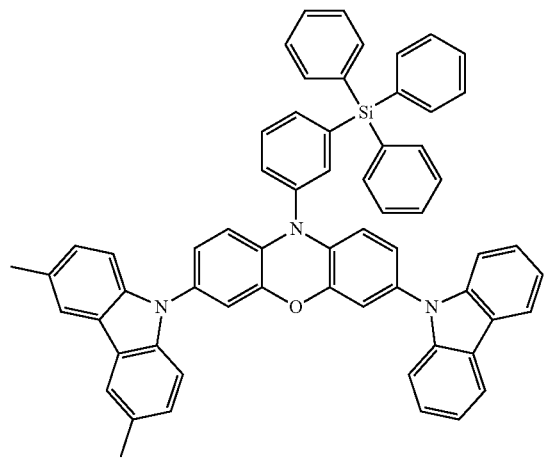
153
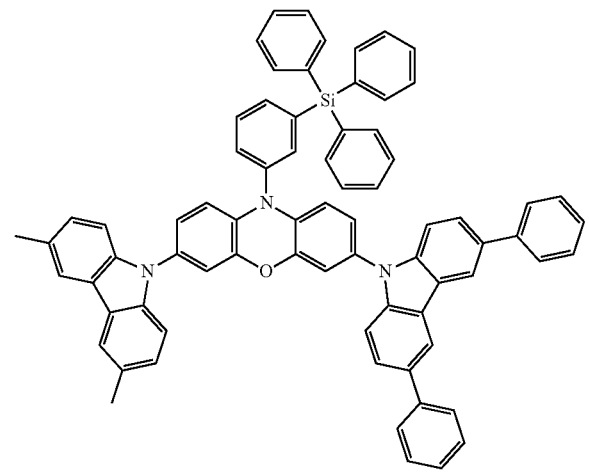
154
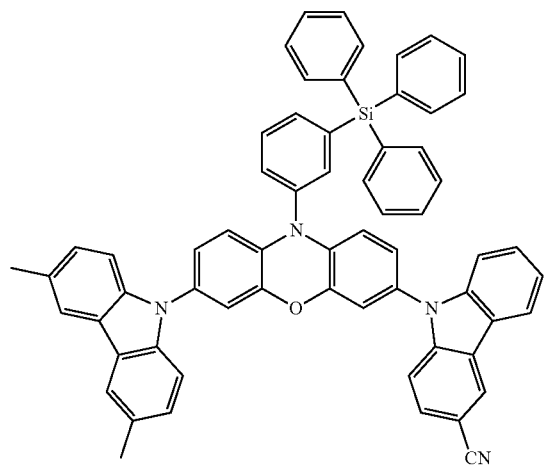
155
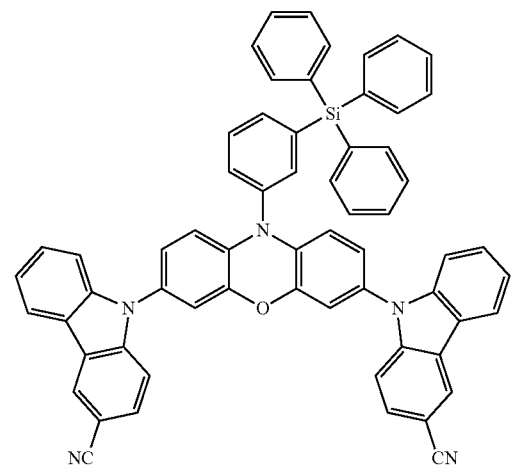
156
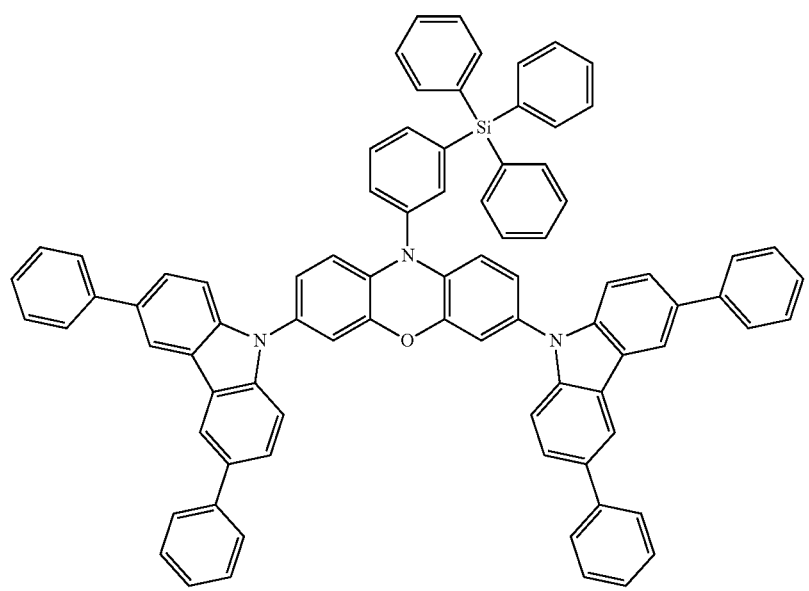

157

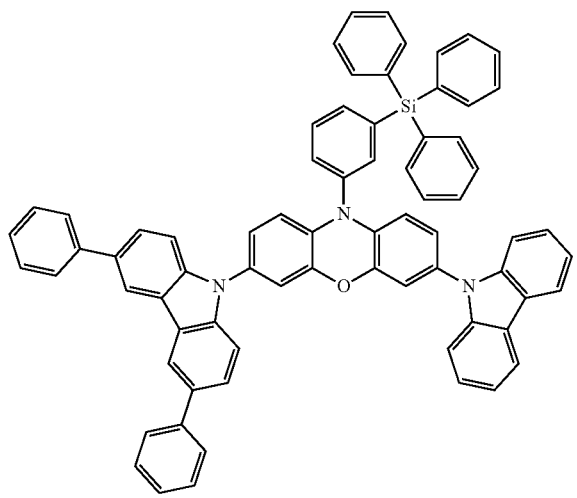

158

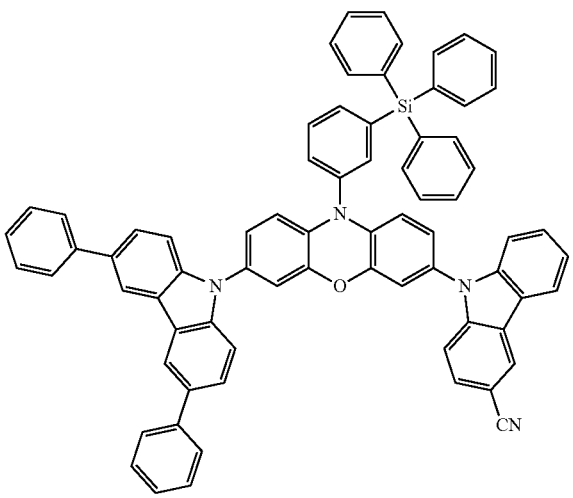

159

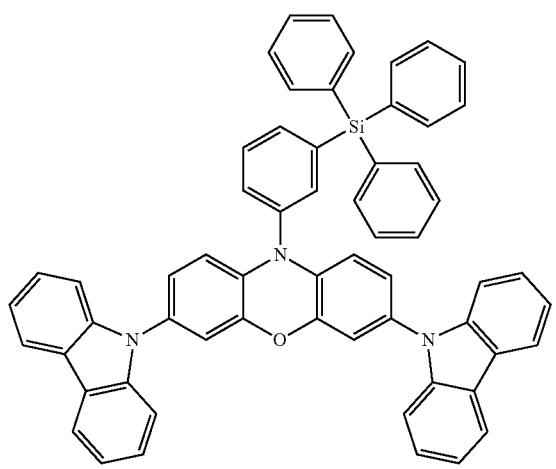

160

In an embodiment, the plurality of functional layers may include a hole transport layer, an emission layer, and an electron transport layer. The hole transport region may be on the first electrode. The emission layer may be on the hole transport region. The electron transport region may be on the emission layer. The emission layer may include the polycyclic compound.

The emission layer may include a host and a phosphorescent dopant. The emission layer may emit blue light.

An embodiment of the present disclosure provides a polycyclic compound represented by Formula 1 described above.

BRIEF DESCRIPTION OF THE DRAWINGS

The accompanying drawings are included to provide a further understanding of the subject matter of the present disclosure, and are incorporated in and constitute a part of this specification. The drawings illustrate exemplary embodiments of the present disclosure and, together with the description, serve to explain principles of the subject matter of the present disclosure. In the drawings.

DETAILED DESCRIPTION

Figure 1:
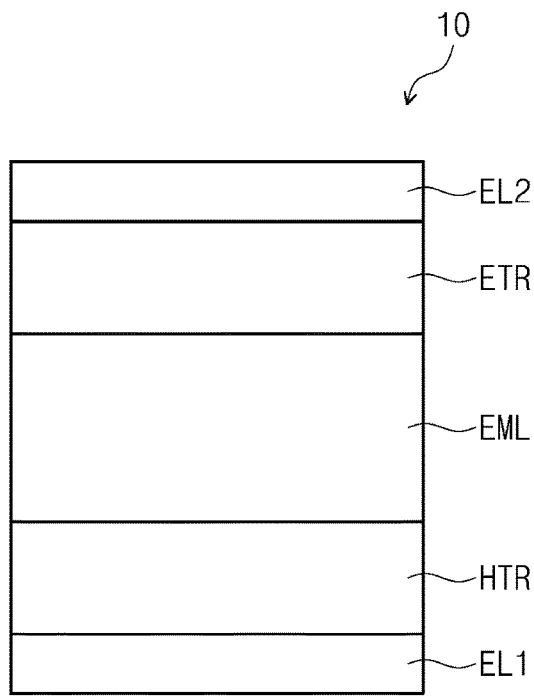
FIG. 1 is a cross-sectional view schematically illustrating an organic electroluminescence device according to an embodiment of the present disclosure.

The subject matter of the present disclosure may have various modifications and may be embodied in different forms, and thus specific embodiments will be exemplified in the drawings and described in the detailed description. It should be understood, however, that it is not intended to limit the present disclosure to the particular form disclosed, but rather, the subject matter of the present disclosure covers all the modifications, equivalents, and replacements within the spirit and technical scope of the present disclosure.

In explaining each of drawings, like reference numerals are used for referring to similar elements. In the accompanying drawings, the dimensions of structures are exaggeratingly illustrated for clarity of the present disclosure. Although the terms such as first and second are used herein to describe various components, these components should not be limited by these terms. The terms are only used to distinguish one component from other components. For example, a first component may be referred to as a second component, and similarly a second component may be referred to as a first component without departing from the scope of the present disclosure. The expression of a singular form may include plural forms unless the context clearly indicates otherwise. In the present application, it will be understood that the meaning of "comprise" or "have" specifies the presence of a feature, a fixed number, a step, a process, an element, a component, or a combination thereof disclosed in the specification, but does not exclude the possibility of presence or addition of one or more other features, fixed numbers, steps, processes, elements, components, or combinations thereof.

In the present application, when a layer, a film, a region, or a plate is referred to as being "above" or "in an upper portion of" another layer, film, region, or plate, it can be directly on the other layer, film, region, or plate, or intervening layers, films, regions, or plates may also be present. Similarly, when a layer, a film, a region, or a plate is referred to as being "under", "in a lower portion of" another layer, film, region, or plate, it can be directly under the layer, film, region, or plate, or intervening layers, films, regions, or plates may also be present. In addition, it will be understood that when a layer, a film, a region, or a plate is referred to as being "on" another layer, film, region, or plate, it can be not only disposed on the layer, film, region, or plate, but also disposed under the layer, film, region, or plate.

In the description, the term "substituted or unsubstituted" may refer to an unsubstituted group, or a group substituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents may be substituted or unsubstituted. For example, a biphenyl group may be interpreted as an aryl group, or a phenyl group substituted with a phenyl group.

In the description, the expression "being bonded to an adjacent group to form a ring" may refer to being bonded to an adjacent group to form a substituted or unsubstituted hydrocarbon ring, or a substituted or unsubstituted heterocyclic ring. The hydrocarbon ring includes an aliphatic hydrocarbon ring and an aromatic hydrocarbon ring. The heterocyclic ring includes an aliphatic heterocyclic ring and an aromatic heterocyclic ring. The hydrocarbon ring and the heterocyclic ring may be monocyclic or polycyclic. In addition, a ring formed by (one group) being bonded to an adjacent group may be linked to another ring to form a spiro structure.

In the description, the term "adjacent group" may refer to a substituent which is substituted for an atom directly linked to an atom for which the substituent is substituted, another substituent which is substituted for an atom for which the substituent is substituted, or a substituent sterically closest to the substituent. For example, the two methyl groups in 1,2-dimethylbenzene may be interpreted as "adjacent groups" to each other, and the two ethyl groups in 1,1-diethylcyclopentane may be interpreted as "adjacent groups" to each other.

In the description, examples of the halogen atom may include a fluorine atom, a chlorine atom, a bromine atom, and an iodine atom.

In the description, the alkyl group may be a linear, branched or cyclic alky group. The number of carbon atoms in the alkyl group may be 1 to 50, 1 to 30, 1 to 20, 1 to 10, or 1 to 6. Examples of the alkyl group may include, but are not limited to, methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the present disclosure, the above explanation on the alkyl group may be applied to the alkylene group except that the alkylene group is a divalent group.

In the description, the term "hydrocarbon ring group" refers to an optional functional group or substituent derived from an aliphatic hydrocarbon ring. The hydrocarbon ring group may be a saturated hydrocarbon ring group having a carbon number to form a ring of 5 to 20.

In the description, the term "aryl group" refers to an optional functional group or substituent derived from an aromatic hydrocarbon ring. The aryl group may be a monocyclic aryl group or a polycyclic aryl group. The carbon number to form a ring in the aryl group may be 6 to 30, 6 to 20, or 6 to 15. Examples of the aryl group may include, but are not limited to, phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc.

In the description, the heteroaryl group may include one or more selected from B, O, N, P, Si, and S as a heteroatom. In the case where the heteroaryl group includes two or more heteroatoms, the two or more heteroatoms may be the same as or different from each other. The heteroaryl group may be a monocyclic heterocyclic group or a polycyclic heterocyclic group. The number of carbon atoms to form a ring of the heteroaryl group may be 2 to 30, 2 to 20, or 2 to 10. Examples of the heteroaryl group may include, but are not limited to, thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuranyl, etc.

In the present disclosure, the above explanation on the aryl group may be applied to the arylene group except that the arylene group is a divalent group. The above explanation on the heteroaryl group may be applied to the heteroarylene group except that the heteroarylene group is a divalent group.

In the description, the silyl group includes an alkyl silyl group and an aryl silyl group. Examples of the silyl group may include, but are not limited to, trimethylsilyl, triethylsilyl, t-butyldimethylsilyl, vinyldimethylsilyl, propyldimethylsilyl, triphenylsilyl, diphenylsilyl, phenylsilyl, etc.

In the description, the oxy group may include an alkoxy group and an aryl oxy group. The alkoxy group may be a linear, branched or cyclic chain. The number of carbons in the alkoxy group may be, for example, 1 to 20, or 1 to 10, but the present disclosure is not limited thereto. Examples of the oxy group may include, but are not limited to, methoxy, ethoxy, n-propoxy, isopropoxy, butoxy, pentyloxy, hexyloxy, octyloxy, nonyloxy, decyloxy, cyclopropoxy, cyclobutoxy, etc. The number of carbons in the aryloxy group may be, for example, 6 to 30, but the present disclosure is not limited thereto. Examples of the aryloxy group may include, but are not limited to, phenoxy group, etc.

In the description, the number of carbon atoms in the amine group may be 1 to 30, but the present disclosure is not limited thereto. The amine group may include an alkyl amine group and an aryl amine group. Examples of the amine group may include, but are not limited to, methylamine, dimethylamine, phenylamine, dephenyl amine, naphthyl amine, 9-methyl-anthracenyl amine, triphenyl amine, etc.

In the description, the aryl group included in the aryloxy group, the arylthio group, the arylsulfoxy group, the arylamino group, the arylboron group, the arylsilyl group, and the arylamine group may be the same as the examples of the aryl group described above.

In the description, the term "direct linkage" may refer to a single bond.

FIG. 1 is a cross-sectional view schematically illustrating an organic electroluminescence device according to an embodiment of the present disclosure. An organic electroluminescence device 10 according to an embodiment of the present disclosure may include a first electrode EL1, a second electrode EL2 disposed on the first electrode EL1, and a plurality of functional layers disposed between the first electrode EL1 and the second electrode EL2. The plurality of functional layers may include a hole transport region HTR, an emission layer EML, an electron transport region ETR, and a second electrode EL2.

Figure 2:
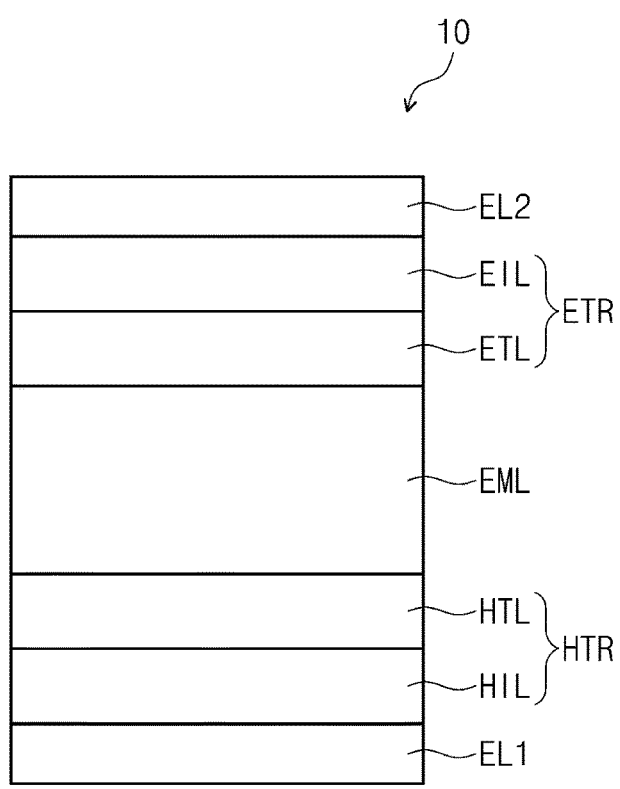
FIG. 2 is a cross-sectional view schematically illustrating an organic electroluminescence device according to an embodiment of the present disclosure.
Figure 3:
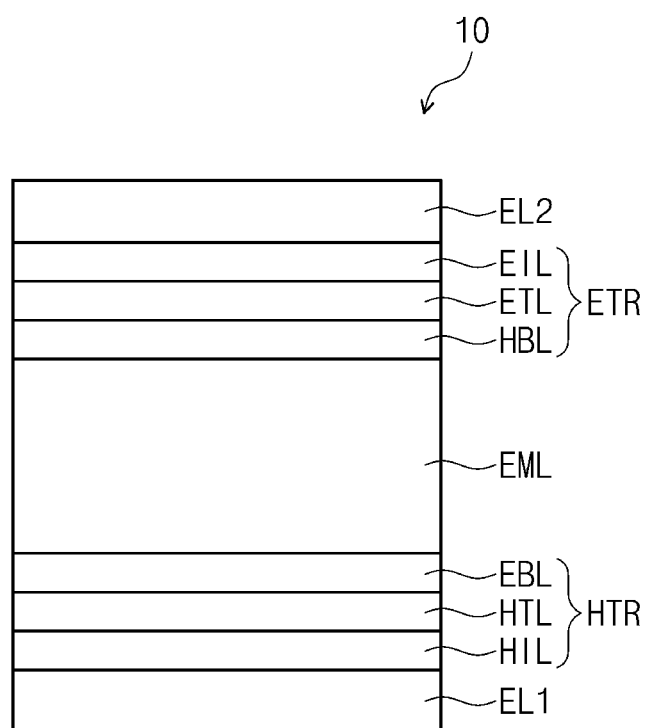
FIG. 3 is a cross-sectional view schematically illustrating an organic electroluminescence device according to an embodiment of the present disclosure.

When compared with FIG. 1, FIG. 2 shows the cross-sectional view of an organic electroluminescence device 10 of an embodiment, wherein the hole transfer region HTR includes a hole injection layer HIL and a hole transport layer HTL, and the electron transfer region ETR includes an electron injection layer EIL and an electron transport layer ETL. Furthermore, when compared with FIG. 1, FIG. 3 shows the cross-sectional view of an organic electroluminescence device 10 of an embodiment, wherein the hole transfer region HTR includes a hole injection layer HIL, a hole transport layer HTL, and an electron blocking layer EBL, and the electron transfer region ETR includes an electron injection layer EIL, an electron transport layer ETL, and a hole blocking layer HBL.

In the organic electroluminescence device 10 of an embodiment of the present disclosure, at least one functional layer selected from the plurality of functional layers may include a polycyclic compound represented by Formula 1 below:

[Formula 1]

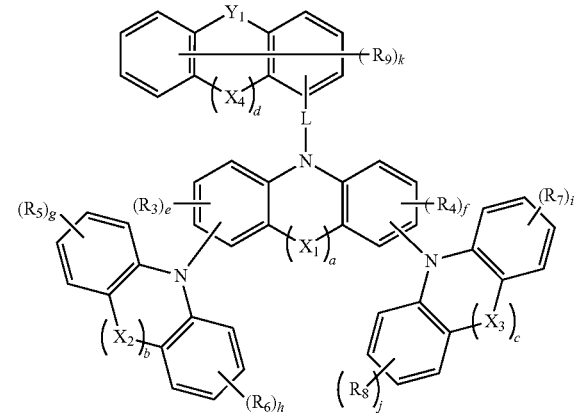

In Formula 1 above, $X_1$ to $X_4$ each independently may be a direct linkage, O, or S. $Y_1$ may be O, S, or $SiR_1R_2$.

L may be a direct linkage, an alkylene group, an arylene group, or a heteroarylene group. The alkylene group may be a substituted or unsubstituted alkylene group having 1 to 10 carbon atoms. The arylene group may be a substituted or unsubstituted arylene group having 6 to 30 carbon atoms to form a ring. The heteroarylene group may be a substituted or unsubstituted heteroarylene group having 2 to 30 carbon atoms to form a ring. For example, L may be a substituted or unsubstituted phenylene group.

$R_1$ and $R_2$ may be each independently a hydrogen atom, a deuterium atom, an alkyl group, an aryl group, or a heteroaryl group, or may be combined with an adjacent group to form a ring. The alkyl group may be a substituted or unsubstituted alkyl group having 1 to 20 carbon atoms. The aryl group may be a substituted or unsubstituted aryl group having 6 to 30 carbon atoms to form a ring. The heteroaryl group may be a substituted or unsubstituted heteroaryl group having 2 to 30 carbon atoms to form a ring. For example, $R_1$ and $R_2$ may be each independently a substituted or unsubstituted phenyl group. In one embodiment, $R_1$ and $R_2$ may be each independently an unsubstituted phenyl group.

$R_3$ to $R_9$ may be each independently a hydrogen atom, a deuterium atom, a halogen atom, a cyano group, an amine group, a silyl group, an oxy group, an alkyl group, an aryl group, or a heteroaryl group, or may be combined with an adjacent group to form a ring. The amine group may be a substituted or unsubstituted amine group. The silyl group may be a substituted or unsubstituted silyl group. The oxy group may be a substituted or unsubstituted oxy group having 1 to 20 carbon atoms. The alkyl group may be a substituted or unsubstituted alkyl group having 1 to 20 carbon atoms. The aryl group may be a substituted or unsubstituted aryl group having 6 to 30 carbon atoms to form a ring. The heteroaryl group may be a substituted or unsubstituted heteroaryl group having 2 to 30 carbon atoms to form a ring.

The substituted or unsubstituted silyl group may be, for example, a triphenylsilyl group. The substituted or unsubstituted oxy group may be, for example, a substituted or unsubstituted alkoxy group, or a substituted or unsubstituted aryloxy group. The substituted or unsubstituted alkoxy group may be, for example, a linear alkoxy group, or a cyclic alkoxy group. The cyclic alkoxy group may be a substituted or unsubstituted cyclic alkoxy group having 3 to 20 carbon atoms to form a ring. The substituted or unsubstituted alkyl group may be, for example, a methyl group, an ethyl group, a propyl group, an isopropyl group, a t-butyl group, an i-butyl group, or a halogenated methyl group. The halogenated methyl group may be a trifluoromethyl group. The aryl group may be, for example, an unsubstituted phenyl group. For example, $R_1$ and $R_9$ may be combined with each other to form a ring.

a to d may be each independently 0 or 1. e and f may be each independently an integer of 0 to 3. g and j may be each independently an integer of 0 to 4. k may be an integer of 0 to 7.

That "e is 0" has the same meaning as "$R_3$ is a hydrogen atom." When e is 1 or more, $R_3$ may be a group other than a hydrogen atom of the groups described above. When e is 2 or more, the 2 or more $R_3$s may be the same as or different from each other. Because the same described as those in e may be applied with regard to f to k, detailed descriptions thereof will be omitted (e.g., not be provided).

For instance, both e and f may be 0. a to d may each be 1; a to c may each be 1, and d may be 0; a and b may each be 1, and c and d may each be 0; or a may be 0, b to d may each be 1.

In one embodiment, $Y_1$ may be O or S, and when $X_4$ is a direct linkage, at least one selected from $X_1$ to $X_3$ may be O or S. Alternatively, when $Y_1$ is O or S, and when $X_4$ is a direct linkage, at least one selected from a to c may be 0.

The polycyclic compound represented by Formula 1 may be represented by Formula 2-1 below:

[Formula 2-1]

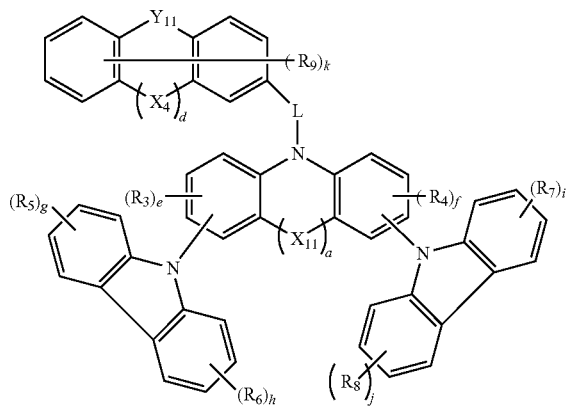

In Formula 2-1, $X_{11}$ and $Y_{11}$ may be each independently O or S. $X_4$, L, $R_3$ to $R_9$, a, and d to k may be the same as respectively defined in connection with Formula 1 above. For example, in Formula 2-1, $X_4$ may be a direct linkage, and d may be 1.

The polycyclic compound represented by Formula 2-1 may be represented by at least one selected from Formula 2-1-1 to Formula 2-1-3 below:

[Formula 2-1-1]

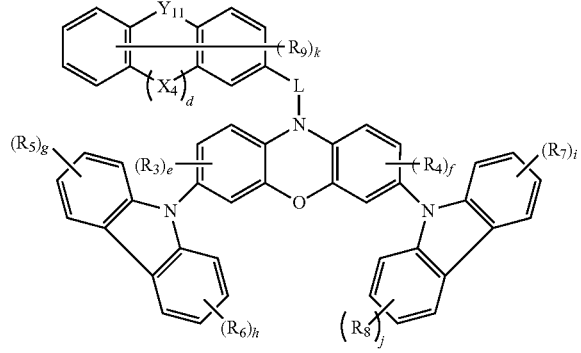

[Formula 2-1-2]

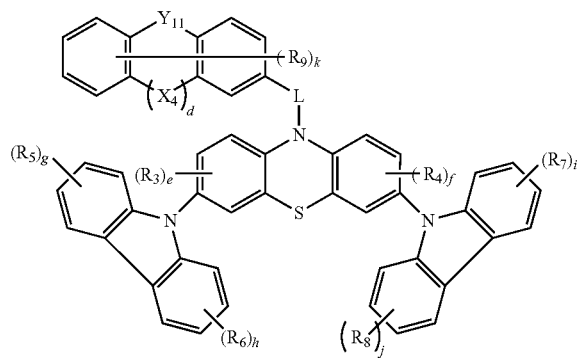

[Formula 2-1-3]

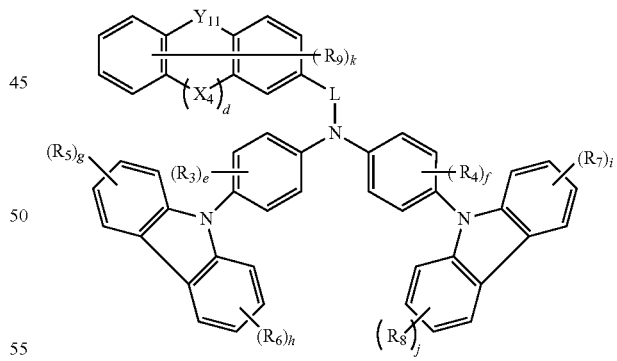

Formula 2-1-1 is a formula specifying that $X_{11}$ is O, and a is 1 in Formula 2-1. Formula 2-1-2 is a formula specifying that $X_{11}$ is S, and a is 1 in Formula 2-1. Formula 2-1-3 is a formula specifying that a is 0 in Formula 2-1. In Formula 2-1-1 to Formula 2-1-3, $X_4$, $Y_{11}$, L, $R_3$ to $R_9$, and d to k may be the same as respectively defined in connection with Formula 2-1. For example, in Formula 2-1-1 to Formula 2-1-3, $X_4$ may be a direct linkage, and d may be 1.

The polycyclic compound represented by Formula 1 may be represented by Formula 2-2 below:

[Formula 2-2]

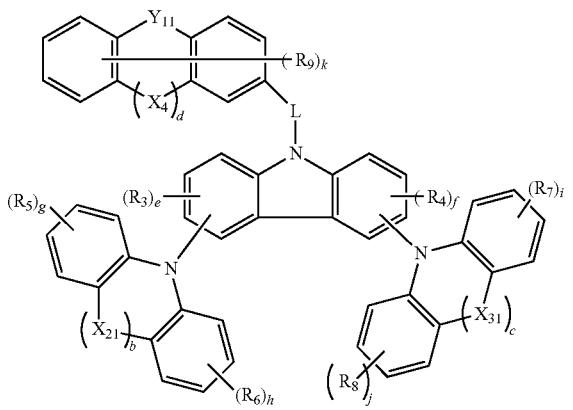

In Formula 2-2 above, $X_{21}$, $X_{31}$, and $Y_{11}$ may be each independently O or S. $X_4$, L, $R_3$ to $R_9$, and b to k may be the same as respectively defined in connection with Formula 1 above. For example, in Formula 2-2, $X_4$ may be a direct linkage, and d may be 1.

The polycyclic compound represented by Formula 2-2 may be represented by Formula 2-2-1 to Formula 2-2-3 below:

[Formula 2-2-1]

[Formula 2-2-2]

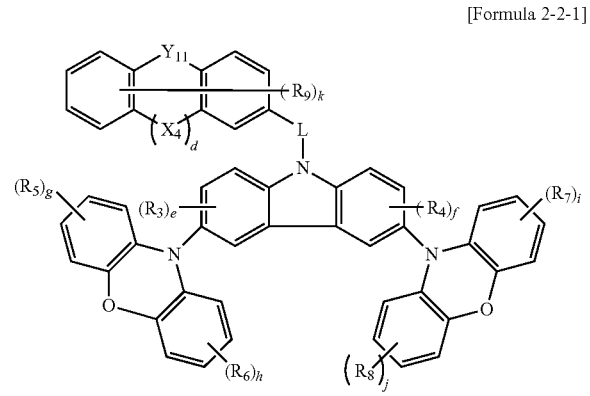

[Formula 2-2-3]

Formula 2-2-1 is a formula specifying that $X_{21}$ and $X_{31}$ are each O, and b and c are each 1 in Formula 2-2. Formula 2-2-2 is a formula specifying that $X_{21}$ and $X_{31}$ are each S, and b and c are each 1 in Formula 2-2. Formula 2-2-3 is a formula specifying that b and c are each 0 in Formula 2-2. In Formula 2-2-1 to Formula 2-2-3, $X_4$, $Y_{11}$, L, $R_3$ to $R_9$, and d to k may be the same as respectively defined in connection with Formula 2-2 above. For example, in Formula 2-2-1 to Formula 2-2-3, $X_4$ may be a direct linkage, and d may be 1.

The polycyclic compound represented by Formula 1 may be represented by Formula 3 below:

[Formula 3]

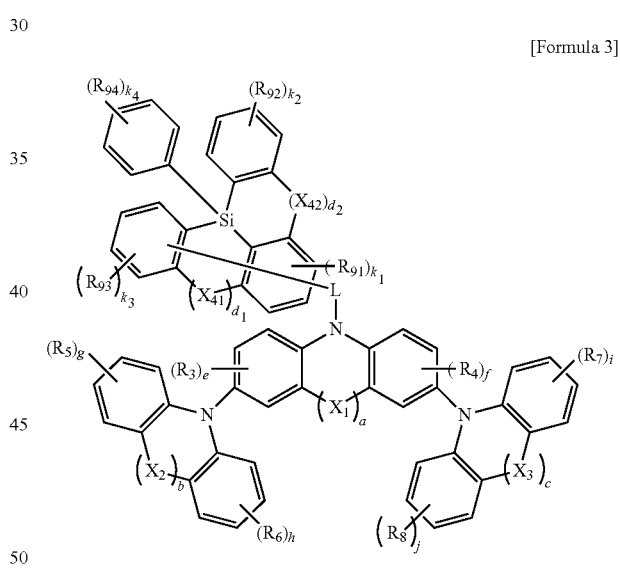

In Formula 3 above, $X_{41}$ and $X_{42}$ may each be O. $R_{91}$ to $R_{94}$ may be each independently a hydrogen atom, a deuterium atom, a halogen atom, a cyano group, an amine group, a silyl group, an oxy group, an alkyl group, an aryl group, or a heteroaryl group. When $R_{91}$ to $R_{94}$ are the hydrogen atom, the deuterium atom, the halogen atom, the cyano group, the amine group, the silyl group, the oxy group, the alkyl group, the aryl group, or the heteroaryl group, the same description in definition of R in Formula 1 may be applied thereto, and thus the detailed description is omitted (not repeated).

$d_1$ and $d_2$ may be each independently 0 or 1. $k_1$ may be an integer of 0 to 3. $k_2$ and $k_3$ may be each independently an integer of 0 to 4. $k_4$ may be an integer of 0 to 5. For example, both $d_1$ and $d_2$ may be 0, at least one selected from $d_1$ to $d_2$ may be 1.

$k_1$ to $k_4$ may each be 0.

$X_1$ to $X_3$, L, $R_3$ to $R_8$, a to c, and e to j may be the same as respectively defined in connection with Formula 1 above.

The polycyclic compound represented by Formula 3 may be represented by Formula 3-1 below:

[Formula 3-1]

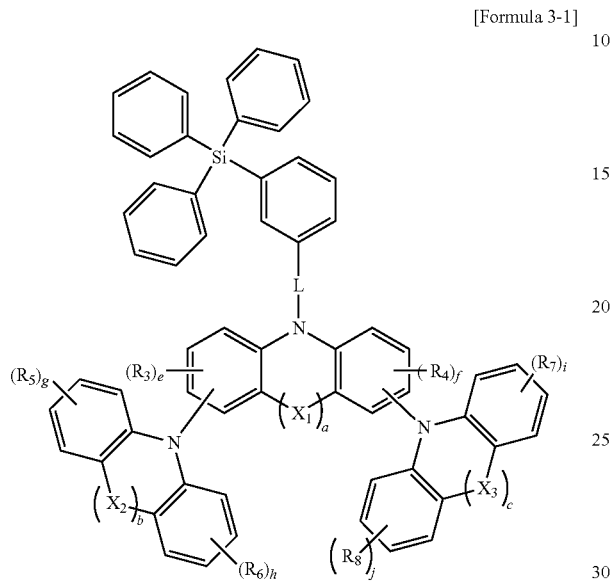

Formula 3-1 is a formula specifying that $d_1$ and $d_2$ are each 0, and specifying the substitution position of the linker L in Formula 3.

In Formula 3-1 above, $X_1$ to $X_3$, L, $R_3$ to $R_8$, a to c, and e to j may be the same as respectively defined in connection with Formula 3 above.

The polycyclic compound represented by Formula 3-1 may be represented by at least one selected from Formula 3-1-1 to Formula 3-1-3 below:

[Formula 3-1-1]

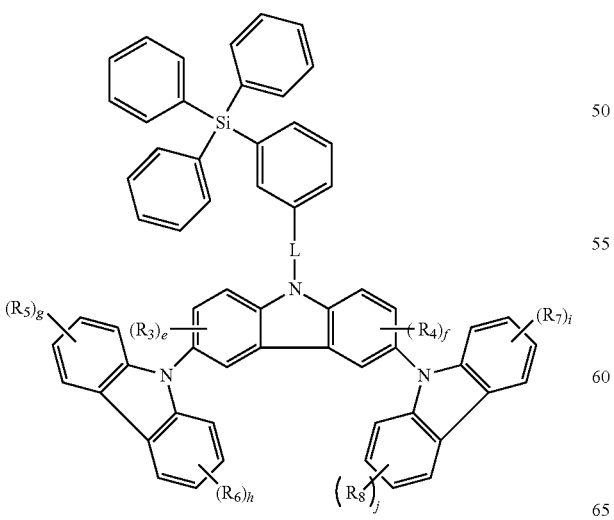

[Formula 3-1-2]

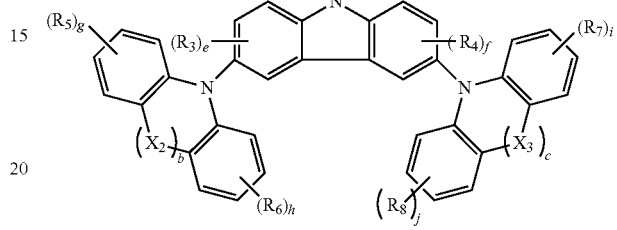

[Formula 3-1-3]

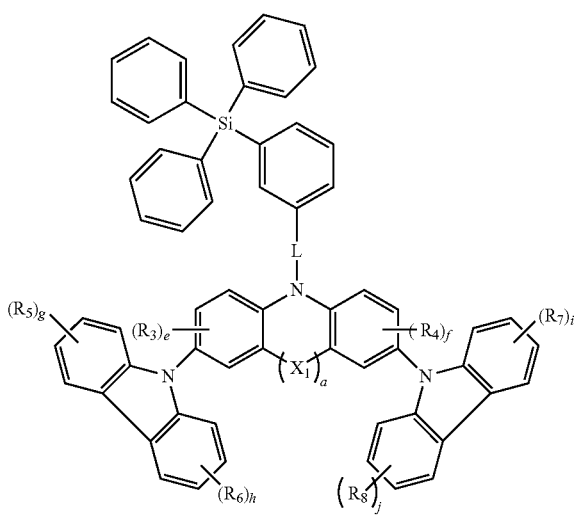

In Formula 3-1-1 to Formula 3-1-3, $X_1$ to $X_3$, L, $R_3$ to $R_8$, a to c, and e to j may be the same as respectively defined in connection with Formula 3-1 above.

The polycyclic compound represented by Formula 3 may be represented by Formula 3-2 and Formula 3-3 below:

[Formula 3-2]
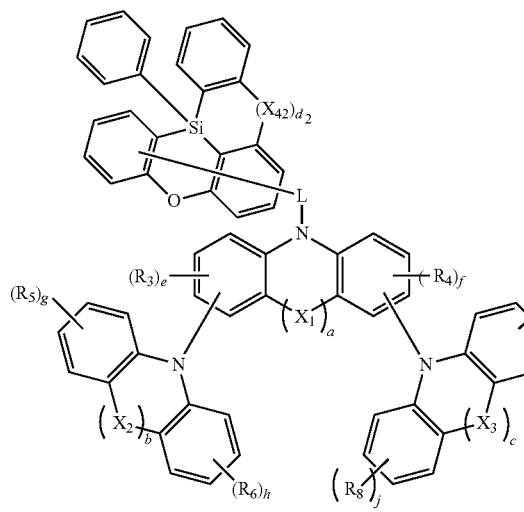
[Formula 3-3]
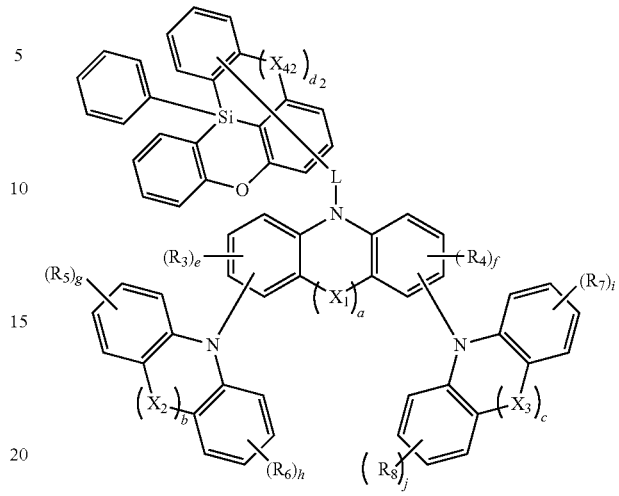
In Formula 3-2 and Formula 3-3, $X_1$ to $X_3$, $X_{42}$, L, $R_3$ to $R_8$, a to c, $d_2$, and e to j may be the same as respectively defined in connection with Formula 3 above.
A polycyclic compound of an embodiment may be any one selected from compounds represented by Compound Group 1 below:
[Compound Group 1]
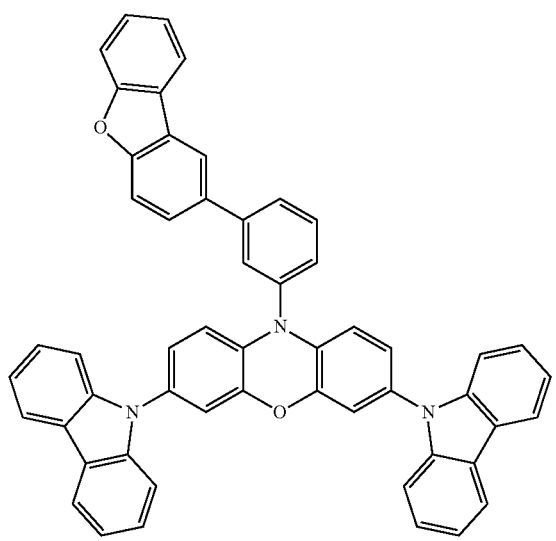
1
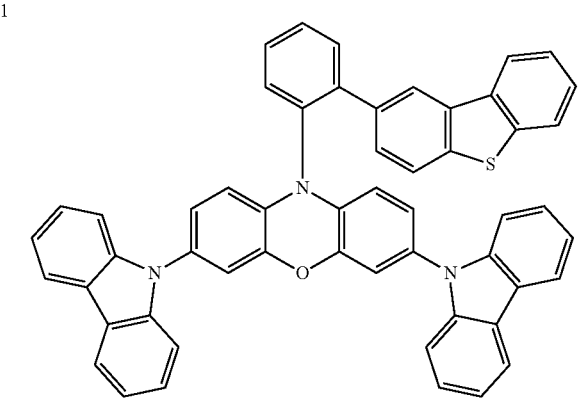
2

-continued
3
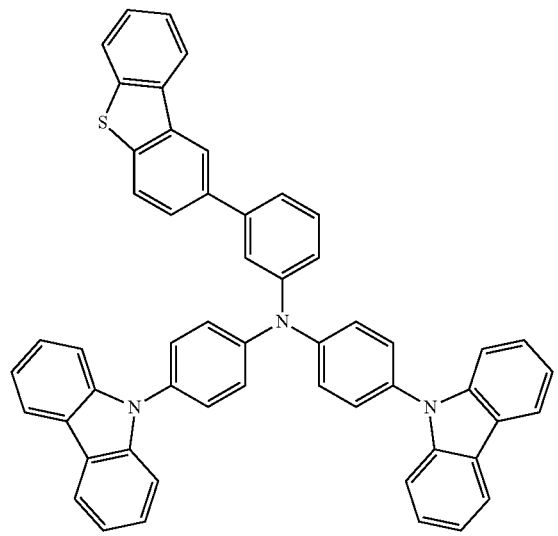
4
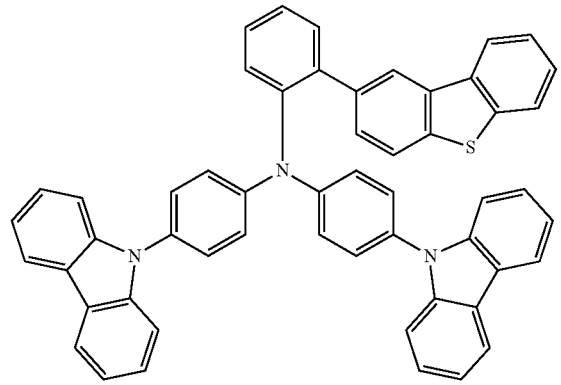
5
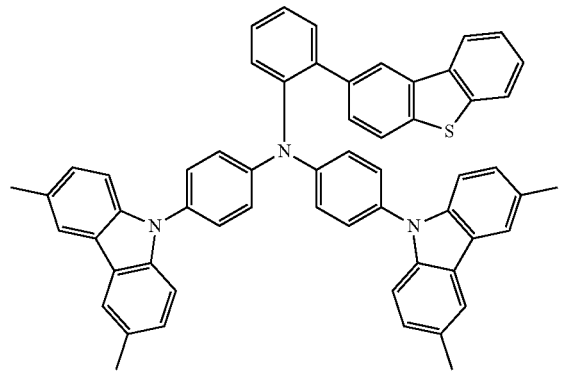
6
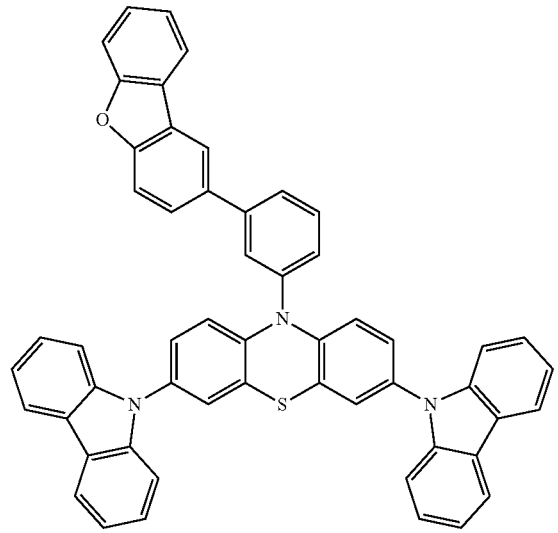
7
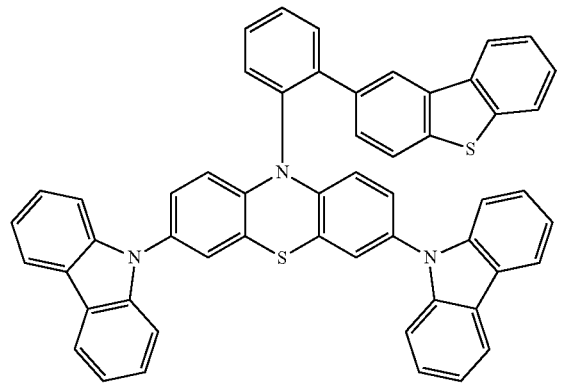
8
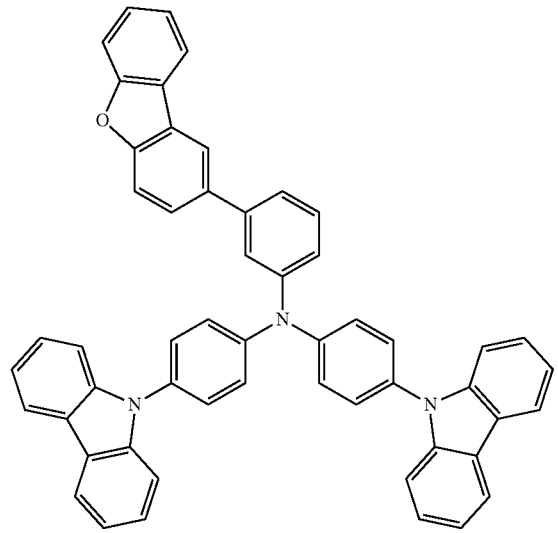

-continued
9
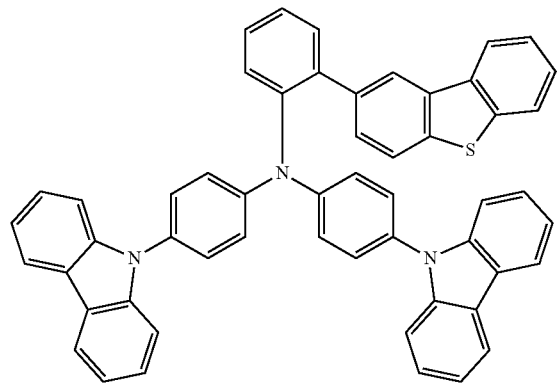
10
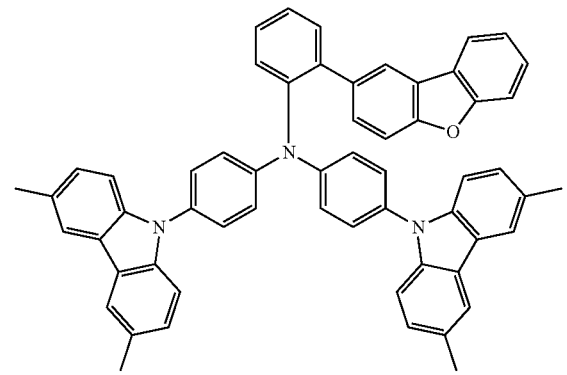
11
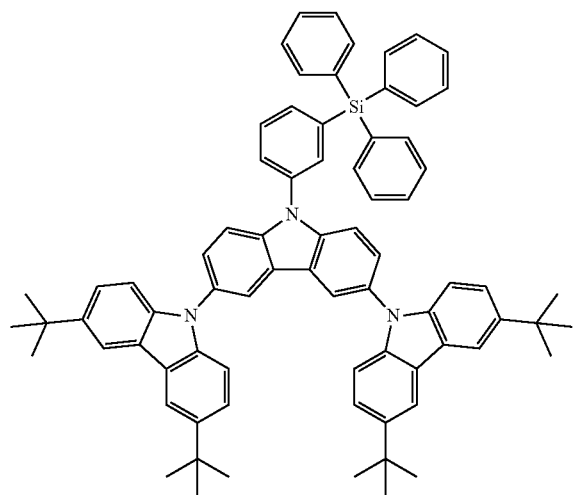
12
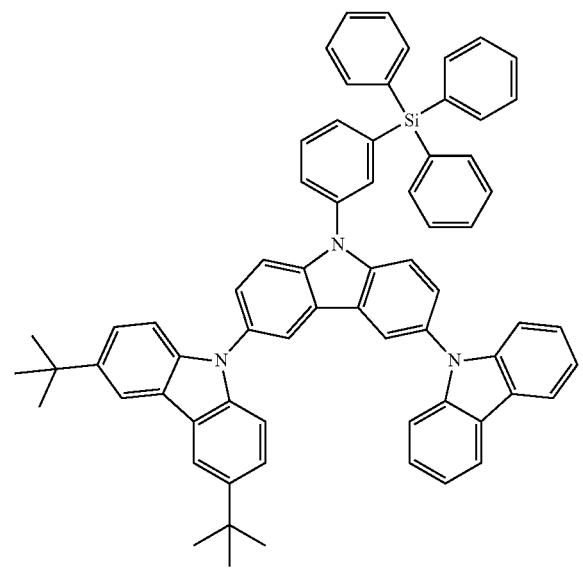
13
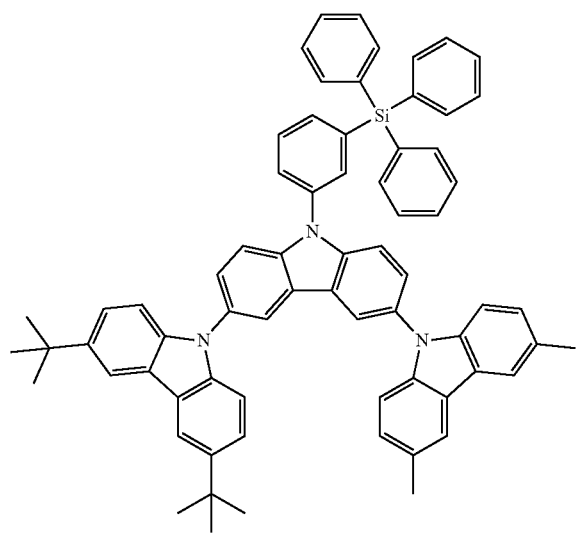
14
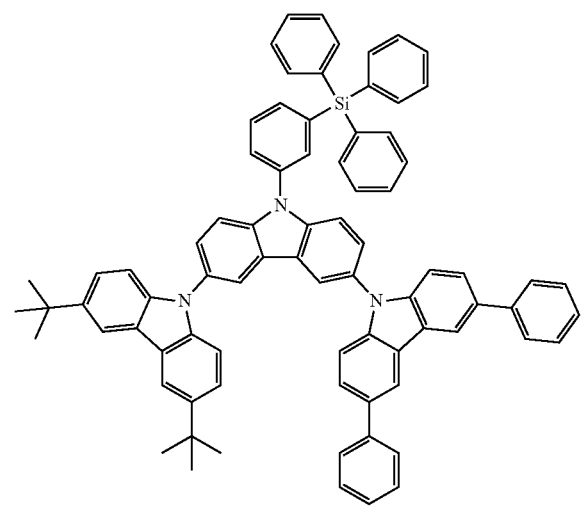

15
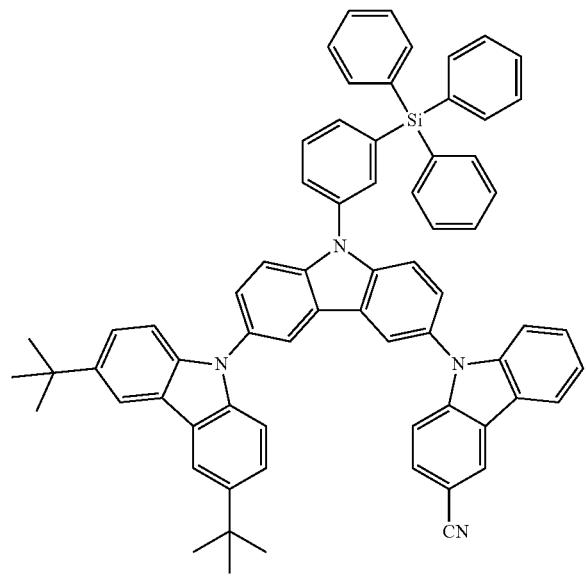
16
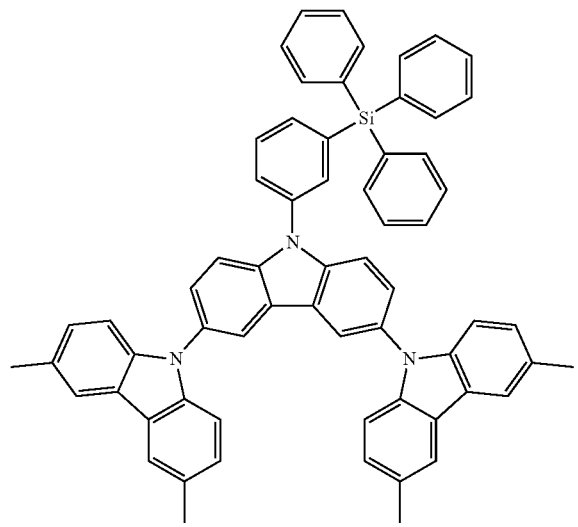
17
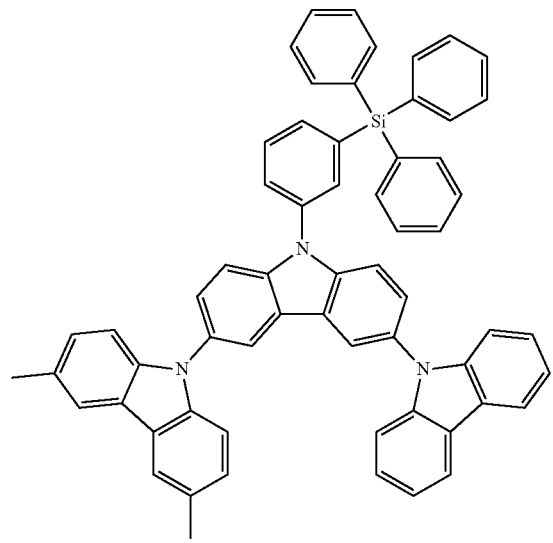
18
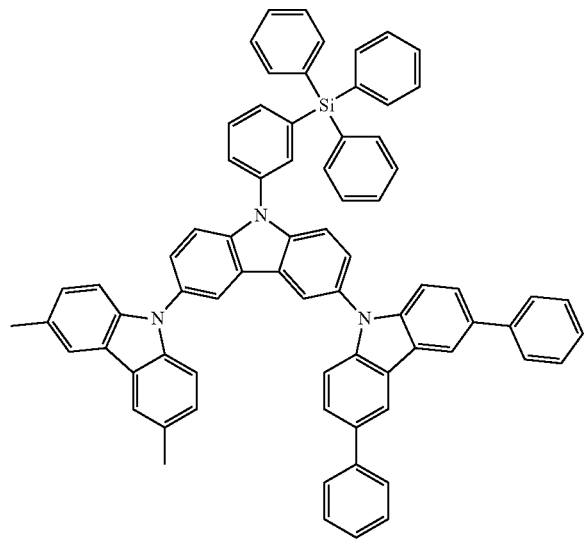

19
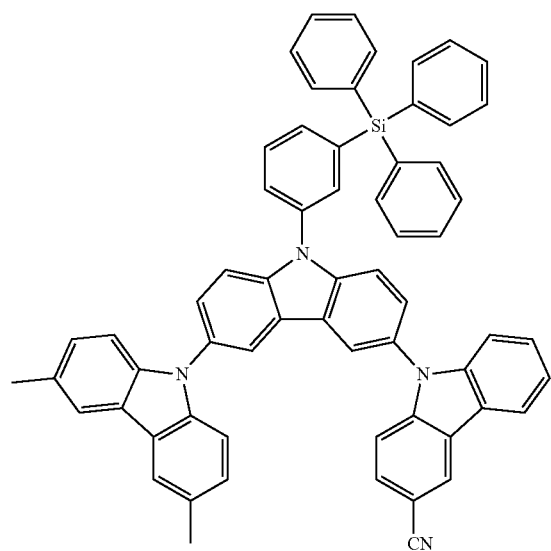
20
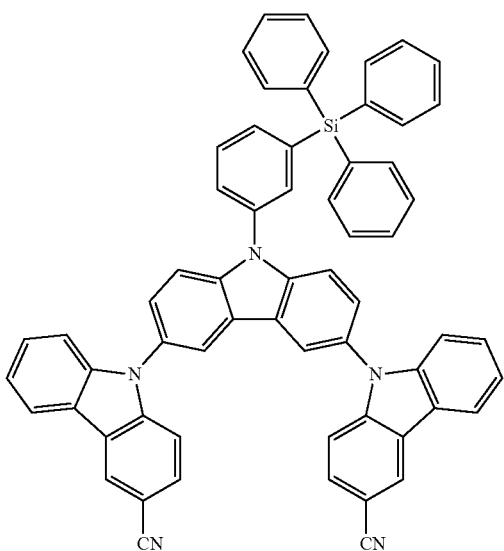
21
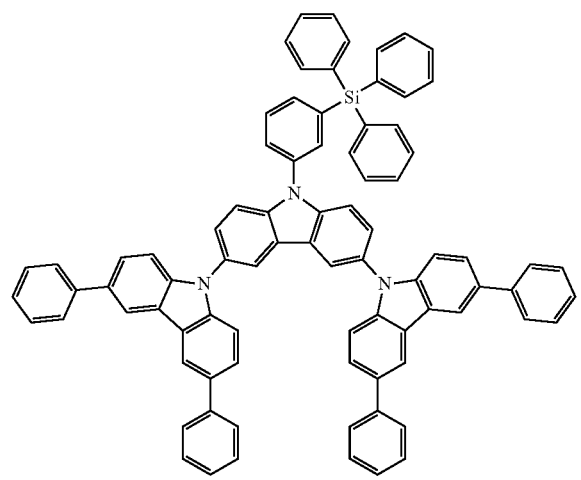
22
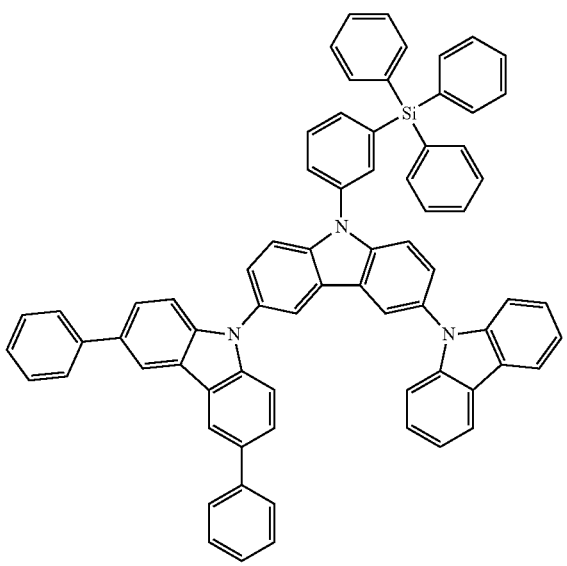

23
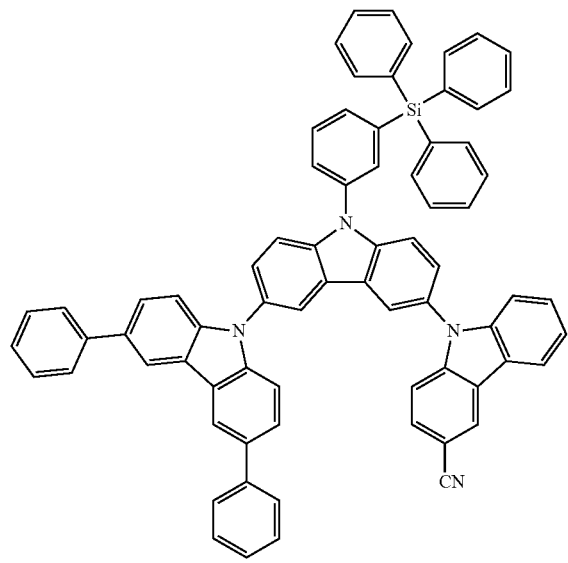
24
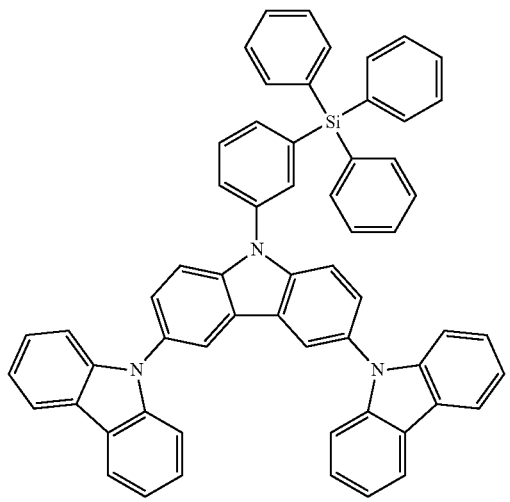
25
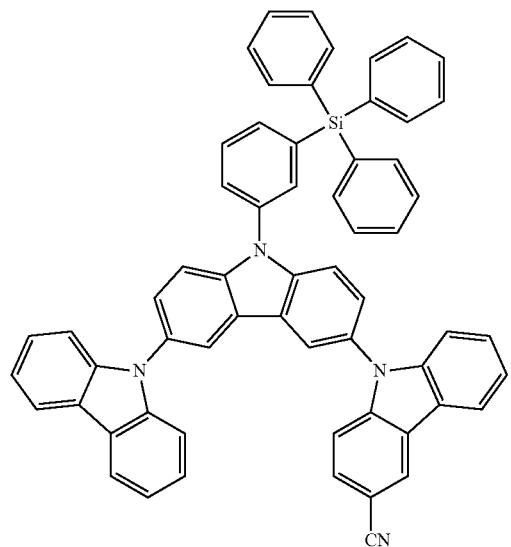
26
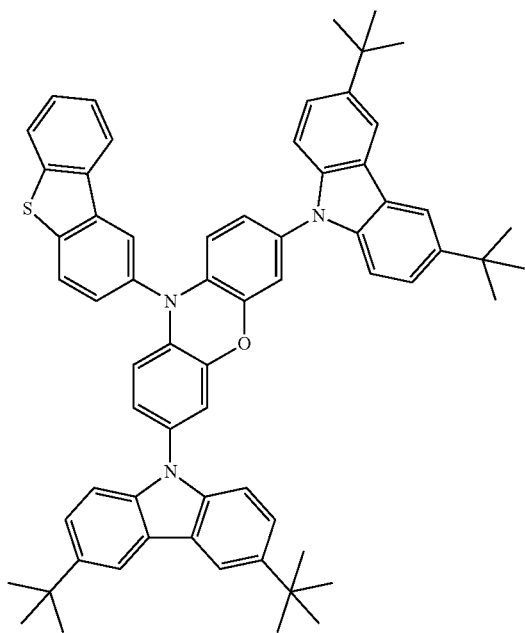

27
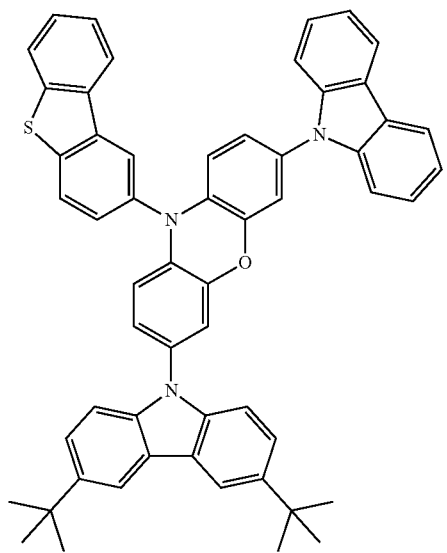
28
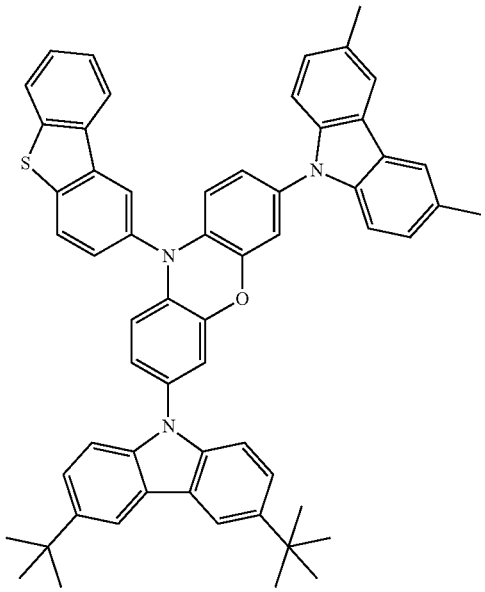
29
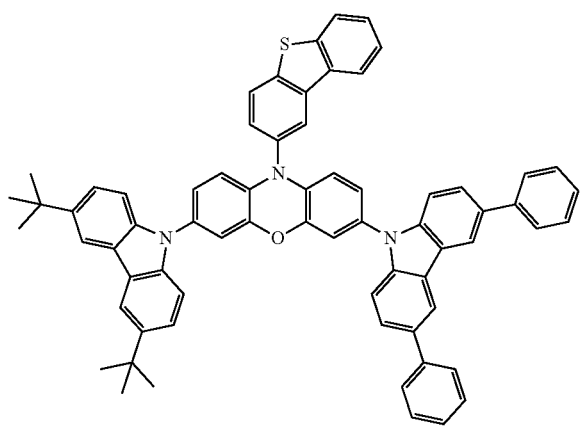
30
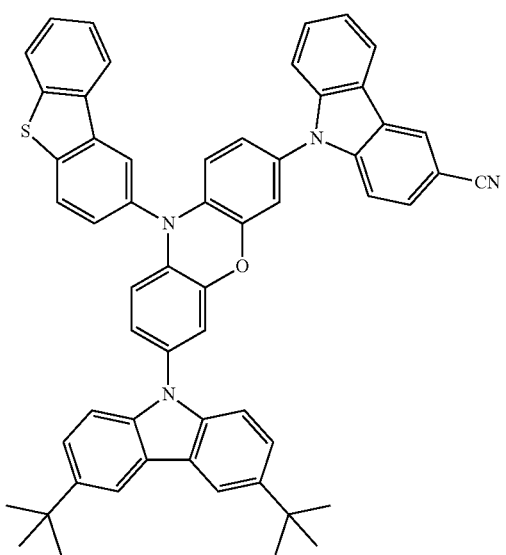

-continued
31
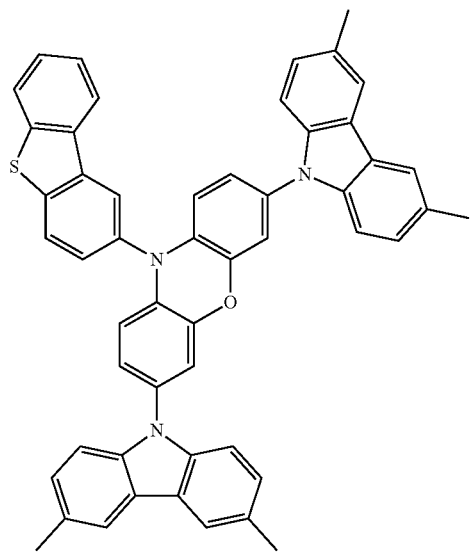
32
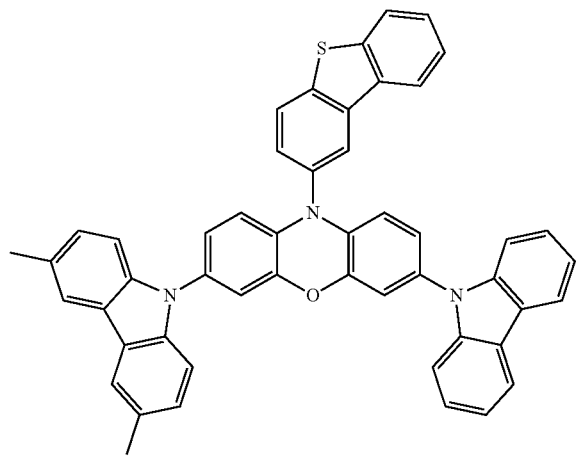
33
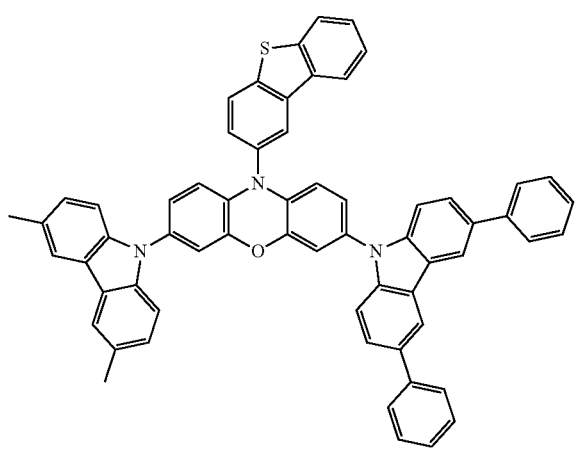
34
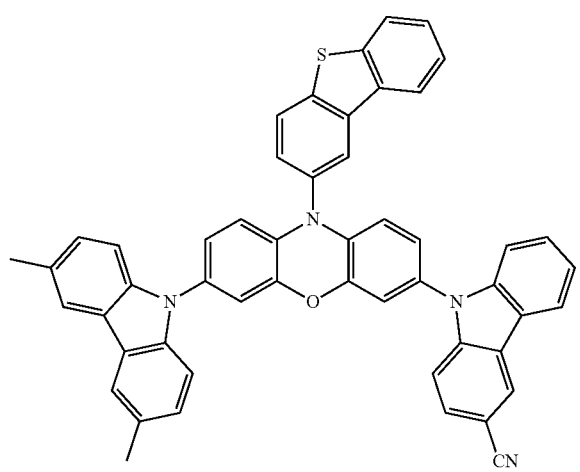
35
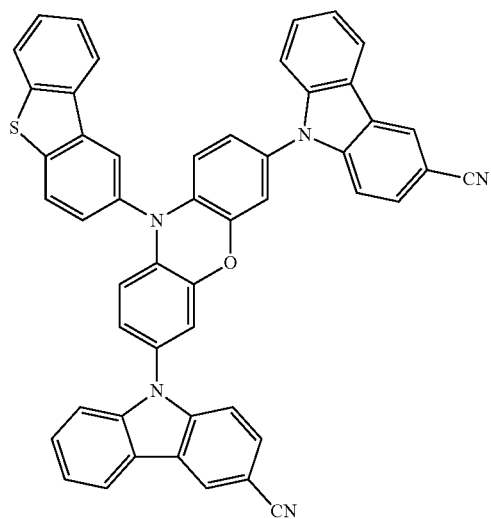

36
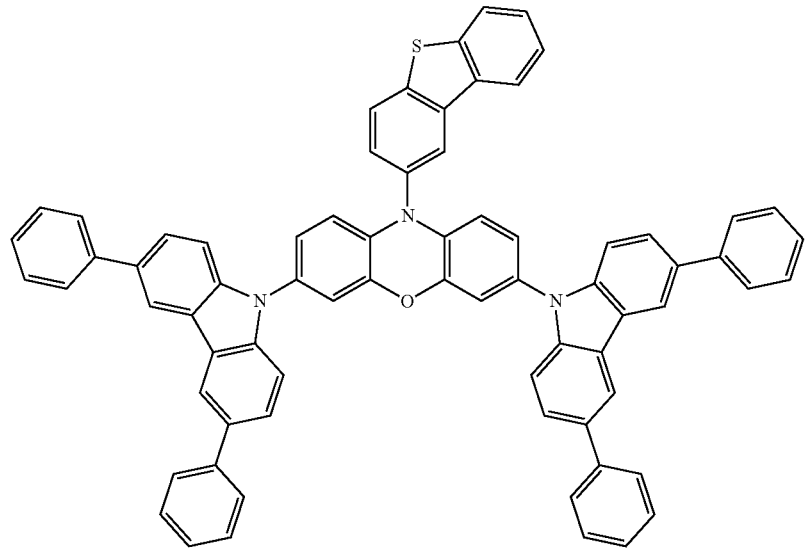
37
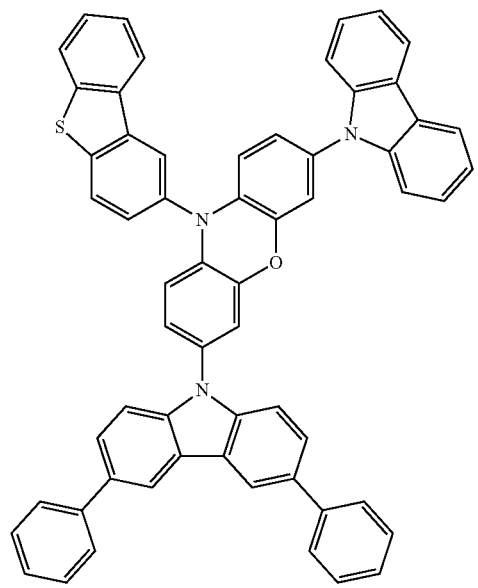
38
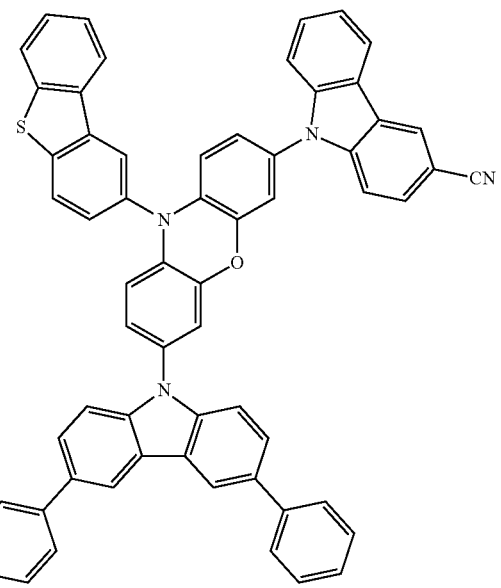
39
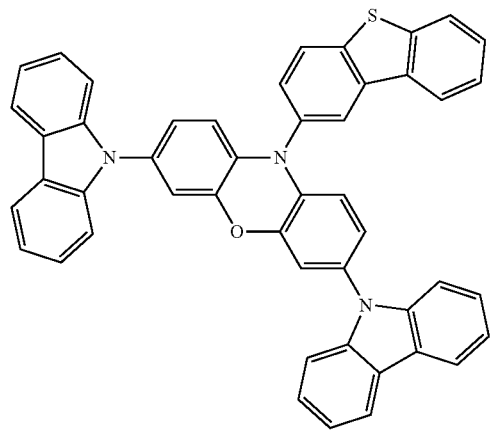
40
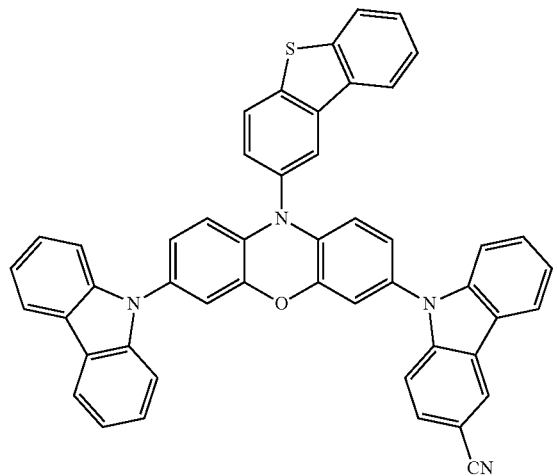

41
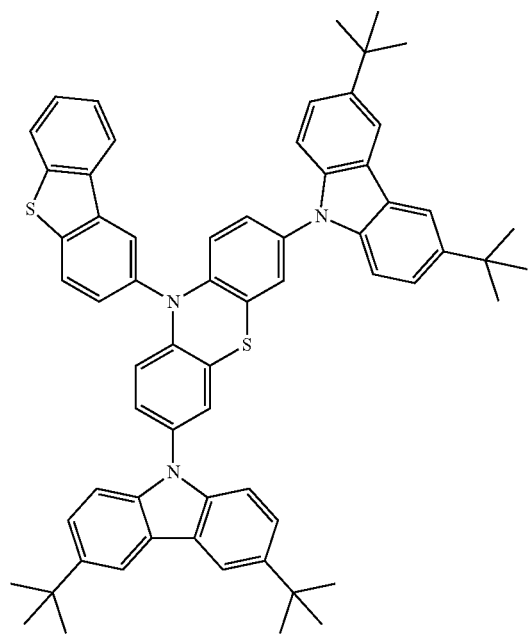
42
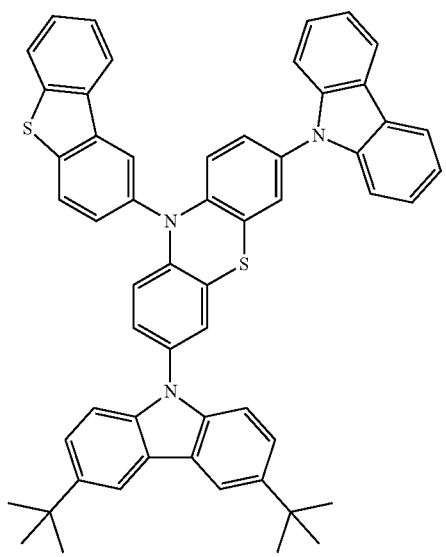
43
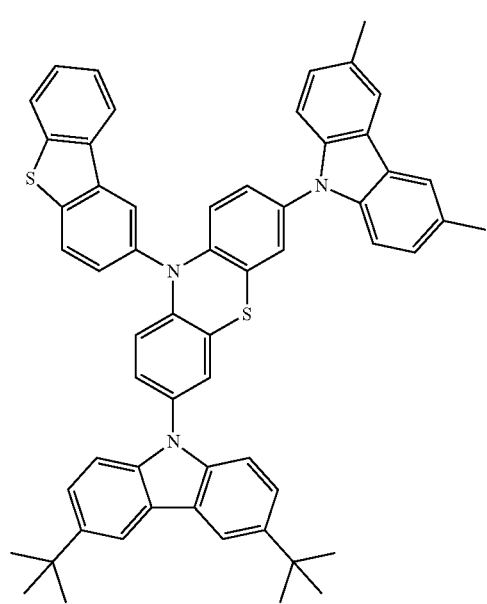
44
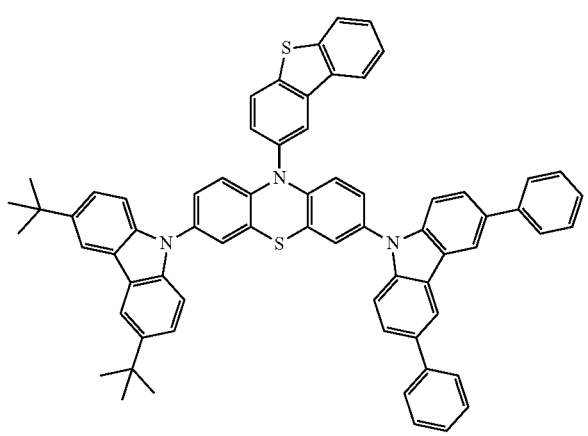

45
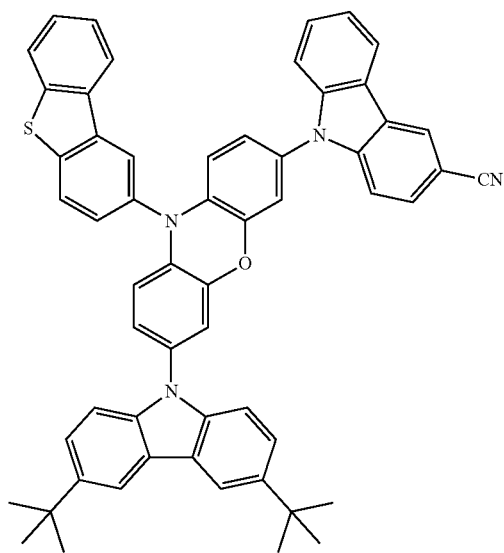
46
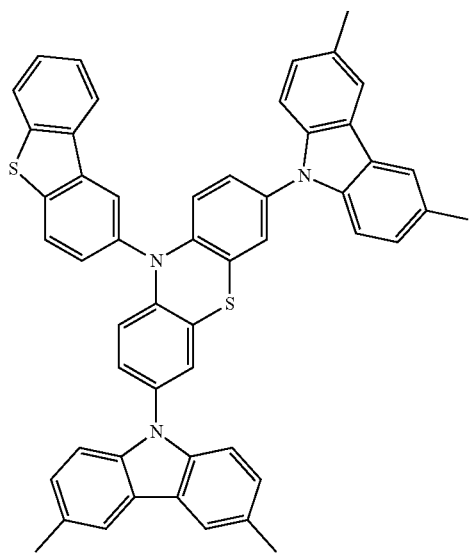
47
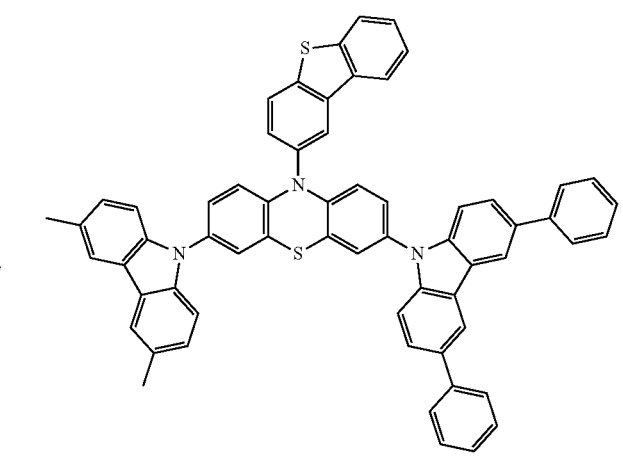
48
49
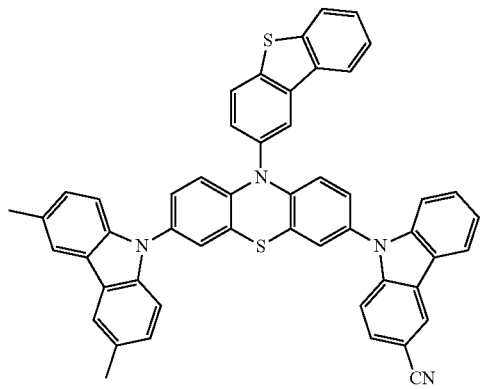
50
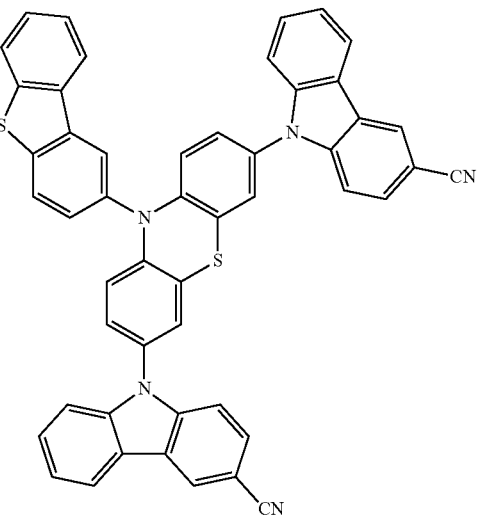

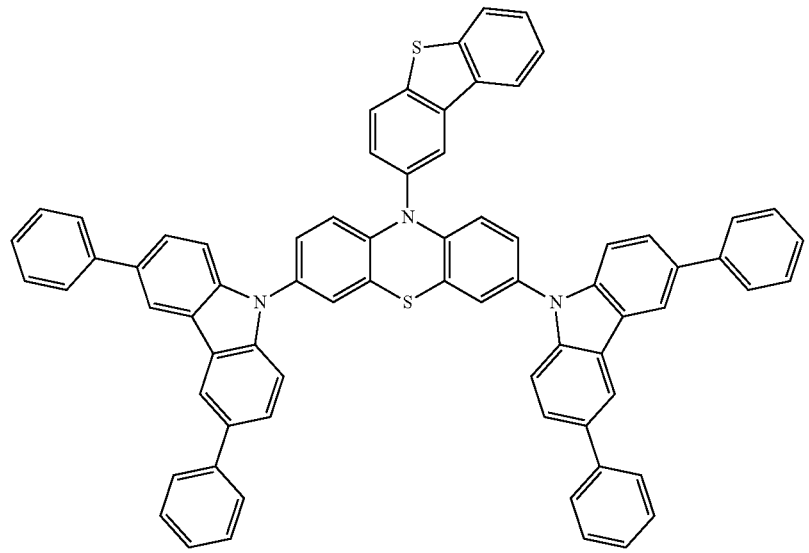
51
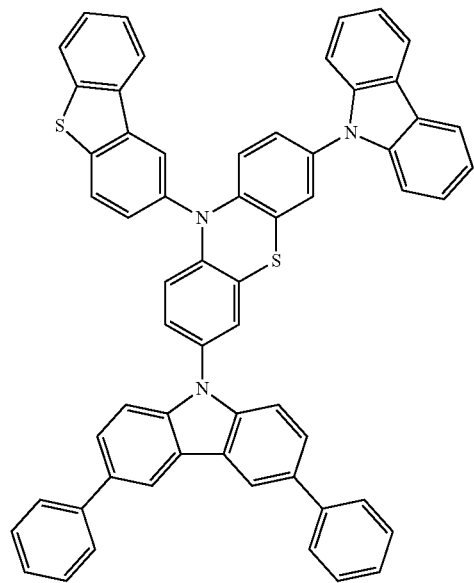
52
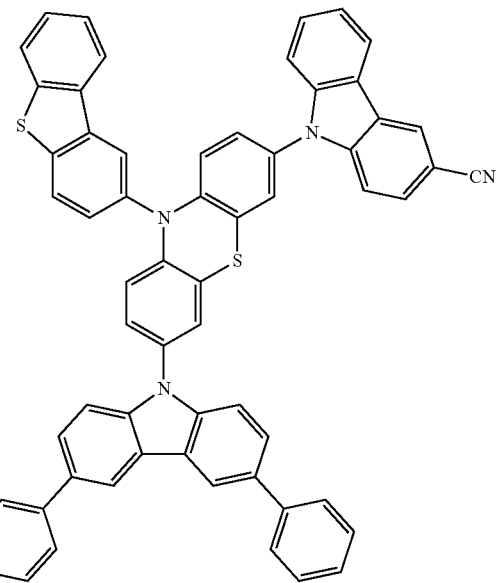
53
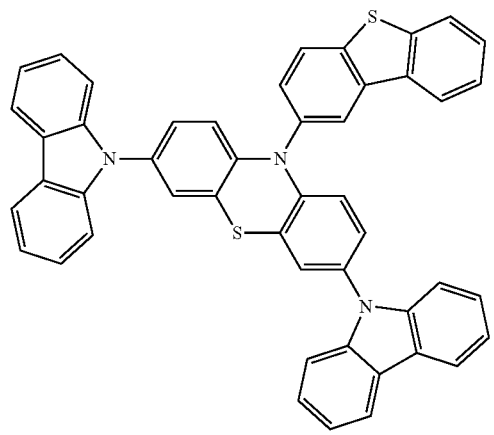
54
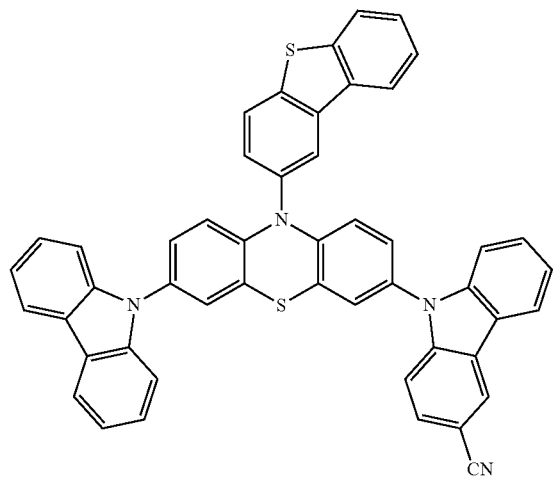
55

56
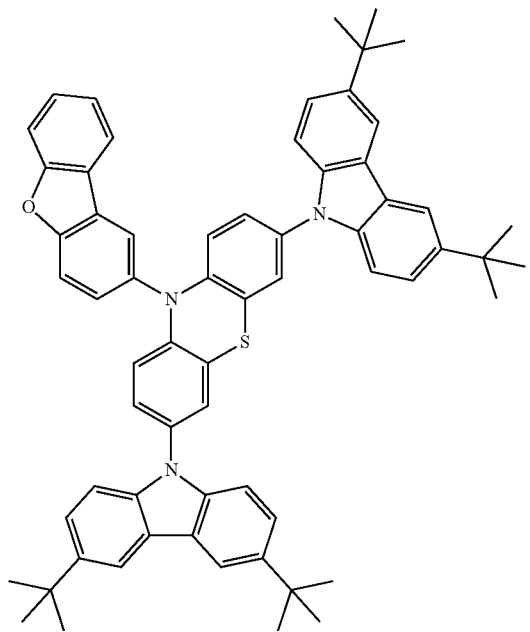
57
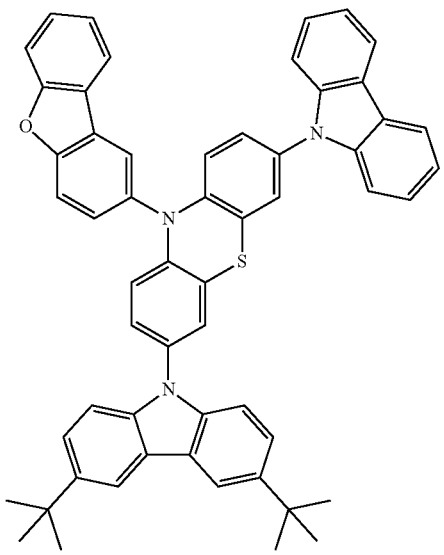
58
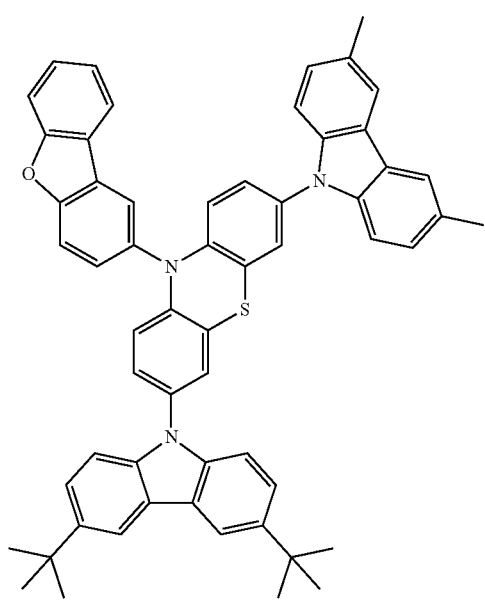
59
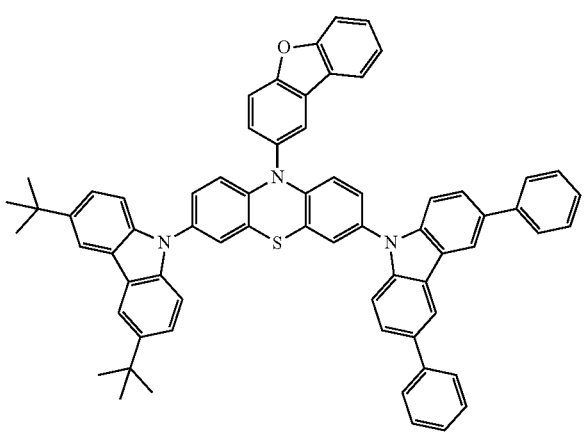

60
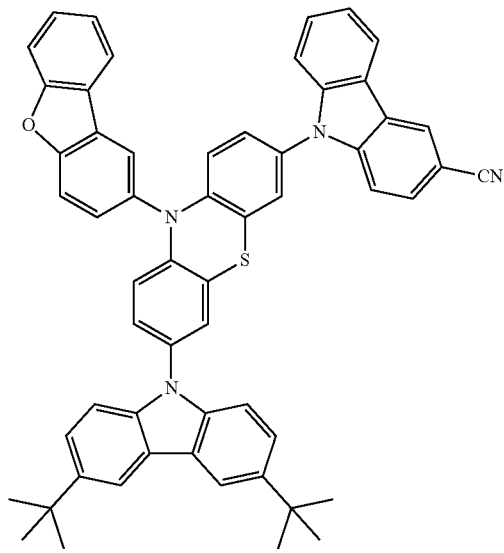
61
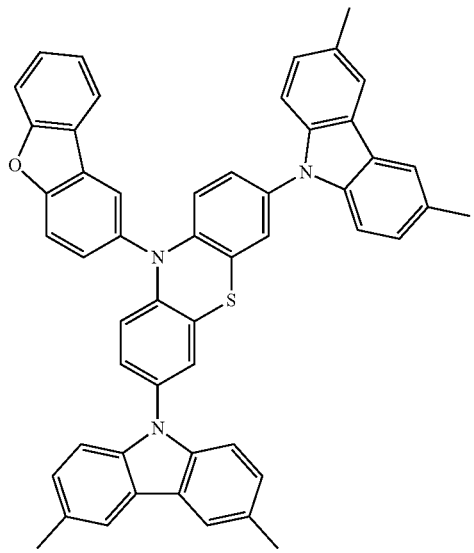
62
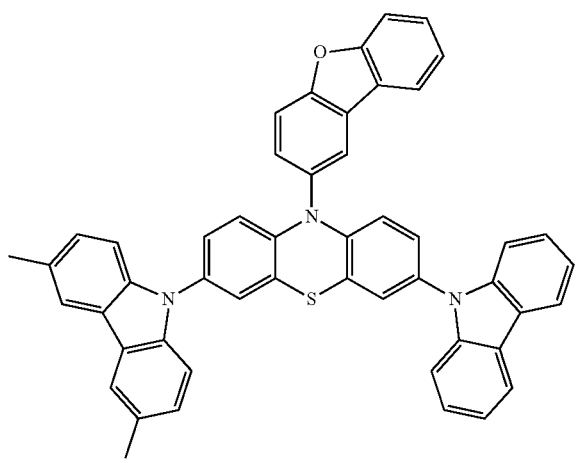
63
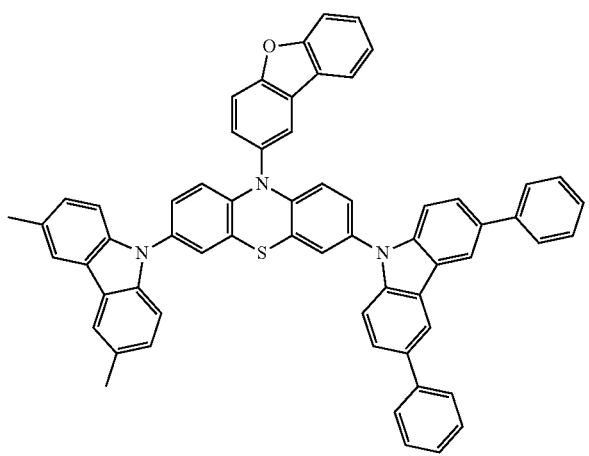
64
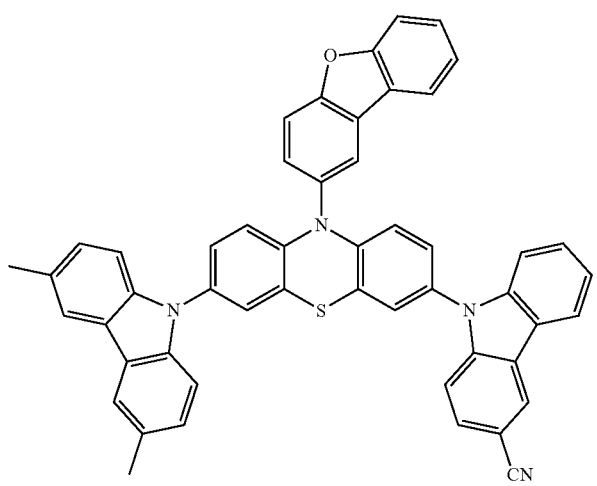
65
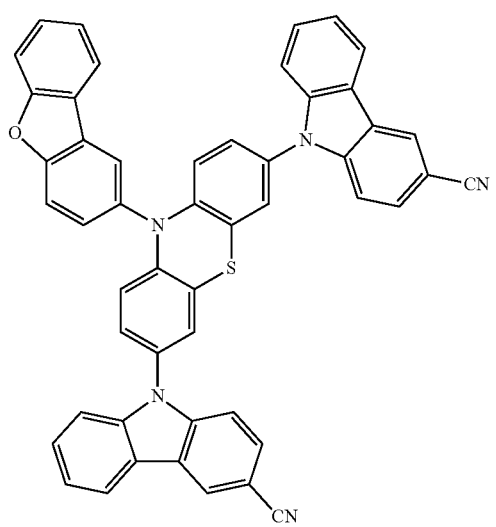

-continued
66
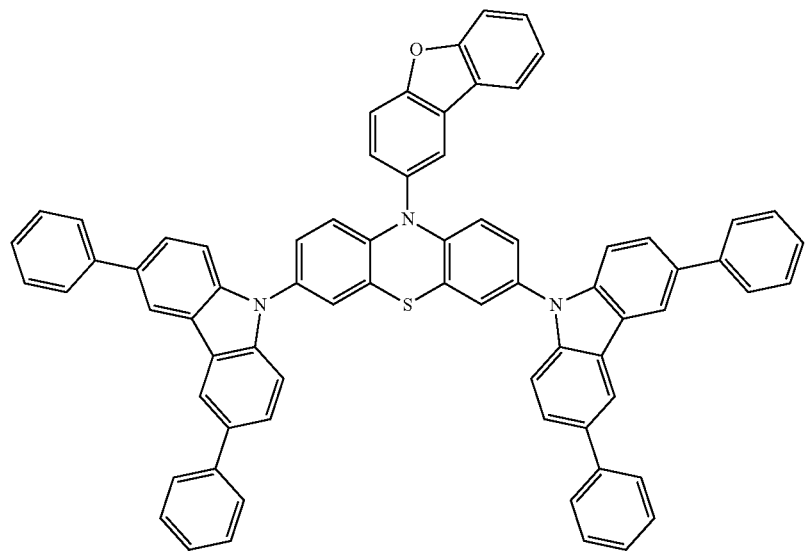
67
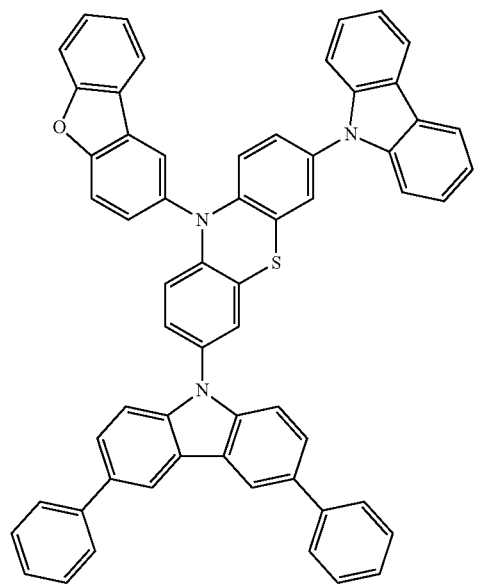
68
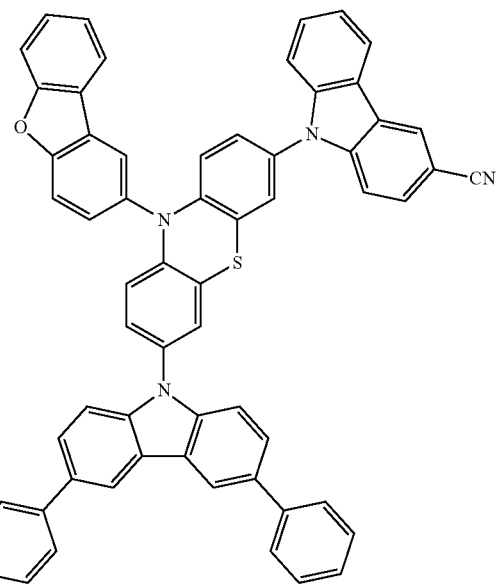
69
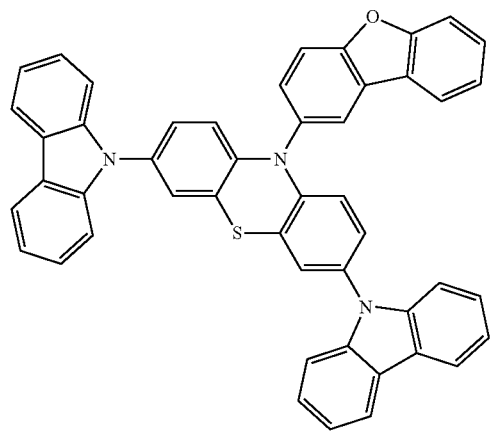
70
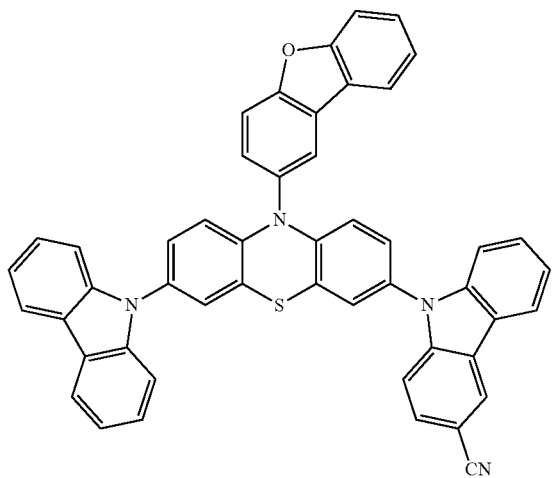

-continued
71
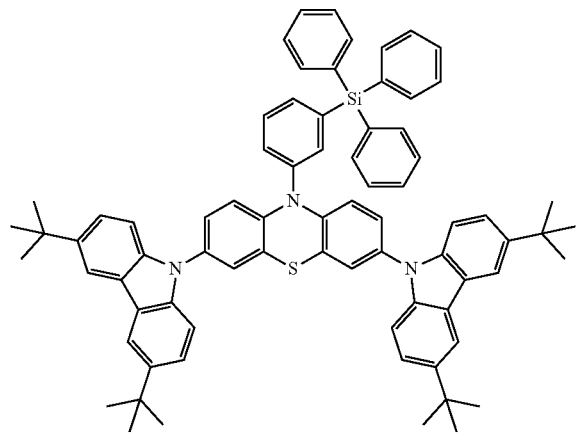
72
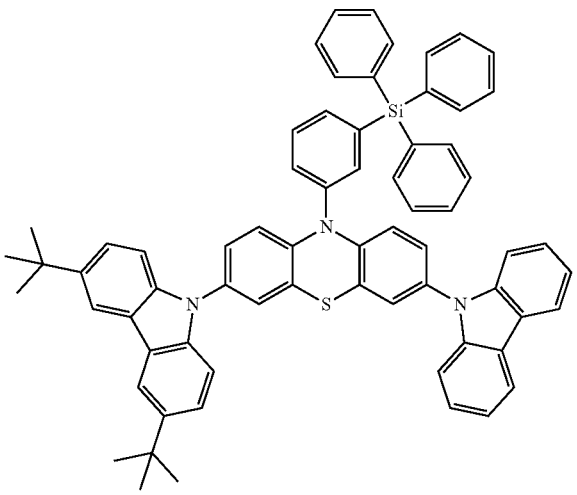
73
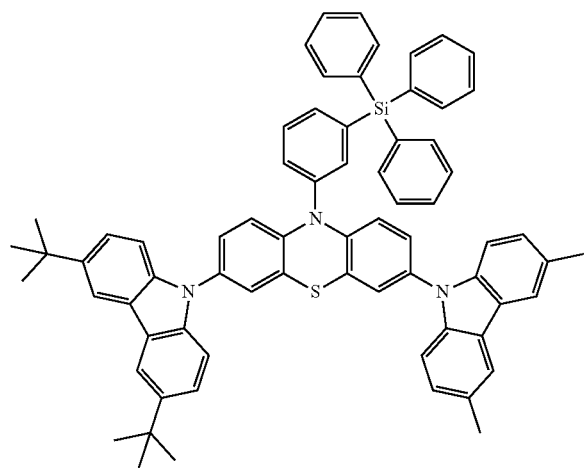
74
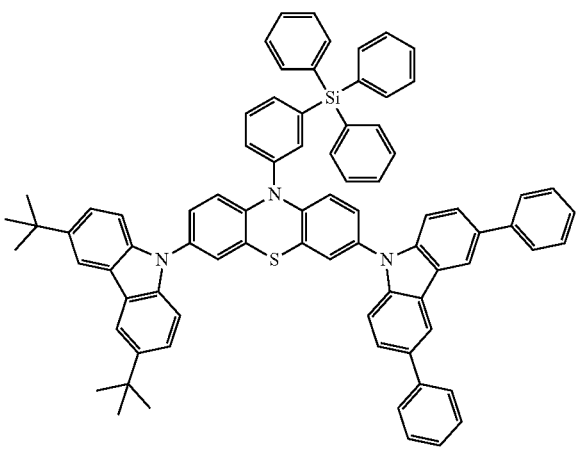
75
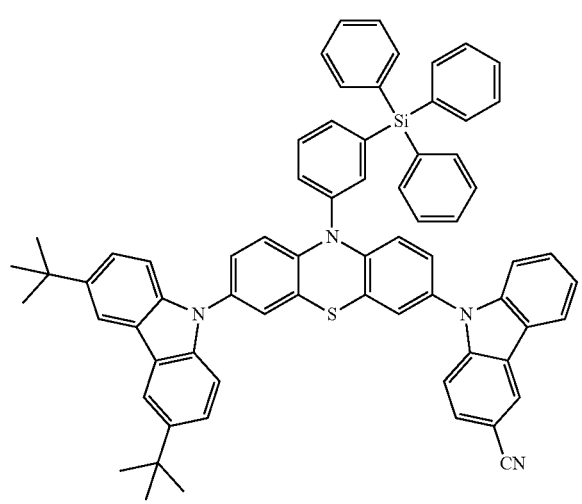
76
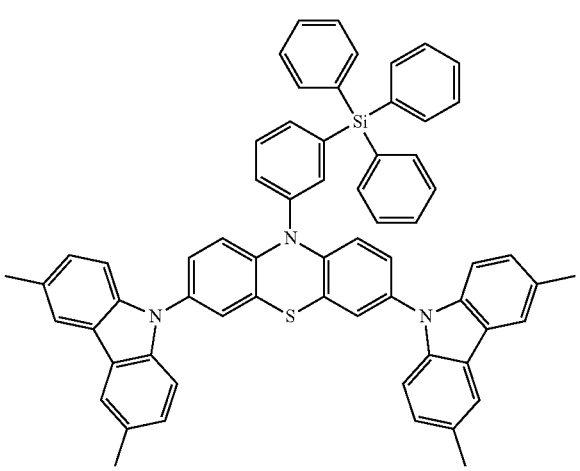

-continued
77
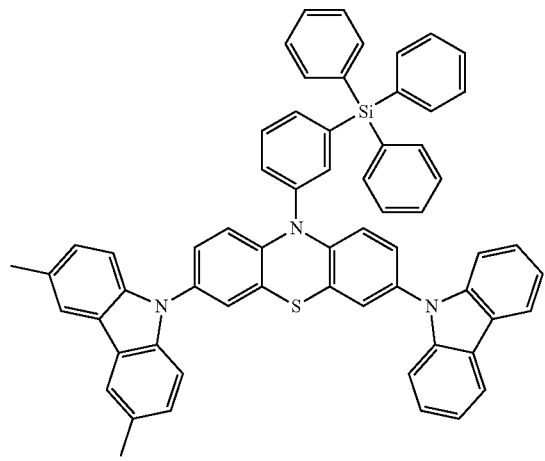
78
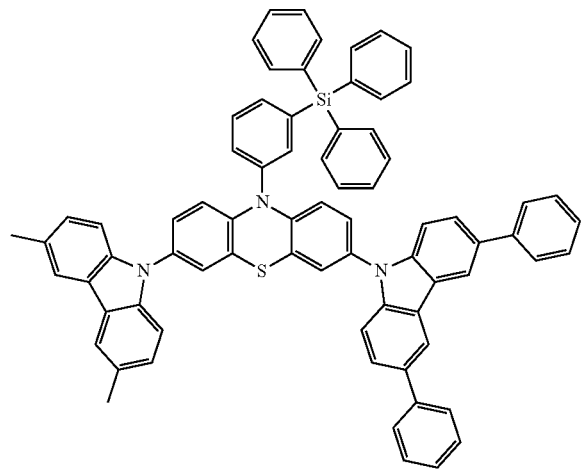
79
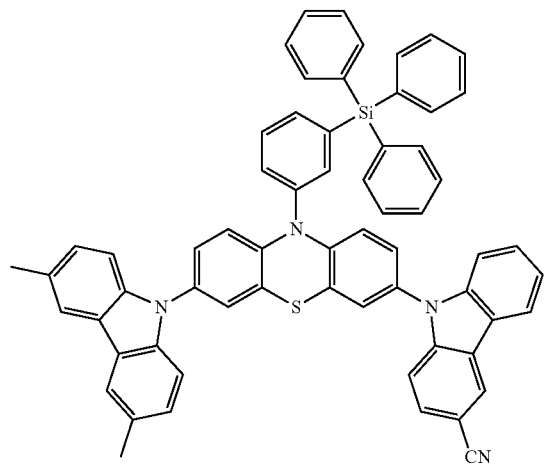
80
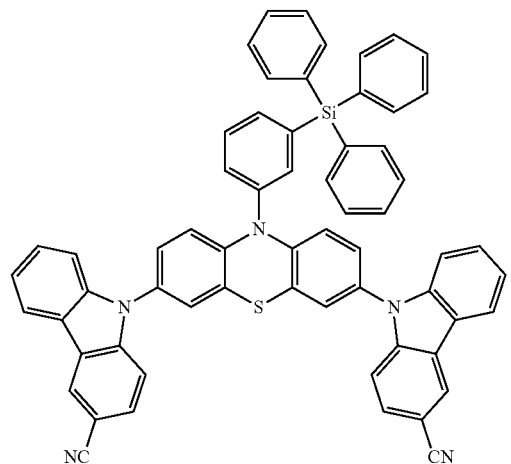
81
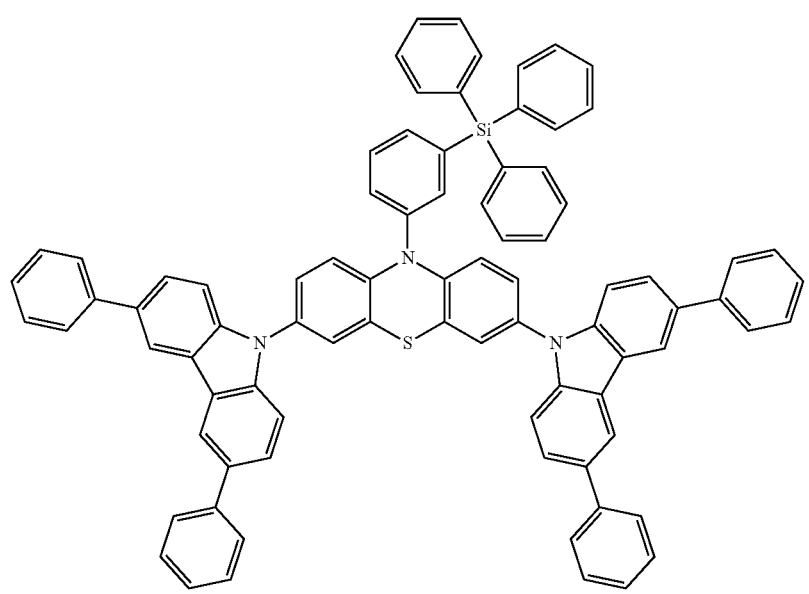

-continued
82
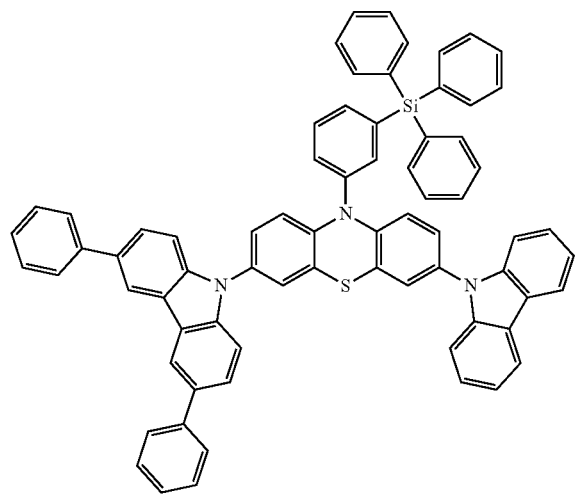
83
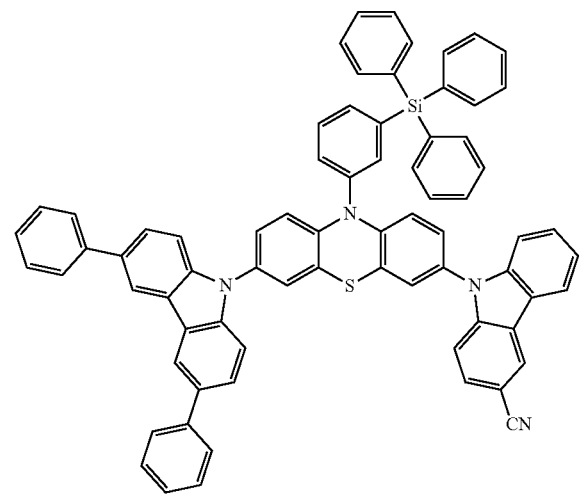
84
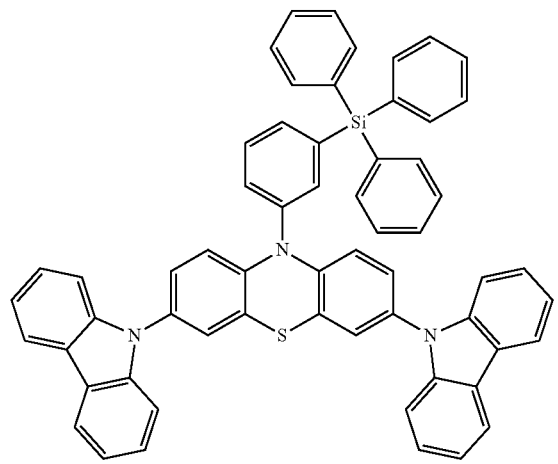
85
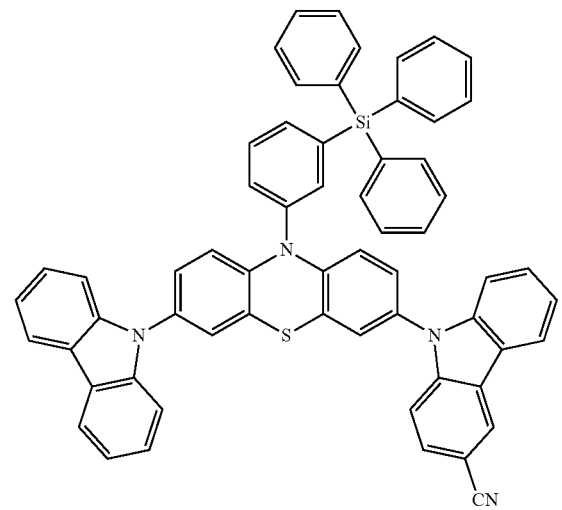
86
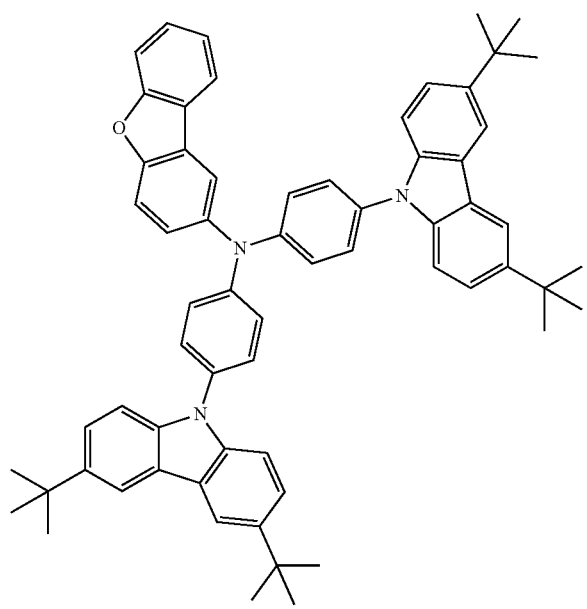
87
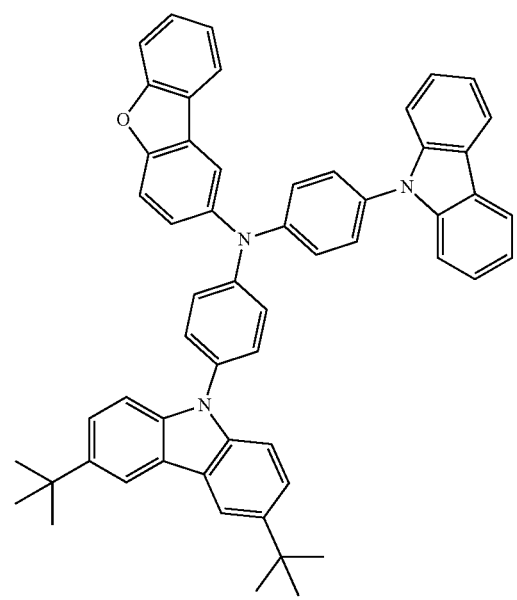

88
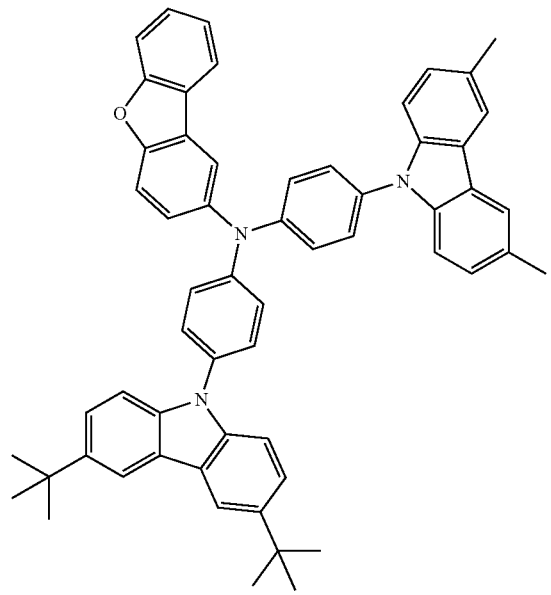
89
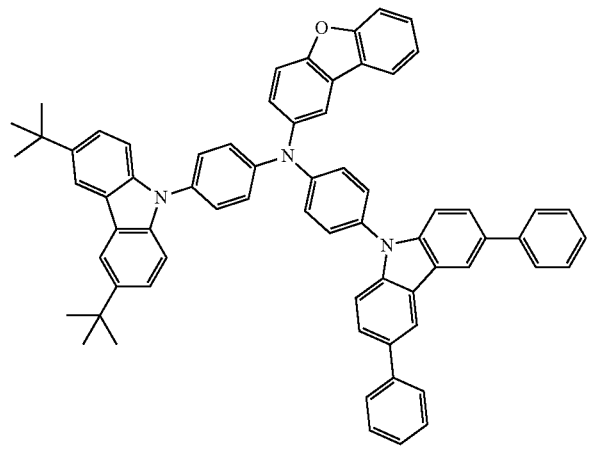
90
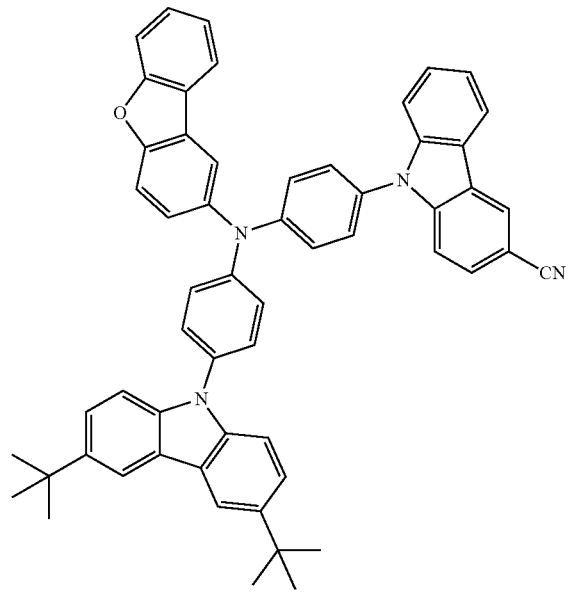
91
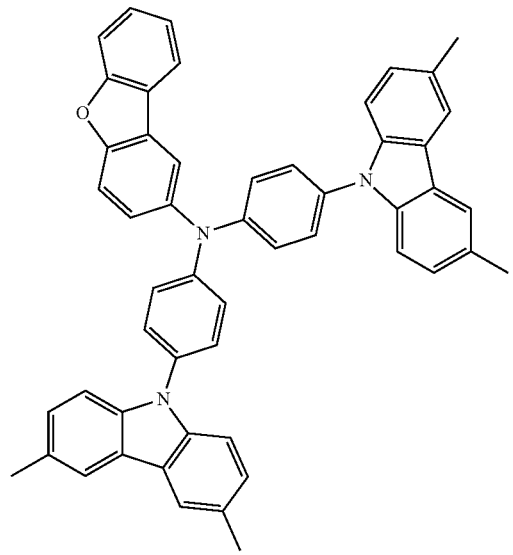

-continued
92
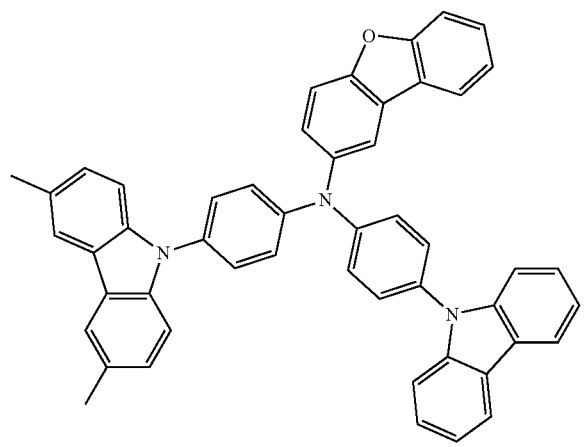
93
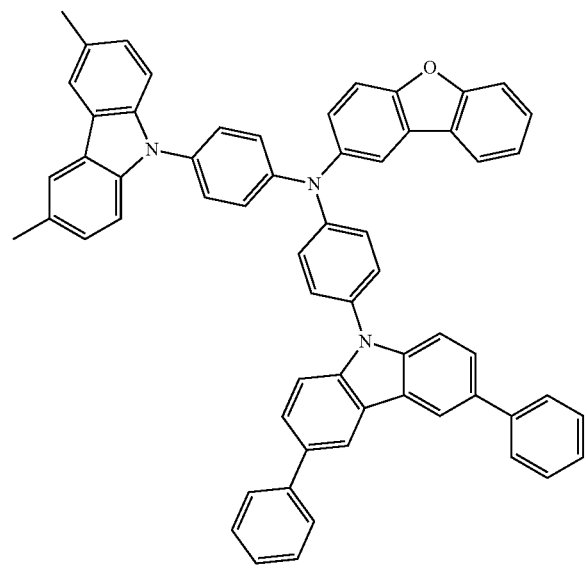
94
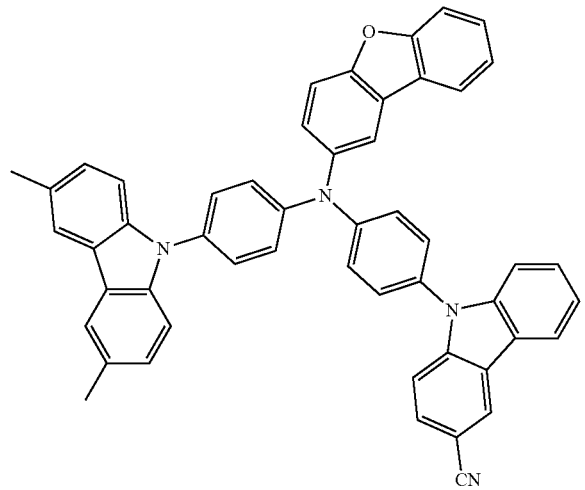
95
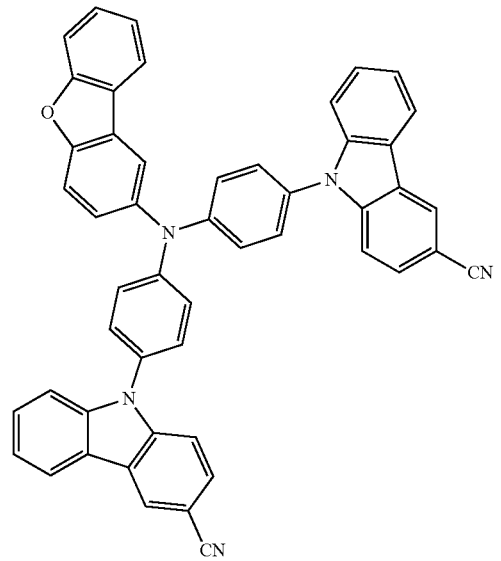

96
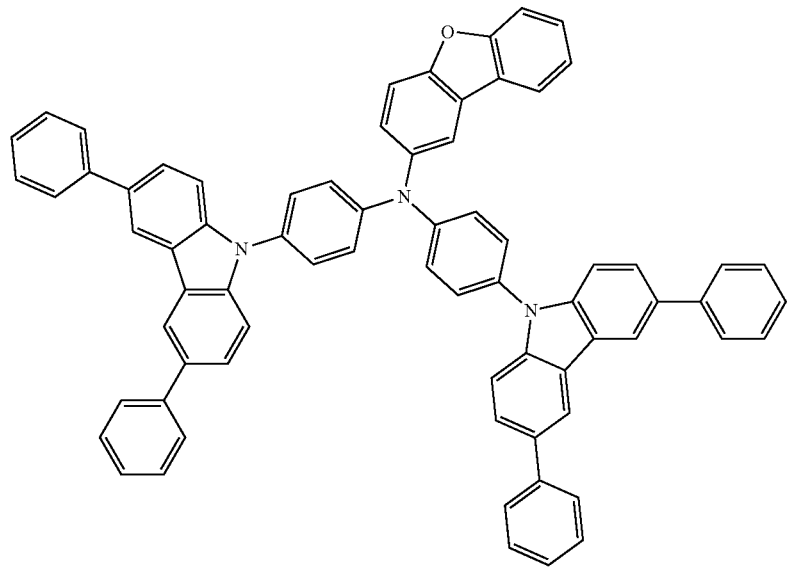
97
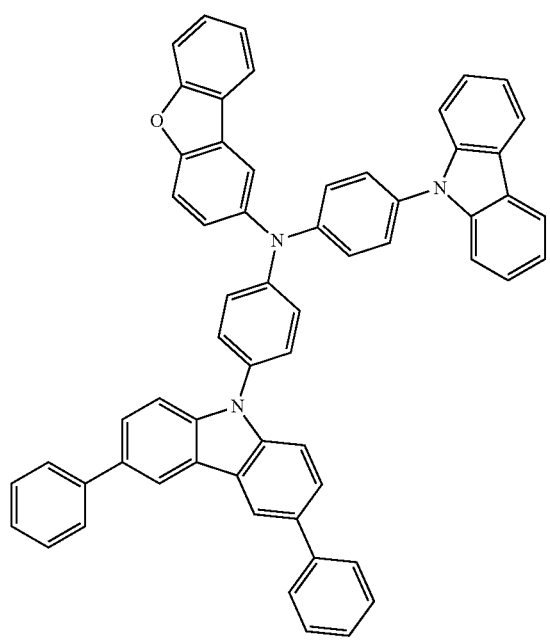
98
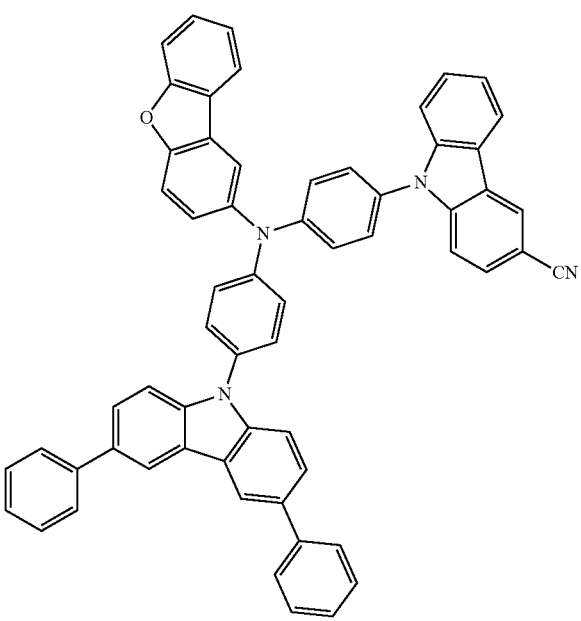

127                                      128
-continued
99
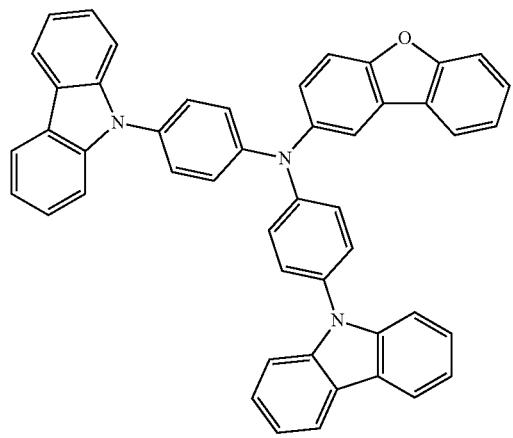
100
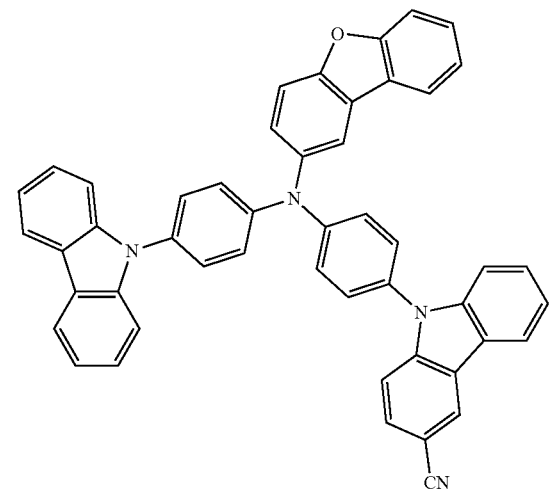
101
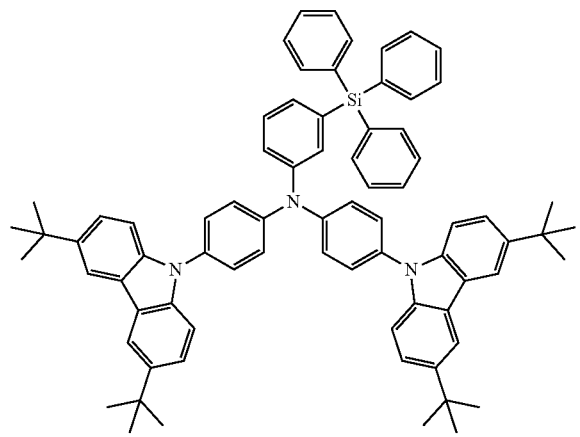
102
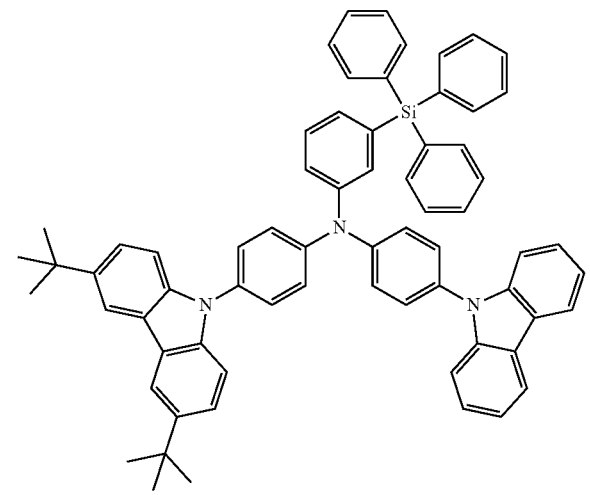
103
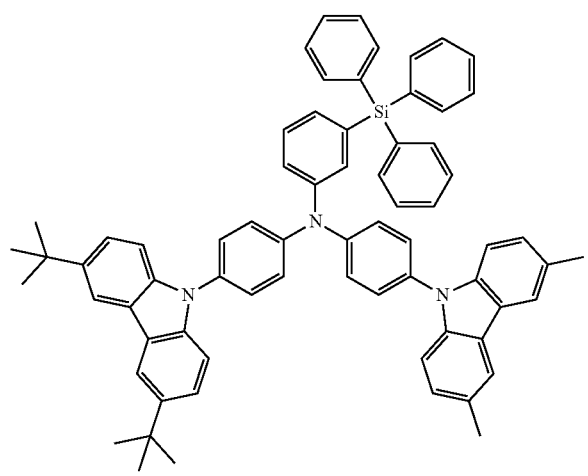
104
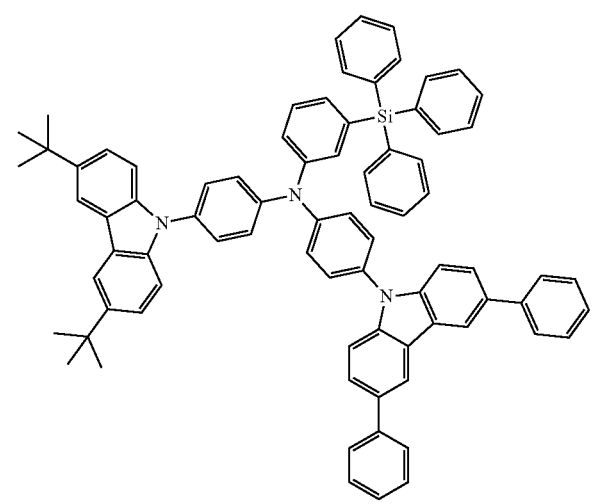

-continued
105
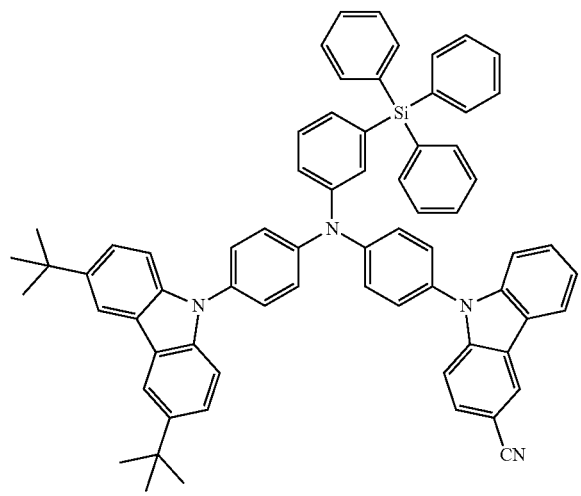
106
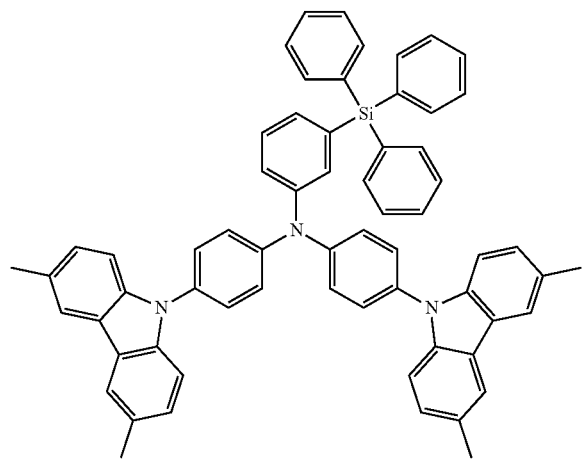
107
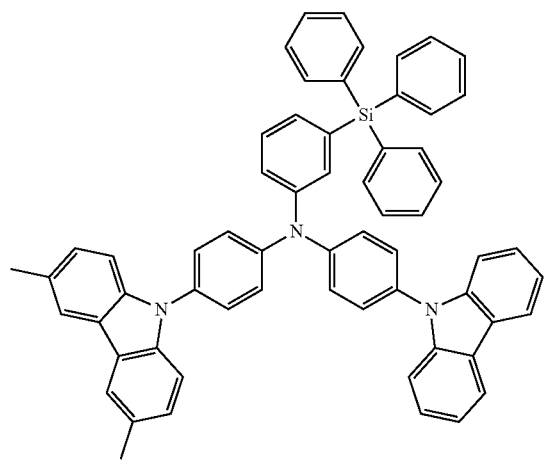
108
109
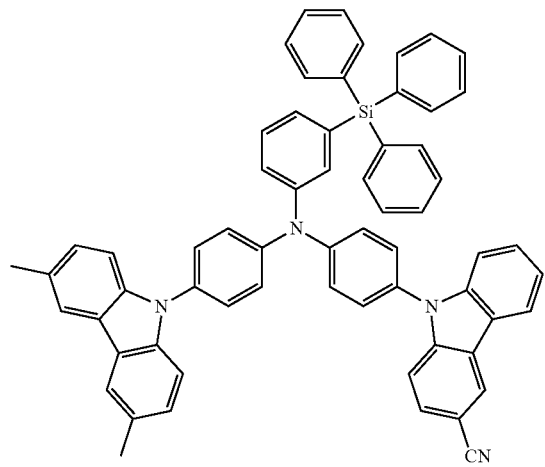
110
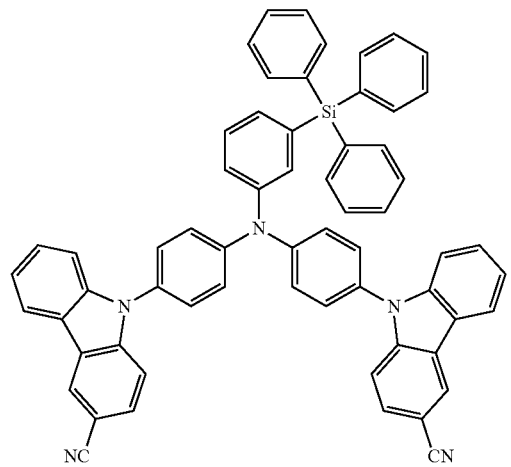

111
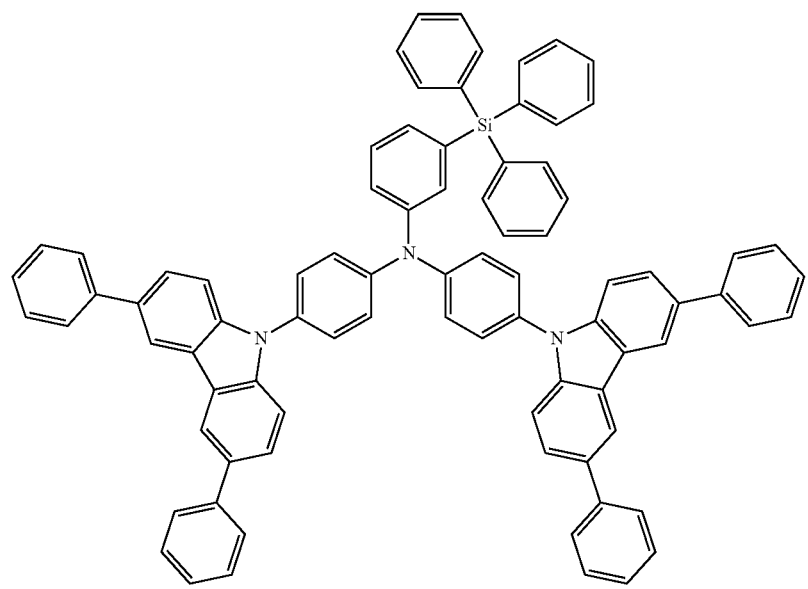
112 113
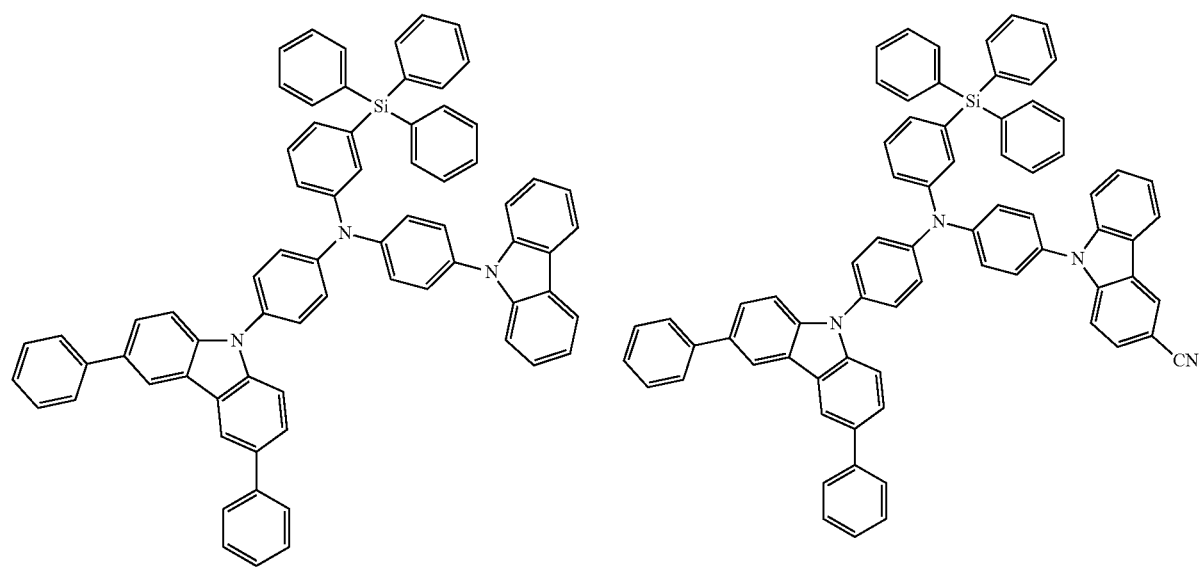

114
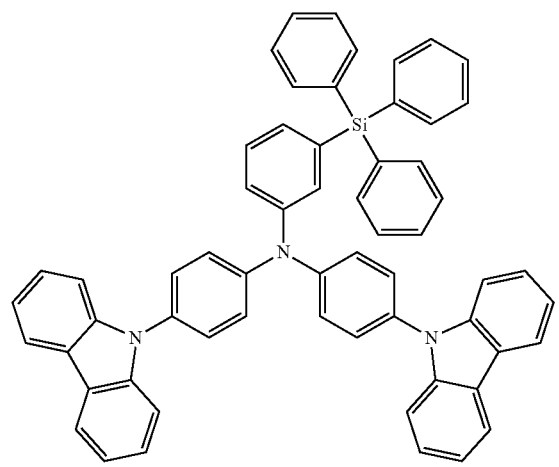
115
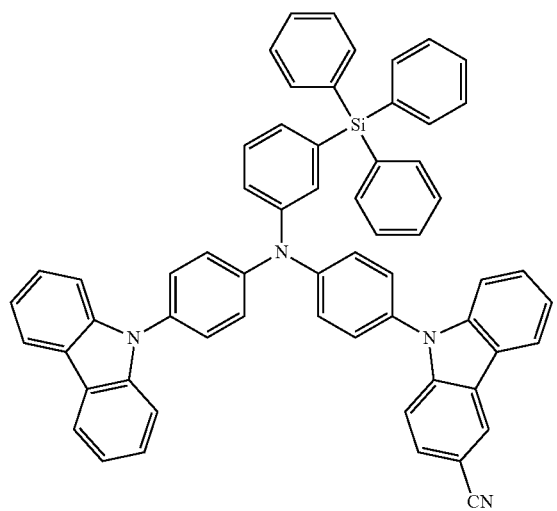
116
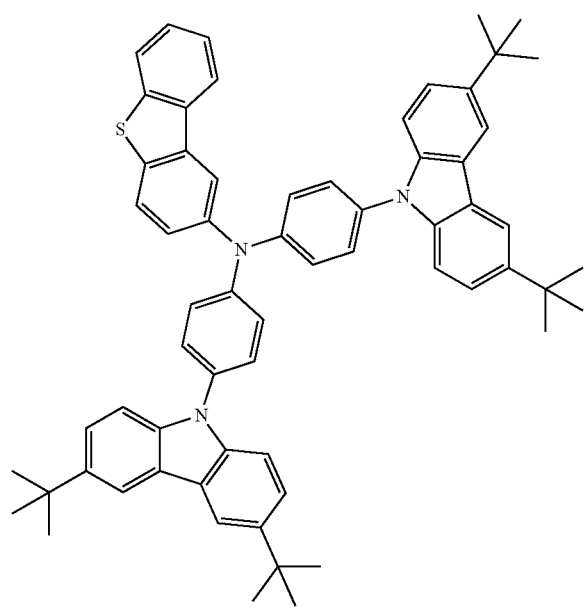
117
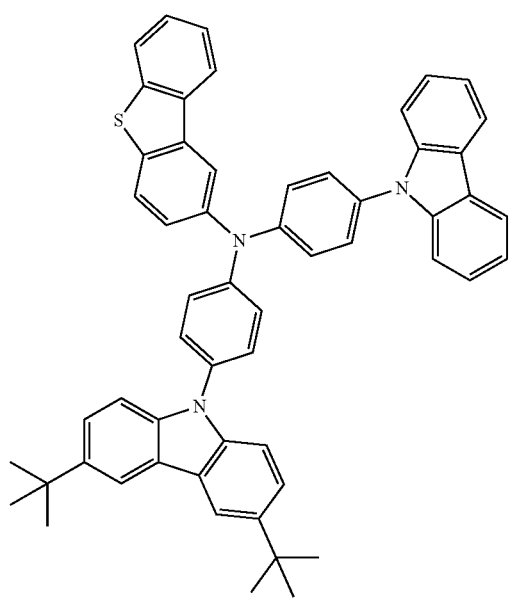

118
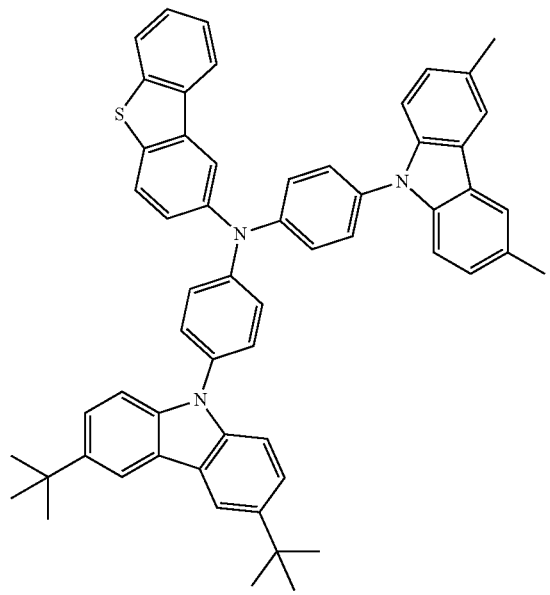
119
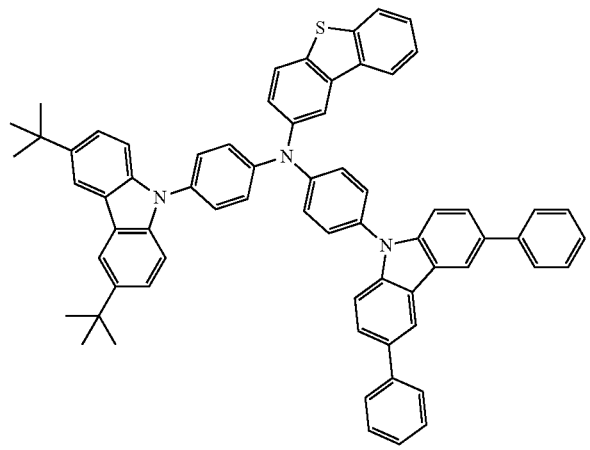
120
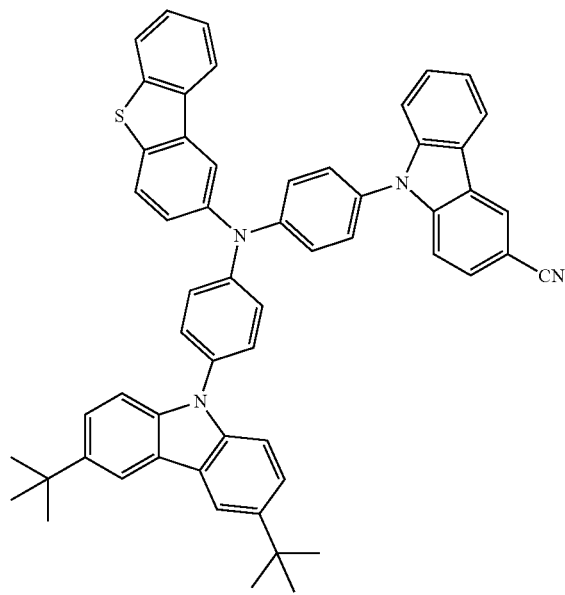
121
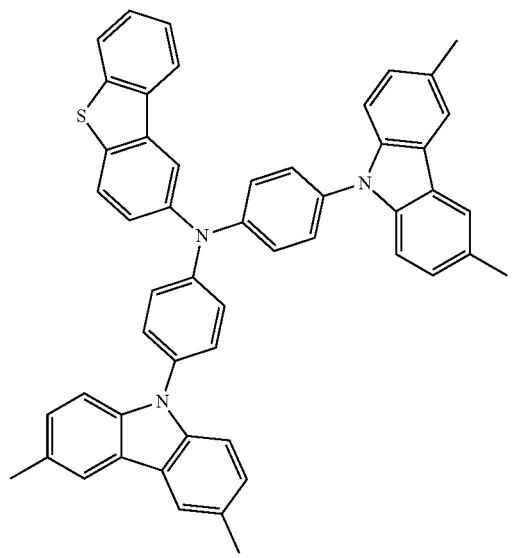

-continued
122
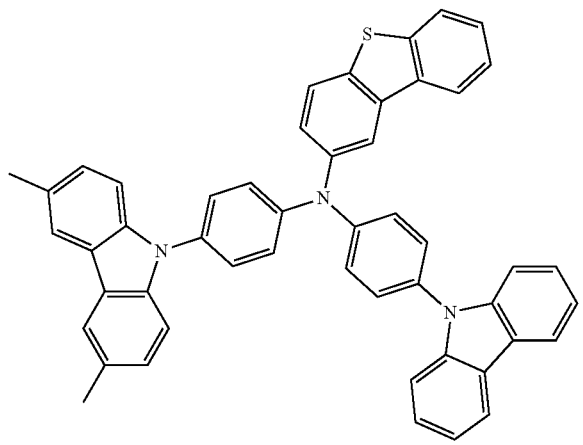
123
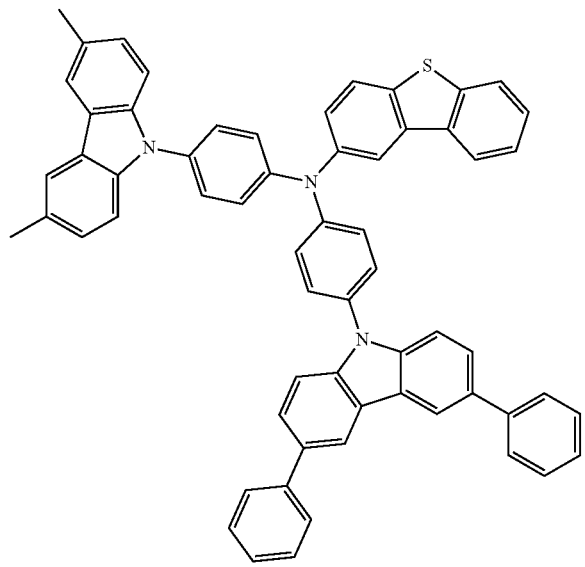
124
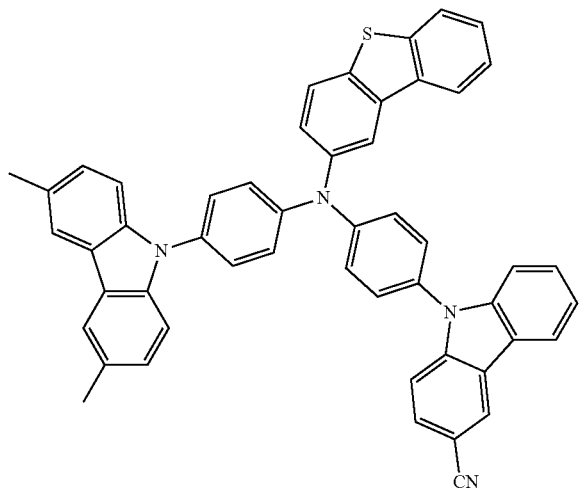
125
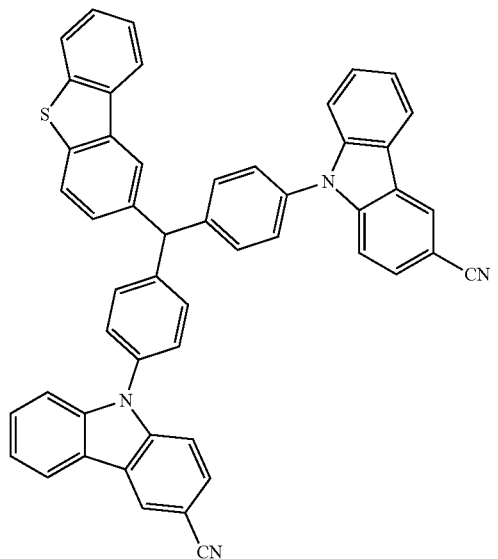

-continued
126
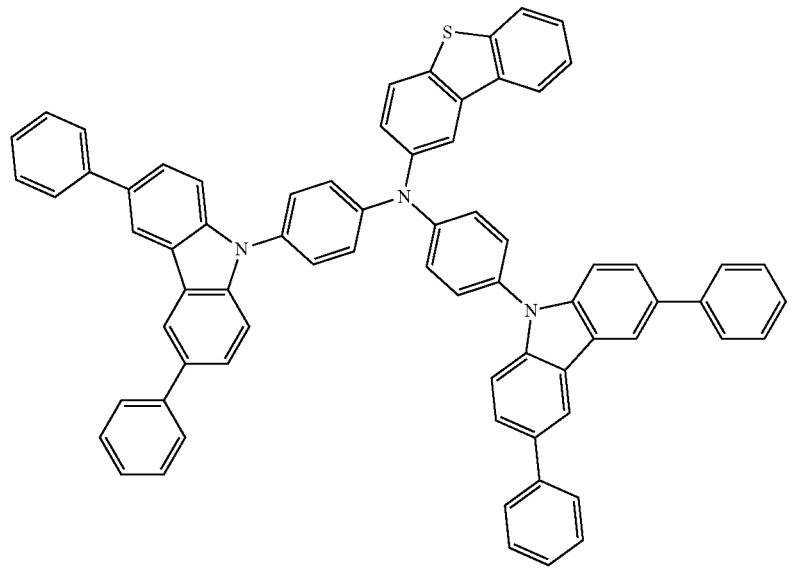
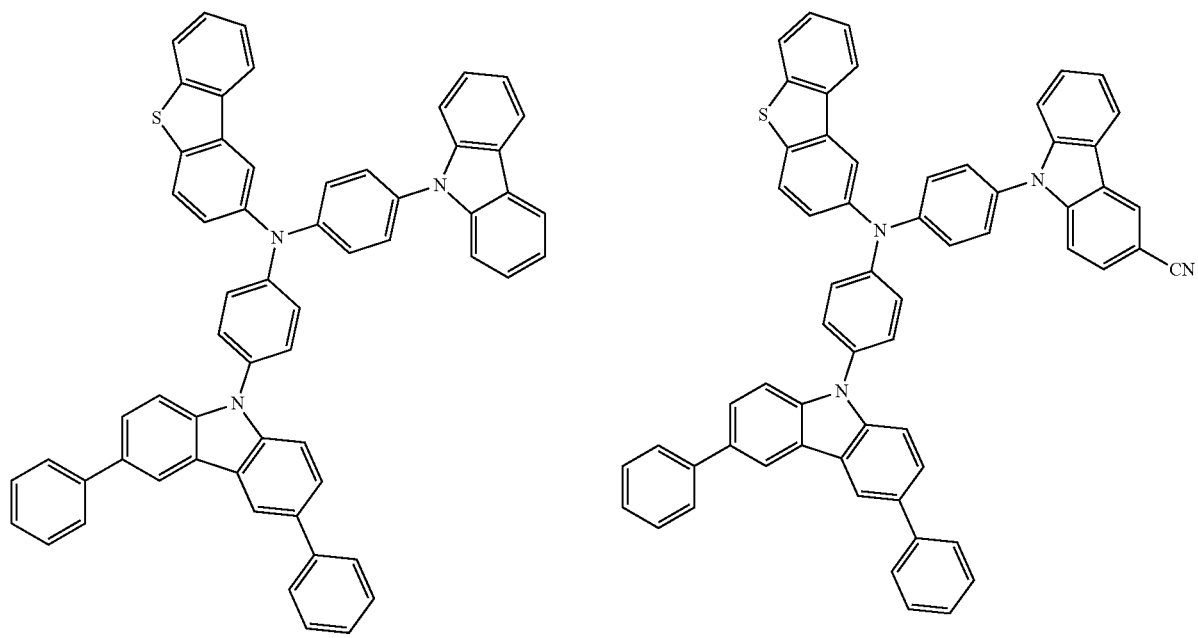

-continued
129
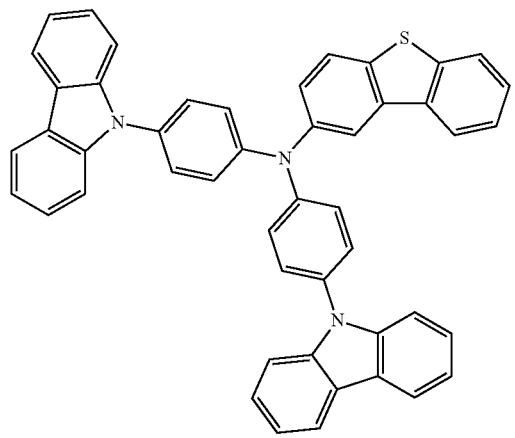
130
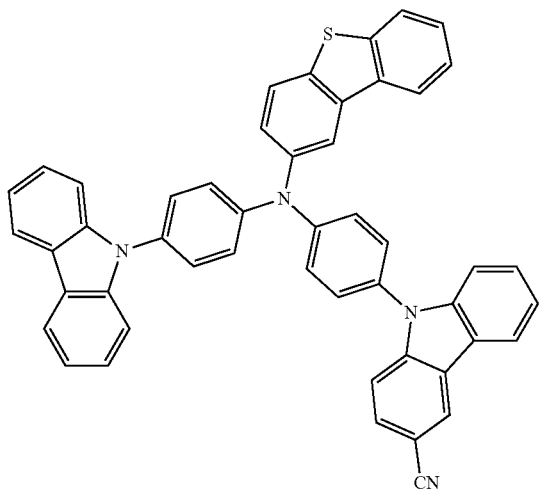
131
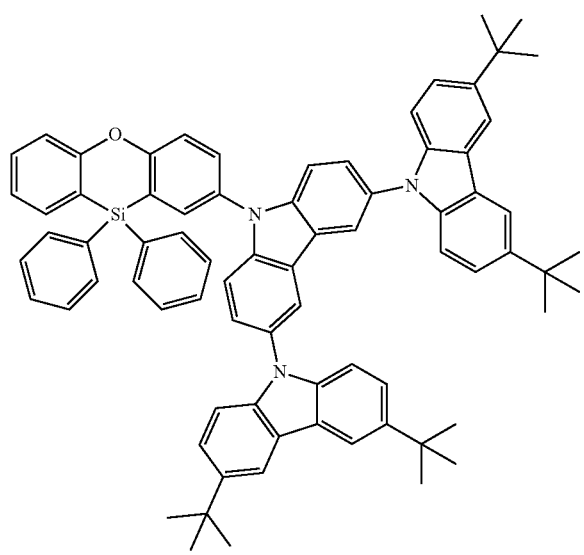
132
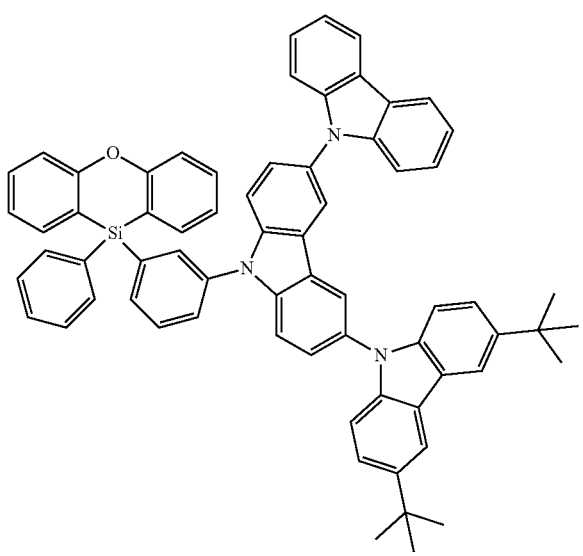
133
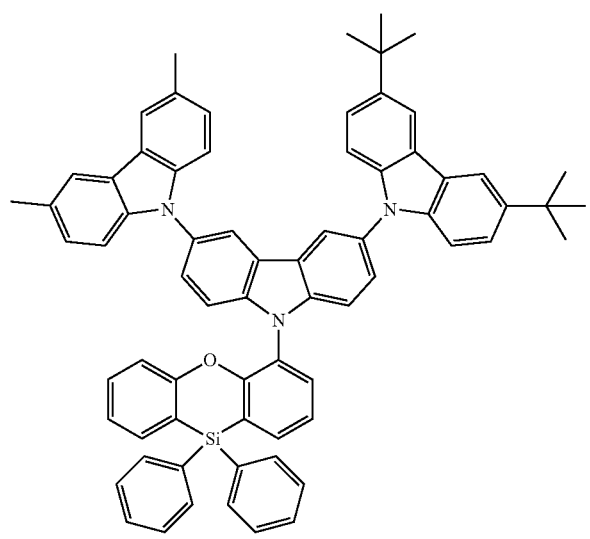
134
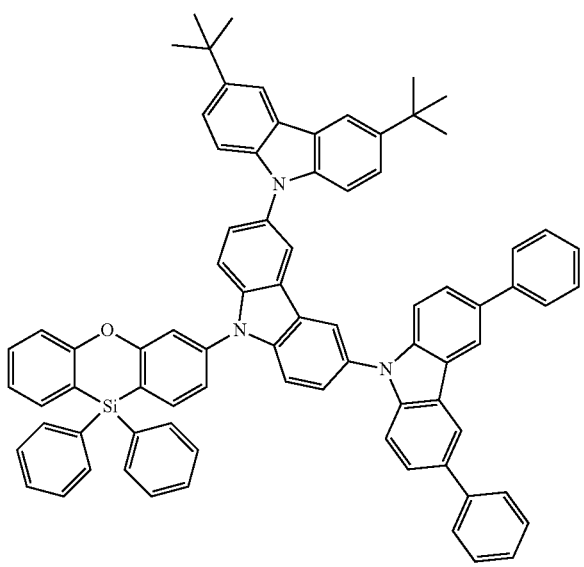

-continued
135
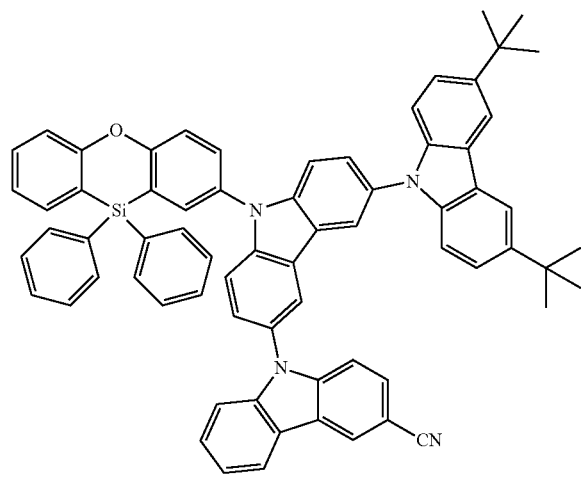
136
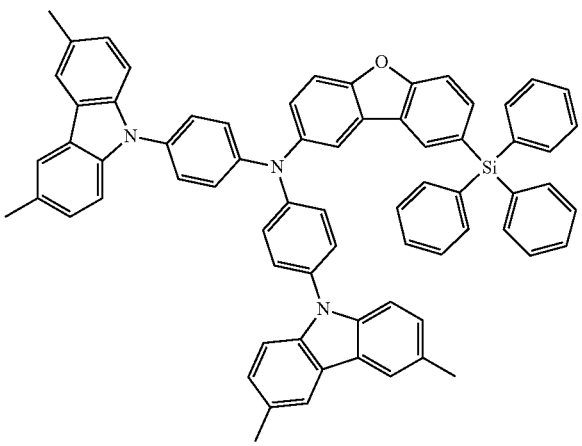
137
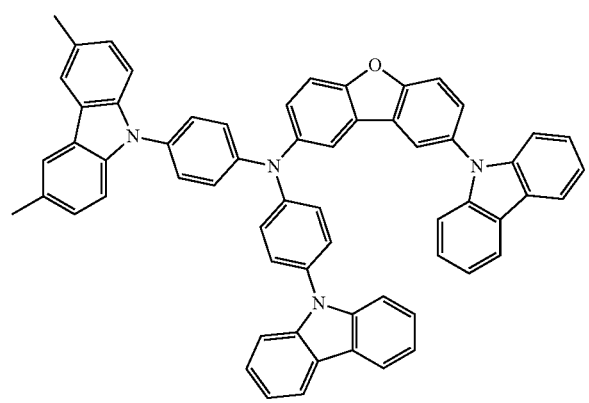
138
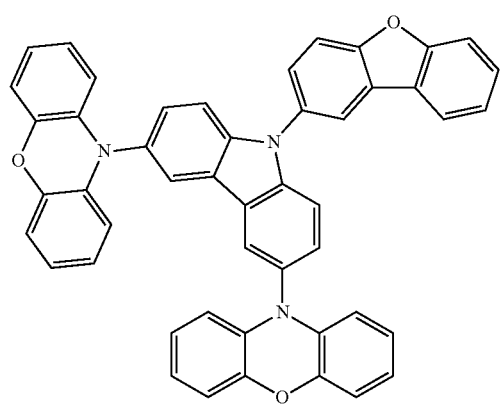
139
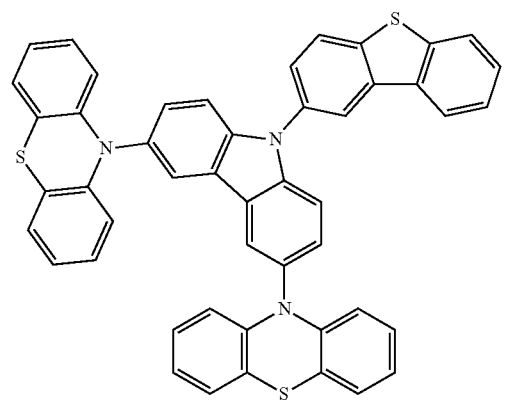
140
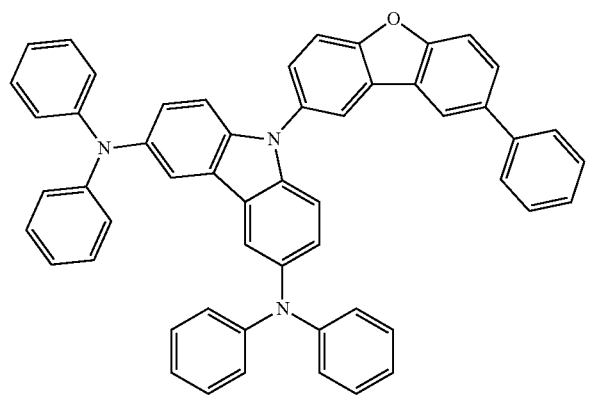

141
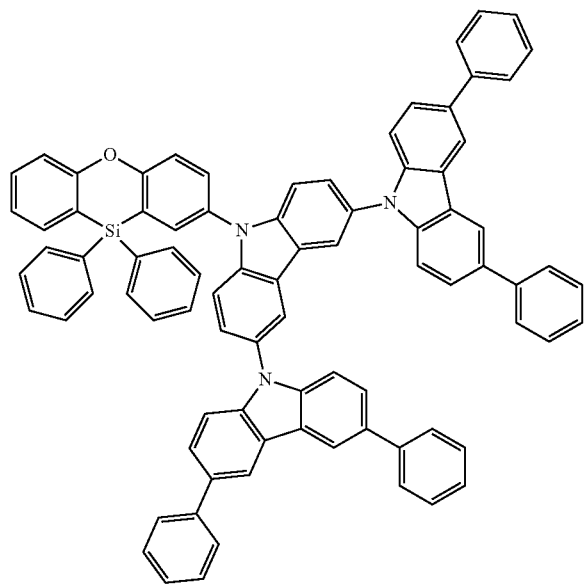
142
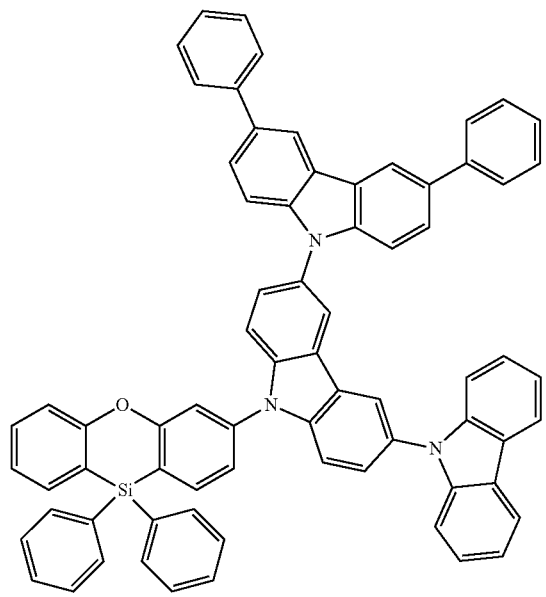
143
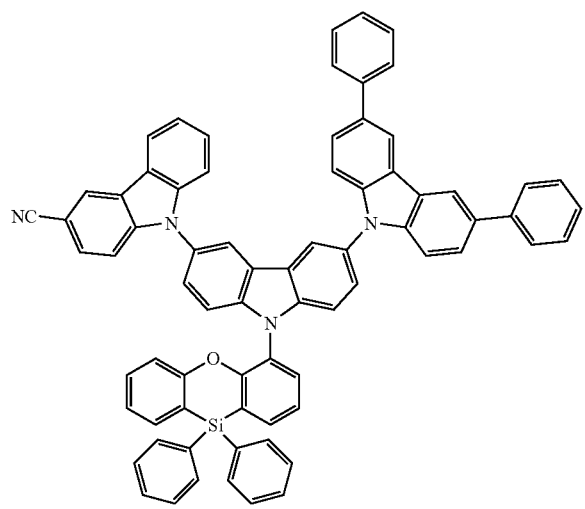
144
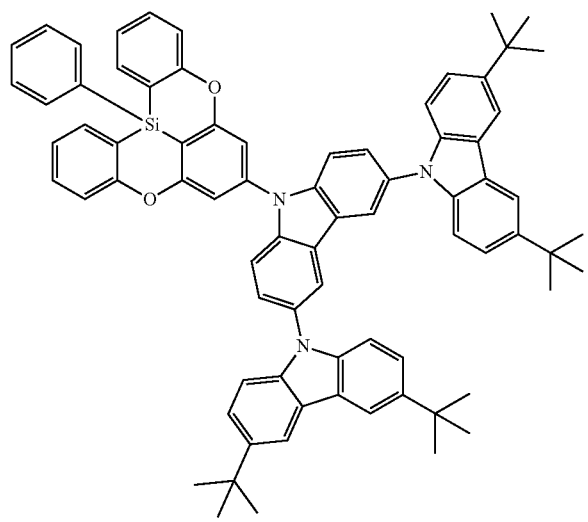
145
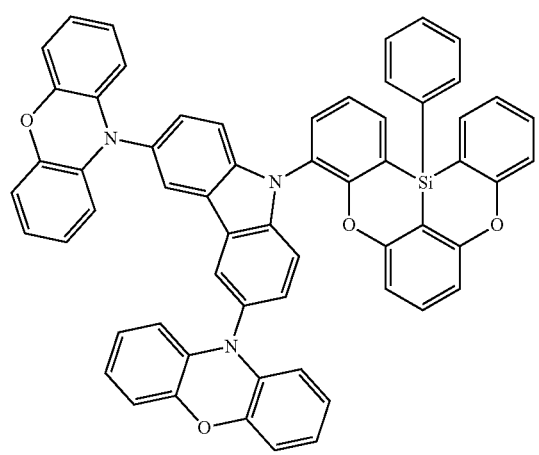

-continued
146
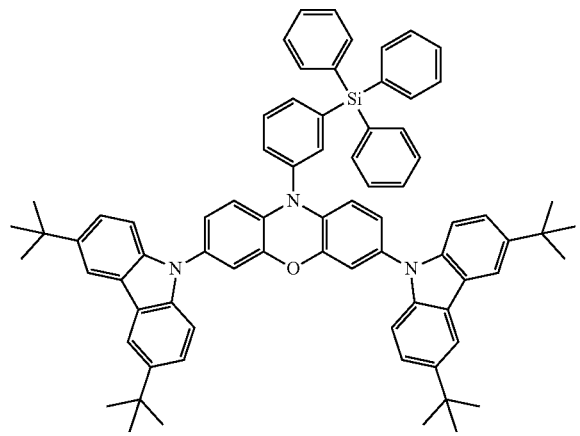
147
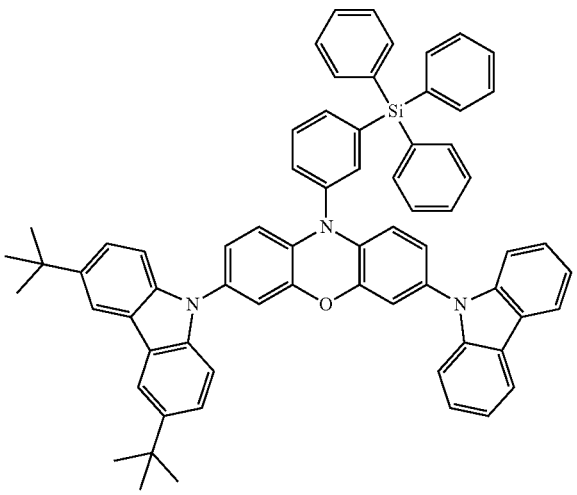
148
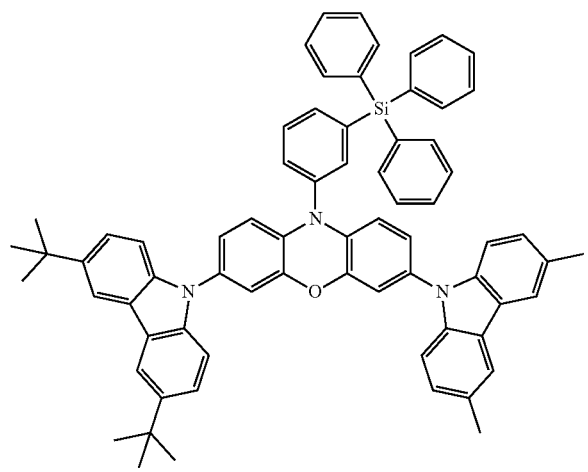
149
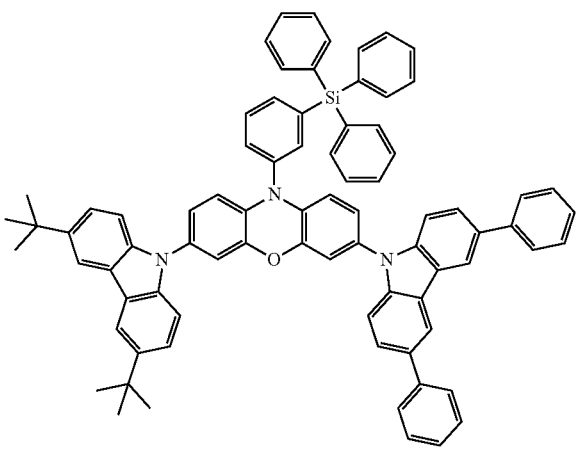
150
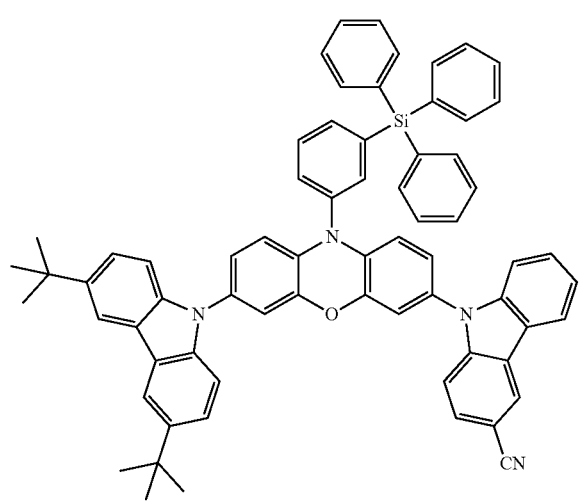
151
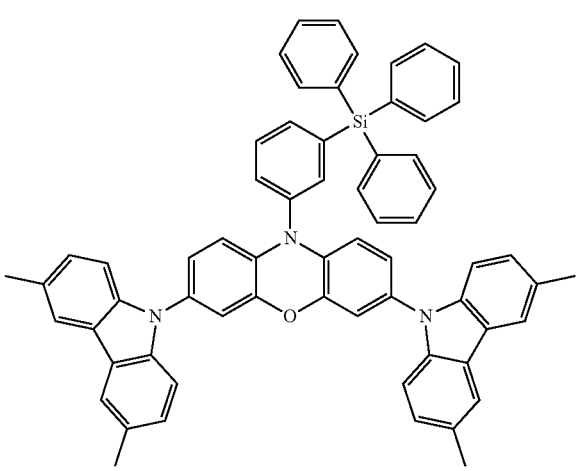

-continued
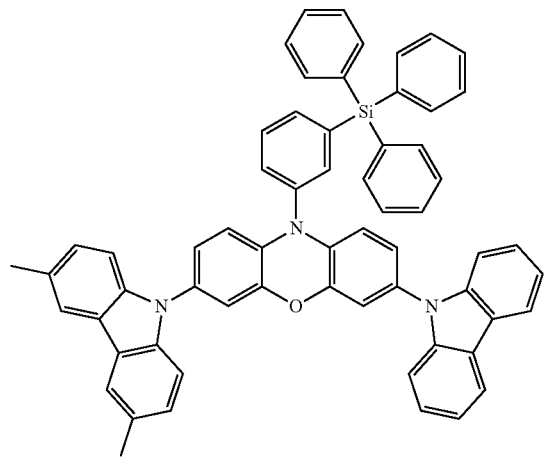
152
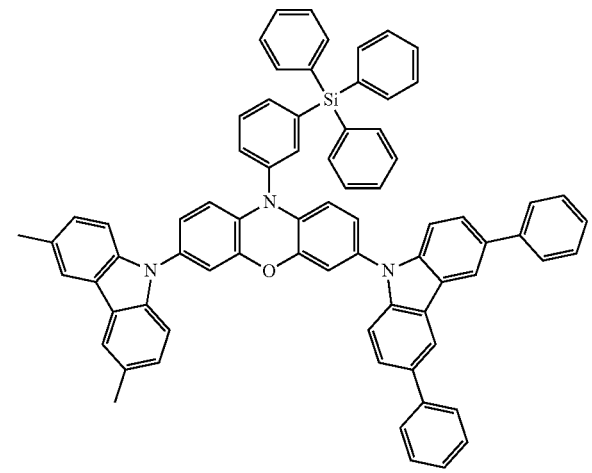
153
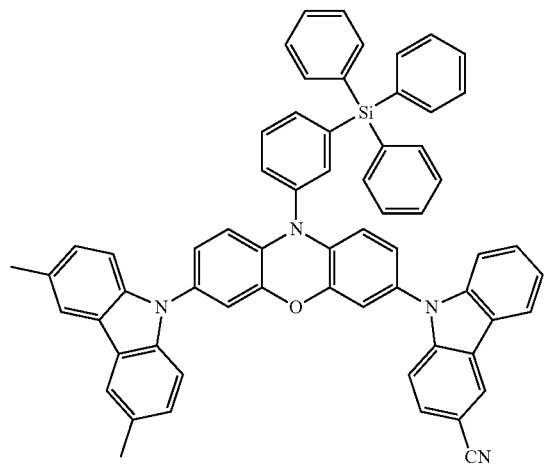
154
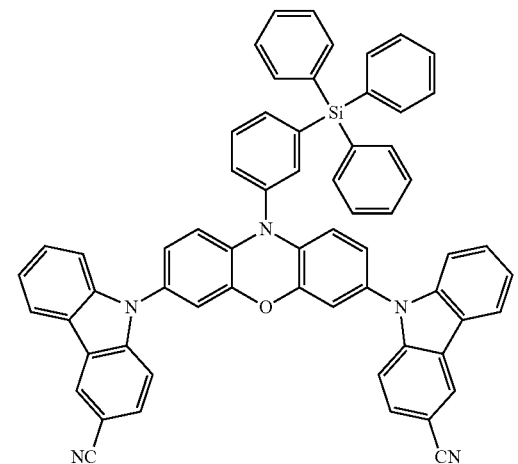
155
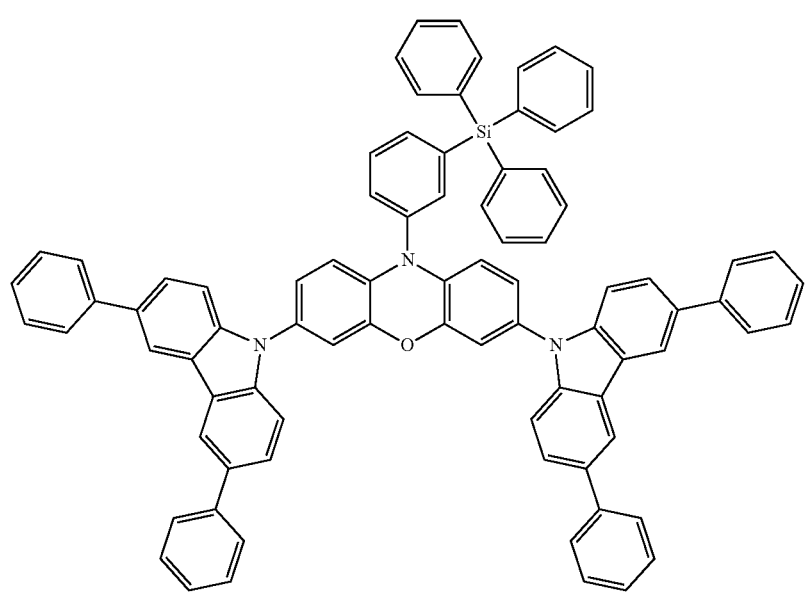
156

157

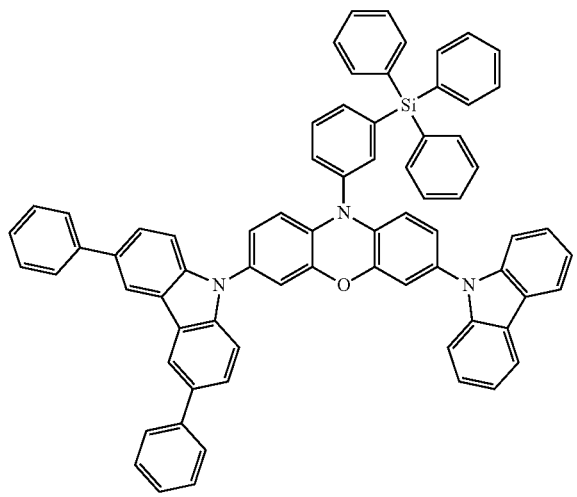

158

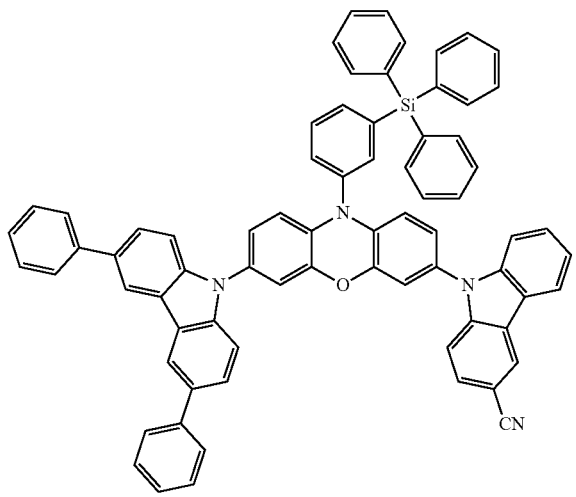

159

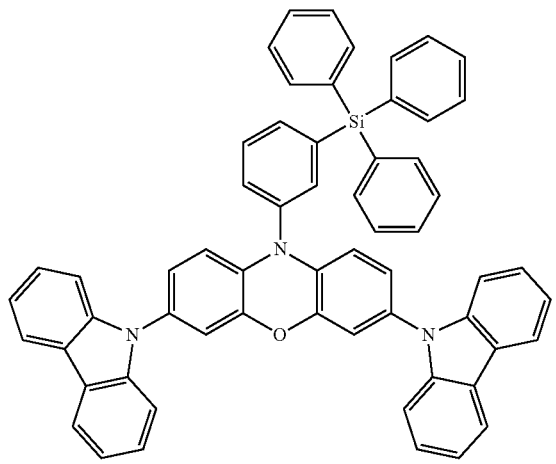

160

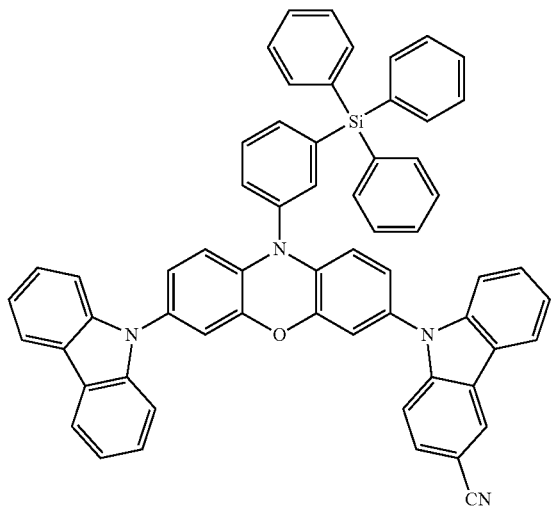

The first electrode EL1 may have conductivity. The first electrode EL1 may be formed of a metal alloy or a conductive compound. The first electrode EL1 may be an anode. In addition, the first electrode EL1 may be a pixel electrode. The first electrode EL1 may be a transmissive electrode, a transflective electrode, or a reflective electrode. When the first electrode EL1 is the transmissive electrode, the first electrode EL1 may include a transparent metal oxide, for example, indium tin oxide (ITO), indium zinc oxide (IZO), zinc oxide (ZnO), or indium tin zinc oxide (ITZO). When the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, or a compound or mixture (e.g., a mixture of Ag and Mg) thereof. Alternatively, the first electrode EL1 may have a multi-layered structure including a reflective layer or transflective layer and a transparent conductive layer formed of indium tin oxide (ITO), indium zinc oxide (IZO), zinc oxide (ZnO), or indium tin zinc oxide (ITZO). For example, the first electrode EL1 may have, but is not limited to, a three-layer structure of ITO/Ag/ITO. The first electrode EL1 may have a thickness from about 1,000 Å to about 10,000 Å, for example, from about 1,000 Å to about 3,000 Å.

The hole transport region HTR is disposed on the first electrode EL1. The hole transport region HTR may include at least one of a hole injection layer HIL, a hole transport layer HTL, a hole buffer layer, and/or an electron blocking layer EBL.

The hole transport region HTR may have a multilayer structure having a single layer formed of a single material, a single layer formed of materials different from each other, or a plurality of layers formed of materials different from each other.

For example, the hole transport region HTR may have a single layer structure of a hole injection layer HIL or a hole transport layer HTL, or a single layer structure formed of a hole injection material and a hole transport material. In addition, the hole transport region HTR has a single layer structure formed of a plurality of materials different from each other, or a structure of a hole injection layer HIL/a hole transport layer HTL, a hole injection layer HIL/a hole transport layer HTL/a hole buffer layer, a hole injection layer HIL/a hole buffer layer, a hole transport layer HTL/a hole buffer layer, or a hole injection layer HIL/a hole transport layer HTL/an electron blocking layer EBL, which are sequentially laminated from the first electrode EL1, but embodiments are not limited thereto.

The hole transport region HTR may be formed by utilizing various suitable methods such as a vacuum deposition method, a spin coating method, a casting method, a Langmuir-Blodgett (LB) method, an inkjet printing method, a laser printing method, and/or a laser induced thermal imaging (LITI) method.

The hole injection layer HIL may include, for example, a phthalocyanine compound (such as copper phthalocyanine), N,N'-diphenyl-N,N'-bis-[4-(phenyl-m-tolyl-amino)-phenyl]-biphenyl-4,4'-diamine (DNTPD), 4,4',4'-tris(3-methylphenylphenylamino)triphenylamine (m-MTDATA), 4,4',4'-tris(N,N-diphenylamino)triphenylamine (TDATA), 4,4',4'-tris{N,-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-I-yl)-N,N'-diphenyl-benzidine (NPB), triphenylamine-containing polyetherketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), and/or the like.

The hole transport layer HTL may further include, for example, carbazole derivatives (such as N-phenyl carbazole and/or polyvinyl carbazole), fluorene derivatives, N,N'-bis (3-methylphenyl)-N,N'-diphenyl-[1,1-biphenyl]-4,4'-diamine (TPD), triphenylamine derivatives (such as 4,4',4'-tris(N-carbazolyl)triphenylamine (TCTA)), N,N'-di(naphthalene-l-yl)-N,N'-diphenyl-benzidine (NPB), 4,4'-cyclohexylidenebis[N,N-bis(4-methylphenyl]benzenamine] (TAPC), 4,4'-bis[N,N'-(3-tolyl)amino]-3,3'-dimethylbiphenyl (HMTPD), 1,3-Bis(N-carbazolyl)benzene (mCP), and/or the like.

The hole transport region HTR may have a thickness from about 100 Å to about 10,000 Å, for example, from about 100 Å to about 5,000 Å. The hole injection region HIL may have a thickness, for example, from about 30 Å to about 1,000 Å, the hole transport layer HTL may have a thickness from about 30 Å to about 1,000 Å. For example, the electron blocking layer EBL may have a thickness from about 10 Å to about 1,000 Å. When the thicknesses of the hole transport region HTR, the hole injection layer HIL, the hole transport layer HTL, and the electron blocking layer EBL satisfy the above-described ranges, satisfactory hole transport characteristics may be achieved without a substantial increase in driving voltage.

The hole transport region HTR may further include a charge generating material in addition to the above-described materials to improve conductivity. The charge generating material may be uniformly or non-uniformly dispersed into the hole transport region HTR. The charge generating material may be, for example, a p-dopant. The p-dopant may be one selected from quinone derivatives, metal oxides, and cyano group-containing compounds, but the present disclosure is not limited thereto. For example, non-limiting examples of the p-dopant may include, quinone derivatives (such as tetracyanoquinodimethane (TCNQ) and 2,3,5,6-tetrafluoro-7,7,8,8-tetracyanoquinodimethane (F4-TCNQ)), and metal oxides (such as tungsten oxides and molybdenum oxides).

As described above, the hole transport region HTR may further include at least one of the hole buffer layer or the electron blocking layer EBL in addition to the hole injection layer HIL and the hole transport layer HTL. The hole buffer layer may compensate for a resonance distance according to the wavelength of light emitted from the emission layer EML to increase light emission efficiency. A material that can be contained in the hole transport region HTR may be utilized as a material that may be contained in the hole buffer layer. The electron blocking layer EBL is a layer playing a role in blocking the electrons injected from the electron transport region ETR to the hole transport region HTR.

The emission layer EML is disposed on the hole transport region HTR. The emission layer EML may have a thickness, for example, from about 100 Å to about 1,000 Å, or from about 100 Å to about 300 Å. The emission layer EML may have a single layer structure having a single layer formed of a single material, a single layer formed of materials different from each other, or a multiplayer structure having a plurality of layers formed of materials different from each other.

In the organic electroluminescence device 10 of an embodiment, the emission layer EML may include anthracene derivatives, pyrene derivatives, fluoranthene derivatives, chrysene derivatives, dehydrobenzanthracene derivatives, and/or triphenylene derivatives. In one embodiment, the emission layer EML may include anthracene derivatives and/or pyrene derivatives.

In the organic electroluminescence device 10 of an embodiment illustrated in FIGS. 1-3, the emission layer EML may include the polycyclic compound according to an embodiment of the present disclosure. The emission layer EML may include one, two, or more of the polycyclic compounds according to an embodiment of the present disclosure. The emission layer EML may further include suitable (e.g., known) materials other than the polycyclic compounds of an embodiment of the present disclosure.

The emission layer EML may include a host and a dopant, and the host may include polycyclic compounds. The polycyclic compound represented by Formula 1 may be included in the emission layer EML as a host. The polycyclic compound represented by Formula 1 may be included in the emission layer EML as a phosphorescent host. Alternatively, the polycyclic compound represented by Formula 1 may be included in the emission layer EML as a thermally activated delayed fluorescence host. However, embodiments are not limited thereto, and the polycyclic compound in an embodiment may be included in the emission layer EML as a dopant material.

The emission layer EML may include the polycyclic compound according to an embodiment of the present disclosure to emit blue light having a wavelength region of 420-485 nm.

The emission layer EML may further include, as host materials, general suitable materials (e.g., that are well known to the person skilled in the art). For example, the emission layer EML may include, as host materials, at least one selected from bis[2-(diphenylphosphino)phenyl] ether oxide (DPEPO), 4,4'-Bis(carbazol-9-yl)biphenyl (CBP), 1,3-bis(carbazol-9-yl)benzene (mCP), 2,8-Bis(diphenylphosphoryl)dibenzo[b,d]furan (PPF), tris(4-carbazoyl-9-ylphenyl)amine (TCTA), and 1,3,5-tris(1-phenyl-1H-benzo[d]imidazol-2-yl)benzene (TPBi). However, embodiments are not limited thereto, and for example, tris(8-hydroxyquinolino)aluminum ($Alq_3$), 4,4'-bis(N-carbazolyl)-1,1'-biphenyl (CBP), poly(n-vinylcabazole) (PVK), 9,10-di(naphthalene-2-yl)anthracene (ADN), tris(carbazol-9-yl)-triphenylamine (TCTA), 1,3,5-tris(1-phenyl-1H-benzo[d]imidazol-2-yl)benzene (TPBi), 3-tert-butyl-9,10-di(naphth-2-yl)anthracene (TBADN), distyrylarylene (DSA), 4,4'-bis (9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenylcyclotriphosphazene (CP1), 1,4-bis(triphenylsilyl)benzene (UGH2), hexaphenylcyclotrisiloxane (DPSiO3), octaphenylcyclotetra siloxane (DPSiO$_4$), 2,8-bis(diphenylphosphoryl)dibenzofuran (PPF), etc. may be utilized as host materials.

In an embodiment, the emission layer EML may include, as dopant materials, styryl derivatives (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi)), perylene and the derivatives thereof (e.g., 2,5,8,11-tetra-t-butylperylene (TBP)), pyrene and the derivatives thereof (e.g., 1-dipyrene, 1,4-dipyrenylbenzene, 1,4-bis(N,N-diphenylamino)pyrene)), etc.

The emission layer EML of an embodiment may include suitable (e.g., known) phosphorescence materials as dopant materials. The phosphorescence materials may include, but are not limited to, a metal complex or an organometallic complex, coumarin and derivatives thereof, etc. The metal complex or the organometallic complex may be selected from Ir, Pt, Os, Au, Cu, Re, and Ru. For example, the emission layer EML may include, as phosphorescence dopant materials, at least one selected from bis(2,4-difluorophenylpyridinato)-tetrakis(1-pyrazolyl)borate iridium(III) (FIr6), bis[2-(4,6-difluorophenyl)pyridinato-C2,N](picolinato)iridium(III) (FIrpic), iridium (III) tris[3-(2,6-dimethylphenyl)-7-methylimidazo[1,2-f] phenanthridine](Ir(dmp)3), iridium (III) tris[1-(2,4-diisopropyldibenzo[b,d]furan-3-yl)-2-phenylimidazole](Ir(dbi)3), and iridium (III) tris[2-(4-fluorophenyl)-1-(5'-isopropyl-(1,1':3',1''-terphenyl]-2'-yl)-1H-imidazole (Ir(itpim)3). However, embodiments are not limited thereto.

The emission layer EML of an embodiment may include a suitable (e.g., known) thermally activated delayed fluorescence (TADF) emitting material as a dopant material. The emission layer EML of an embodiment may include a suitable (e.g., known) compound as a thermally activated delayed fluorescence material. For example, the emission layer EML of an embodiment may include, as a thermally activated delayed fluorescence dopant, at least one of a donor-acceptor type thermally activated delayed fluorescence compound and a boron-containing thermally activated delayed fluorescence compound. The boron-containing thermally activated delayed fluorescence compound may be a polycyclic compound, and may include nitrogen. The boron-containing thermally activated delayed fluorescence compound may be a compound which separates HOMO-LUMO by the multiple resonance effect to function as TADF.

The polycyclic compound of an embodiment described above may be included in functional layers other than the emission layer EML.

In the organic electroluminescence device 10 of an embodiment shown in FIGS. 1-3, the electron transport region ETR is disposed on the emission layer EML. The electron transport region ETR may include, but is not limited to, at least one of the hole blocking layer HBL, the electron transport layer ETL, or the electron injection layer EIL.

The electron transport region ETR may have a single layer structure having a single layer formed of a single material, a single layer formed of materials different from each other, or a multilayer structure including a plurality of layers formed of materials different from each other.

For example, the electron transport region HTR may have a single layer structure of an electron injection layer EIL or an electron transport layer ETL, or a single layer structure formed of electron injection materials and/or electron transport materials. In addition, the electron transport region ETR may have a single layer structure formed of materials different from each other, or a structure of an electron transport layer ETL/an electron injection layer EIL, or a hole blocking layer HBL/an electron transport layer ETL/an electron injection layer (EIL), which are sequentially laminated from the emission layer EML, but embodiments are not limited thereto. The electron transport region ETR may have a thickness, for example, from about 1,000 Å to about 1,500 Å.

The electron transport region ETR may be formed by utilizing various suitable methods such as a vacuum deposition method, a spin coating method, a casting method, a Langmuir-Blodgett (LB) method, an inkjet printing method, a laser printing method, and/or a laser induced thermal imaging (LITI) method.

If the electron transport region ETR includes the electron transport layer ETL, the electron transport region ETR may include an anthracene-based compound. However, embodiments are not limited thereto, and the electron transport region ETR may include, for example, tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tris(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq2), 9,10-di(naphthalene-2-yl)anthracene (ADN), or a mixture thereof. The thicknesses of the electron transport layers ETL may be from about 100 Å to about 1,000 Å, for example, from about 150 Å to about 500 Å. When the thicknesses of the electron transport layers ETL satisfy the above-described ranges, satisfactory electron transport characteristics may be achieved without a substantial increase in driving voltage.

When the electron transport region ETR includes the electron injection layer EIL, metal halides such as LiF, NaCl, CsF, RbCl, RbI, and CuI, lanthanum metals such as Yb, metal oxide such as Li$_2$O, BaO, or lithium quinolate (LiQ), and/or the like may be utilized in the electron transport region ETR, but embodiments are not limited thereto. The electron injection layer EIL may be also formed of a mixture of an electron transport material and an organo metal salt. The organo metal salt may be a material having an energy band gap of about 4 eV or more. For example, the organo metal salt may include metal acetate, metal benzoate, metal acetoacetate, metal acetylacetonate and/or metal stearate. The electron injection layers EIL may have a thickness from about 1 Å to about 100 Å, or from about 3 Å to about 90 Å. When the thicknesses of the electron injection layers EIL satisfy the above-described ranges, satisfactory electron injection characteristics may be achieved without a substantial increase in driving voltage.

As described above, the electron transport region ETR may include the hole blocking layer HBL. The hole blocking layer HBL may include, for example, at least one of 2,9-dimethyl-4,7-diphenyl-1,10-phenanthroline (BCP), or 4,7-diphenyl-1,10-phenanthroline (Bphen), but the present disclosure is not limited thereto.

The second electrode EL2 is disposed on the electron transport region ETR. The second electrode EL2 may be a common electrode or a negative electrode. The second electrode EL2 may be a transmissive electrode, a transflective electrode, or a reflective electrode. When the second electrode EL2 is the transmissive electrode, the second electrode EL2 may be formed of a transparent metal oxide, for example, indium tin oxide (ITO), indium zinc oxide (IZO), zinc oxide (ZnO), indium tin zinc oxide (ITZO), and/or the like.

When the second electrode EL2 is a transflective electrode or a reflective electrode, the second electrode EL2 may include Ag, Mg Cu, Al, Pt, Pd, Au, Ni, Nd, Ir, Cr, Li, Ca, LiF/Ca, LiF/Al, Mo, Ti, or a compound or mixture (e.g., a mixture of Ag and Mg) including the same. Alternatively, the second electrode EL2 may have a multi-layered structure including a reflective layer or transflective layer and a transparent conductive layer formed of indium tin oxide (ITO), indium zinc oxide (IZO), zinc oxide (ZnO), or indium tin zinc oxide (ITZO).

The second electrode EL2 may have a thickness from about 50 Å to about 10,000 Å. For example, the second electrode EL2 may have a thickness from about 100 Å to about 5,000 Å, or from about 1,000 Å to about 3,000 Å.

In one embodiment, the second electrode EL2 may be connected to an auxiliary electrode. When the second electrode EL2 is connected to the auxiliary electrode, resistance of the second electrode EL2 may be decreased.

In one embodiment, a capping layer may be further disposed on the second electrode EL2 of the organic electroluminescence device 10 of an embodiment. The capping layer may include, for example, α-NPD, NPB, TPD, m-MTDATA, Alq₃, CuPc, N4,N4,N4',N4'-tetra(biphenyl-4-yl)biphenyl-4,4'-diamine (TPD15), tris(4-carbazoyl-9-ylphenyl) amine (TCTA), N,N'-bis(naphthalen-1-yl), and/or the like.

The polycyclic compound of an embodiment described above may be included in functional layers other than the hole transport region HTR as a material for the organic electroluminescence device 10. The organic electroluminescence device 10 of an embodiment of the present disclosure may also include the above-described polycyclic compound in at least one functional layer disposed between the first electrode EL1 and the second electrode EL2, or in the capping layer disposed on the second electrode EL2.

In the organic electroluminescence device 10, as a voltage is applied to the first electrode EL1 and the second electrode EL2, respectively, the holes injected from the first electrode EL1 are moved through the hole transport region HTR to the emission layer EML, and the electrons injected from the second electrode EL2 are moved through the electron transport region ETR to the emission layer EML. The electrons and holes are recombined in the emission layer EML to generate excitons and emit light when the excitons return to a ground state from an excited state.

Hereinafter, the polycyclic compound according to an embodiment of the present disclosure and the organic electroluminescence device of an embodiment including the polycyclic compound of an embodiment will be explained in particular referring to examples and comparative examples. In addition, the examples below are exemplified for assisting the understanding of the present disclosure, and the scope of the present disclosure is not limited thereto.

1. Synthetic Examples

A polycyclic compound according to an embodiment of the present disclosure may be synthesized as, for example, the following. However, a synthetic method of the polycyclic compound according to an embodiment of the present disclosure is not limited thereto.

1-1. Synthesis of Compound 1

Polycyclic compound 16 of an embodiment of the present disclosure may be synthesized by, for example, Reaction Formula 1 below:

[Reaction Formula 1]

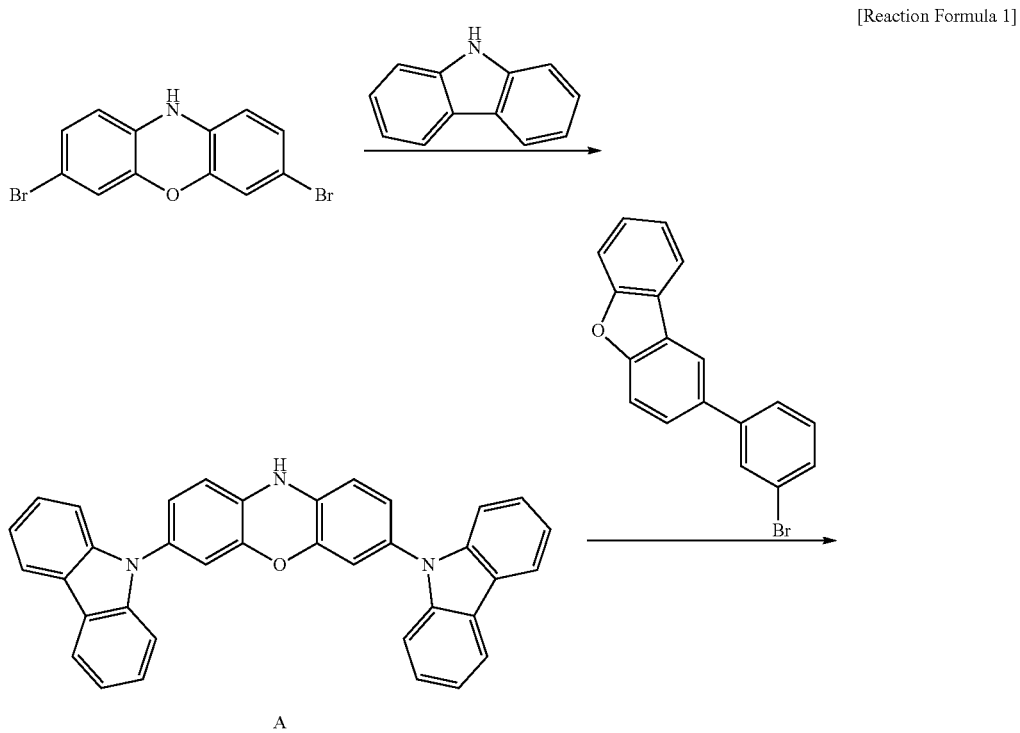

A

-continued

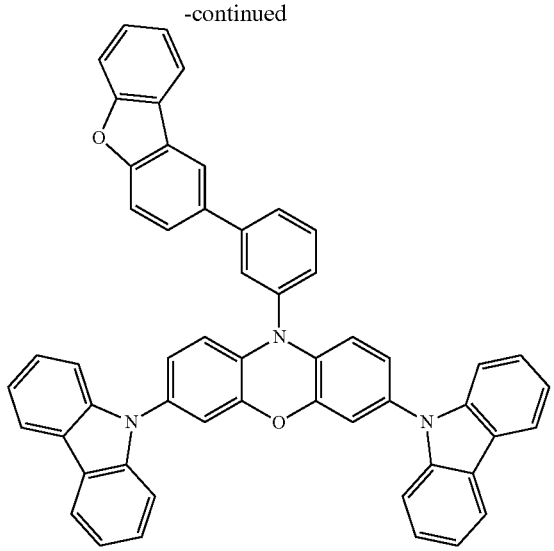

1

(Synthesis of Intermediate A)
Intermediate A was obtained by a coupling reaction between 3,7-dibromo-10H-phenoxazine and 9H-carbazole in the presence of a Pd catalyst.
(Synthesis of Compound 1)
Intermediate A (1.3 g), 2-(3-bromophenyl)dibenzo[b,d]furan (0.82 g), $Pd_2(dba)_3$ (0.1 g), $(tBu)_3P$ (0.04 g), and tBuONa (0.61 g) were dissolved in DMF (13 mL) and refluxed for 24 hours. After the reaction was completed, the reaction solution was extracted with ethyl acetate. The extracted organic layer was dried with $MgSO_4$, and the solvent was evaporated to obtain residuals. The obtained residuals were separated and purified by silica gel column chromatography to obtain Compound 1 (1.64 g, yield: 86%).

1-2. Synthesis of Compound 11
Polycyclic compound 11 of an embodiment of the present disclosure may be synthesized by, for example, Reaction Formula 2 below:

[Reaction Formula 2]

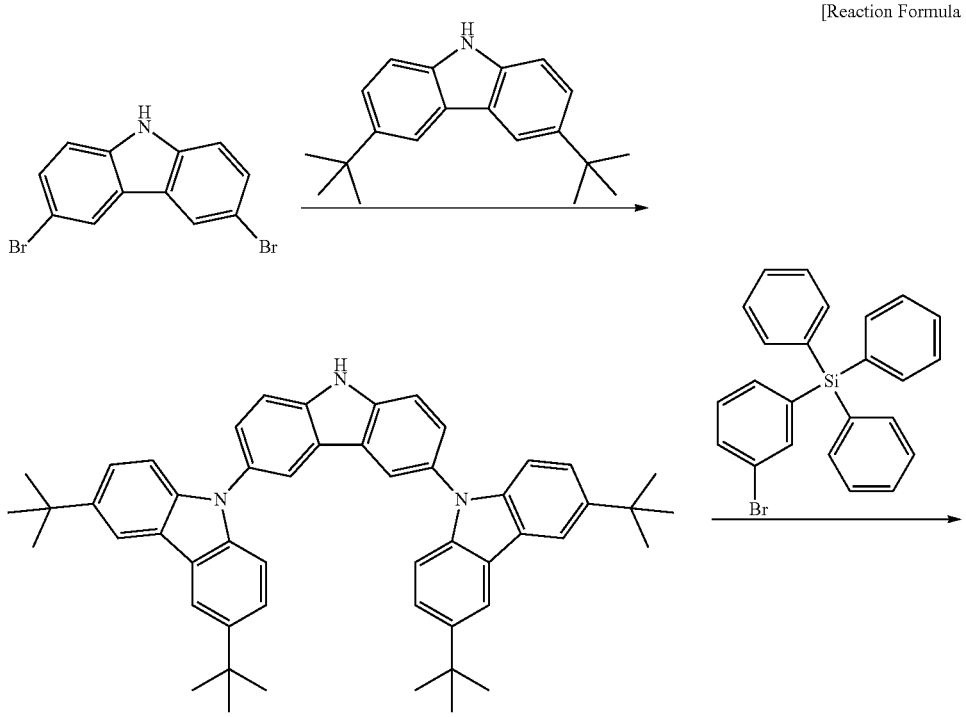

B

-continued

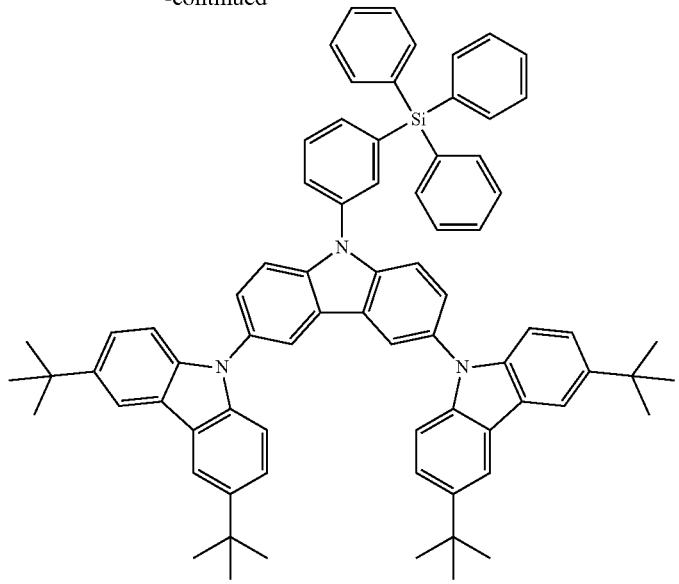

11

(Synthesis of Intermediate B)

Intermediate B was obtained by a coupling reaction between 3,6-dibromo-9H-carbazole and 3,6-di-tert-butyl-9H-carbazole in the presence of a Pd catalyst.

(Synthesis of Compound 11)

Intermediate B (1.7 g), (3-bromophenyl)triphenylsilane (0.98 g), Pd$_2$(dba)$_3$ (0.08 g), (tBu)$_3$P (0.04 g), and tBuONa (0.56 g) were dissolved in DMF (12 mL) and refluxed for 24 hours. After the reaction was completed, the reaction solution was extracted with ethyl acetate. The extracted organic layer was dried with MgSO$_4$, and the solvent was evaporated to obtain residuals. The obtained residuals were separated and purified by silica gel column chromatography to obtain Compound 11 (2.26 g, yield: 91%).

1-3. Synthesis of Compound 40

Polycyclic compound 40 of an embodiment of the present disclosure may be synthesized by, for example, Reaction Formula 3 below:

[Reaction Formula 3]

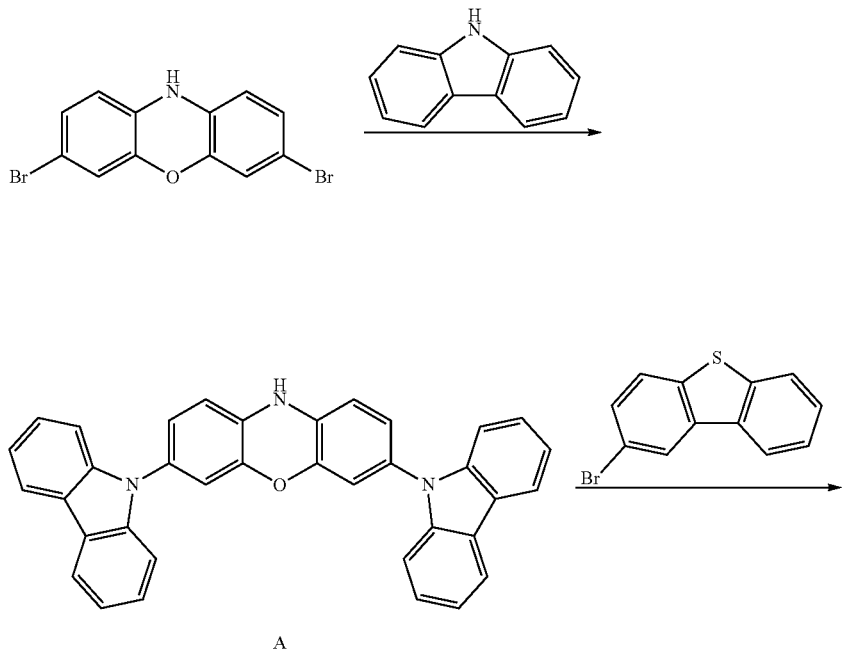

A

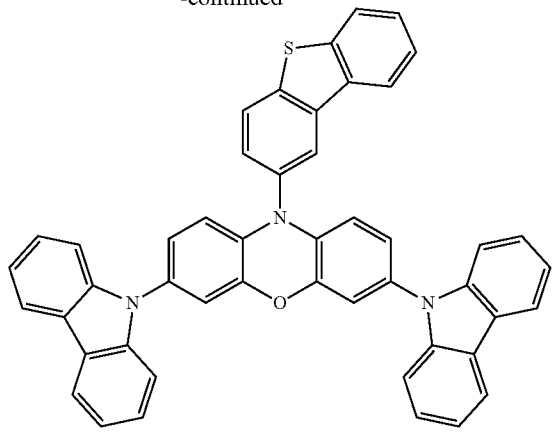

40

(Synthesis of Compound 40)

Intermediate A (1.4 g), 2-bromodibenzo[b,d]thiophene (0.71 g), $Pd_2(dba)_3$ (0.1 g), $(tBu)_3P$ (0.04 g), and tBuONa (0.65 g) were dissolved in DMF (14 mL) and refluxed for 24 hours. After the reaction was completed, the reaction solution was extracted with ethyl acetate. The extracted organic layer was dried with $MgSO_4$, and the solvent was evaporated to obtain residuals. The obtained residuals were separated and purified by silica gel column chromatography to obtain Compound 40 (1.67 g, yield: 88%).

1-4. Synthesis of Compound 51

Polycyclic compound 51 of an embodiment of the present disclosure may be synthesized by, for example, Reaction Formula 4 below:

[Reaction Formula 4]

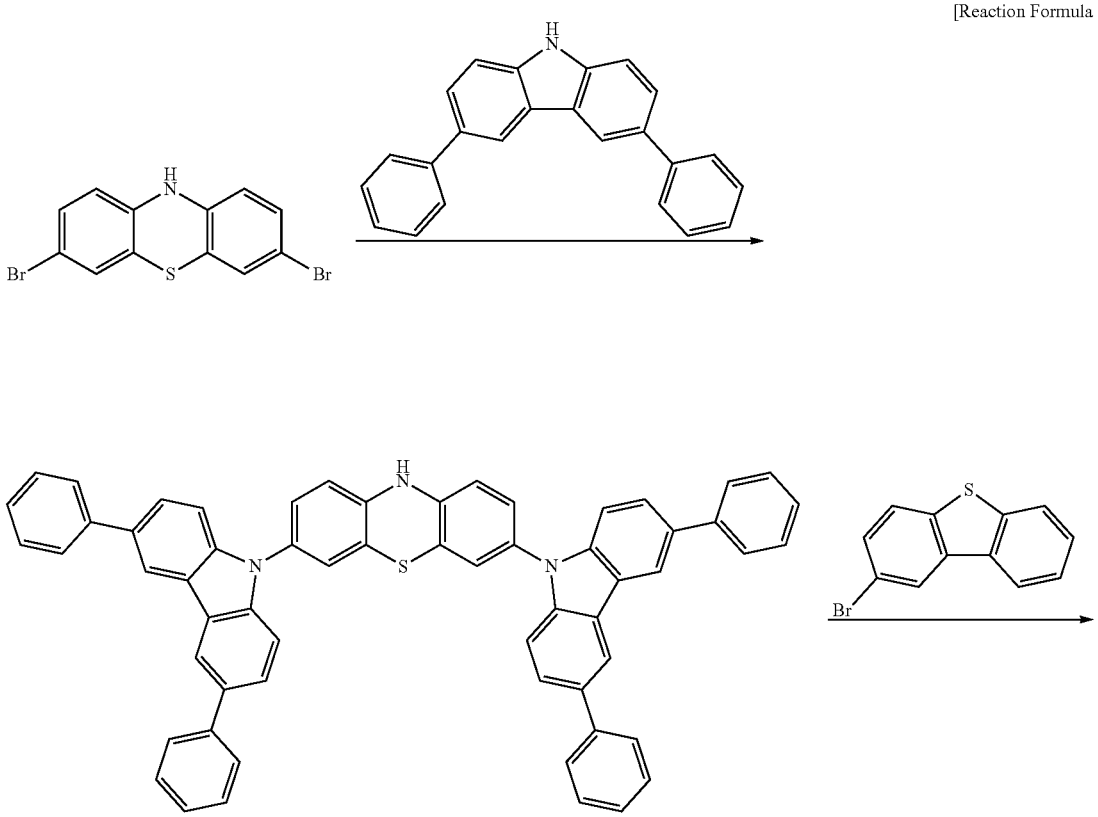

C

-continued

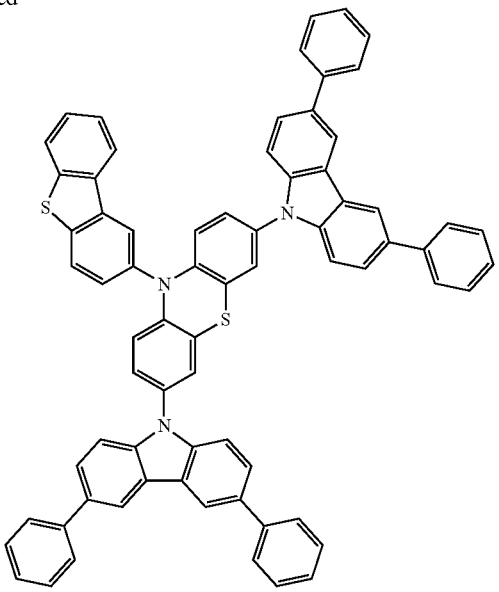

51

(Synthesis of Intermediate C)
Intermediate C was obtained by a coupling reaction between 3,7-dibromo-10H-phenothiazine and 3,6-diphenyl-9H-carbazole in the presence of a Pd catalyst.
(Synthesis of Compound 51)
Intermediate C (2.0 g), 2-bromodibenzo[b,d]thiophene (0.63 g), Pd$_2$(dba)$_3$ (0.087 g), (tBu)$_3$P (0.04 g), and tBuONa (0.57 g) were dissolved in DMF (12 mL) and refluxed for 24 hours. After the reaction was completed, the reaction solution was extracted with ethyl acetate. The extracted organic layer was dried with MgSO$_4$, and the solvent was evaporated to obtain residuals. The obtained residuals were separated and purified by silica gel column chromatography to obtain Compound 51 (2.04 g, yield: 84%).

1-5. Synthesis of Compound 61
Polycyclic compound 61 of an embodiment of the present disclosure may be synthesized by, for example, Reaction Formula 5 below:

[Reaction Formula 5]

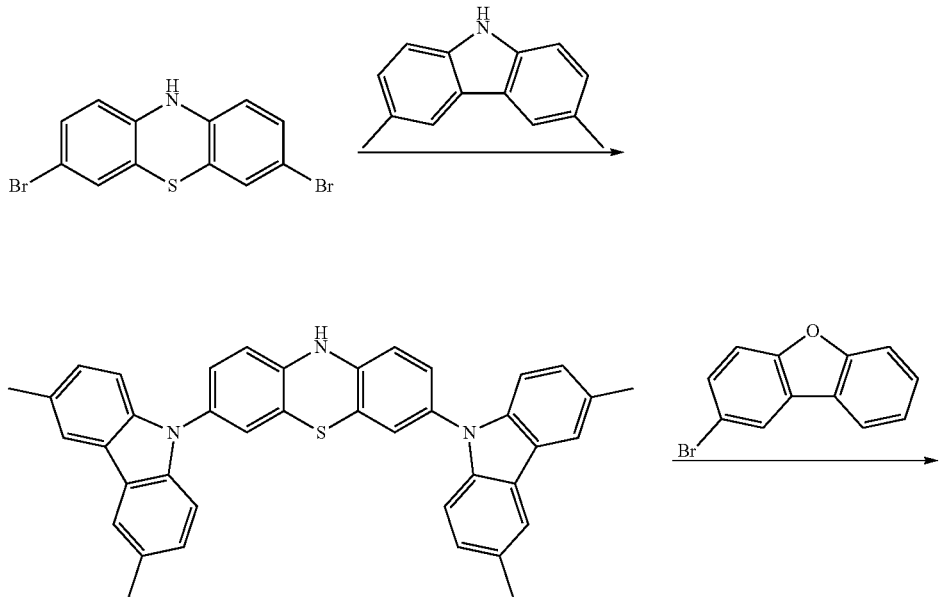

C

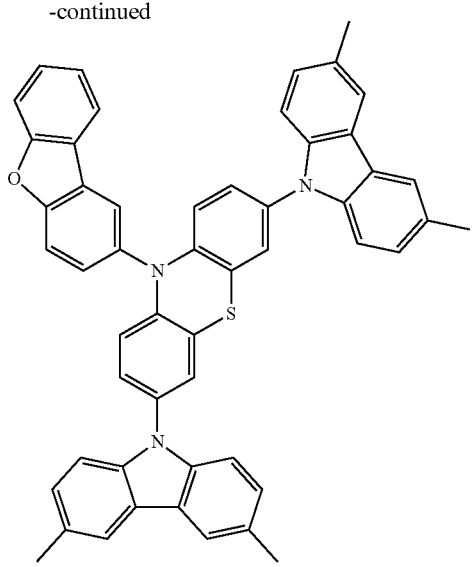

61

(Synthesis of Intermediate D)

Intermediate D was obtained by a coupling reaction between 3,7-dibromo-10H-phenoxazine and 3,6-dimethyl-9H-carbazole in the presence of a Pd catalyst.

(Synthesis of Compound 61)

Intermediate D (1.5 g), (3-bromophenyl)dibenzo[b,d]furan (0.63 g), Pd$_2$(dba)$_3$ (0.09 g), (tBu)$_3$P (0.04 g), and tBuONa (0.58 g) were dissolved in DMF (13 mL) and refluxed for 24 hours. After the reaction was completed, the reaction solution was extracted with ethyl acetate. The extracted organic layer was dried with MgSO$_4$, and the solvent was evaporated to obtain residuals. The obtained residuals were separated and purified by silica gel column chromatography to obtain Compound 61 (1.66 g, yield: 86%).

1-6. Synthesis of Compound 71

Polycyclic compound 71 of an embodiment of the present disclosure may be synthesized by, for example, Reaction Formula 6 below:

[Reaction Formula 6]

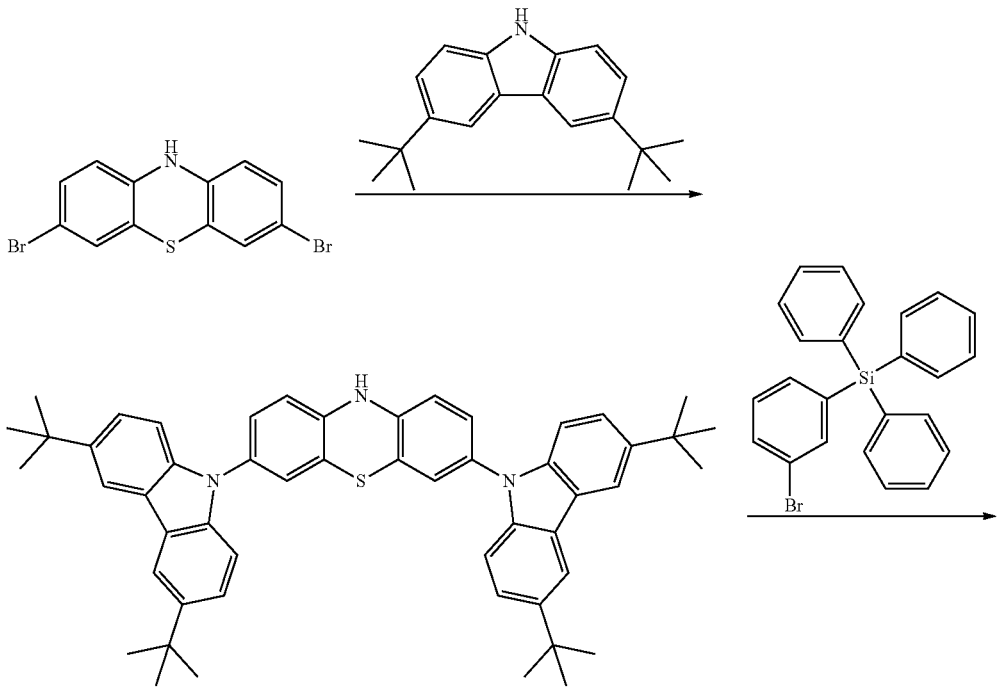

E

-continued

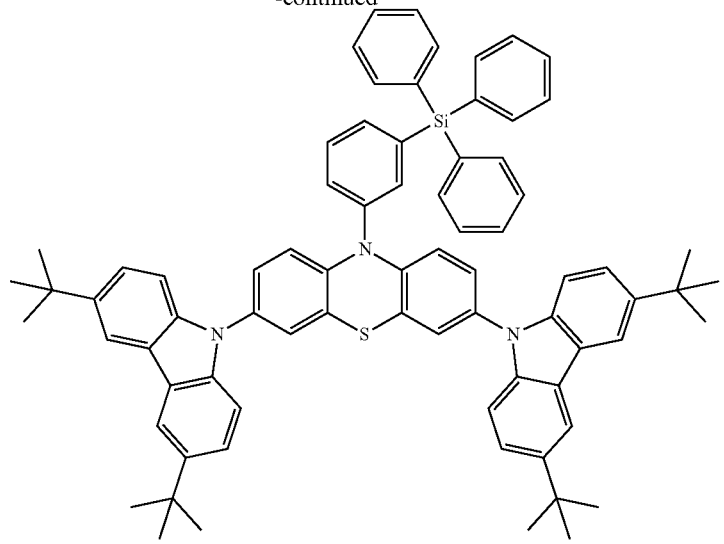

71

(Synthesis of Intermediate E)

Intermediate E was obtained by a coupling reaction between 3,7-dibromo-10H-phenothiazine and 3,6-di-tert-butyl-9H-carbazole in the presence of a Pd catalyst.

(Synthesis of Compound 71)

Intermediate E (1.8 g), (3-bromophenyl)triphenylsilane (0.99 g), $Pd_2(dba)_3$ (0.87 g), $(tBu)_3P$ (0.04 g), and tBuONa (0.57 g) were dissolved in DMF (12 mL) and refluxed for 24 hours. After the reaction was completed, the reaction solution was extracted with ethyl acetate. The extracted organic layer was dried with $MgSO_4$, and the solvent was evaporated to obtain residuals. The obtained residuals were separated and purified by silica gel column chromatography to obtain Compound 71 (2.26 g, yield: 87%).

1-7. Synthesis of Compound 86

Polycyclic compound 91 of an embodiment of the present disclosure may be synthesized by, for example, Reaction Formula 7 below:

[Reaction Formula 7]

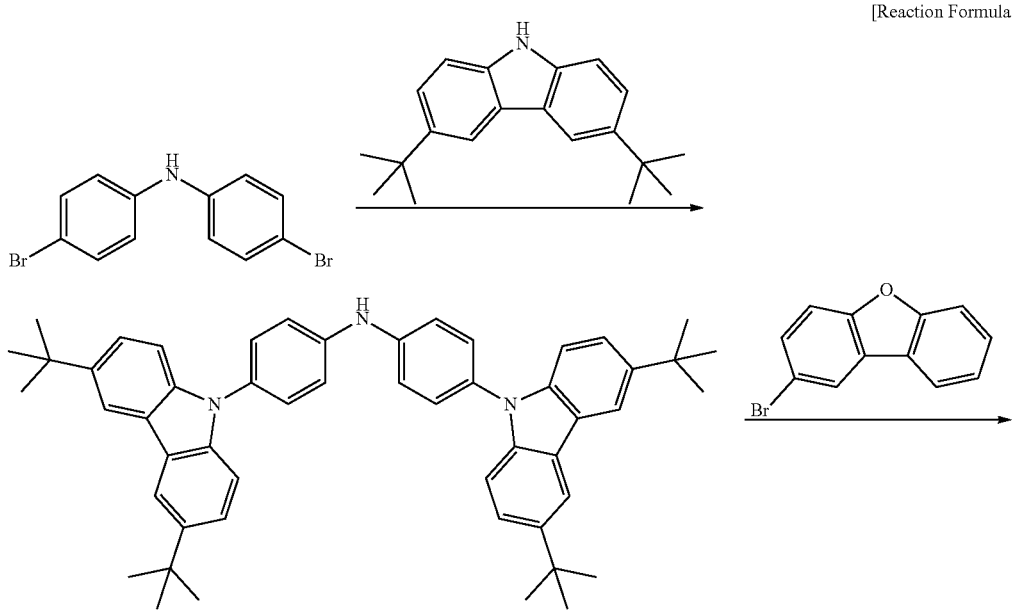

F

-continued

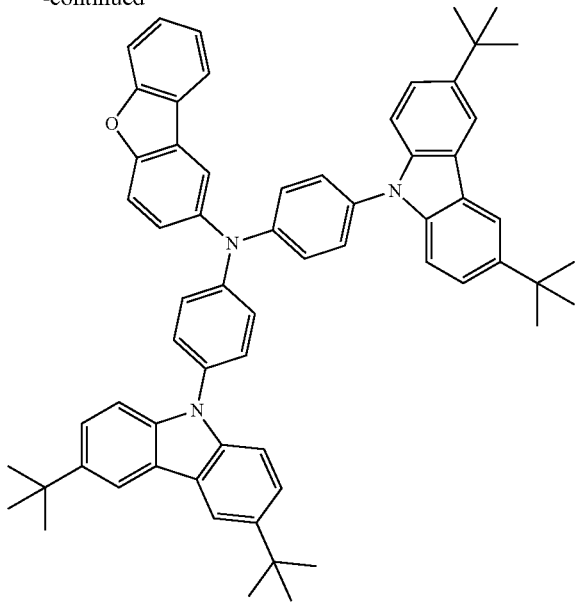

86

(Synthesis of Intermediate F)

Intermediate F was obtained by a coupling reaction between bis(4-bromophenyl)amine and 3,6-di-tert-butyl-9H-carbazole in the presence of a Pd catalyst.

(Synthesis of Compound 86)

Intermediate F (1.8 g), (3-bromophenyl)dibenzo[b,d]furan (0.61 g), Pd$_2$(dba)$_3$ (0.09 g), (tBu)$_3$P (0.04 g), and tBuONa (0.59 g) were dissolved in DMF (12 mL) and refluxed for 24 hours. After the reaction was completed, the reaction solution was extracted with ethyl acetate. The extracted organic layer was dried with MgSO$_4$, and the solvent was evaporated to obtain residuals. The obtained residuals were separated and purified by silica gel column chromatography to obtain Compound 86 (1.70 g, yield: 77%).

1-8. Synthesis of Compound 101

Polycyclic compound 101 of an embodiment of the present disclosure may be synthesized by, for example, Reaction Formula 8 below:

[Reaction Formula 8]

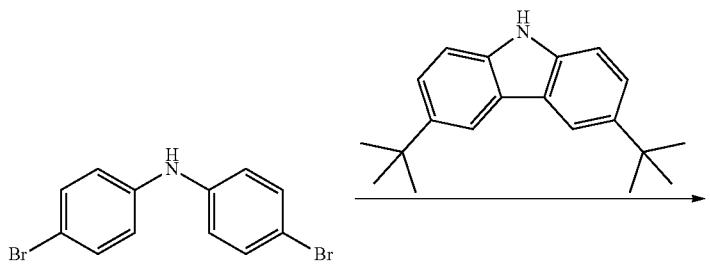

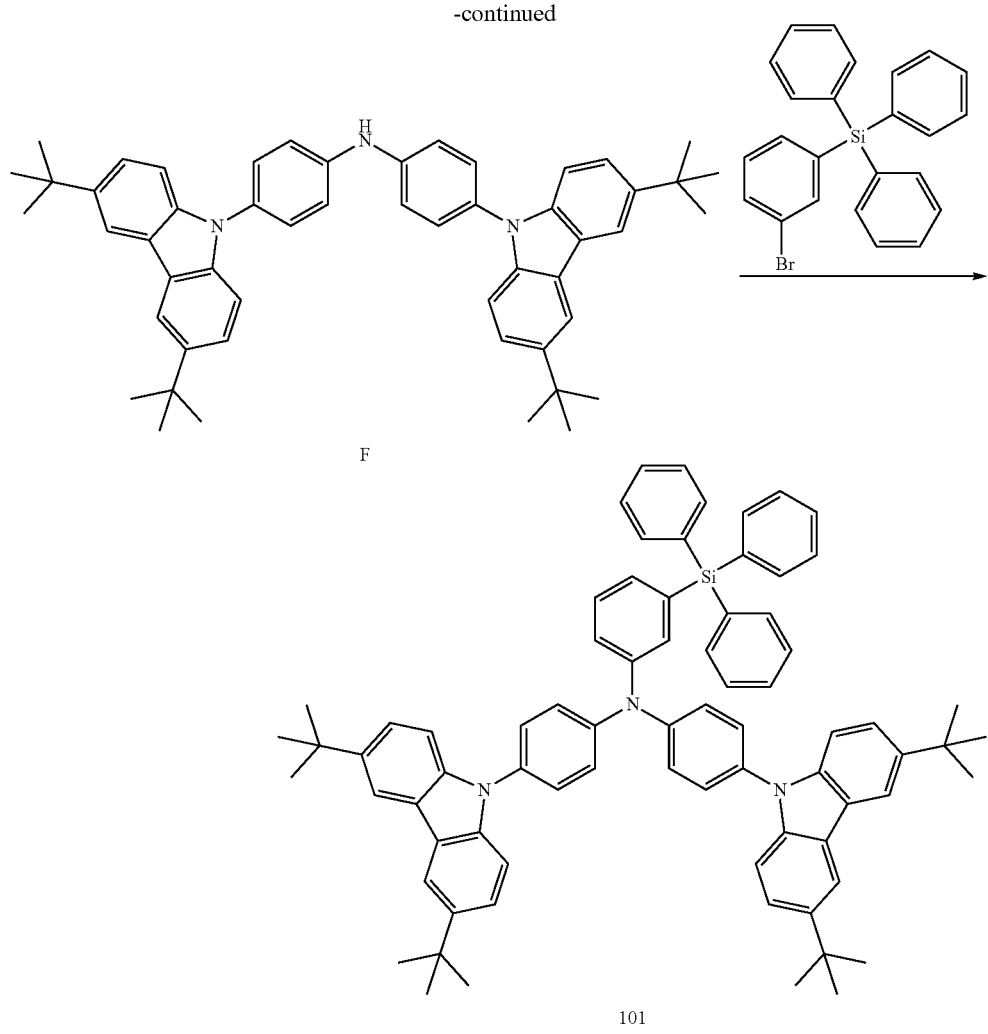

(Synthesis of Compound 101)

Intermediate F (1.7 g), (3-bromophenyl)triphenylsilane (0.98 g), $Pd_2(dba)_3$ (0.09 g), $(tBu)_3P$ (0.04 g), and tBuONa (0.56 g) were dissolved in DMF (12 mL) and refluxed for 24 hours. After the reaction was completed, the reaction solution was extracted with ethyl acetate. The extracted organic layer was dried with $MgSO_4$, and the solvent was evaporated to obtain residuals. The obtained residuals were separated and purified by silica gel column chromatography to obtain Compound 101 (2.03 g, yield: 82%).

1-9. Synthesis of Compound 116

Polycyclic compound 116 of an embodiment of the present disclosure may be synthesized by, for example, Reaction Formula 9 below:

[Reaction Formula 9]

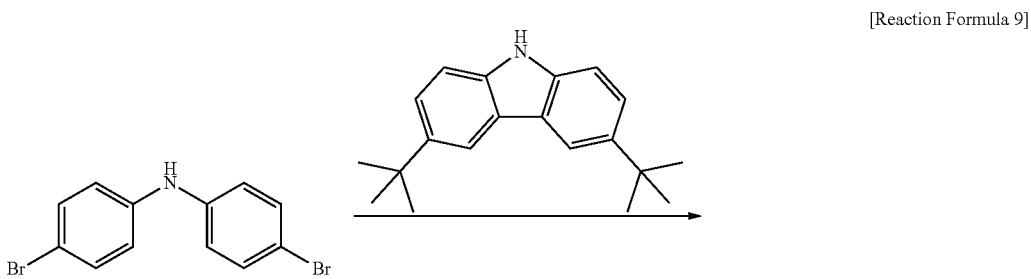

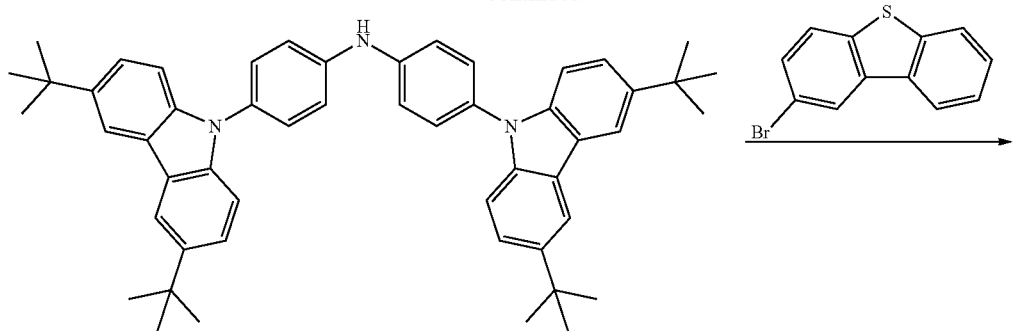

-continued

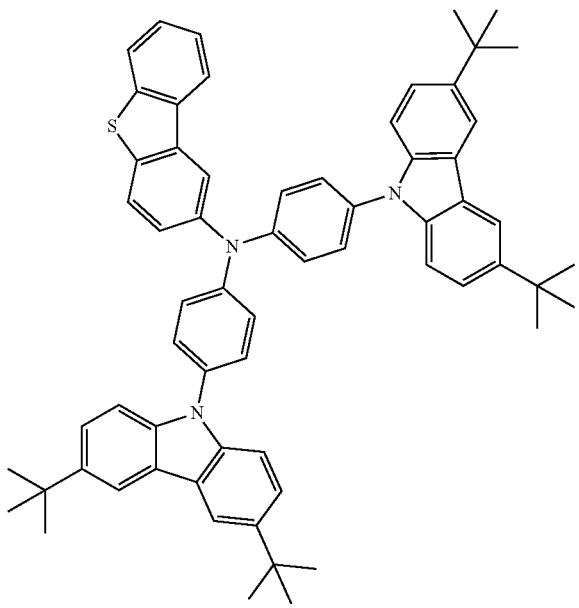

116

(Synthesis of Compound 116)

Intermediate F (1.3 g), (2-bromophenyl)dibenzo[b,d]thiophene (0.82 g), Pd$_2$(dba)$_3$ (0.1 g), (tBu)$_3$P (0.04 g), and tBuONa (0.61 g) were dissolved in DMF (13 mL) and refluxed for 24 hours. After the reaction was completed, the reaction solution was extracted with ethyl acetate. The extracted organic layer was dried with MgSO$_4$, and the solvent was evaporated to obtain residuals. The obtained residuals were separated and purified by silica gel column chromatography to obtain Compound 116 (1.64 g, yield: 86%).

1-10. Synthesis of Compound 131

Polycyclic compound 131 of an embodiment of the present disclosure may be synthesized by, for example, Reaction Formula 10 below:

[Reaction Formula 10]

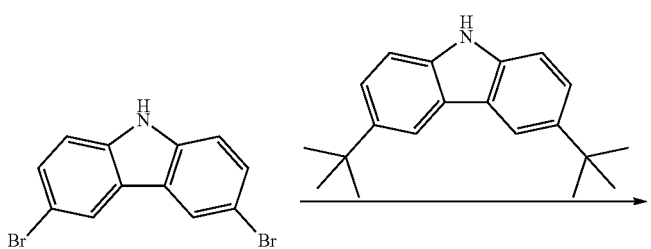

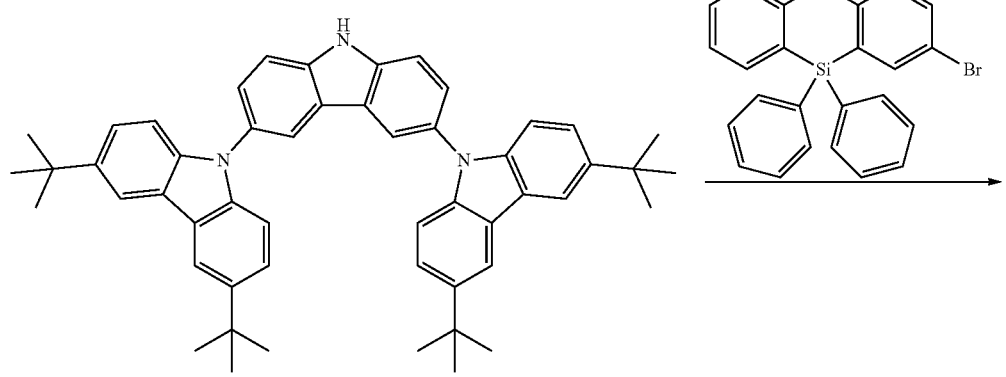

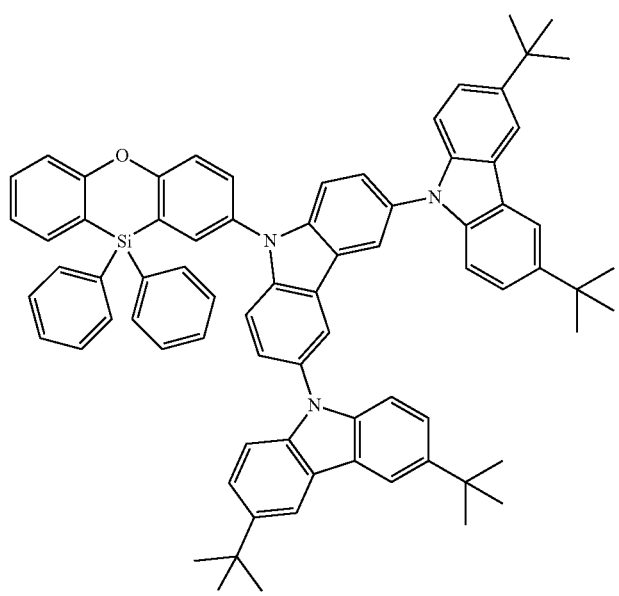

(Synthesis of Compound 131)

Intermediate F (1.5 g), 2-bromo-10,10-diphenyl-10H-dibenzo[b,e][1,4]oxasiline (0.89 g), $Pd_2(dba)_3$ (0.7 g), $(tBu)_3P$ (0.03 g), and tBuONa (0.5 g) were dissolved in DMF (10 mL) and refluxed for 24 hours. After the reaction was completed, the reaction solution was extracted with ethyl acetate. The extracted organic layer was dried with $MgSO_4$, and the solvent was evaporated to obtain residuals. The obtained residuals were separated and purified by silica gel column chromatography to obtain Compound 131 (1.89 g, yield: 85%).

1-11. Synthesis of Compound 138

Polycyclic compound 143 of an embodiment of the present disclosure may be synthesized by, for example, Reaction Formula 11 below:

[Reaction Formula 11]

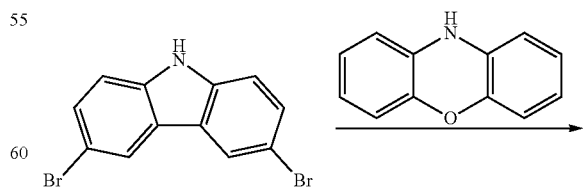

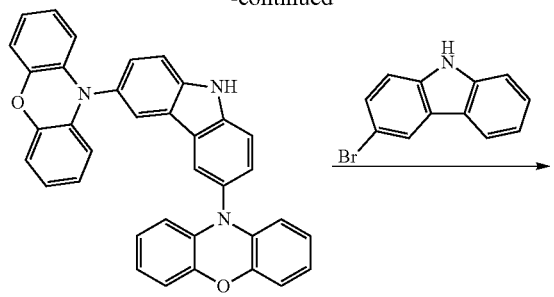

G

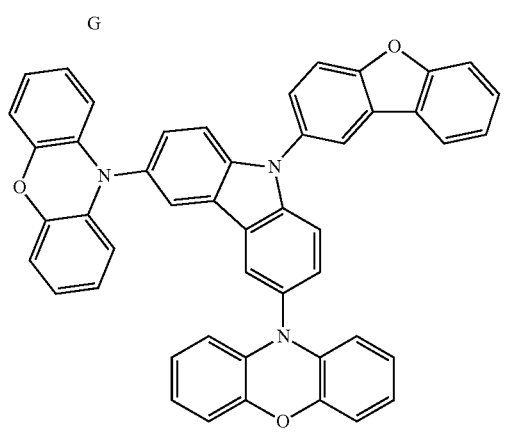

138

(Synthesis of Intermediate G)

Intermediate G was obtained by a coupling reaction between 3,6-dibromo-9H-carbazole and 10H-phenoxazine in the presence of a Pd catalyst.

(Synthesis of Compound 143)

Intermediate G (1.4 g), 2-bromodibenzo[b,d]furan (0.65 g), Pd$_2$(dba)$_3$ (0.1 g), (tBu)$_3$P (0.04 g), and tBuONa (0.63 g) were dissolved in DMF (13 mL) and refluxed for 24 hours. After the reaction was completed, the reaction solution was extracted with ethyl acetate. The extracted organic layer was dried with MgSO$_4$, and the solvent was evaporated to obtain residuals. The obtained residuals were separated and purified by silica gel column chromatography to obtain Compound 138 (1.45 g, yield: 79%).

1-12. Synthesis of Compound 159

Polycyclic compound 159 are classified as an embodiment of the present disclosure may be synthesized by, for example, Reaction Formula 12 below:

[Reaction Formula 12]

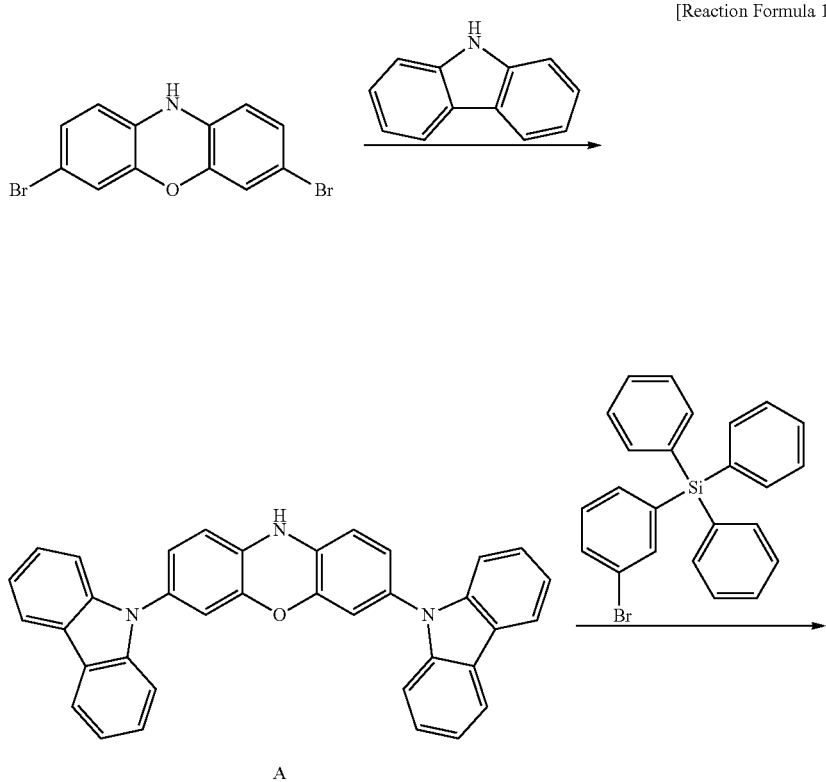

A

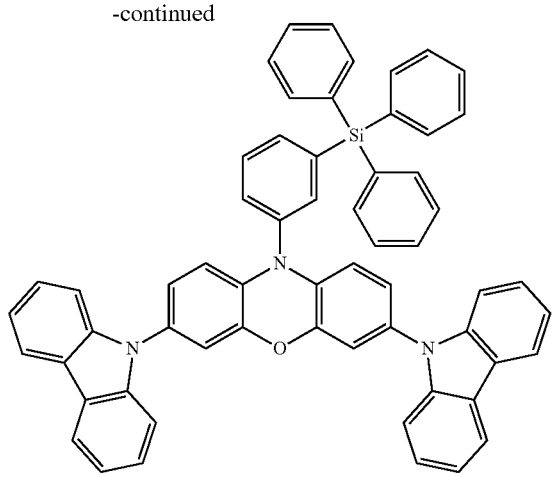

159

(Synthesis of Compound 159)

Intermediate A (1.3 g), (3-bromophenyl)triphenylsilane (1.05 g), Pd$_2$(dba)$_3$ (0.09 g), (tBu)$_3$P (0.04 g), and tBuONa (0.61 g) were dissolved in DMF (13 mL) and refluxed for 24 hours. After the reaction was completed, the reaction solution was extracted with ethyl acetate. The extracted organic layer was dried with MgSO$_4$, and the solvent was evaporated to obtain residuals. The obtained residuals were separated and purified by silica gel column chromatography to obtain Compound 159 (1.73 g, yield: 81%).

1-13. Confirmation of Structure of Synthesized Compound $^1$H NMR measurement values and molecular weights measured by MS/FAB in Synthesized Compounds 1, 11, 39, 51, 61, 71, 86, 101, 116, 131, 138, and 159 are shown in Table 1 below. $^1$H NMR represents a chemical shift value, the number of hydrogen atoms having the chemical shift value, and a degree of peak splitting. s means a singlet peak, d means a doublet peak, t means a triplet peak, and m means a multiplet peak.

TABLE 1

| Compound | $^1$H NMR (CDCl$_3$, 400 MHz) | MS/FAB found | MS/FAB calc |
|---|---|---|---|
| Compound 1 | 8.23(1H, s), 8.11(4H, d), 7.91(1H, d), 7.70(1H, d), 7.61(2H, d), 7.53(1H, t), 7.35-7.27(13H, m), 7.23(1H, d), 7.12(1H, t), 7.08(2H, d), 6.96(1H, s), 6.90(2H, d), 6.33(2H, s), 6.16(1H, d) | 756.92 | 755.88 |
| Compound 11 | 8.14(2H, s), 8.07(3H, s), 7.66(6H, d), 7.49-7.24(25H, m), 1.39(36H, t) | 1056.27 | 1056.53 |
| Compound 39 | 8.13-8.04(5H, d), 7.82(1H, d), 7.73-7.72(2H, m), 7.60(1H, t), 7.44(1H, t), 7.37-7.26(12H, m), 7.09-7.06(2H, d), 6.96-6.94(2H, d), 6.33(2H, s) | 696.88 | 695.84 |
| Compound 51 | 8.23(4H, s), 8.06-8.04(1H, d), 7.83-7.81(1H, d), 7.73-7.67(10H, m), 7.62-7.57(5H, d), 7.52-7.47(8H, t), 7.44-7.38(5H, t), 7.25(1H, d), 7.22(1H, d), 7.15-7.13(4H, d), 7.01-6.99(2H, d), 6.93-6.90(1H, d), 6.28(2H, s) | 1017.34 | 1016.29 |
| Compound 61 | 7.84-7.81(1H, d), 7.75-7.71(5H, m), 7.63-7.60(1H, d), 7.57(1H, s), 7.55-7.51(1H, t), 7.44-7.40(1H, t), 7.25-7.22(6H, d), 7.19-7.16(4H, d), 7.01-6.99(2H, d), 6.96-6.93(1H, d), 6.28(2H, s), 2.56(12H, t) | 752.99 | 751.95 |
| Compound 71 | 8.07(4H, s), 7.64-7.61(6H, m), 7.34-7.18(22H, m), 6.93-6.90(2H, d), 6.48-6.41(1H, m), 6.28(2H, s), 1.39(36H, t) | 1089.54 | 1088.59 |
| Compound 86 | 8.01(4H, s), 7.81-7.84(1H, d), 7.74-7.71(1H, d), 7.59-7.51(3H, m), 7.44-7.40(1H, t), 7.33-7.26(8H, m), 7.17-7.13(4H, d), 6.96-6.93(1H, d), 6.84-6.80(4H, d), 1.39(36H, t) | 891.07 | 890.23 |
| Compound 101 | 8.01(4H, s), 7.64-7.61(6H, m), 7.33-7.22(18H, m), 7.17-7.13(4H, d), 7.02-6.98(2H, t), 6.79-6.75(4H, d), 6.35(1H, t), 1.38(36H, t) | 1059.51 | 1058.54 |
| Compound 116 | 8.06-8.04(1H, d), 8.01(4H, s), 7.83-7.81(1H, d), 7.73-7.70(1H, d), 7.67(1H, s), 7.62-7.58(1H, t), 7.46-7.42(1H, t), 7.33-7.26(8H, d), 7.17-7.13(4H, d), 6.93-6.90(1H, d), 6.84-6.80(4H, d), 1.39(36H, t) | 907.34 | 906.29 |
| Compound 131 | 8.07-8.05(4H, m), 7.95(1H, s), 7.73-7.71(4H, d), 7.34-7.19(19H, m), 7.13-7.11(1H, d), 7.08(1H, t), 7.04(1H, t), 6.99-6.96(1H, d), 1.39(36H, t) | 1071.67 | 1070.51 |
| Compound 138 | 7.91-7.88(1H, d), 7.78(1H, s), 7.77-7.75(1H, d), 7.68-7.65(1H, d), 7.55-7.51(1H, t), 7.40-7.34(6H, m), 6.92-6.90(4H, d), 6.85-6.81(4H, t), 6.66(2H, d), 6.54-6.52(4H, d) | 696.82 | 695.78 |
| Compound 159 | 8.12-8.10(4H, d), 7.64-7.61(6H, m), 7.37-7.21(23H, m), 7.09-7.06(2H, d), 6.90-6.83(3H, m), 6.59-6.56(1H, d), 6.33(2H, s) | 849.12 | 848.09 |

2. Manufacture and Evaluation of Organic Electroluminescence Device Including Polycyclic Compound 2-1. Examples of Organic Electroluminescence Device Including Polycyclic Compound Example Compounds, 11, 39, 51, 61, 71, 86, 101, 116, 131, 138, 159, and Comparative Compounds C1 to C4 were utilized as materials for emission layers to manufacture the organic electroluminescence devices of Examples 1 to 12 and Comparison Examples 1 to 4.

(Example Compound)
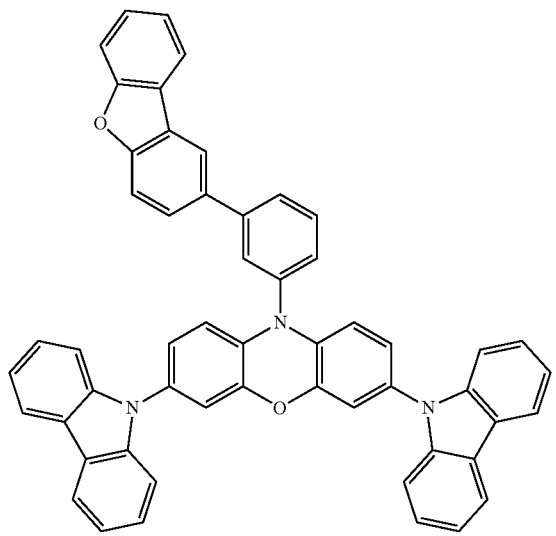
1
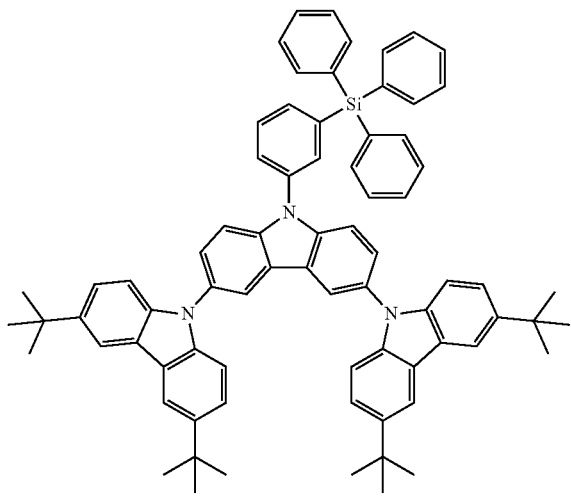
11
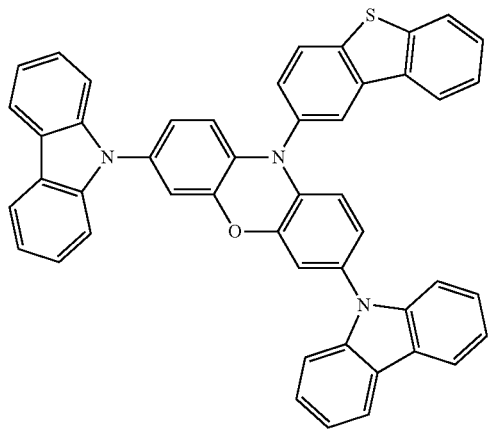
39
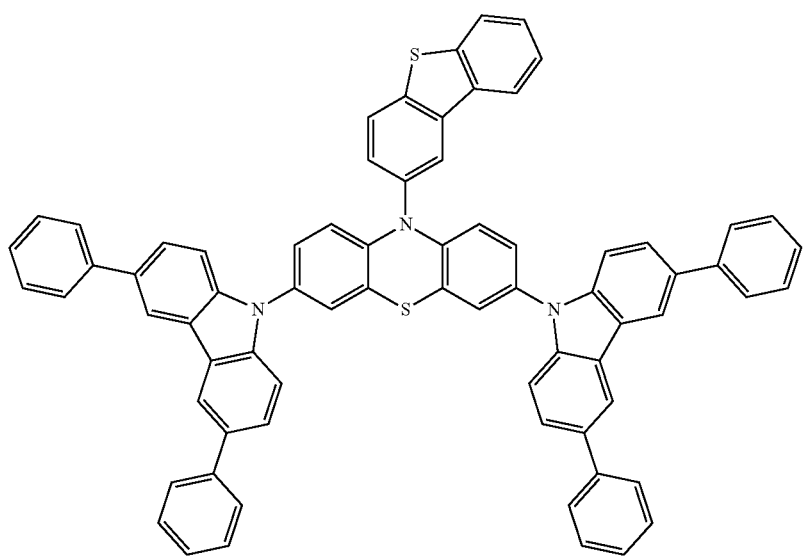
51

-continued
61
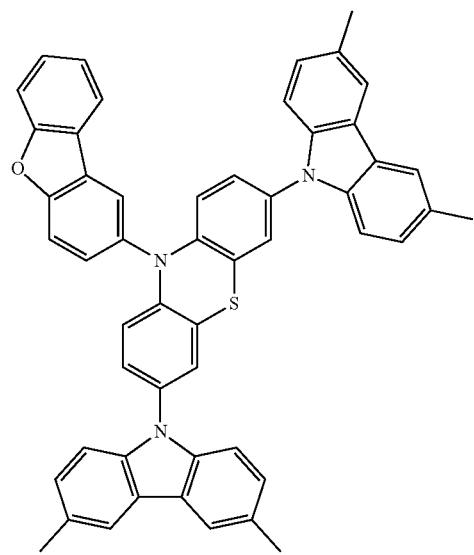
71
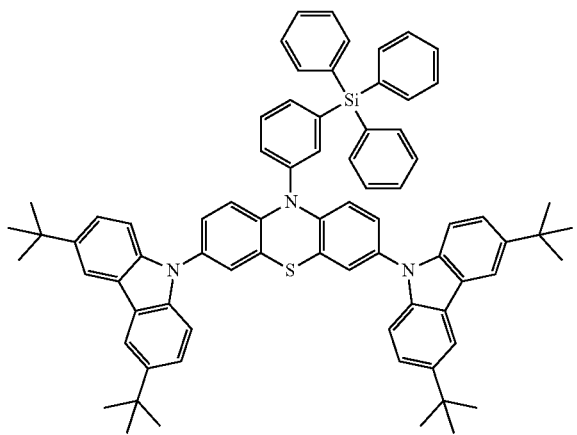
86
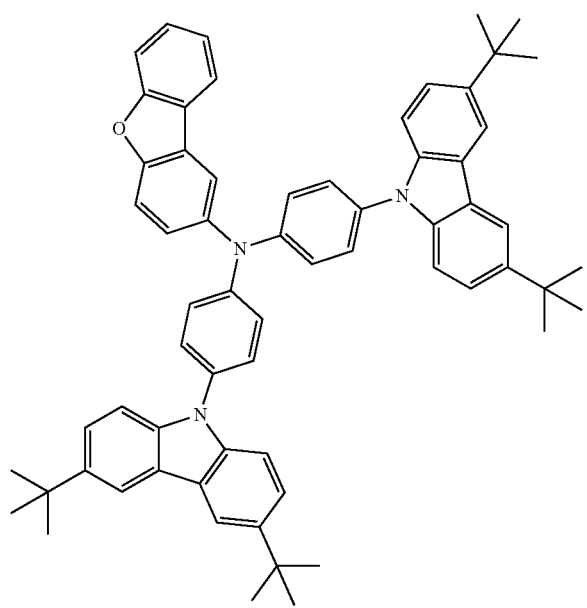
101
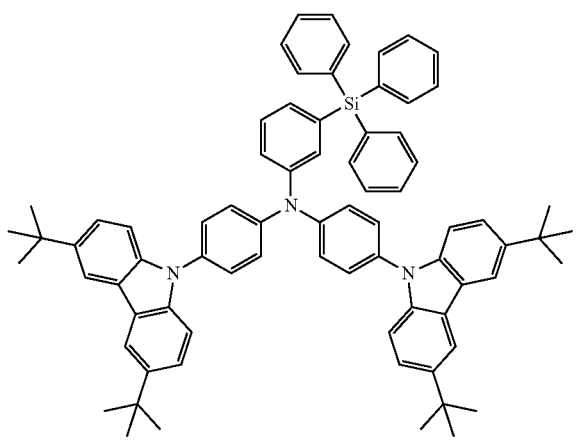

-continued
116
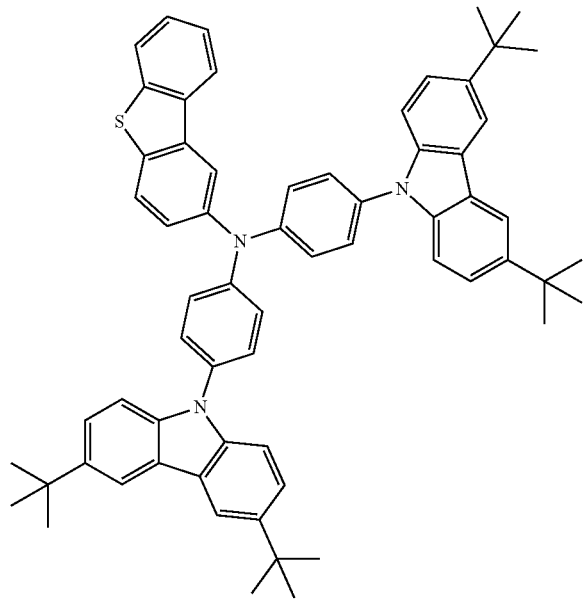
131
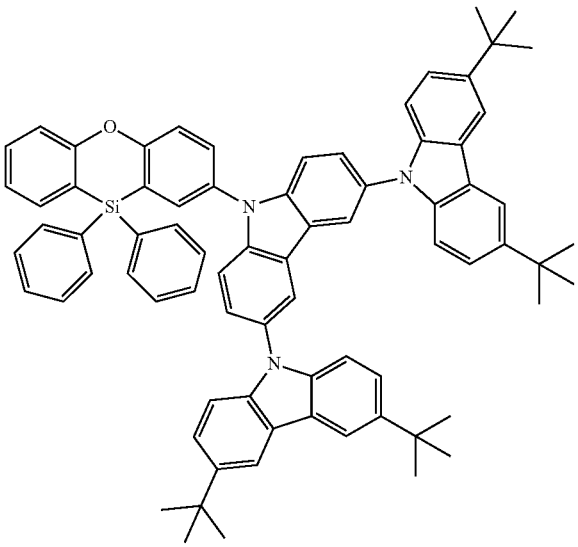
138
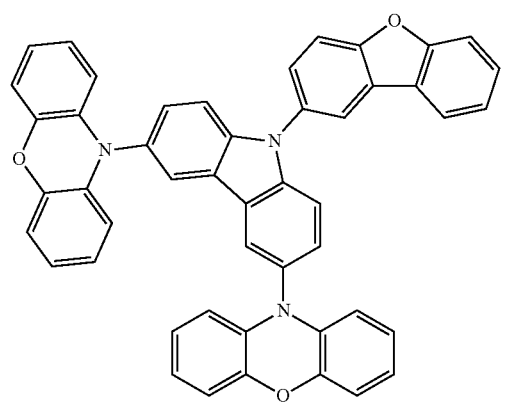
(Comparative Compound)
159
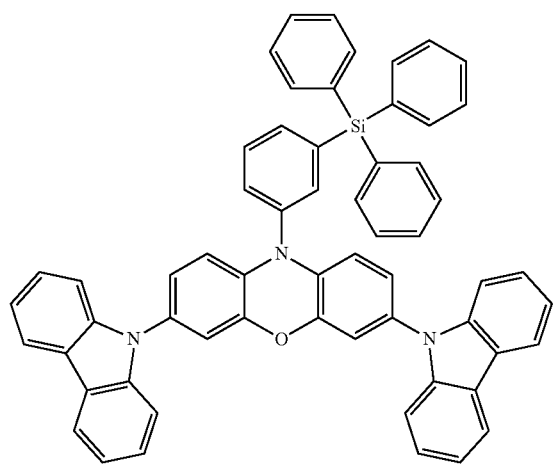
C1
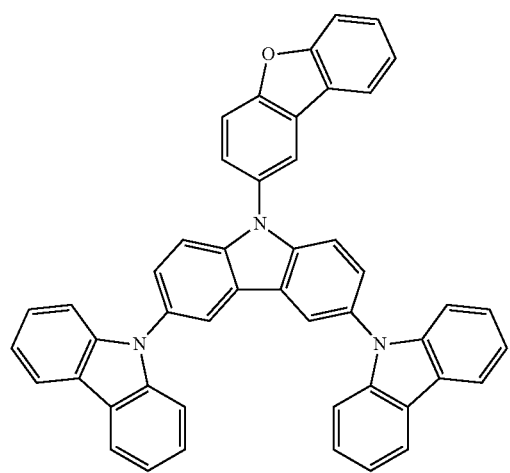
C2
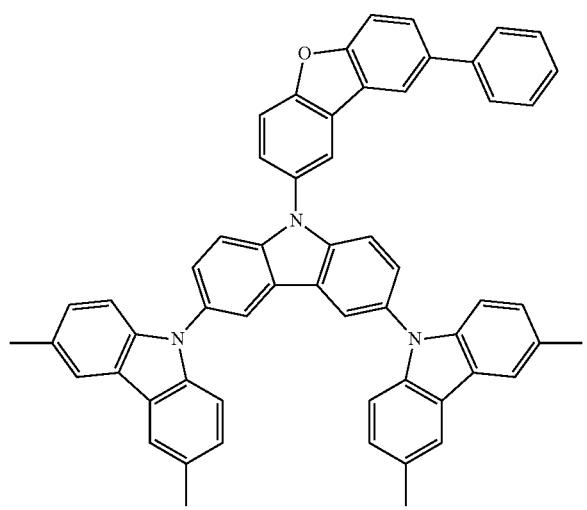

-continued

C3
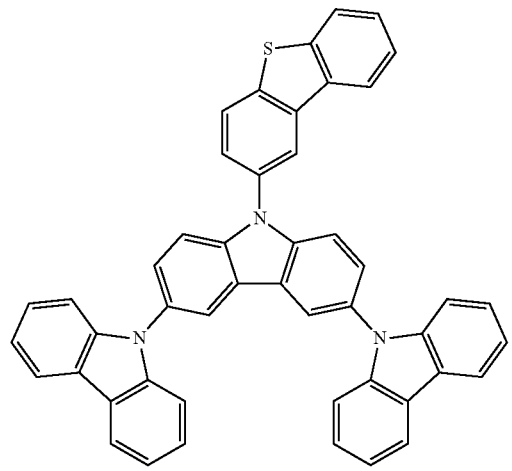

C4
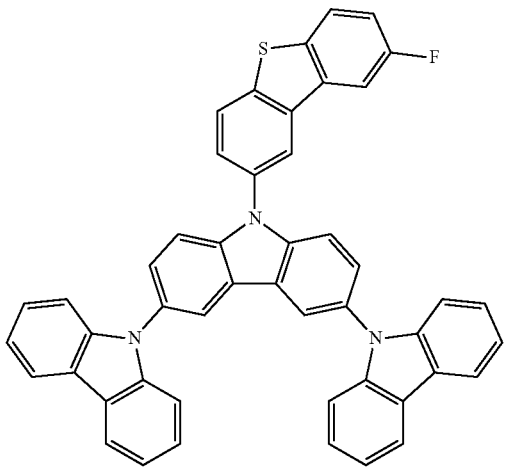

(Manufacture of Organic Electroluminescence Device)

With respect to each of the organic electroluminescence devices of Examples 1 to 12 and Comparison Examples 1 to 4, ITO was cleansed by ultrasonic waves utilizing isopropyl alcohol and distilled water for about 5 minutes each, then irradiated with ultraviolet rays for about 30 minutes, and exposed to ozone for cleaning to form a first electrode having a thickness of 1,200 Å. A hole injection layer HIL having a thickness of about 300 Å was formed of NPD, and a hole transport layer HTL having a thickness of about 200 Å was formed of mCP. An emission layer EML having a thickness of about 250 Å (in which Firpic (about 8%) was doped) per each of Example Compounds and Comparative Compounds was formed. An electron transport layer ETL having a thickness of about 200 Å was formed of TAZ, and an electron injection layer EIL having a thickness of about 10 Å was formed of LiF. A second electrode EL2 having a thickness of about 100 Å was formed of Al. Each layer was formed by a vacuum deposition method.

(Evaluation of Property of Organic Electroluminescence Device)

A luminescence property of the manufactured organic electroluminescence device was evaluated utilizing 2400 series SourceMeter made by Keithley Instrument. To evaluate properties of the organic electroluminescence device according to each of Examples and Comparative Examples, drive voltage (driving voltage), current density, and maximum quantum efficiency (maximum emission efficiency) were measured. Drive voltage and maximum quantum efficiency were values obtained with respect to current density of 10 mA/cm$^2$. The luminescence devices utilized in Examples and Comparative Examples are organic luminescence devices emitting blue light. For the evaluation of maximum quantum efficiency, brightness/current density is measured utilizing brightness photometer in which wavelength sensitivity is calibrated, and maximum quantum efficiency is converted by assuming angular brightness distribution (Lambertian distribution) in which ideal diffuse reflecting surface is contemplated. The results of evaluation of properties of the organic electroluminescence devices are shown in Table 2 below.

TABLE 2

| Device | Emission layer Materials | Drive voltage (V) | Current efficiency (cd/A) | Maximum quantum efficiency (%) |
|---|---|---|---|---|
| Example 1 | Compound 1 | 5.4 | 13.9 | 23.5 |
| Example 2 | Compound 11 | 5.0 | 15.3 | 25.1 |
| Example 3 | Compound 39 | 5.4 | 13.5 | 22.9 |
| Example 4 | Compound 51 | 5.3 | 14.3 | 23.7 |

TABLE 2-continued

| Device | Emission layer Materials | Drive voltage (V) | Current efficiency (cd/A) | Maximum quantum efficiency (%) |
|---|---|---|---|---|
| Example 5 | Compound 61 | 5.5 | 14.4 | 24.1 |
| Example 6 | Compound 71 | 5.2 | 15.1 | 24.9 |
| Example 7 | Compound 86 | 5.1 | 15.4 | 25.5 |
| Example 8 | Compound 101 | 5.2 | 15.4 | 25.3 |
| Example 9 | Compound 116 | 5.3 | 15.1 | 25.3 |
| Example 10 | Compound 131 | 5.2 | 14.7 | 24.8 |
| Example 11 | Compound 138 | 5.1 | 14.4 | 24.1 |
| Example 12 | Compound 159 | 5.4 | 14.3 | 24.5 |
| Comparative Example 1 | C1 | 5.7 | 12.8 | 22.4 |
| Comparative Example 2 | C2 | 5.6 | 12.9 | 22.6 |
| Comparative Example 3 | C3 | 5.8 | 12.8 | 22.3 |
| Comparative Example 4 | C4 | 5.9 | 12.5 | 22.1 |

Referring to the results of Table 2, it can be seen that when the polycyclic compounds according to examples of the present disclosure are applied to the organic electroluminescence devices as materials for the emission layers, high efficiency and a long lifespan can be achieved.

Specifically, high efficiency and low drive voltage are achieved in Examples 1 to 12 compared to Comparative Examples 1 to 4.

Specifically, the drive voltage of each of the Examples is less than or equal to that of each of the Comparative Examples, for example, drive voltage of up to about 20% lower than the Comparative Examples is achieved. Current efficiency of each of the Examples is from about 4% to about 25% higher than that of each of the Comparative Examples. In the case of maximum quantum (emission) efficiency, the maximum quantum efficiency of each of the Examples is from about 5% to about 15% higher than that of the Comparative Examples.

Example Compounds 1, 39, 51, 61, 71, 86, 101, 116, and 159 each have a core structure of phenothiazine, phenoxazine, or arylamine (particularly, biphenylamine). Therefore, it is found that the Example Compounds have different electrical properties or sterical properties compared to Comparative Compounds (having a trivalent carbazole group as a core structure), and thus the above-described low drive voltage and high efficiency properties are achieved.

Example Compounds 11, 131, and 138 each have a trivalent carbazole core group as the Comparative Compounds, but a triphenyl silyl group, a dibenzoxasilyl group, or the like is substituted in a carbazole core structure. Therefore, it is found that the Examples including these compounds have different electrical properties or sterical properties compared to the Comparative Examples in which dibenzothiophene group or dibenzofuran group is substituted in a carbazole core structure, and thus the above-described low drive voltage and high efficiency properties are achieved.

The polycyclic compounds according to an embodiment may be utilized as materials of the organic electroluminescence device to achieve high efficiency of the organic electroluminescence device.

The organic electroluminescence device according to an embodiment may achieve high efficiency by including the polycyclic compound of an embodiment.

The organic electroluminescence device and the polycyclic compound utilized therein according to an embodiment of the present disclosure may achieve high efficiency.

As used herein, the term "and/or" includes any and all combinations of one or more of the associated listed items. Throughout the disclosure, the expression "at least one of a, b or c" indicates only a, only b, only c, both a and b, both a and c, both b and c, all of a, b, and c, or variations thereof.

The terminology used herein is for the purpose of describing particular example embodiments only and is not intended to be limiting of the invention.

As used herein, the term "substantially," "about," and similar terms are used as terms of approximation and not as terms of degree, and are intended to account for the inherent deviations in measured or calculated values that would be recognized by those of ordinary skill in the art. Moreover, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112, first paragraph, or 35 U.S.C. § 112(a), and 35 U.S.C. § 132(a).

Expressions such as "at least one of," when preceding a list of elements, modify the entire list of elements and do not modify the individual elements of the list. Further, the use of "may" when describing embodiments of the inventive concept refers to "one or more embodiments of the inventive concept."

Although described with reference to preferred embodiments of the present disclosure, it will be understood that various changes and modifications of the present disclosure may be made by one skilled in the art or one having ordinary knowledge in the art without departing from the spirit and technical field of the present disclosure as hereinafter claimed.

Hence, the technical scope of the present disclosure is not limited to the detailed descriptions in the specification, but it should be determined only by reference of the claims, and equivalents thereof.

What is claimed is:

1. An organic electroluminescence device comprising:
a first electrode;
a second electrode on the first electrode; and
a plurality of functional layers between the first electrode and the second electrode,
the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, or a compound of two or more selected from them, a mixture of two or more selected from them, or oxides thereof,
wherein at least one functional layer of the plurality of functional layers comprises a polycyclic compound, the polycyclic compound being at least one selected from compounds 28 to 38, 40, 43 to 45, 47 to 53, 55, 58 to 60, 62 to 70, and 138 to 140:

193
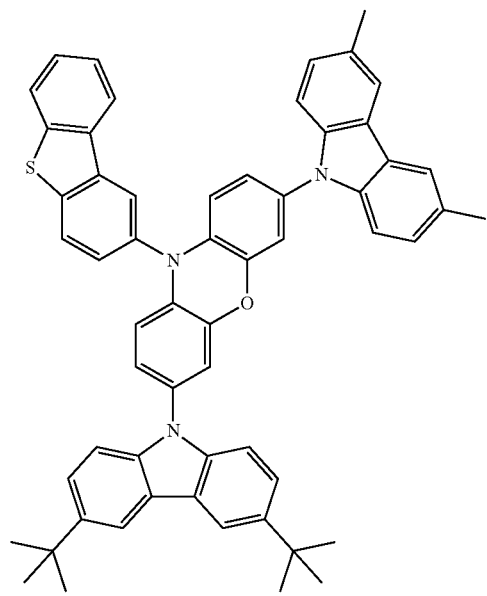
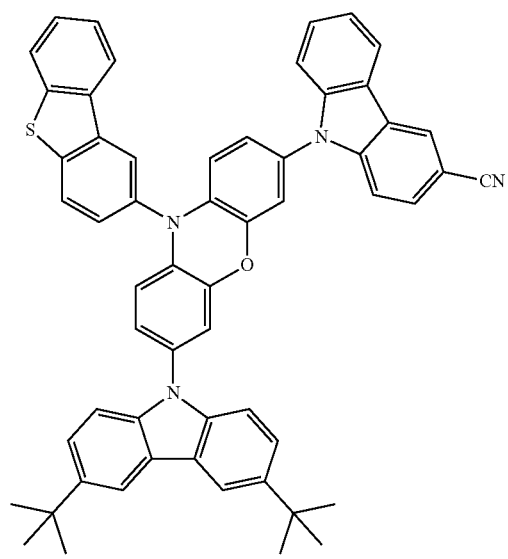
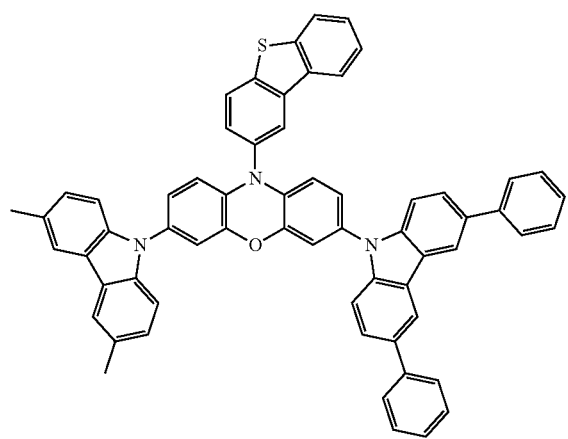
194
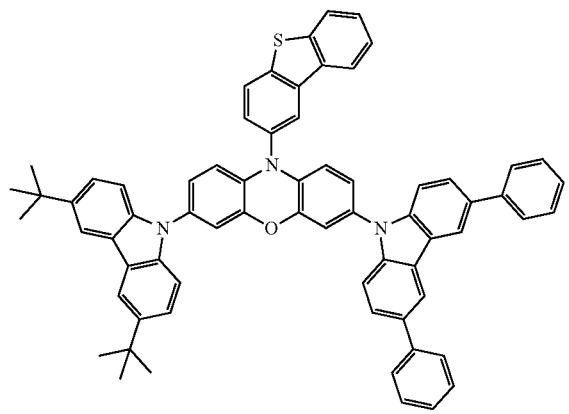
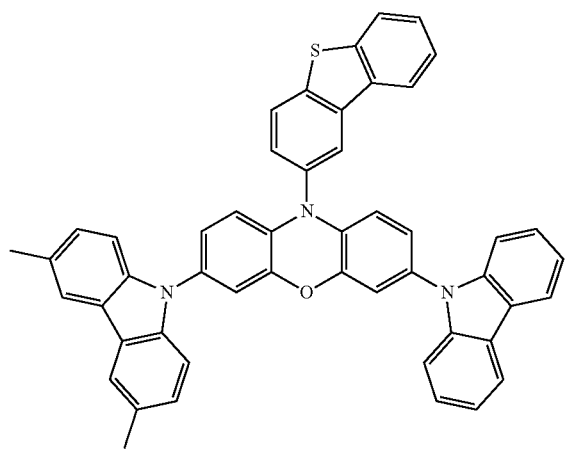
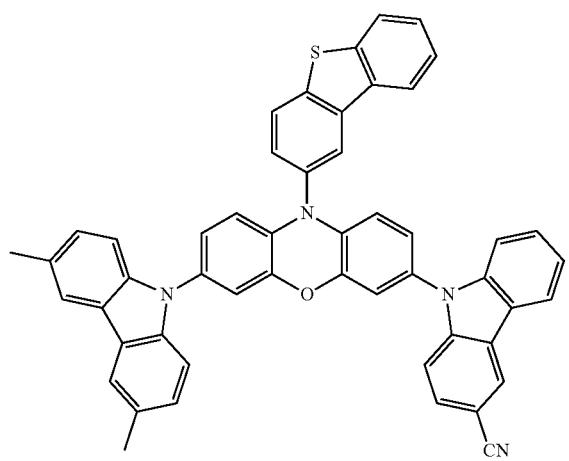

-continued
35
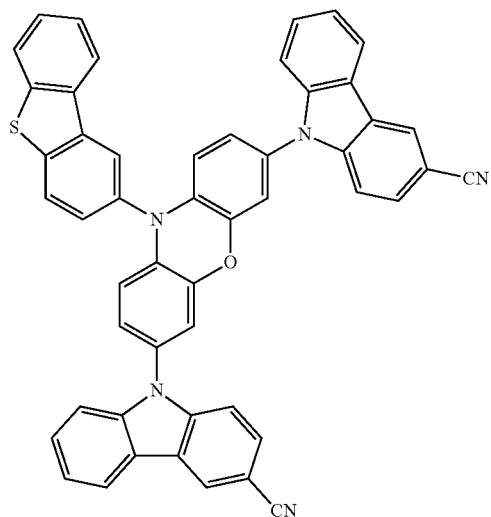
36
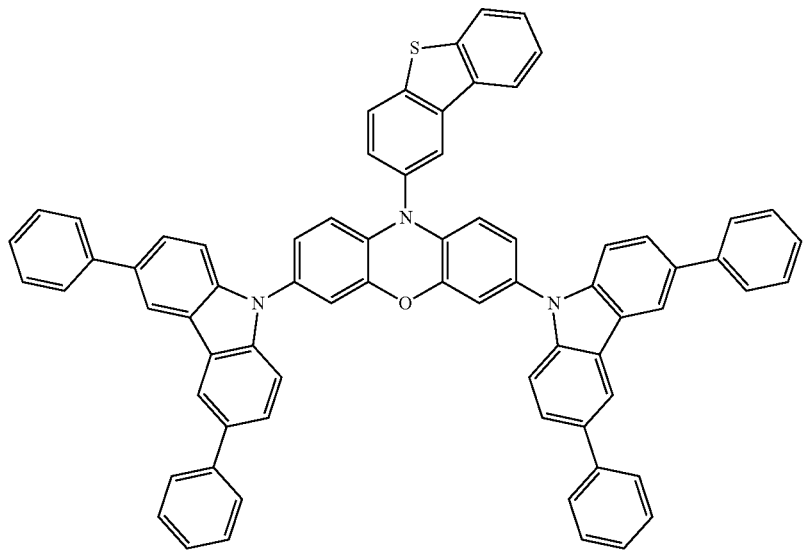
37
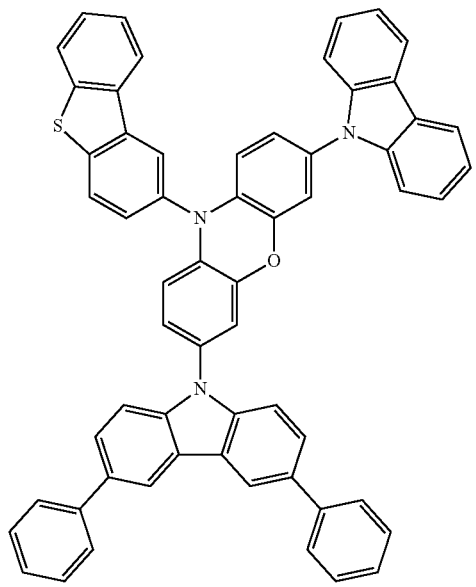
38
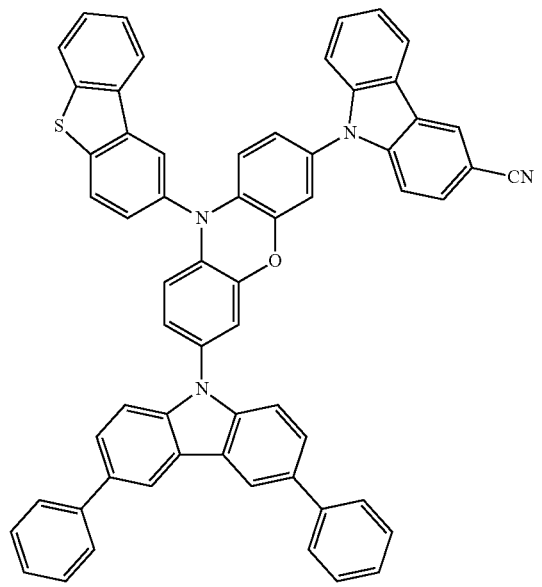

40
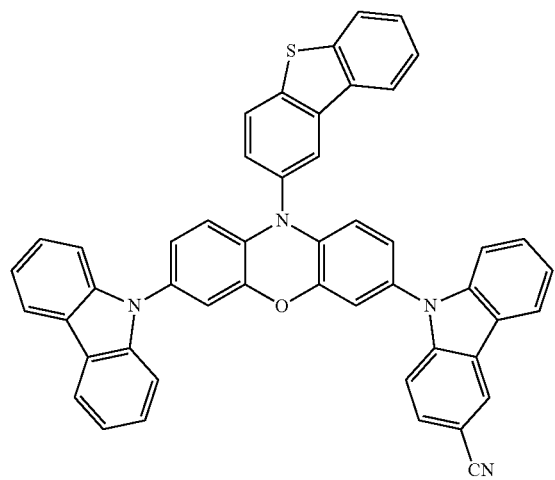
43
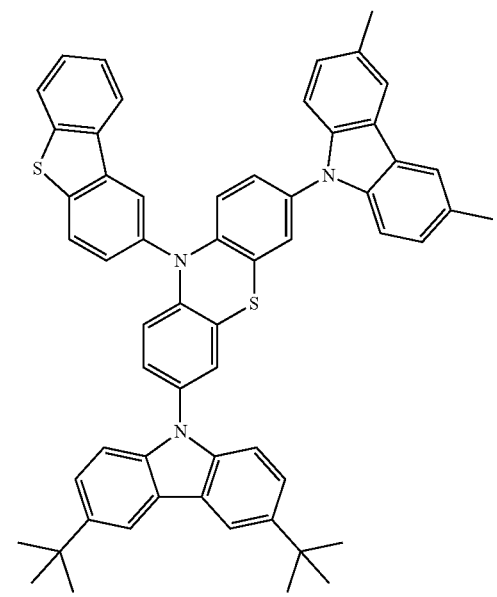
44
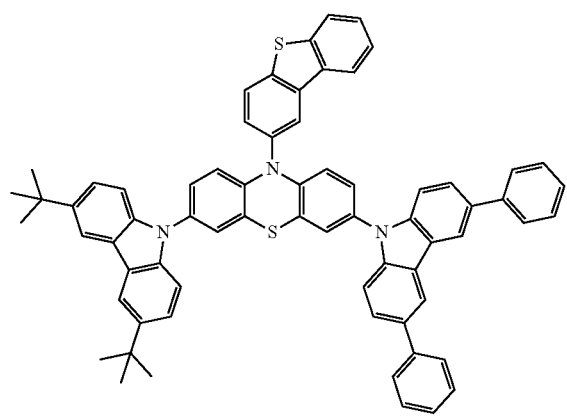
45
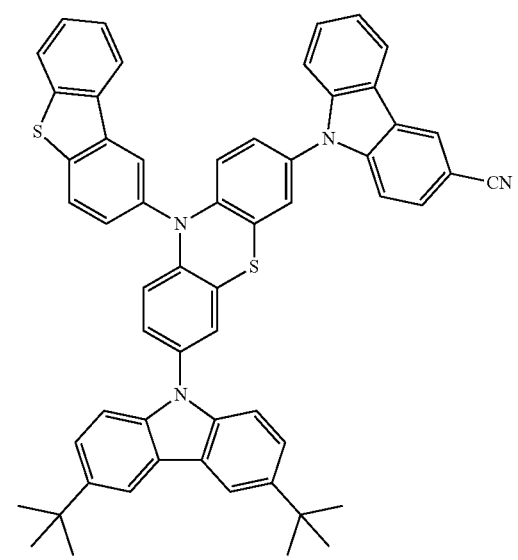
47
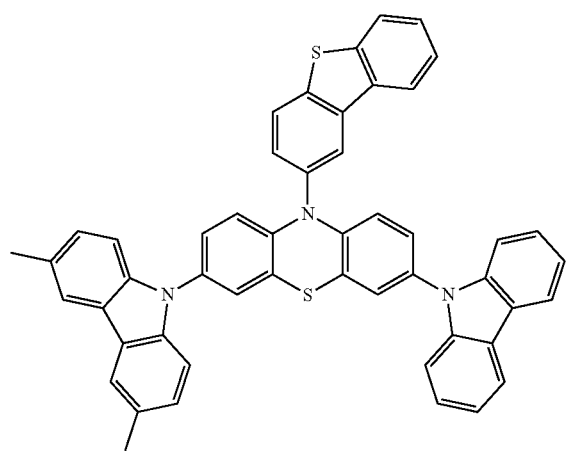
48
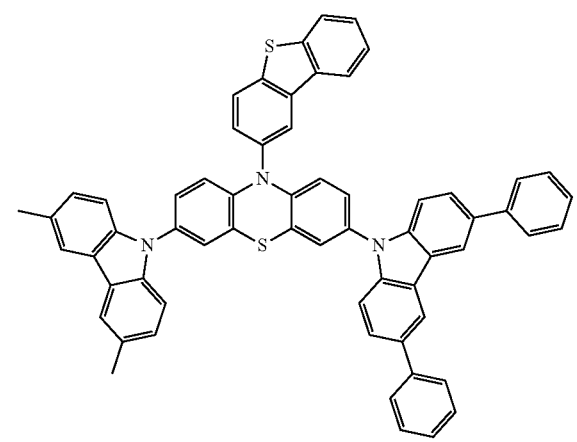

49
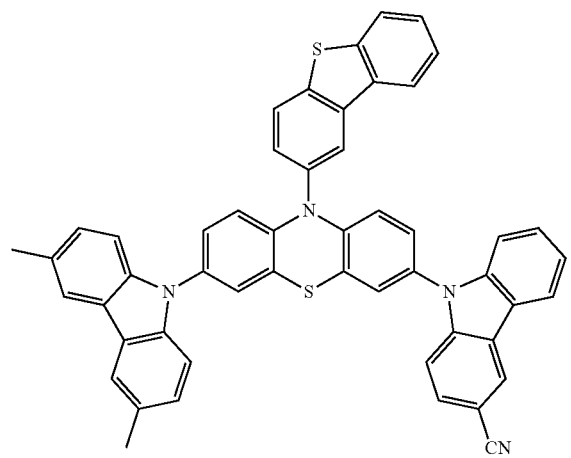
50
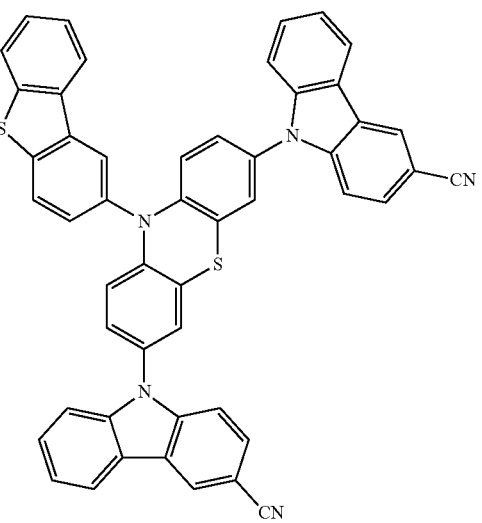
51
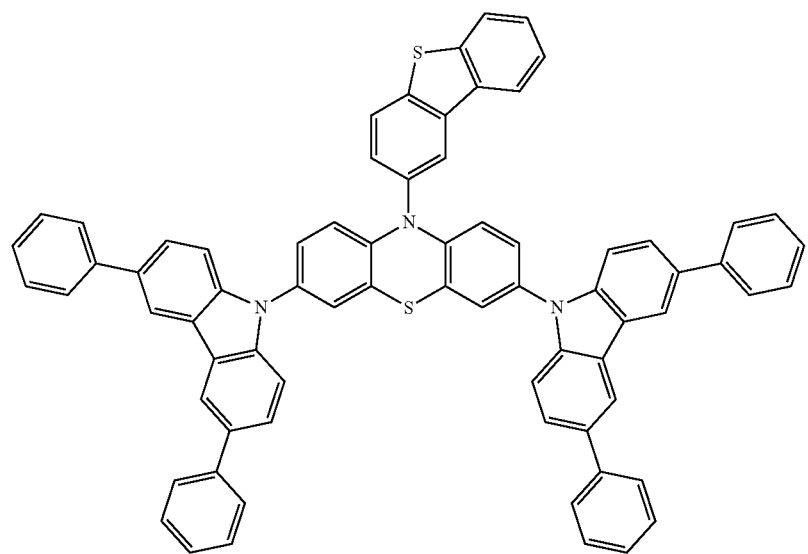

201
202
-continued
52 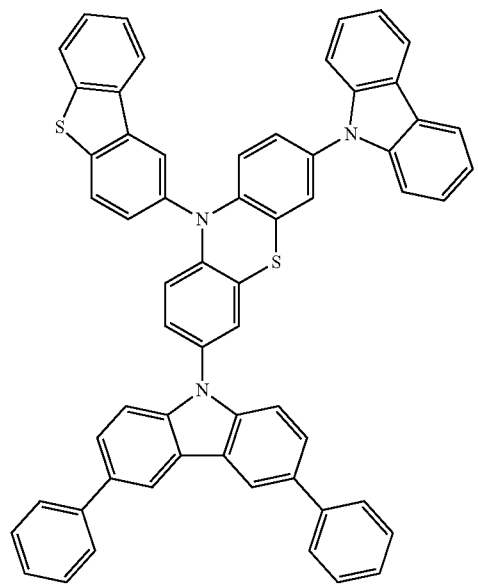
53 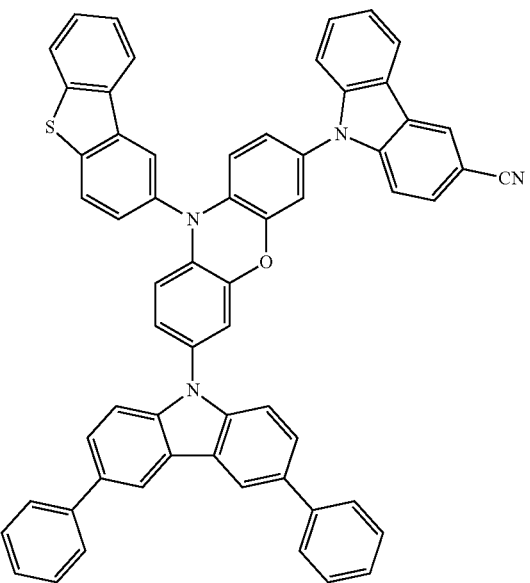
55 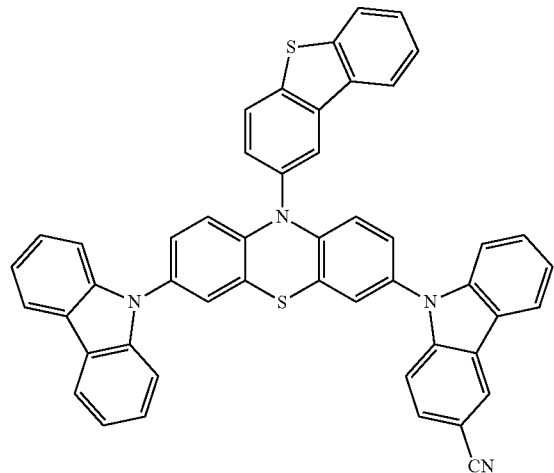
58 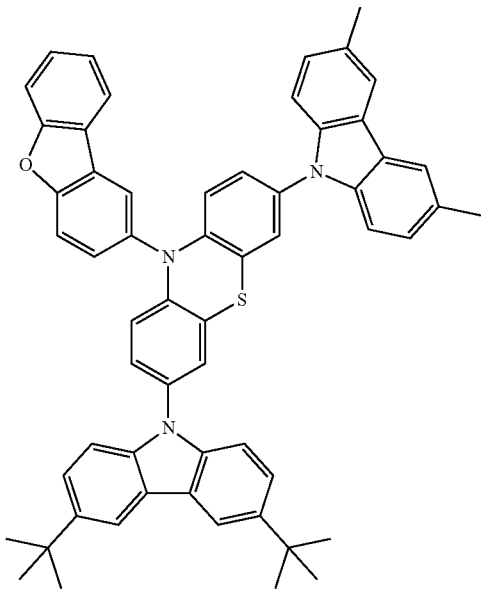

| 59 | 60 |
|---|---|
| 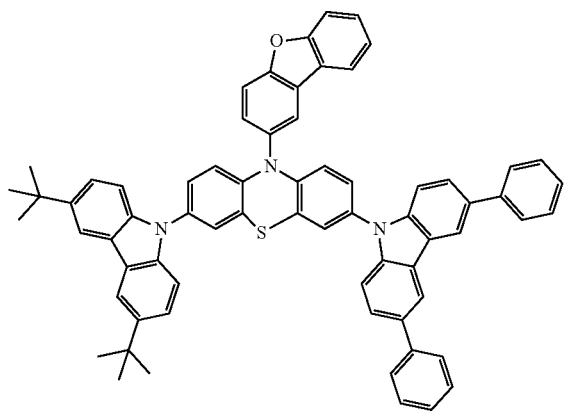 | 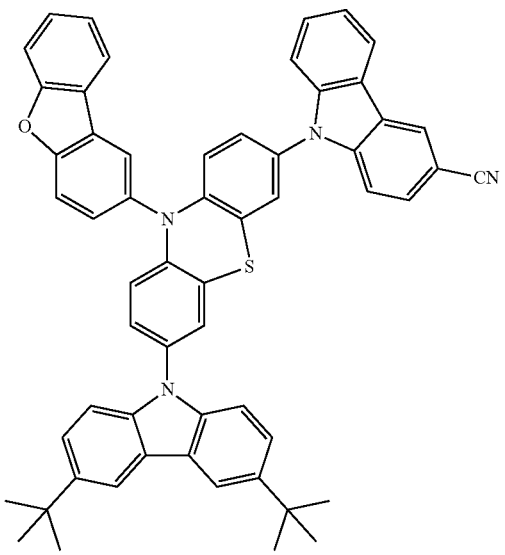 |
| 62 | 63 |
| 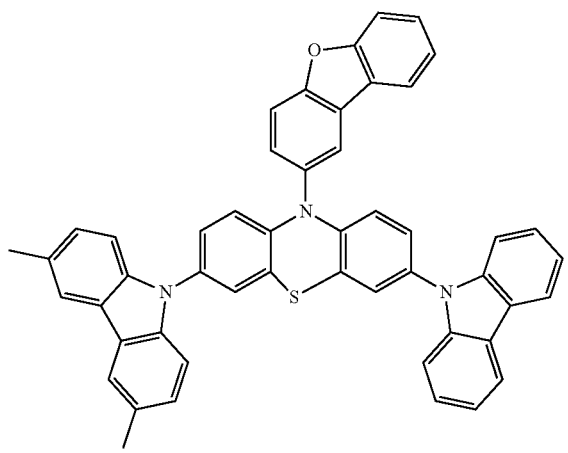 | 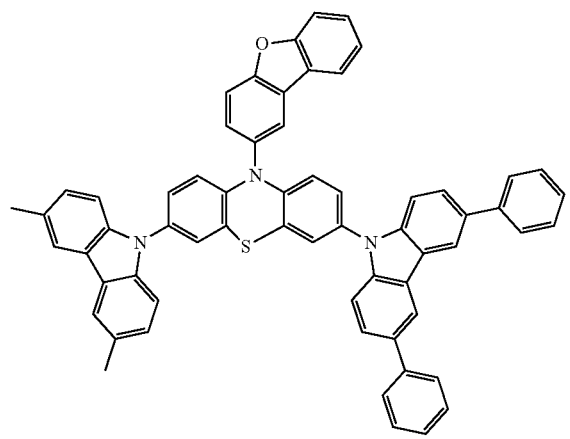 |
| 64 | 65 |
| 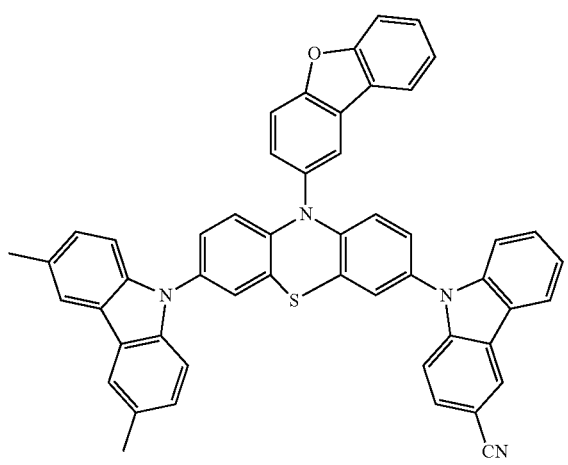 | 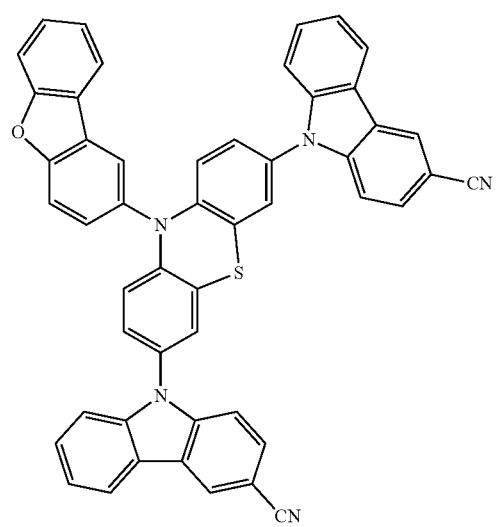 |

-continued
66
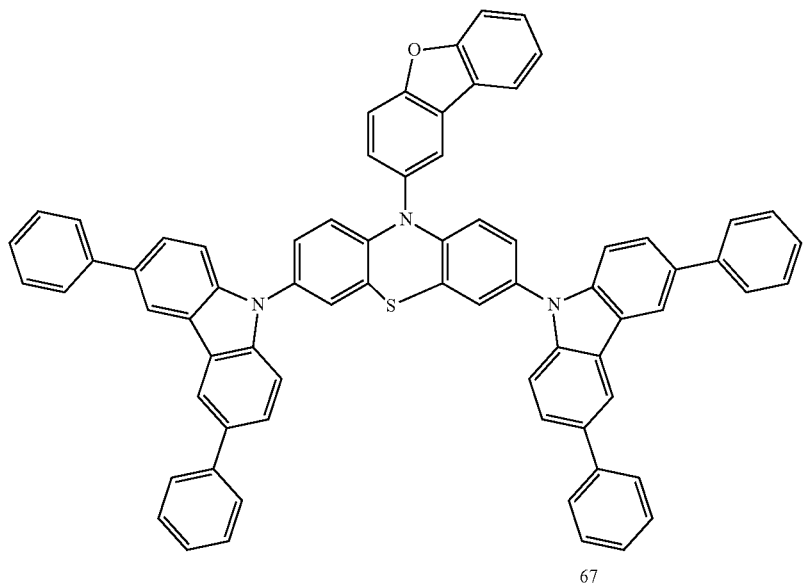
67
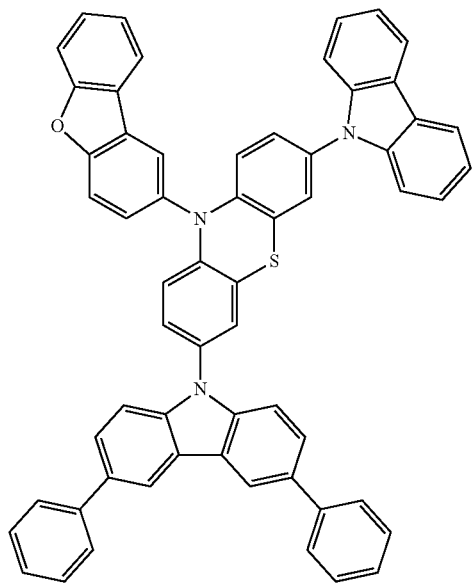
68
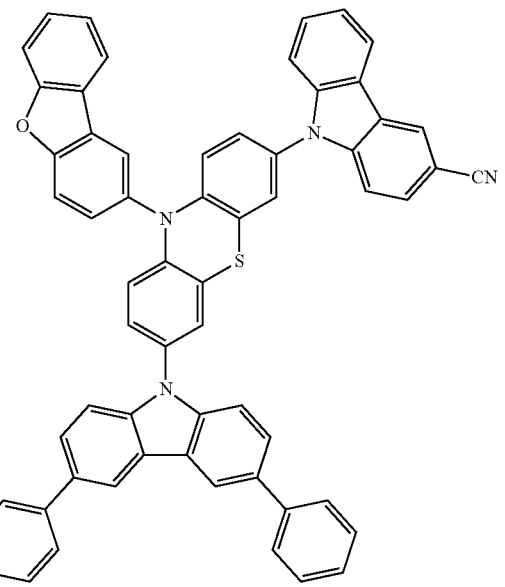
70
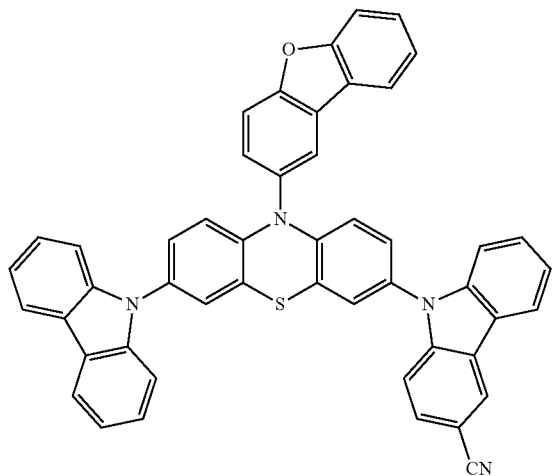

2. The organic electroluminescence device of claim 1, wherein: the plurality of functional layers comprise:
   a hole transport region on the first electrode;
   an emission layer on the hole transport region; and
   an electron transport region on the emission layer, and
   the emission layer comprises the polycyclic compound.

3. The organic electroluminescence device of claim 2, wherein:
   the emission layer comprises a host and a phosphorescent dopant, and
   the host comprises the polycyclic compound.

4. The organic electroluminescence device of claim 2, wherein the emission layer is to emit blue light.

5. A polycyclic compound being at least one selected from compounds 28 to 38, 40, 43 to 45, 47 to 53, 55, 58 to 60, 62 to 70, and 138 to 140:

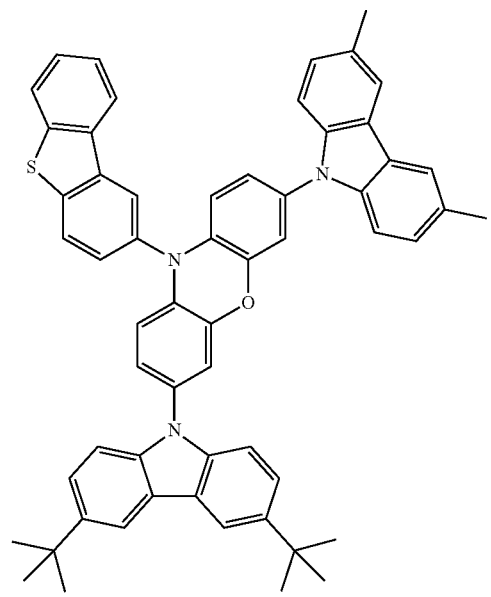

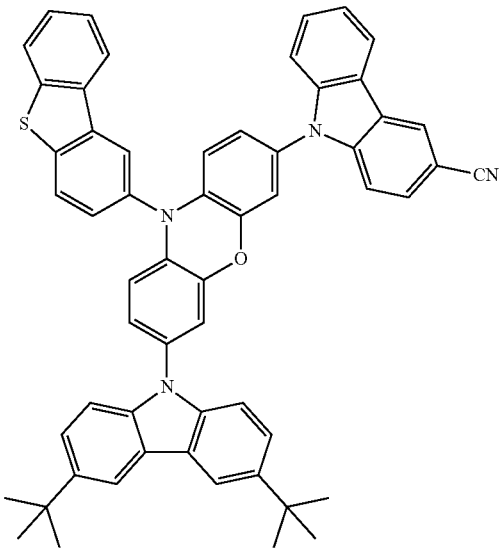

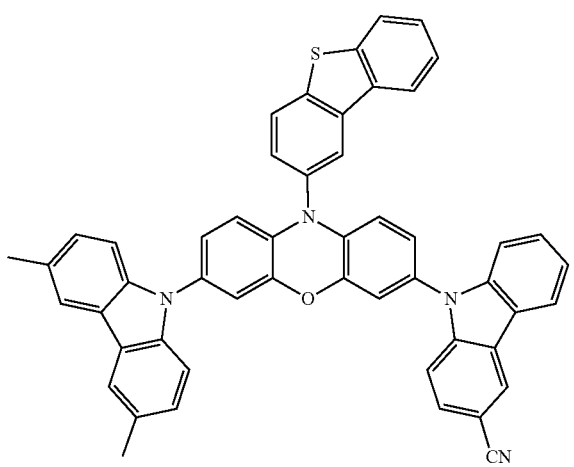
34
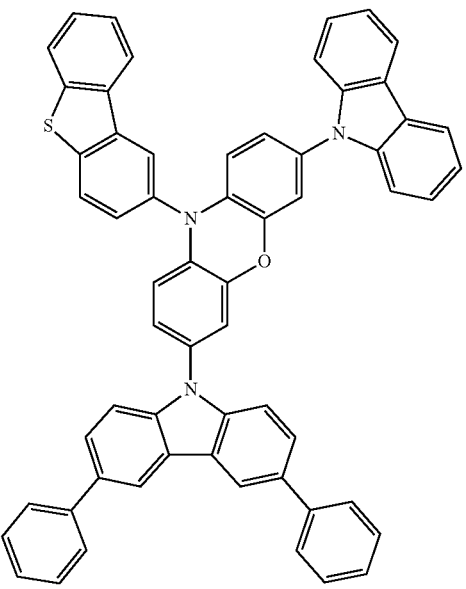
37
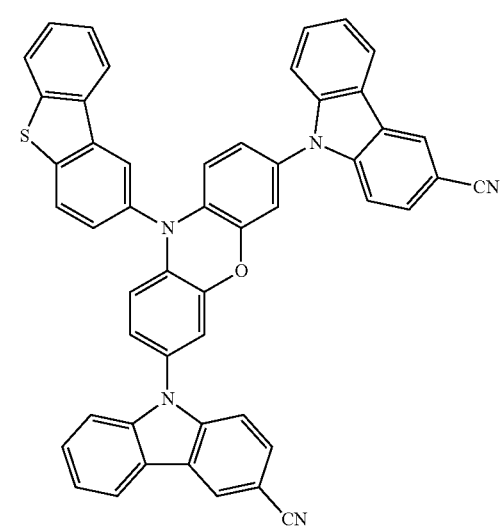
35
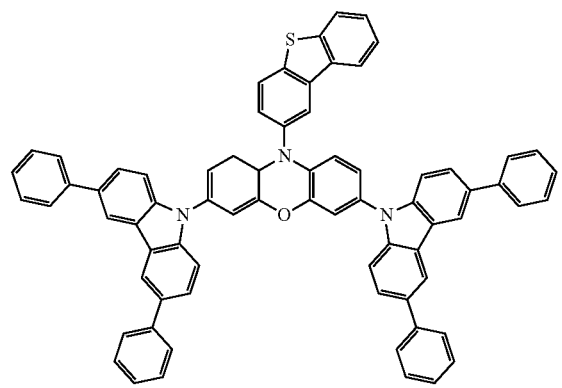
36
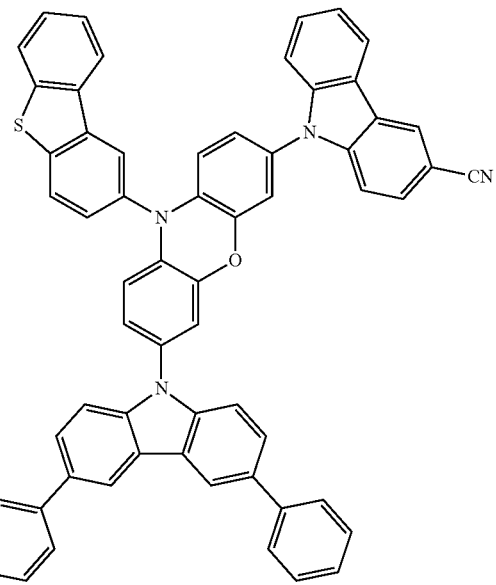
38

211
-continued
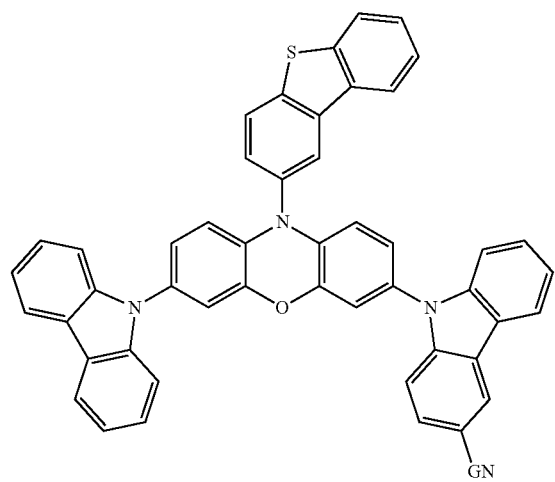
40
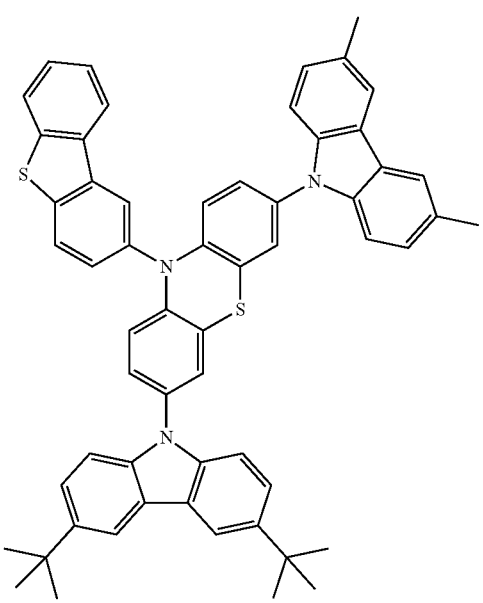
43
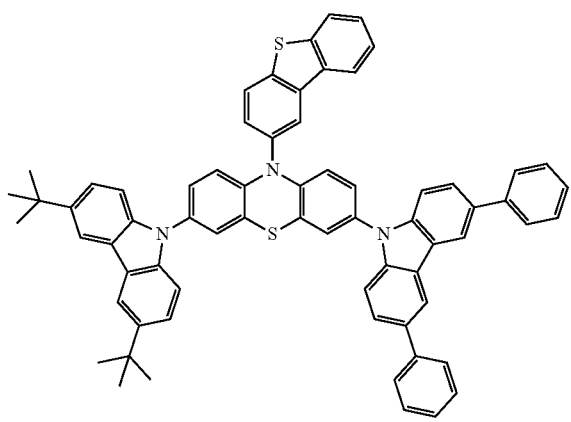
44
212
-continued
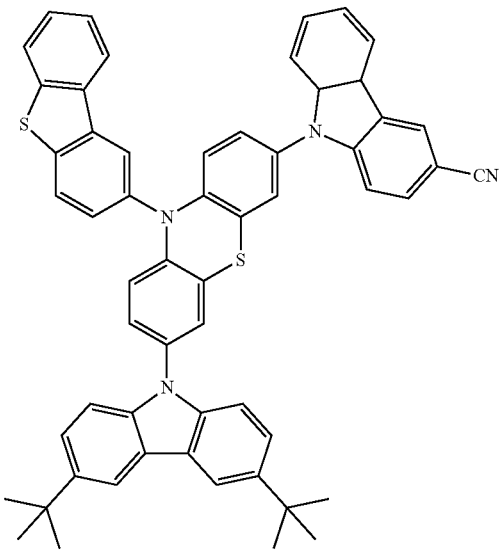
45
47
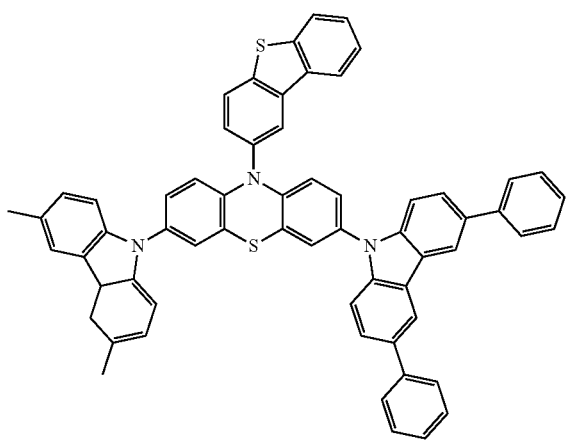
48

49
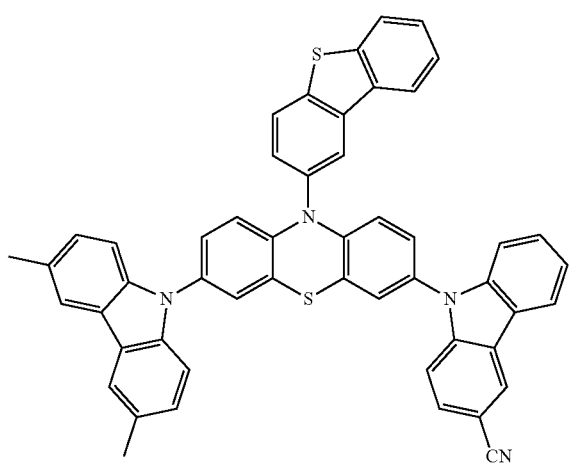
50
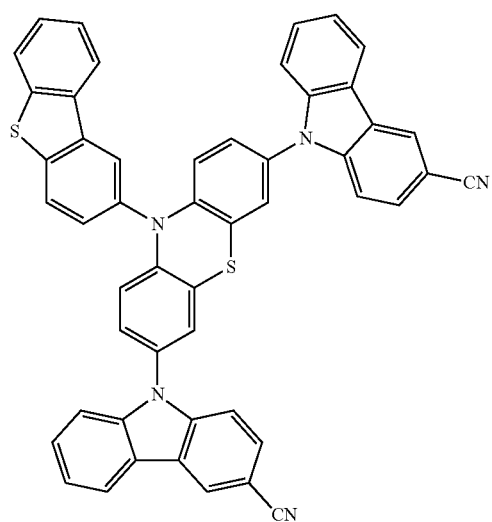
51
52
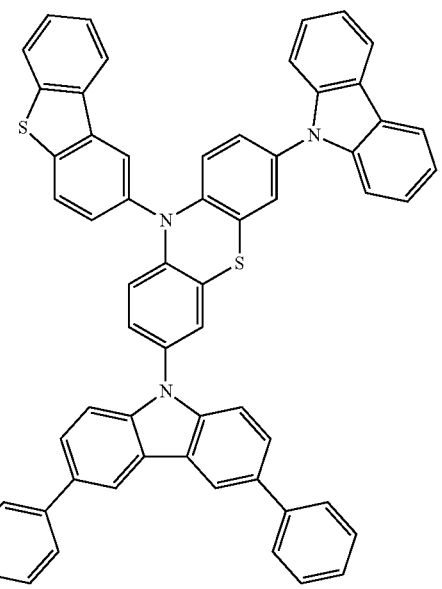
53
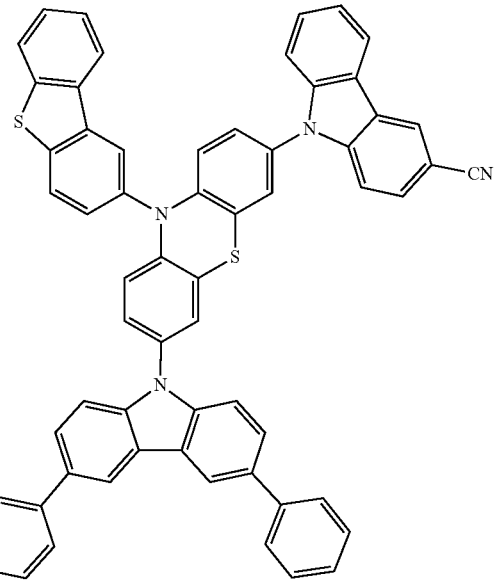

215
-continued
216
-continued
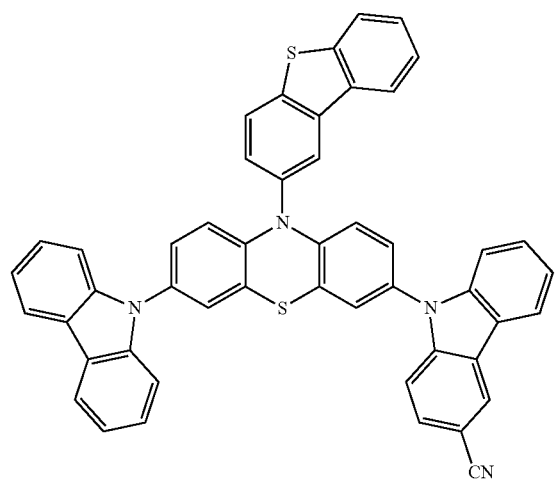
57
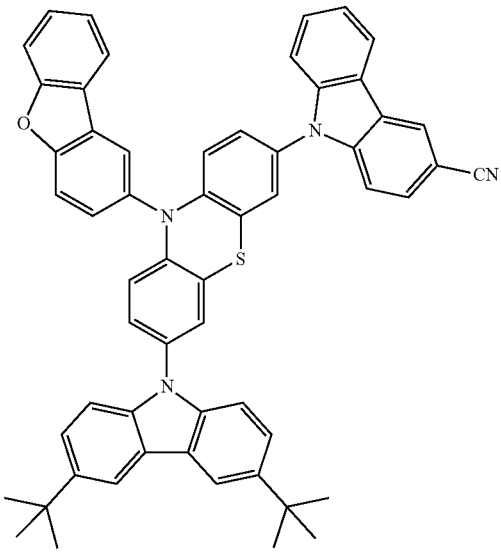
60
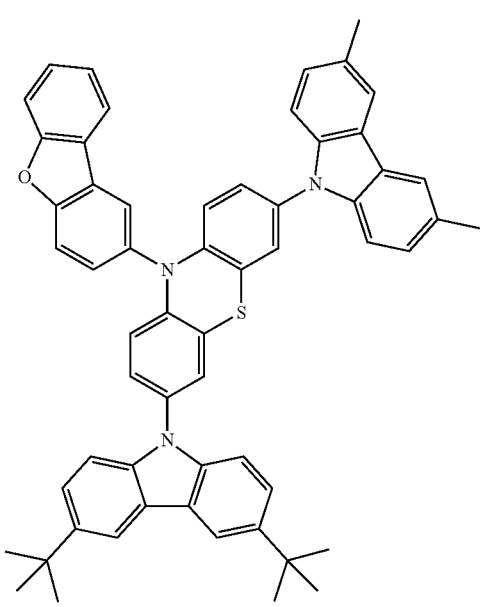
58
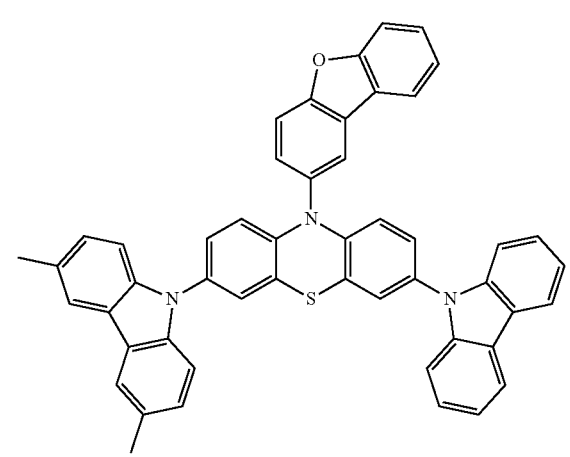
62
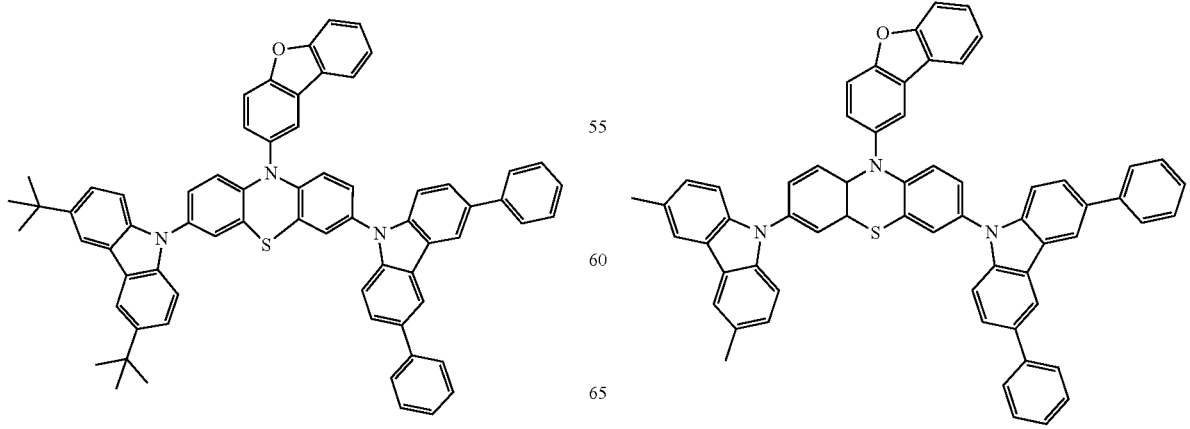
59
63

64
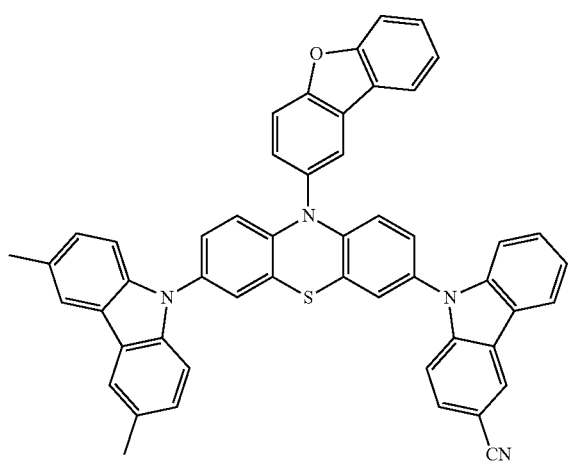
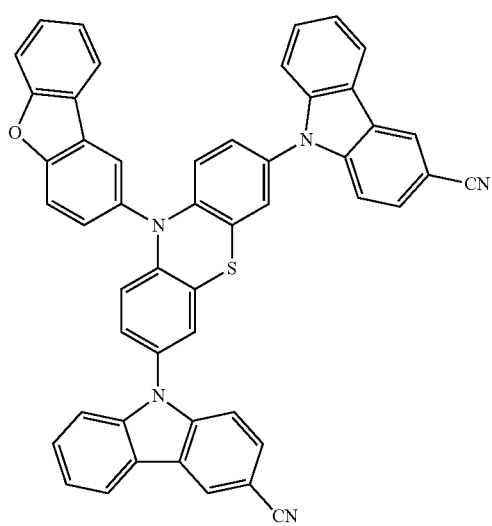
67
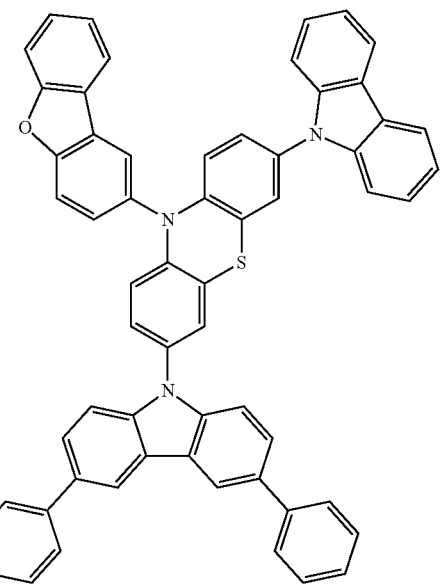
68
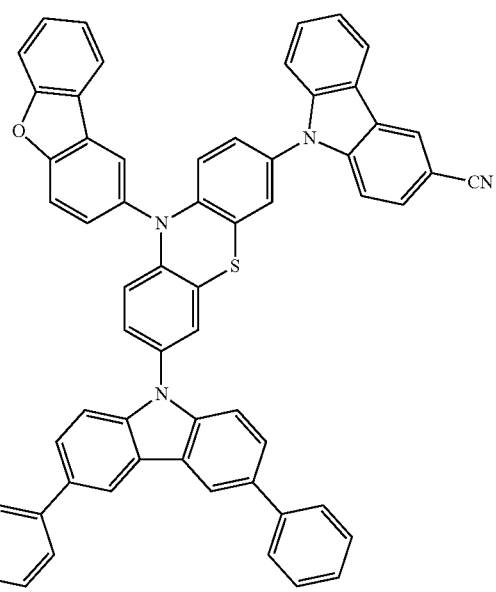

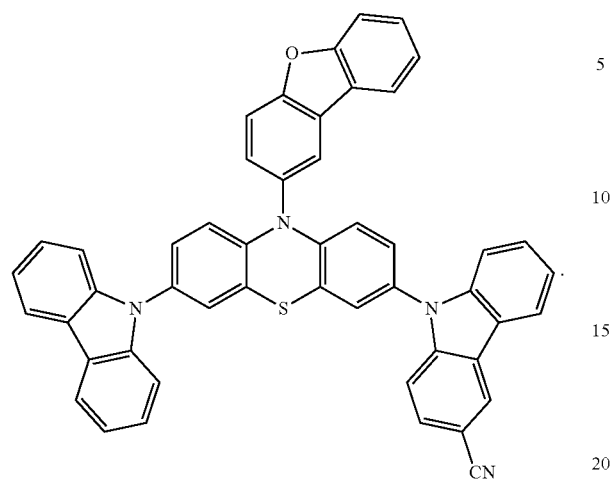
* * * * *